US006794137B2

(12) United States Patent
Blumenberg

(10) Patent No.: US 6,794,137 B2
(45) Date of Patent: Sep. 21, 2004

(54) GENE MARKERS USEFUL FOR DETECTING SKIN DAMAGE IN RESPONSE TO ULTRAVIOLET RADIATION

(75) Inventor: Miroslav Blumenberg, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/947,870

(22) Filed: Sep. 6, 2001

(65) Prior Publication Data

US 2002/0090624 A1 Jul. 11, 2002

Related U.S. Application Data

(60) Provisional application No. 60/231,454, filed on Sep. 8, 2000.

(51) Int. Cl.$^7$ .......................... C12Q 1/68; C07H 21/02; C07H 21/04
(52) U.S. Cl. .......................... 435/6; 536/23.1; 536/24.3
(58) Field of Search ........................... 435/6; 536/23.1, 536/24.3

(56) References Cited

U.S. PATENT DOCUMENTS

| 5,770,581 | A | * | 6/1998 | Weichselbaum et al. | |
| 5,908,836 | A | | 6/1999 | Bar-Shalom et al. | .......... 514/53 |
| 5,916,880 | A | | 6/1999 | Bar-Shalom et al. | .......... 514/53 |
| 5,939,082 | A | | 8/1999 | Oblong et al. | .............. 424/401 |
| 5,939,457 | A | | 8/1999 | Miser | ......................... 514/557 |
| 5,962,534 | A | | 10/1999 | Gudas et al. | ............... 514/690 |
| 6,258,536 | B1 | * | 7/2001 | Oliner et al. | |

OTHER PUBLICATIONS

Strickland et al., J. of Investigative Dermatology 108(5):763–768 (1997).*
Maytin et al., J. of Biological Chemistry 267(32) : 23, 189–23196 (1992).*
Huang et al., J. of Cellular Biochemistry 73(2) : 227–236 (1999).*
Herdegen et al., Neuroscience 81(1) : 199–212 (1997).*
Marshall et al. Cell 64 : 313–326 (1991).*
Weinberg et al. Science 251 : 1138–1146 (1991).*
Latkowski et al., "Epidermal Cell Kinetics, Epidermal Differentiation, and Keratinization," Fitzpatrick's Dermatology in Medicine (book) 1999 McGraw Hill pp 133–144.
Herrlich et al., "The Mammalian UV Response: Mechanism of DNA Damage Induced Gene Expression," Advan. Enzyme Regul. vol. 34, 1995, 381–395.
Ullrich et al., "The Role of Cytokines in UV–Induced Systemic Immune Suppression," Journal of Dermatological Science, vol. 23, 2000 Abstract.
Ouhtit et al., "Temporal Events in Skin Injury and the Early Adaptive Responses in Ultraviolet–irradiated Mouse Skin," American Journal of Pathology, vol. 156, No. 1, Jan. 2000, pp 201–207.

Beissert et al., "Mechanisms Involved in Ultraviolet Light–Induced Immunosuppression," J. Investig. Dermatol. Symp. Proc., vol. 4, No. 1, pp 61–63.
Zhuang et al., "Molecular Mechanism of Ultraviolet–Induced Keratinocyte Apoptosis," Journal of Interferon and Cytokine Research, vol. 20, 2000, pp 445–454.
Assefa et al., "Differential Stimulation of ERK and JNK Activities by Ultraviolet B Irradiation and Epidermal Growth Factor in Human Keratinocytes," vol. 108, No. 6, Jun. 1997, pp 886–890.
Kilgman et al., "The Nature of Photoaging: Its Prevention and Repair," Photodermatology, vol. 3, 1986, pp 215–227.
Lavker et al., "Aged Skin: A Study by Light, Transmission Electron, and Scanning Electron Microscopy," The Journal of Investigative Dermatology, vol. 88, No. 3, 1987.
Lavker et al., "Structural Alterations in Exposed and Unexposed Aged Skin," The Journal of Investigative Dermatology, vol. 73, No. 1, pp 80–85.
Gilchrest, "Skin and Aging Process" (Book) Copyright 1984 by CRC Press, Inc.
Darljand et al., "JNK1: A Protein Kinase Stimulated by UV Light and Ha–Ras That Blinds and Phosphorylaties the o–Jun Activation Domain," Cell, vol. 76, pp 1026–1037, Mar. 25, 1994.
Kyriakis et al., "The Stress–Activated Protein Kinase Subfamily of c–Jun Kinases," Nature, vol. 389, pp 156–160, May 12, 1994.
Rosett et al., "Ultraviolet Light and Osmotic Stress: Activation of the JNK Cascade Through Multiple Growth Factor and Cytokine Receptors," Science, vol. 274, Issue 5290, No. 15, 1998, pp 1194–1197.
Cavigelli et al., "The Tumor Promoter Arsante Stimulates AP–1 Activity by Inhibiting a JNK Phosphatase," The EMBO Journal, vol. 15, No. 22, pp. 6269–6279, 1996.
Kallunki et al., "c–Jun Can Recruit JNK to Phosphorylate Dimerization Partners via Specific Docking Interactions," Cell, vol. 87, pp 929–939, Nov. 29, 1996.
Fanger et al., "MEKKs, GCKs, MLKs, PAKs, TAKs and Tple: Upstream Regulators of the c–Jun Amino–Terminal Kinases," Oncogenes and Cell Proliferation, pp 67–74.

(List continued on next page.)

Primary Examiner—Ethan Whisenant
(74) Attorney, Agent, or Firm—Hale and Dorr LLP

(57) ABSTRACT

The cellular response to ultraviolet radiation exposure has been characterized on the molecular level through the use of high density gene array technology. Nucleic acid molecules and protein molecules, the expression of which are repressed or induced in response to ultraviolet radiation exposure, are identified according to a temporal pattern of altered expression post ultraviolet radiation exposure. Methods are disclosed that utilized these ultraviolet radiation-regulated molecules as markers for ultraviolet radiation exposure. Other screening methods of the invention are designed for the identification of compounds that modulate the response of a cell to ultraviolet radiation exposure. The invention also provides compositions useful for drug screening or pharmaceutical purposes.

92 Claims, 6 Drawing Sheets

OTHER PUBLICATIONS

Devary et al., "NK$–Kappa$B Activation by Ultraviolet Light Not Dependent on a Nuclear Signal," Science, vol. 261, Sep. 10, 1993, pp 1441–1446.

Simon et al., "UVB Light Induces Nuclear Factor kB(NFkB) Activity Independently From Chromosomal DNA Damage in Cell–Free Cytosolic Extracts," The Society for Investigative Dermatology, vol. 102, No. 4, Apr. 1984, pp 422–427.

Barnes et al., "Mechanisms of Disease," The New England Journal of Medicine, vol. 336, No. 15, Apr. 10, 1997, pp 1066–1071.

Li et al., "Ionizing Radiation and Short Wavelength UV Activate NF–$kappa$B Through Two Distinct Mechanisms," Proceedings of the National Academy of Science of the United States of America, vol. 95, Issue 22, Oct. 27, 1996, pp 13012–13017.

Garmayn et al., "Immediate and Delayed Molecular Response of Human Keratinocytes to Solar–Stimulated Irradiation," Laboratory Investigation, vol. 65, No. 4, 1991, pp 471–478.

Able et al., "Analysis of UVB–modulated Gene Expression in Human Keratinocytes by mRNA Differential Display Polymerase Chain Reaction," Photochemistry and Photobiology, vol. 66, No. 3, 1997, pp 383–387.

Eller, "Photodamage (book)" Blackwell Ed. 1995, pp 26–56.

Lockhart et al., "Expression Monitoring by Hybridization to High–Density Oligonucleotide Arrays," Nature Biotechnology, vol. 14, Dec. 1996, pp 1875–1880.

Johnston et al., "Gebe Chips: Array of Hope for Understanding Gene Regulation," Current Biology, vol. 8, 1996, pp R171–R174.

Scharf et al., "A Gene Expression Database for the Molecular Pharmacology of Cancer," Nature Genetics, vol. 24, Mar. 2000, pp 236–244.

Ross et al., "Systematic Variation In Gene Expression Patterns in Human Cancer Cell Lives," Nature Genetics,, vol. 24,,Mar. 2000, pp 227–235.

Welford et al., "Detection of Differentially Expressed Genes in Primary Tumor Tissues Using Representational Differences Analysis Coupled to Microarray Hybridization," Nucleic Acids Research, vol. 28, No. 12, 1998, 3059–3055.

Alon et al., "Broad Patterns of Gene Expression Revealed by Clustering Analysis of Tumor and Normal Colon Tissues Probed by Oligonucleotide Arrays," Proceedings of the National Academy of Science of the United States of America, vol. 96, Issue 12, Jun. 8, 1999, pp 6745–6750.

Golub et al.,"Molecular Classification of Cancer: Class Discovery and Class Prediction by Gene Expression Monitoring," Science, vol. 286, Oct. 15, 1999, pp 531–537.

Farnbrough et al., Diverse Signaling Pathways Activated by Growth Factor Receptors Induce Broadly Overlapping Rather Than Independent, Sets of Genes, Cell, vol. 97, Jun. 11, 1999, pp 727–741.

Galitski et al., "Pioidy Regulation of Gene Expression," Science, vol. 265, Jul. 9, pp 251–253.

Lee et al., "Gene Expression Profile of Aging and Its Retardation by Caloric Restriction," Science, vol. 298, Aug. 27, 1999, pp 1390–1392.

Ly et al., "Mitolic Misregulation and Human Aging," Science, vol. 287, Mar. 31, 2000, pp 2486–2492.

Harkin et al., "Induction of GADD–45 and JNK/SAPK–Dependent Apoptosis Following Inducible Expression of BRCAI," Cell, vol. 97, May 28, 1999, pp 575–585.

Jelinsky et al., "Global Response of *Saccharomyces cerevisiae* to an Alkylating Agent," Proceedings of the National Academy of Sciences of the United States of America, vol. 96, Issue 4, Feb. 15, 1999, pp 1486–1491.

Kilgman et al., "Photoaging," Fitzpatrick's Dermatology in Medicine (book) 1999 McGraw Hill, pp 1717–1721.

Zhao Rantin et al., "Analysis of p53–regulated Gene Expression Patterns Using Oligonucleotide Arrays," Genes & Development, vol. 14, No. 8, Apr. 15, 2000, pp 981–993 and Abstract.

Miyazawa M., et al., "Moscatilin From Dendrobium Noble, a Naturally Occurring Bibenzyl Compound With Potential Antimulagenic Activity," Journal of Agricultural and Food Chemistry, May 1999, vol. 47, No. 5, pp 2163–2167.

Rosen et al., "UVB Radiation–Activated Genes Induced by Transcriptional and Posttranscriptional Mechanisms in Rat Keratinocytes," The American Journal of Physiology, Apr. 1995, vol. 268, No. 4, pp C846–C856.

Fukunaga, et al., "MNK1, a New MAP Kinase–activated Portein Kinase, isolated by a Novel Expression Screening Method for Identifying Protein Kinase Substrates," The Embo Journal, Apr. 15, 1997, vol. 16, No. 6, pp 1921–1933.

Li et al., "Rays and Arrays: the Transcriptional Program in the Response of Human Epidermal Keratinocytes to UVB Illumination," Nov 2001, vol. 15, No. 13, pp 2533–2535.

Takao et al., "Genomic Scale Analysis of the Human Keratinocyte Response to Broad–band Ultraviolet–B Irradiation," vol. 18, No. 1, Feb. 2002, pp 5–13.

Kartasova et al., "Isolation, Characterization and UV–Stimulated Expression of Two Families of Genes Encoding Polypeptides of Related Structure in Human Epidermal Keratinocytes," vol. 8, No. 5, pp 2195–2203 and Abstract.

Shimizu et al., "Expression of a Novel Immediate Early Gene During 12–0 Tetradecanoylphorbol–13–Acetate–Induced Cells", Journal of Biol. Chemistry, vol. 266, No. 19, 1991, pp 12157–12161.

Iida et al., "Cloning and Sequencing of a New Gro Transcript From Activated Human Monocytes: Expression in Leukocytes and Wound Tissue," Mol. Cell. Biol., vol. 10, No. 10, 1990, pp 5596–5598.

Isoherranen et al., "UV Irradiation Induces Downregulation of bci–2 Expression In Vitro and In Vivo," Archives of Dermatological Research, vol. 291, No. 4, Apr. 1999, pp 212–216.

Buckman et al, "COX–2 Expression Is Induced by UVB Exposure In Human Skin: Implications for the Development of Skin Cancer," Carcinogenesis, May 1996, vol. 19, No. 5, pp 723–729.

\* cited by examiner

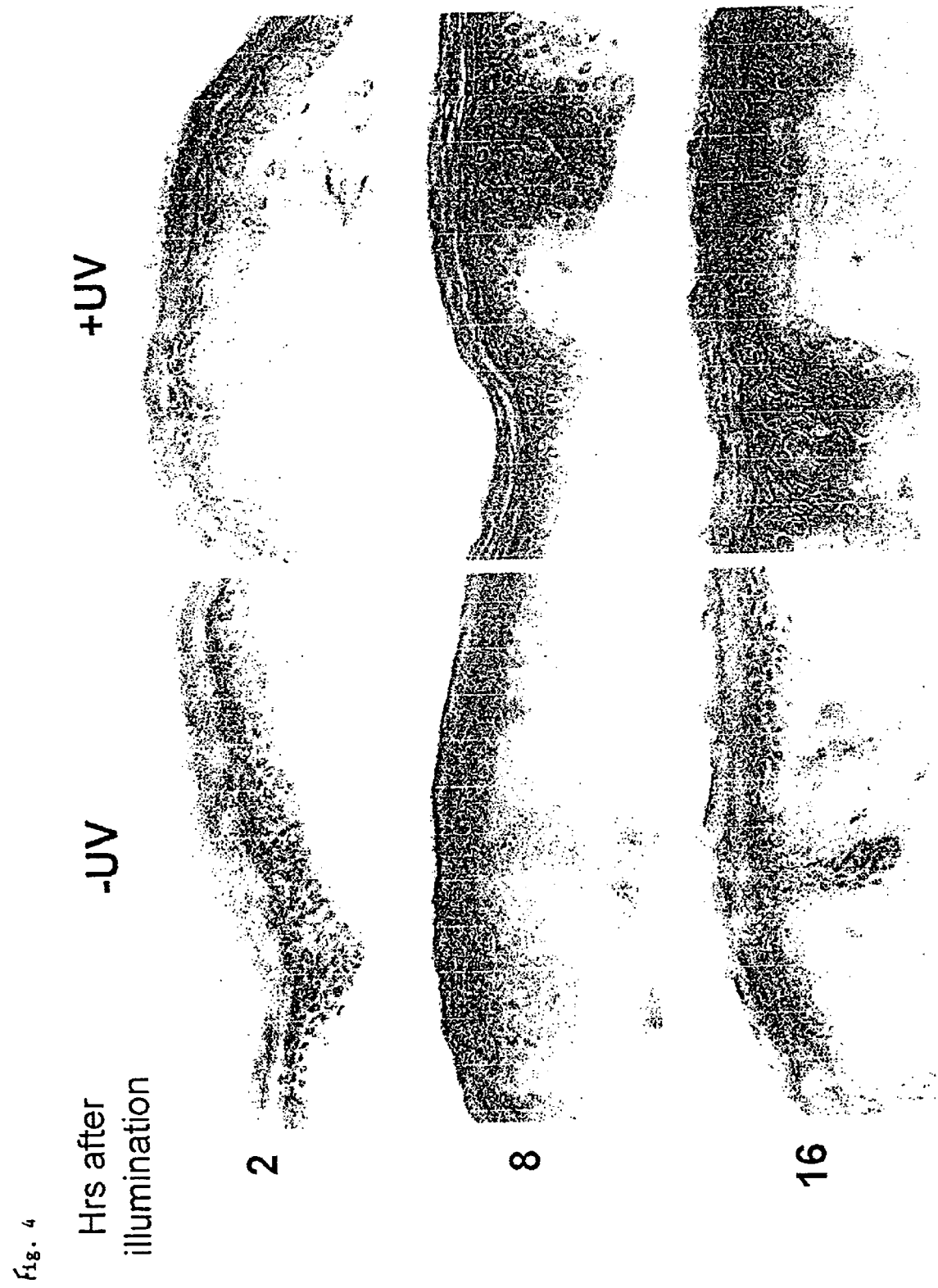

GENE MARKERS USEFUL FOR DETECTING SKIN DAMAGE IN RESPONSE TO ULTRAVIOLET RADIATION

CROSS-REFERENCE TO RELATED APPLICATION

This application claims the benefit of U.S. Provisional Application No. 60/231,454, filed Sep. 8, 2000.

FIELD OF THE INVENTION

The invention relates to the fields of molecular biology, cell biology and dermatology. More specifically, the invention relates to the molecular events underlying the response of a cell to exposure to ultraviolet radiation and, thereby, to the molecular processes contributing towards the development of premature tissue aging and cancer.

BACKGROUND OF THE INVENTION

Human skin is relatively simple tissue that performs varied and complex functions such as temperature regulation, the processing of vitamin D precursors, the excretion of urea, and the storage of carbohydrate and fat. The skin contains many unique cell types to effect its specialized functions. On a gross level, the skin consists of epidermis and a basement membrane zone overlying dermis and subcutaneous fat. Skin tissue arises embryologically from ectoderm, neuroectoderm, and mesoderm. The epidermis, hair and sebaceous glands (pilosebaceous units), sweat glands (eccrine units), and nails are all ectodermal derivatives. Neuroectodermal derivatives include melanocytes, nerves, and special neuroreceptors, while mesenchymal derivatives include collagen, reticulin and elastic fibers, blood vessels, muscle, and fat. Probably the most important function of the skin is that of protection; the skin produces a scaling surface impermeable to many substances, has an elaborate network of immunocompetent cells constantly monitoring for potentially harmful antigens, and produces pigment which filters out harmful rays of ultraviolet radiation from the sun.

Ultraviolet radiation is a major environmental damaging agent causing photodamage to the skin, including cutaneous malignancies and photoaging (see generally, *Fitzpatrick's Dermatology in Medicine,* Fifth Edition, I. M. Freedberg, et at, eds., McGraw-Hill (1999)). Clinical features of photoaging include wrinkles, skin laxity and coarseness, and pigmentation disorders. While histological manifestations of photoaging have been well known for some time, the molecular mechanisms that cause them have only recently become a focus of concerted studies.

Solar light contains a broad spectrum of energy wavelengths, and ultraviolet radiation which is among the relatively short wavelengths occurring at between 100 and 400 nanometers (in contrast to the visible light spectrum which occurs at between about 490 and 690 nanometers). Ultraviolet radiation is composed of three segments, designated as A, B, and C, Ultraviolet-C radiation (between 100 and 280 nanometers) is filtered out by the earth's ozone layer and is not known to pose a health threat. There is evidence, however, that exposure to both ultraviolet-A radiation (between 315 and 400 nanometers) and ultraviolet-B radiation (between 280 and 315 nanometers) can have adverse short-term and long-term effects on skin health and visual health. For example, ultraviolet radiation is known to play an important a role in both the development of skin cancers and premature aging of the skin.

The cell type most affected by ultraviolet radiation in humans is the keratinocyte. When illuminated by ultraviolet radiation, the keratinocyte reacts in three generally non-overlapping ways. First, it initiates a DNA repair response, which is activated by the DNA damage itself (Herrlick et al. (1994) *Adv. Enzyme Reg.* 34:381–95). Second, it signals to the surrounding tissue by releasing pro-inflammatory cytokines, such as IL-1 and TNFα (Ullrich et al. (2000) *J. Dermatol. Sci.* 23:S10–2; Ouhtit et al. (2000) *Am. J. Pathol.* 156:201–7; and Beissert et al. (1999) *J. Investig. Dermatol. Symp. Proc.* 4:61–4). Third, the keratinocyte activates its inherent responses to ultraviolet radiation by changing its physiology, including regulation of gene expression, cytoskeletal rearrangements, and induction of apoptosis (Zhuang et al. (2000) *J. Interferon Cytokine Res.* 20:445–54; and Assefa et al. (1997) *J. Invest. Dermatol.* 108:886–891).

The inherent responses of keratinocytes to ultraviolet radiation, by analogy with responses to other extracellular signals, can be separated into two phases, the immediate and delayed. The immediate phase contains the ultraviolet radiation-specific signal transduction cascades and results in activation of transcription factors. In the delayed phase one sees the changes in gene expression. The invention herein provides a characterization of the ultraviolet radiation-responsive induced and suppressed genes in human epidermal keratinocytes.

The histological signs of photoaging at the epidermal level include the following: (1) variation in the thickness of the epidermis (atrophy or hyperplasia according to the zones observed); (2) a cellular atypia (Kligman et al. (1986) *Photodermatol.* 3:215–227); (3) a loss of cell polarity; (4) an unevenness of the horny layer; (5) a reduction in the number of Langerhans' cells (Lavker et al. (1987) *J. Invest. Dermatol.* 88:44s–51s); (6) a pigmentation characterized by a mosaic appearance with hypo- or hyperpigmentation zones; and (7) a linearization of the dermo-epidermal junction (Lavker (1979) *J. Invest. Dermatol.* 73:59). For a review of photoaging of the skin, see Gilchourest, *Skin and Aging Processes,* 1989, CRC Press.

The biologic responses of cells exposed to ultraviolet radiation have been studied in a wide variety of systems, from *Esherichia coli* to man. In humans, the molecular effects of ultraviolet radiation include DNA damage, apoptosis and activation of the Jun N-terminal kinase (JNK) and the nuclear factor kappa-beta (NFkB). Both studied recently, although not extensively in epidermal keratinocytes, which are the primary target of ultraviolet radiation. A major impetus for studies of the molecular response to ultraviolet radiation came with the identification of the protein kinase that bound to and activated the c-Jun transcription factor in response to ultraviolet radiation (Derijard et al. (1994) *Cell* 76:1025–1037). The kinase was named "JNK" for Jun N-terminal kinase, or "SAPK" for stress activated protein kinase (Kyriakis et al. (1994) *Nature* 369:156–160). Soon it was realized that JNK responds to several extracellular signals in addition to ultraviolet radiation, such as osmotic shock, arsenate, and pro-inflammatory cytokines (Rosette et al. (1996) *Science* 274:1194–7; Cavigelli et al. (1996) *E.M.B.O. Journal* 15:6269–79). JNK can phosphorylate additional transcription factors, including Elk1 and ATF2 (Kallunki et al. (1996) *Cell* 87:929–39). JNK is itself activated by a small number of relatively specific kinases, designated "JNKKs." Many kinases, designated JNKKKs, respond to a large variety of stimuli to phosphorylate and activate "JNKKs;" the ultraviolet radiation-responsive JNKKK has not yet been identified (Fanger et al. (1997) *Curr. Opin. Genet. Dev.* 7:67–74).

Another clear molecular effect of ultraviolet radiation is the activation of the NFkB transcription factor (Devary et al. (1993) *Science* 261:1442–5). The activation of NFkB by ultraviolet radiation is not associated with DNA damage and occurs even in cytoplasts devoid of nuclear DNA (Devary et al. (1993) *Science* 261:1442–5; Simon et al. (1994) *J. Invest. Dermatol.* 102:422–7). Inactive NFkB resides in the cytoplasm complexed with IkB protein. Upon activation by a very large and varied set of extracellular stimuli, IkB is phosphorylated and thus designated for proteolysis. This results in the release of NFkB, which is then free to enter the nucleus and activate gene transcription (Barnes et al. (1997) *NE J. Med.* 336:1066–71). The ultraviolet radiation-responsive kinases that mark IkB for degradation have not yet been identified (Li et al. (1998) *Proc. Natl. Acad. Sci (USA)* 95:13012–13017).

Methods to evaluate photodamage to skin or to cells contained therein have been described in the art. For example, U.S. Pat. No. 6,079,415 provides methods and markers useful for establishing ultraviolet-A radiation damage to the dermis, and more specifically, to the production of collagen by fibroblasts of the dermis. Moreover, methods useful for the prevention of ultraviolet radiation damage to the skin or cells contained therein have been described. For example, U.S. Pat. No. 5,908,836 provides methods for protecting skin from ultraviolet radiation damage using sulphated sugars, and U.S. Pat. No. 5,916,880 provides a method to reduce wrinkles by treatment with sulfated sugars. Numerous other examples have been described in the field. For example, U.S. Pat. No. 5,939,457 describes the use of a hydroxy acid product useful for the reduction of wrinkles, U.S. Pat. No. 5,939,082 describes the use of a vitamin B compound for the regulation of signs of skin aging, and U.S. Pat. No. 5,962,534 describes the use of certain retenoids.

However, studies to date examining the response at the molecular level of skin and the specialized skin cells to exposure to ultraviolet radiation almost exclusively have been limited to the examination of one or several genes and/or proteins specific to a particular cellular process. For example, the study by Garmyn et al. ((1991) *Lab. Invest.* 65:471–478) describes an immediate and early temporal pattern of keratinocyte response to exposure to ultraviolet radiation, but this study was limited to an analysis of the expression patterns of only a few genes. Moreover, no study has successfully provided an analysis of the complete response of the skin and/or the specialized cells of the skin to exposure to ultraviolet radiation. For example, while the study by Abts et al. ((1997) *Photochem. Photobio.* 66(3):363–367) utilized the methodology of mRNA differential display to study alterations in gene expression mediated by ultraviolet radiation exposure, the study identified only a very small number of ultraviolet radiation-regulated genes due to the difficulty of the technique used.

The role of the ultraviolet-B radiation has been clearly demonstrated in the induction of ultraviolet radiation-induced skin cancers. It has, as a principal chromophore, nucleic acids and, in particular, deoxyribonucleic acid, in which it induces lesions and/or notations (Eller, in *Photodamage*, pp. 26–56, Blackwell, ed. (1995)). In addition, ultraviolet-B radiation has been linked to premature aging of the skin, characterized by a dry, rough clinical appearance associated with a loss of elasticity, as well as marked wrinkles.

Gene array technology is a powerful, new technique for gene expression monitoring, enabling a global view into changes of expression for an extremely large set of genes. The technology has been applied to the study of many biologic processes (see, e, Lockhart et al. (1966) *Nat. Biotechnol.* 14:1675–1680; Johnston (1998) *Curr. Biol.* 8:171–174). For example, the technique has been used in the study of cancer (Scherf et al. (2000) *Nat. Genet.* 24:236–44; Ross et al. (2000) *Nat. Genet.* 24:227–35; Welford et al. (1998) *Nuc. Acids Res.* 26:3059–3065; Alon et al. (1999) *Proc. Natl. Acad. Sci.* (*USA*) 96:6745–6750; and Golub et al. (1999) *Science* 286:531–537); for the study of complex pathways of gene expression (Fambrough et al. (1999) *Cell* 97:727–741; and Galitski et al. (1999) *Science* 285:251–254); for the study of the aging process (Cheol-Koo Lee (1999) *Science* 285:1390–1393; Ly et al. (2000) *Science* 287:2486–92; Harkin (1999) *Cell* 97:575–586); and for the study of the stress response of cells to particular damaging agents (Jelinsky et al. (1999) *Proc. Natl. Acad. Sci.* (*USA*) 96:1486–1491)).

Pharmacological agents useful in the treatment of photodamaged skin have been identified. For example, the normal repair processes in photodamaged skin have been enhanced pharmacologically. The first to be assessed for this property was Tretinoin (all-trans-retinoic acid). Studies have demonstrated that the reconstruction zone of new collagen was significantly deeper in tretinoin-treated mice, with the enhanced repair being dose and time related. In addition, new collagen was histochemically, ultrastructurally, and biochemically normal. As determined by radioimmunoassay, collagen content was increased twofold, and mRNAs for types I and III collagen were increased two- to threefold in the tretinoin-treated skin. New collagen synthesis was localized with immunofluorescence techniques in the histologically defined reconstruction zone, and the presence of new elastin and increased fibronectin were also established in the region. Isotretinoin (13-cis-retinoic acid) has also been demonstrated to enhance dermal repair in mice. This repair activity remains retinoid-specific. *Fitzpatrick's Dermatology in Medicine*, Fifth Edition, I. M. Freedberg, et al., eds., McGraw-Hill (1999), pp. 1717–1721).

Studies at the molecular level have shown that ultraviolet-B radiation up-regulates the collagen-degrading enzymes collagenase and gelatinase, and that tretinoin reduces the mRNA's, protein, and activities of these enzymes by 50 to 80 percent. Id. at 1721. Thus, pharmacological agents may be used to reverse skin damage resulting from altered expression of proteins and nucleic acid molecules due to ultraviolet radiation exposure.

Because exposure of specialized cells of the skin to ultraviolet radiation plays an important role in the generation of skin cancer and in the process of premature aging, it would be beneficial to characterize at the molecular level the full response of the skin to exposure to ultraviolet radiation. The present invention provides such information, which was previously lacking in the field. Moreover, epidermal keratinocytes, the main target of environmental ultraviolet radiation, have seldom been used as the model system. The invention described herein redresses this deficiency in the art. Furthermore, nucleic acid molecules and protein molecules in skin cells that are regulated by ultraviolet radiation and the methods provided herein are useful resources for the identification of pharmacological agents for the prevention and treatment of skin cancer and premature aging of the skin.

SUMMARY OF THE INVENTION

It has been discovered that certain molecular events occur in the response of a cell to exposure to ultraviolet radiation.

More particularly, it has been determined that the expression of a plurality of specific nucleic acid molecules and proteins are regulated in response to ultraviolet radiation exposure. The term "regulated" is used herein to mean that the expression of RNA molecules and/or proteins encoded therein are increased or decreased in response to ultraviolet radiation exposure of a cell relative to the expression levels found in a non-ultraviolet radiation irradiated cell. These ultraviolet radiation-regulated nucleic acid molecules and proteins are further characterized temporally in relation to the cellular response (a first response, a second response, and a third response) and in a quantitative fashion (induced or repressed) in relation to the expression levels found in a cell not exposed to ultraviolet radiation.

These discoveries have been exploited to provide the present invention, which includes compositions of matter, pharmaceutical compositions, methods of identifying a cell exposed to ultraviolet radiation, and screening methods for the identification of compounds that modulate a response by a cell to ultraviolet radiation exposure, the response comprising the altered expression of nucleic acid molecules and/or proteins in the cell.

The cellular responses defined by the present invention relate to the altered expression of RNA molecules and/or protein molecules in a cell exposed to ultraviolet radiation. These responses include the following: (1) a primary first response, a primary second response, and a primary third response, all of which relate to the altered expression of RNA molecules in a cell exposed to ultraviolet radiation; (2) a secondary first response, a secondary second response, and a secondary third response, all of which relate to the altered expression of RNA molecules in a cell exposed to ultraviolet radiation; (3) a tertiary first response, a tertiary second response, and a tertiary third response, all of which relate to the altered expression of proteins in a cell exposed to ultraviolet radiation; and (4) a quaternary first response, a quaternary second response, and a quaternary third response, all of which relate to the altered expression of proteins in a cell exposed to ultraviolet radiation. Thus, the invention provides for a number of groups of RNA molecules or proteins that are regulated in response the exposure of a cell to ultraviolet radiation. These groups include the following: (1) a primary first response group, a primary second response group, and a primary third response group, all of which relate to the altered expression of RNA molecules in a cell exposed to ultraviolet radiation; (2) a secondary first response group, a secondary second response group, and a secondary third response group, all of which relate to the altered expression of RNA molecules in a cell exposed to ultraviolet radiation; (3) a tertiary first response group, a tertiary second response group, and a tertiary third response group, all of which relate to the altered expression of proteins in a cell exposed to ultraviolet radiation; and (4) a quaternary first response group, a quaternary second response group, and a quaternary third response group, all of which relate to the altered expression of proteins in a cell exposed to ultraviolet radiation. The specific differences between these groups are detailed below.

In accordance with a further aspect of the invention, there is provided a composition of matter comprising: (1) a plurality of nucleic acid molecules at least 90% identical to the group of polynucleotides regulated by a cell in response to ultraviolet radiation exposure; and (2) a substrate suitable for binding the nucleic acid molecules of (1). The group of polynucleotides regulated by the cell in response to ultraviolet radiation exposure comprises the following: M20030 Human small proline rich protein (sprII) mRNA, clone 930, X53065, M13903 Human involucrin gene, exon 2, L10343 Human elafin gene, complete cds, M21302 Human small proline rich protein (sprII) mRNA, clone 174N, L05188 *H. sapiens* small proline-rich protein 2 (SPRR2B) gene, complete cds, Y00787 Human mRNA for MDNCF (monocyte-derived neutrophil chemotactic factor), D50840 *H. sapiens* mRNA for ceramide glucosyltransferase, complete cds, M22918 Myosin, Light Chain, Alkali, Smooth Muscle (Gb:U02629), Non-Muscle, Alt. Splice, X70326 Macmarcks, X52426 *H. sapiens* mRNA for cytokeratin 13, S81914 IEX-1=radiation-inducible immediate-early gene [human, placenta, mRNA Partial, 1, M80254 *H. sapiens* cyclophilin isoform (hCyP3) mRNA, complete cds, L08069 Human heat shock protein, *E coli* DnaJ homolog mRNA, complete cds, U62800 Human cystatin M (CST6) mRNA, complete cds, L24564 Human Rad mRNA, complete cds, M59465 Human tumor necrosis factor alpha inducible protein A20 mRNA, complete cds, Z49989 *H. sapiens* mRNA for smoothelin, X57985 *H. sapiens* genes for histones H2B.1 and H2A, L19779 *H. sapiens* histone H2A.2 mRNA, complete cds, D42040 Human mRNA for KIAA9001 gene, complete cds, M63573 Human secreted cyclophilin-like protein (SCYLP) mRNA, complete cds, X54489 Human gene for melanoma growth stimulatory activity (MGSA), M92934 Human connective tissue growth factor, complete cds, Z14244 *H. sapiens* coxVIIb mRNA for cytochrome c oxidase subunit VIIb, M60278 Human heparin-binding EGF-like growth factor mRNA, complete cds, M72885 Human GOS2 gene, 5' flank and cds, X62083 *H. sapiens* mRNA for Drosophila female sterile homeotic (FSH) homolog, X67325 *H. sapiens* p27 mRNA, U04636 Human cyclooxygenase-2 (hCox-2) gene, complete cds, M26311 Human cystic fibrosis antigen mRNA, complete cds, L20688 Human GDP-dissociation inhibitor protein (Ly-GDI) mRNA, complete cds, M27436 Human tissue factor gene, complete cds, with a Alu repetitive sequence in the 3', AF001294 *H. sapiens* IPL (IPL) mRNA, complete cds, M22918 Myosin, Light Chain, Alkali, Smooth Muscle (Gb:U02629), Non-Muscle, All. Splice, X74874 *H. sapiens* gene for RNA pol II largest subunit, exon 1, M22919 Myosin, Light Chain, Alkali, Smooth Muscle (Gb:U02629), Smooth Muscle, Alt. Spli, V00594 Human mRNA for metallothionein from cadmium-treated cells, V00599 Tubulin, Beta, X99920 *H. sapiens* mRNA for S100 calcium-binding protein A13, M21005 Human migration inhibitory factor-related protein 8 (MRP8) gene, complete cds, U07919 Human aldehyde dehydrogenase 6 mRNA, complete cds, M37583 Human histone (H2A.Z) mRNA, complete cds, S54005 thymosin beta-10 [human, metastatic melanoma cell line, mRNA, 453 nt], D49824 Human HLA-B null allele mRNA, S78771 NAT=CpG island-associated gene [human, mRNA, 1741 nt], M90657 Human tumor antigen (L6) mRNA, complete cds, U09937 Human urokinase-type plasminogen receptor, exon 7, X77794 *H. sapiens* mRNA for cyclin G1, M28130 Human interleukin 8 (IL8) gene, complete cds, X14850 Human H2AX mRNA encoding histone H2A.X, AB000584 *H. sapiens* mRNA for TGF-beta superfamily protein, complete cds, U52101 Human YMP mRNA, complete cds, M57731 Human gro-beta mRNA, complete cds, D45248 Human mRNA for proteasome activator hPA28 subunit beta, complete cds, X83416 *H. sapiens* PrP gene, exon 2, X52882 Human t-complex polypeptide 1 gene, X57351 Human 1-8D gene from interferon-inducible gene family, X53800 Human mRNA for macrophage inflammatory protein-2beta (MIP2beta), Z69043 *H. sapiens* mRNA translocon-associated protein delta subunit precursor, D38305 Human mRNA for Tob, complete cds, X52979

Human gene for small nuclear ribonucleoproteins SmB and SmB', S80437 fatty acid synthase {3' region} [human, breast and HepG2 cells, mRNA Partial, 22, X87679 Major Histocompatibility Complex, Class I, E (Gb:M21533), Z29505 *H. sapiens* mRNA for nucleic acid binding protein sub2.3, D21853 Human mRNA for KIAA0111 gene, complete cds, X78687 *H. sapiens* G9 gene encoding sialidase, M13755 Human interferon-induced 17-kD/15-kD protein mRNA, complete cds, M21186 Human neutrophil cytochrome b light chain p22 phagocyte b-cytochrome mRNA, compl, D28235 Human PTGS2 gene for prostaglandin endoperoxide synthase-2, complete cds, M14328 Human alpha enolase mRNA, complete cds, V00599 Tubulin, Beta 2, U90546 Human butyrophilin (BTF4) mRNA, complete cds, K02574, X15729 Human mRNA for nuclear p68 protein, D89052 *H. sapiens* mRNA for proton-ATPase-like protein, complete cds, M60974 Human growth arrest and DNA-damage-inducible protein (gadd45) mRNA, complete cds, X06956 Tubulin, Alpha 1, Isoform 44, X04654 Human mRNA for U1 RNA-associated 70K protein, M79463 Human PML-2 mRNA, complete CDS, L76568 *H. sapiens* excision and cross link repair protein (ERCC4) gene, complete genome, Y09022 *H. sapiens* mRNA for Not56-like protein, X57579 *H. sapiens* activin beta-A subunit (exon 2), U37690 Human RNA polymerase II subunit (hsRPB10) mRNA, complete cds, X61123 Human BTG1 mRNA, J04456 Human 14 kD lectin mRNA, complete cds, Z49254 *H. sapiens* L23-related mRNA, U70660 Human copper transport protein HAH1 (HAH1) mRNA, complete cds, D86974 Human mRNA for KIAA0220 gene, partial cds, Y07604 *H. sapiens* mRNA for nucleoside-diphosphate kinase, AF006084 *H. sapiens* Arp2/3 protein complex subunit p41-Arc (ARC41) mRNA, complete cds, Y00503 Human mRNA for keratin 19, L26336 Heat Shock Protein, 70 KD (Gb:Y00371), M62831 Human transcription factor ETR101 mRNA, complete cds, Z22548 *H. sapiens* thiol-specific antioxidant protein mRNA, U40369 Human spermidine/spermine N1-acetyltransferase (SSAT) gene, complete cds, M12125 Human fibroblast muscle-type tropomyosin mRNA, complete cds, X51345 Human jun-B mRNA for JUN-B protein, Z21507 *H. sapiens* EF-1delta gene encoding human elongation factor-1-delta, U20734 Human transcription factor junB (junB) gene, 5' region and complete cds, D13413 Human mRNA for tumor-associated 120 kD nuclear protein p120, partial cds(carbox, LA2379 *H. sapiens* bone-derived growth factor (BPGF-1) mRNA, complete cds, X15822 Human COX VIIa-L mRNA for liver-specific cytochrome c oxidase (EC 1.9.3.1.), D86988 Human mRNA for KIAA0221 gene, complete cds, M26730 Human mitochondrial ubiquinone-binding protein (QP) gene, exon 4, M69043 *H. sapiens* MAD-3 mRNA encoding IkB-like activity, complete cds, D38251 Human mRNA for RPB5 (XAP4), complete cds, M30703 Human amphiregulin (AR) gene, exon 6, clones lambda-ARH(6, 12), L76200 Human guanylate kinase (GUK1) mRNA, complete cds, M34516 Human omega light chain protein 14.1 (Ig lambda chain related) gene, exon 3, U26727 Human p16INK4/MTS1 mRNA, complete cds, U53830 *H. sapiens* interferon regulatory factor 7A mRNA, complete cds, M22960 Human protective protein mRNA, complete cds, D89667 *H. sapiens* mRNA for c-myc binding protein, complete cds, L16862 *H. sapiens* G protein-coupled receptor kinase (GRK6) mRNA, complete cds, M19309 Human slow skeletal muscle troponin T mRNA, clone H22h, D64142 Human mRNA for histone H1x, complete cds, U41515 Human deleted in split hand/split foot 1 (DSS1) mRNA, complete cds, J04611 Human lupus p70 (Ku) autoantigen protein mRNA, complete cds, U35048 Human TSC-22 protein mRNA, complete cds, X82693 *H. sapiens* mRNA for E48 antigen, M92843 *H. sapiens* zinc finger transcriptional regulator mRNA, complete cds, U72649 Human BTG2 (BTG2) mRNA, complete ed, X92896 *H. sapiens* mRNA for ITBA2 protein, X74104 *H. sapiens* mRNA for TRAP beta subunit, M84332 Human ADP-ribosylation factor 1 gene, exons 2–5, D15050 Human mRNA for transcription factor AREB6, complete cds, D10923 Human mRNA for HM74, M84739 Human autoantigen calreticulin mRNA, complete cds, U09813 Human mitochondrial ATP synthase subunit 9, P3 gene copy, mRNA, nuclear gene enc, X67951 *H. sapiens* mRNA for proliferation-associated gene (pag), X82200 *H. sapiens* Staf50 mRNA, L27706 Human chaperonin protein (Tcp20) gene complete cds, U69126 Human FUSE binding protein 2 (FBP2) mRNA, partial cds, M12529 Human apolipoprotein E mRNA, complete cds, X71129 *H. sapiens* mRNA for electron transfer flavoprotein beta subunit, U28386 Human nuclear localization sequence receptor hSRP1alpha mRNA, complete cds, U41766 Human metalloprotease/disintegrin/cysteine-rich protein precursor (MDC9) mRNA, c, AF006041 *H. sapiens* Fas-binding protein (DAXX) mRNA, partial cds, U28749 Human high-mobility group phosphoprotein isoform I-C (HMGIC) mRNA, complete cds, M60483 Human protein phosphatase 2A catalytic subunit-alpha gene, complete cds, U07664 Human HB9 homeobox gene, exons 2 and 3 and complete cds, U13991 Human TATA-binding protein associated factor 30 kD subunit (taffII30) mRNA, comp, J04794 Human aldehyde reductase mRNA, complete cds, U51586 Human siah binding protein 1 (SiahBP1) mRNA, partial cds, M58026 Human NB-1 mRNA, complete cds, X52425 Human IL4R mRNA for the interleukin 4 receptor, X94563 *H. sapiens* dbi/acbp gene exon 1 & 2, X68277 *H. sapiens* CL 100 mRNA for protein tyrosine phosphatase, X56681 Human junD mRNA, V01512 Human cellular oncogene c-fos (complete sequence), U09578 *H. sapiens* MAPKAP kinase (3 pK) mRNA, complete cds, L13391 Human helix-loop-helix basic phosphoprotein (GOS8) gene, complete cds, U62317 Chromosome 22q13 BAC Clone C11987SK-384D8 complete sequence, M16364 Human creatine kinase-B mRNA, complete cds, L19437 Human transaldolase mRNA containing transposable element, complete cds, X53416 Human mRNA for actin-binding protein (filamin) (ABP-280), X52560 Nuclear Factor Nf-I16, X78549 *H. sapiens* brk mRNA for tyrosine kinase, L11066 Human mRNA sequence, X74008 *H. sapiens* mRNA for protein phosphatase 1 gamma, X87241 *H. sapiens* mRNA for hFat protein, S68616 Na+H+ exchanger NHE-1 isoform [human, heart, mRNA, 4516 nt], D13705 Human mRNA for fatty acids omega-hydroxylase (cytochrome P-450HKV), complete cds, D86966 Human mRNA for KIAA0211 gene, complete cds, U17327 Human neuronal nitric oxide synthase (NOS1) mRNA, complete cds, U89336 Human HLA class III region containing NOTCH4 gene, partial sequence, homeobox PB, D85527 *H. sapiens* mRNA for LIM domain, partial cds, L07517 Mucin 6, Gastric (Gb:L07517), M58459 Human ribosomal protein (RPS4Y) isoform mRNA, complete cds, U65579 Human mitochondrial NADH dehydrogenase-ubiquinone Fe—S protein 8, 23 kD subunit, M19961 Human cytochrome c oxidase subunit Vb (coxVb) mRNA, complete cds, M29064 Human hnRNP B1 protein mRNA, X64330 *H. sapiens* mRNA for ATP-citrate lyase, X89267 *H. sapiens* DNA for uroporphyrinogen decarboxylase gene, X91247 *H. sapiens* mRNA for thioredoxin reductase, L11672 Human Kruppel related zinc finger protein (HTF10) mRNA, complete cds, X78992 *H. sapiens* ERF-2 mRNA, L19314 Human HRY gene, complete cds, D90086 Human pyruvate dehydrogenase (EC 1.2.4.1) beta subunit gene, exons 1–10, X12794 Human v-erbA related ear-2 gene, L22005 Human ubiquitin conjugating enzyme mRNA, partial cds, U01337 Human Ser/Thr protein kinase (A-RAF-1) gene, complete cds, M34182 Human testis-specific protein kinase gamma-subunit mRNA, complete cds, L08246 Human myeloid cell differentiation protein (MCL1) mRNA, L37042 *H. sapiens* casein kinase I alpha isoform (CSNK1A1) mRNA, complete cds, L04731 *H. sapiens* translocation T(4:11) of ALL-1 gene to chromosome 4, D87071 Human mRNA for KIAA0233 gene, complete cds, S74017 Nrf2=NF-E2-like basic leucine zipper transcriptional activator [human, hemin-ind, L41351 *H. sapiens* prostasin mRNA, complete cds, L00352 Human low density lipoprotein receptor gene, exon 18, D50683 *H. sapiens* mRNA for TGF-betaIIR alpha, complete cds, X89750 *H. sapiens* mRNA for TGIF protein, D13988 Human rab GDI mRNA, complete cds, M12886 Human T-cell receptor active beta-chain mRNA, complete cds, M55265 Human casein kinase II alpha subunit mRNA, complete cds, J03161 Human serum response factor (SRF) mRNA, complete cds, M58286 *H. sapiens* tumor necrosis factor receptor mRNA, complete cds, U88629 Human RNA polymerase II elongation factor ELL2, complete cds, X04412 Human mRNA for plasma gelsolin, L27943 *H. sapiens* cytidine deaminase (CDA) mRNA, complete cds, U90716 Human cell surface protein HCAR mRNA, complete cds, M24547 Amyloid Beta (A4) Precursor Protein, Alt. Splice 2, A4(751), U05875 Human clone pSK1 interferon gamma receptor accessory factor-1 (AF-1) mRNA, compl, Z11585 Potassium Channel Protein (Gb:Z11585), M58603 Human nuclear factor kappa-B DNA binding subunit (NF-kappa-B) mRNA, complete cds, D87442 Human mRNA for KIAA0253 gene, partial cds, M76482 Human 130-kD pemphigus vulgaris antigen mRNA, complete cds, U56418 Human lysophosphatidic acid acyltransferase-beta mRNA, complete cds, J00120 Proto-Oncogene C-Myc, Alt. Splice 3, Orf 114, U68142 Human RalGDS-like 2 (RGL2) mRNA, partial cds, U88898 Human endogenous retroviral H protease/integrase-derived ORF1 mRNA, complete cds, M91083 Human DNA-binding protein (HRC1) mRNA, complete cds, Z30643 *H. sapiens* mRNA for chloride channel (putative) 2139 bp, X12953 Human rab2 mRNA, YPT1-related and member of ras family, D78129 *H. sapiens* mRNA for squalene epoxidase, partial cds, U63825 Human hepatitis delta antigen interacting protein A (dipA) mRNA, complete cds, S78825 Id1, M54915 Human h-pim-1 protein (h-pim-1) mRNA, complete cds, X04828 Human mRNA for G(i) protein alpha-subunit (adenylate cyclase inhibiting GTP-bind, X06323 Human MRL3 mRNA for ribosomal protein 13 homolog (MRL3=mammalian ribosome L, D14043 Human mRNA for MGC-24, complete cds, L38951 *H. sapiens* importin beta subunit mRNA, complete cds, U34252 Human gamma-aminobutyraldehyde dehydrogenase mRNA, complete cds, M13829 Human putative raf related protein (pks/a-raf) mRNA, partial cds, U33821 Human tax1-binding protein TXBP151 mRNA, complete cds, U66616 Human SWI/SNF complex 170 KD subunit (BAF170) mRNA, complete cds, U29607 Human methionine aminopeptidase mRNA, complete cds, D14520 Human mRNA for GC-Box binding protein BTEB2, complete cds, D14874 *H. sapiens* mRNA for adrenomedullin precursor, complete cds, D85429 *H. sapiens* gene for heat shock protein 40, complete cds, M69181 Human nonmuscle myosin heavy chain-B (MYH10) mRNA, partial cds, U60205 Human methyl sterol oxidase (ERG25) mRNA, complete cds, X75342 *H. sapiens* SHB mRNA, D45906 *H. sapiens* mRNA for LIMK-2, complete cds, X59434 Human rohu mRNA for rhodanese, M96803 Human general beta-spectrin (SPTBN1) mRNA, complete cds, D79994 Human mRNA for KIAA0172 gene, partial cds, D86965 Human mRNA for KIAA0210 gene, complete cds, Y13647 Stearoyl-Coenzymea Desaturase, X52541 Human mRNA for early growth response protein 1 (hEGR1), Z26317 *H. sapiens* mRNA for desmoglein 2, M57763 Human ADP-ribosylation factor (hARF6) mRNA, complete cds, L38490 *H. sapiens* ADP-ribosylation factor mRNA, complete cds, D87438 Human mRNA for KIAA0251 gene, partial cds, M31627 Human X box binding protein-1 (XBP-1) mRNA, complete cds, X80692 *H. sapiens* ERK3 mRNA, U37122 Human adducin gamma subunit mRNA, complete cds, M83667 Human NF-IL6-beta protein mRNA, complete cds, J05211 Desmoplakin I, D42123 *H. sapiens* mRNA for ESP1/CRP2, complete cds, X90858 *H. sapiens* mRNA for uridine phosphorylase, X76717 *H. sapiens* MT-11 mRNA, Y08915 *H. sapiens* mRNA for alpha 4 protein, U30999 Human (memc) mRNA, 3'UTR, L77886 Human protein tyrosine phosphatase mRNA, complete cds, U14603 Human protein-tyrosine phosphatase (HU-PP-1) mRNA, partial sequence, U28480 Uncoupling Protein Ucp, X53586 Human mRNA for integrin alpha 6, M64347 Human novel growth factor receptor mRNA, 3' cds, U52100 Human XMP mRNA, complete cds, D21852 Human mRNA for KIAA0029 gene, partial cds, X05409 Human RNA for mitochondrial aldehyde dehydrogenase I ALDH I (EC 1.2.1.3), D87462 Human mRNA for KIAA0272 gene, partial cds, L40391 *H. sapiens* (clone s153) mRNA fragment, D87469 Human mRNA for KIAA0279 gene, partial cds, S73591 brain-expressed HHCPA78 homolog [human, HL60 acute promyelocytic leukemia cells, L19267 *H. sapiens* 59 protein mRNA, 3' end, M81601 Human transcription elongation factor (SII) mRNA, complete cds, X52611 Human mRNA for transcription factor AP-2, U28811 Human cysteine-rich fibroblast growth factor receptor (CFR-1) mRNA, complete cds, L31801 *H. sapiens* monocarboxylate transporter 1 (SLC16A1) mRNA, complete cds, M13929 Human c-myc-P64 mRNA, initiating from promoter P0, (HLmyc2.5) partial cds, L48546 *H. sapiens* tuberin (TSC2) gene, exons 38, 39, 40 and 41, L00058 Human (GH) germline c-myc proto-oncogene, exon 3 and 3' flank, U09587 Human glycyl-tRNA synthetase mRNA, complete cds, L37127 *H. sapiens* RNA polymerase II mRNA, complete cds, U52426 *H. sapiens* GOK (STIM1) mRNA, complete cds, U72066 *H. sapiens* CtBP interacting protein CtIP (CtIP) mRNA, complete cds, U83115 Human non-lens beta gamma-crystallin like protein (AIM1) mRNA, partial cds, M90656 Human gamma-glutamylcysteine synthetase (GCS) mRNA, complete cds, D90209 Human mRNA for DNA binding protein TAXREB67, D83777 Human mRNA for KIAA0193 gene, complete cds, U42031 Human 54 kD progesterone receptor-associated immunophilin FKBP54 mRNA, partial, M80244 Human E16 mRNA, complete cds, D31883 Human mRNA for KIAA0059 gene, complete cds, J04444 Human cytochrome c-1 gene, complete cds, M38258 Human retinoic acid receptor gamma 1 mRNA, complete cds, M95787 Human 22 kD smooth muscle protein (SM22) mRNA, complete cds, U00968 Human SREBP-1 mRNA, complete cds, K03195 Human (HepG2) glucose transporter gene mRNA, complete cds, X92720 *H. sapiens* mRNA for phosphoenolpyruvate carboxykinase, X77366 *H. sapiens* HBZ17 mRNA, U53347 Human neutral amino acid transporter B mRNA, complete cds, X80695 *H. sapiens* OXA1Hs mRNA, J04102 Human erythroblastosis virus oncogene homolog 2 (ets-2) mRNA, complete cds, S75762 Oncogene Tls/Chop, Fusion Activated, U14550 Human sialyltransferase SThM (sthm) mRNA, complete cds, L09229 Human long-chain acyl-coenzyme A synthetase (FACL1) mRNA, complete cds, X76534 H. sapiens NMB mRNA, M55268 Human casein kinase II alpha' subunit mRNA, complete cds, M27396 Human asparagine synthetase mRNA, complete cds, U37519 Human aldehyde dehydrogenase (ALDH8) mRNA, complete cds, X69111 H. sapiens HLH 1R21 mRNA for helix-loop-helix protein, M77836 Human pyrroline 5-carboxylate reductase mRNA, complete cds, D32050 Human mRNA for alanyl-tRNA synthetase, complete cds, X01630 Human mRNA for argininosuccinate synthetase. This group of ultraviolet radiation-regulated polynucleotides is hereinafter referred to as the "complete response group" of ultraviolet radiation-regulated polynucleotides.

In accordance with a further aspect of the invention, there is provided a composition of matter comprising: (1) a plurality of nucleic acid molecules at least 90% identical to the group of polynucleotides regulated by a cell in response to ultraviolet radiation exposure; and (2) a substrate suitable for binding the nucleic acid molecules of (1). The group of polynucleotides regulated by the cell in response to ultraviolet radiation exposure comprises the following: M20030 Human small proline rich protein (sprII) mRNA, clone 930, X53065, M13903 Human involucrin gene, exon 2, L10343 Human elafin gene, complete cds, M21302 Human small proline a rich protein (sprII) mRNA, clone 174N, L05188 H. sapiens small proline-rich protein 2 (SPRR2B) gene, complete cds, Y00787 Human mRNA for MDNCF (monocyte-derived neutrophil chemotactic factor), D50840 H. sapiens mRNA for ceramide glucosyltransferase, complete cds, M22918 Myosin, Light Chain, Alkali, Smooth Muscle (Gb:U02629), Non-Muscle, Alt. Splice, X70326 Macmarcks, X52426 H. sapiens mRNA for cytokeratin 13, S81914 IEX-1=radiation-inducible immediate-early gene [human, placenta, mRNA Partial, 1, M80254 H. sapiens cyclophilin isoform (hCyP3) mRNA, complete cds, L08069 Human heat shock protein, E. coli DnaJ homolog mRNA, complete cds, U62800 Human cystatin M (CST6) mRNA, complete cds, L24564 Human Rad mRNA, complete cds, M59465 Human tumor necrosis factor alpha inducible protein A20 mRNA, complete cds, Z49989 H. sapiens mRNA for smoothelin, X57985 H. sapiens genes for histones H2B.1 and H2A, L19779 H. sapiens histone H2A.2 mRNA, complete cds, D42040 Human mRNA for KIAA9001 gene, complete cds, M63573 Human secreted cyclophilin-like protein (SCYLP) mRNA, complete cds, X54489 Human gene for melanoma growth stimulatory activity (MGSA), M92934 Human connective tissue growth factor, complete cds, Z14244 H. sapiens coxVIIb mRNA for cytochrome c oxidase subunit VIIb, M60278 Human heparin-binding EGF-like growth factor mRNA, complete cds, M72885 Human GOS2 gene, 5' flank and cds, X62083 H. sapiens mRNA for Drosophila female sterile homeotic (FSH) homolog, X67325 H. sapiens p27 mRNA, U04636 Human cyclooxygenase-2 (hCox-2) gene, complete cds, M26311 Human cystic fibrosis antigen mRNA, complete cds, L20688 Human GDP-dissociation inhibitor protein (LyGDI) mRNA, complete cds, M27436 Human tissue factor gene, complete cds, with a Alu repetitive sequence in the 3', AF001294 H. sapiens IPL (IPL) mRNA, complete cds, M22918 Myosin, Light Chain, Alkali, Smooth Muscle (Gb:U02629), Non-Muscle, Alt. Splice. X74874 H. sapiens gene for RNA pol II largest subunit, exon 1, M22919, Myosin, Light Chain, Alkali, Smooth Muscle (Gb:U02629), Smooth Muscle, Alt. Spli, V00594 Human mRNA for metallothionein from cadmium-treated cells, V00599 Tubulin, Beta, X99920 H. sapiens mRNA for S100 calcium-binding protein A13, M21005 Human migration inhibitory factor-related protein 8 (MRP8) gene, complete cds, U07919 Human aldehyde dehydrogenase 6 mRNA, complete cds, M37583 Human histone (H2A.Z) mRNA, complete cds, S54005 thymosin beta-10 [human, metastatic melanoma cell line, mRNA, 453 nt], D49824 Human HLA-B null allele mRNA, S78771 NAT=CpG island-associated gene [human, mRNA, 1741 nt], M90657 Human tumor antigen (L6) mRNA, complete cds, U09937 Human urokinase-type plasminogen receptor, exon 7, X77794 H. sapiens mRNA for cyclin G1, M28130 Human interleukin 8 (IL8) gene, complete cds, X14850 Human H2A.X mRNA encoding histone H2A.X, AB000584 H. sapiens mRNA for TGF-beta superfamily protein, complete cds, U52101 Human YMP mRNA, complete cds, M57731 Human gro-beta mRNA, complete cds, D45248 Human mRNA for proteasome activator hPA28 subunit beta, complete cds, X83416 H. sapiens PrP gene, exon 2, X52882 Human t-complex polypeptide 1 gene, X57351 Human 1-8D gene from interferon-inducible gene family, X53800 Human mRNA for macrophage inflammatory protein-2beta (MIP2beta), Z69043 H. sapiens mRNA translocon-associated protein delta subunit precursor, D38305 Human mRNA for Tob, complete cds, t X52979 Human gene for small nuclear ribonucleoproteins SmB and SmB', S80437 fatty acid synthase {3' region} (human, breast and HepG2 cells, mRNA Partial, 22, X87679 Major Histocompatibility Complex, Class I, E (Gb:M21533), Z29505 H. sapiens mRNA for nucleic acid binding protein sub2.3, D21853 Human mRNA for KIAA0111 gene, complete cds, X78687 H. sapiens G9 gene encoding sialidase, M13755 Human interferon-induced 17-kD/15-kD protein mRNA, complete cds, M21186 Human neutrophil cytochrome b light chain p22 phagocyte b-cytochrome mRNA, compl, 8235_s_at D28235 Human PTGS2 gene for prostaglandin endoperoxide synthase-2, complete cds, M14328 Human alpha enolase mRNA, complete cds, V00599 Tubulin, Beta 2, U90546 Human butyrophilin (BTF4) mRNA, complete cds, K02574, X15729 Human mRNA for nuclear p68 protein, D89052 H. sapiens mRNA for proton-ATPase-like protein, complete cds, M60974 Human growth arrest and DNA-damage-inducible protein (gadd45) mRNA, complete cds, X06956 Tubulin, Alpha 1, Isoform 44, X04654 Human mRNA for U1 RNA-associated 70K protein, M79463 Human PML-2 mRNA, complete CDS, L76568 H. sapiens excision and cross link repair protein (ERCC4) gene, complete genom, Y09022 H. sapiens mRNA for Not56-like protein, X57579 H. sapiens activin beta-A subunit (exon 2), 37690 Human RNA polymerase II subunit (hsRPB10) mRNA, complete cds, X61123 Human BTG1 mRNA, J04456 Human 14 kD lectin mRNA, complete cds, Z49254 H. sapiens L23-related mRNA, U70660 Human copper transport protein HAH1 (HAH1) mRNA, complete cds, D86974 Human mRNA for KIAA0220 gene, partial cds, AF006084 H. sapiens Arp2/3 protein complex subunit p41-Arc (ARC41) mRNA, complete cds, Y00503 Human mRNA for keratin 19, M62831 Human transcription factor ETR101 mRNA, complete cos, Z22548 H. sapiens thiol-specific antioxidant protein mRNA, U40369 Human spermidine/spermine N1-acetyltransferase (SSAT) gene, complete cds, M12125 Human fibroblast muscle-type tropomyosin mRNA, complete cds, X51345 Human jun-B mRNA for JUN-B protein, Z21507 H. sapiens EF-1delta gene encoding human elongation factor-1-delta, U20734 Human transcription factor junB (junB) gene, 5' region and complete cds, D13413 Human mRNA for tumor-associated 120 kD nuclear protein p120, partial cds(carbox, L42379 H. sapiens bone-derived growth factor (BPGF-1) mRNA, complete cds, X15822 Human COX VIIa-L mRNA for liver-specific cytochrome c oxidase (EC 1.9.3.1.), D86988 Human mRNA for KIAA0221 gene, complete cds, M26730 Human mitochondrial ubiquinone-binding protein (QP) gene, exon 4, M69043 *H. sapiens* MAD-3 mRNA encoding IkB-like activity, complete cds, D38251 Human mRNA for RPB5 (XAP4), complete cds, L76200 Human guanylate kinase (GUK1) mRNA, complete cds, M34516 Human omega light chain protein 14.1 (Ig lambda chain related) gene, exon 3, U26727 Human p16INK4/MTS1 mRNA, complete cds, U53830 *H. sapiens* interferon regulatory factor 7A mRNA, complete cds, M22960 Human protective protein mRNA, complete cds, D89667 *H. sapiens* mRNA for c-myc binding protein, complete cds, M19309 Human slow skeletal muscle troponin T mRNA, clone H22h, D64142 Human mRNA for histone H1x, complete cds, U41515 Human deleted in split hand/split foot 1 (DSS1) mRNA, complete cds, J04611 Human lupus p70 (Ku) autoantigen protein mRNA, complete cds, U35048 Human TSC-22 protein mRNA, complete cds, X82693 *H. sapiens* mRNA for E48 antigen, M92843 *H. sapiens* zinc finger transcriptional regulator mRNA, complete cds, U72649 Human BTG2 (BTG2) mRNA, complete cds, X92896 *H. sapiens* mRNA for ITBA2 protein, D10923 Human mRNA for HM74, M84739 Human autoantigen calreticulin mRNA, complete cds, U09813 Human mitochondrial ATP synthase subunit 9, P3 gene copy, mRNA, nuclear gene enc, X67951 *H. sapiens* mRNA for proliferation-associated gene (pag), L27706 Human chaperonin protein (Tcp20) gene complete cds, U69126 Human FUSE binding protein 2 (FBP2) mRNA, partial cds, M12529 Human apolipoprotein E mRNA, complete cds, X71129 *H. sapiens* mRNA for electron transfer flavoprotein beta subunit, U13991 Human TATA-binding protein associated factor 30 kD subunit (tafII30) mRNA, comp, J04794 Human aldehyde reductase mRNA, complete cds, U51586 Human siah binding protein 1 (SiahBP1) mRNA, partial cds, M58026 Human NB-1 mRNA, complete cds, X68277 *H. sapiens* CL 100 mRNA for protein tyrosine phosphatase, X56681 Human junD mRNA, V01512 Human cellular oncogene c-fos (complete sequence), U09578 *H. sapiens* MAPKAP kinase (3 pK) mRNA, complete cds, L13391 Human helix-loop-helix basic phosphoprotein (G0S8) gene, complete cds, U62317 Chromosome 22q13 BAC Clone CIT987SK-384D8 complete sequence, M16364 Human creatine kinase-B mRNA, complete cds, L19437 Human transaldolase mRNA containing transposable element, complete cds, X53416 Human mRNA for actin-binding protein (filamin) (ABP-280), X52560 Nuclear Factor Nf-I16, M58459 Human ribosomal protein (RPS4Y) isoform mRNA, complete cds, U65579 Human mitochondrial NADH dehydrogenase-ubiquinone Fe—S protein 8, 23 kD subunit, M19961 Human cytochrome c oxidase subunit Vb (coxVb) mRNA, complete cds, M29064 Human hnRNP B1 protein mRNA, D90086 Human pyruvate dehydrogenase (EC 1.2.4.1) beta subunit gene, exons 1–10, L04731 *H. sapiens* translocation T(4:11) of ALL-1 gene to chromosome 4, D87071 Human mRNA for KIAA0233 gene, complete cds, X04412 Human mRNA for plasma gelsolin, L27943 *H. sapiens* cytidine deaminase (CDA) mRNA, complete cds, U68142 Human RalGDS-like 2 (RGL2) mRNA, partial cds, U63825 Human hepatitis delta antigen interacting protein A (dipA) mRNA, complete cds, X04828 Human mRNA for G(i) protein alpha-subunit (adenylate cyclase inhibiting GTP-bind, L38951 *H. sapiens* importin beta subunit mRNA, complete cds, M31627 Human X box binding protein-1 (XBP-1) mRNA, complete cds, J04444 Human cytochrome c-1 gene, complete cds, S75762 Oncogene Tls/Chop, Fusion Activated. This group of ultraviolet radiation-regulated polynucleotides is hereinafter referred to as the "induced response group" of ultraviolet radiation-regulated polynucleotides.

In accordance with a further aspect of the invention, there is provided a composition of matter comprising: (1) a plurality of nucleic acid molecules at least 90% identical to the group of polynucleotides regulated by a cell in response to ultraviolet radiation exposure; and (2) a substrate suitable for binding the nucleic acid molecules of (1). The group of polynucleotides regulated by the cell in response to ultraviolet radiation exposure comprises the following: D50840 *H. sapiens* mRNA for ceramide glucosyltransferase, complete cds, L08069 Human heat shock protein, *E. coli* DnaJ homolog mRNA, complete cds, X77794 *H. sapiens* mRNA for cyclin G1, D89052 *H. sapiens* mRNA for proton-ATPase-like protein, complete cds, L26336 Heat Shock Protein, 70 KD (Gb:Y00371), M30703 Human amphiregulin (AR) gene, exon 6, clones lambda-ARH(6,12), L16862 *H. sapiens* G protein-coupled receptor kinase (GRK6) mRNA, complete cds, M92843 *H. sapiens* zinc finger transcriptional regulator mRNA, complete cds, U72649 Human BTG2 (BTG2) mRNA, complete cds, X74104 *H. sapiens* mRNA for TRAP beta subunit, M84332 Human ADP-ribosylation factor 1 gene, exons 2–5, D15050 Human mRNA for transcription factor AREB6, complete cds, U28386 Human nuclear localization sequence receptor hSRP1alpha mRNA, complete cds, U41766 Human metalloprotease/disintegrin/cysteine-rich protein precursor (MDC9) mRNA, c, AF006041 *H. sapiens* Fas-binding protein (DAXX) mRNA, partial cds, U28749 Human high-mobility group phosphoprotein isoform I-C (HMGIC) mRNA, complete cds, M60483 Human protein phosphatase 2A catalytic subunit-alpha gene, complete cds, U07664 Human HB9 homeobox gene, exons 2 and 3 and complete cds, X52425 Human IL-4-R mRNA for the interleukin 4 receptor, X94563 *H. sapiens* dbi/acbp gene exon 1 & 2, L11066 Human mRNA sequence, X74008 *H. sapiens* mRNA for protein phosphatase 1 gamma, X87241 *H. sapiens* mRNA for hFat protein, S68616 Na+/H+ exchanger NHE-1 isoform [human, heart, mRNA, 4516 nt], D13705 Human mRNA for fatty acids omega-hydroxylase (cytochrome P450HKV), complete cds, D86966 Human mRNA for KIAA0211 gene, complete cds, U17327 Human neuronal nitric oxide synthase (NOS1) mRNA, complete cds, U89336 Human HLA class III region containing NOTCH4 gene, partial sequence, homeobox PB, D85527 *H. sapiens* mRNA for LIM domain, partial cds, L07517 Mucin 6, Gastric (Gb:L07517), X64330 *H. sapiens* mRNA for ATP-citrate lyase, X89267 *H. sapiens* DNA for uroporphyrinogen decarboxylase gene, X91247 *H. sapiens* mRNA for thioredoxin reductase, L11672 Human Kruppel related zinc finger protein (HTF10) mRNA, complete cds, X78992 *H. sapiens* ERF-2 mRNA, L19314 Human HRY gene, complete cds, X12794 Human v-erbA related ear-2 gene, L22005 Human ubiquitin conjugating enzyme mRNA, partial cds, U01337 Human Ser/Thr protein kinase (A-RAF-1) gene, complete cds, M34182 Human testis-specific protein kinase gamma-subunit mRNA, complete cds, L08246 Human myeloid cell differentiation protein (MCL1) mRNA, L37042 *H. sapiens* casein kinase I alpha isoform (CSNK1A1) mRNA, complete cds, D87071 Human mRNA for KIAA0233 gene, complete cds, S74017 Nrf2=NF-E2-like basic leucine zipper transcriptional activator [human, hemin-ind, L41351 *H. sapiens* prostasin mRNA, complete cds, L00352 Human low density lipoprotein receptor gene, exon 18, D50683 H. sapiens mRNA for TGF-betaIIR alpha, complete cds, X89750 H. sapiens mRNA for TGIF protein, t D13988 Human rab GDI mRNA, complete cds, M12886 Human T-cell receptor active beta-chain mRNA, complete cds, M55265 Human casein kinase II alpha subunit mRNA, complete cds, J03161 Human serum response factor (SRF) mRNA, complete cds, M58286 H. sapiens tumor necrosis factor receptor mRNA, complete cds, U88629 Human RNA polymerase II elongation factor ELL2, complete cds, U90716 Human cell surface protein HCAR mRNA, complete cds, M24547 Amyloid Beta (A4) Precursor Protein, Alt. Splice 2, A4(751), U05875 Human clone pSK1 interferon gamma receptor accessory factor-1 (AF-1) mRNA, compl, M58603 Human nuclear factor kappa-B DNA binding subunit (NF-kappa-B) mRNA, complete cds, D87442 Human mRNA for KIAA0253 gene, partial cds, M76482 Human 130-kD pemphigus vulgaris antigen mRNA, complete cds, U56418 Human lysophosphatidic acid acyltransferase-beta mRNA, complete cds, J00120 Proto-Oncogene C-Myc, Alt. Splice 3, Orf 114, U88898 Human endogenous retroviral H protease/integrase-derived ORF1 mRNA, complete cds, M91083 Human DNA-binding protein (HRC1) mRNA, complete cds, Z30643 H. sapiens mRNA for chloride channel (putative) 2139 bp, X12953 Human rab2 mRNA, YPT1-related and member of ras family, D78129 H. sapiens mRNA for squalene epoxidase, partial cds, S78825 Id1, M54915 Human h-pim-1 protein (h-pim-1) mRNA, complete cds, X06323 Human MRL3 mRNA for ribosomal protein U3 homolog (MRL3= mammalian ribosome L, D14043 Human mRNA for MGC-24, complete cds, U34252 Human gamma-aminobutyraldehyde dehydrogenase mRNA, complete cds, M13829 Human putative raf related protein (pks/a-raf) mRNA, partial cds, U33821 Human tax1-binding protein TXBP151 mRNA, complete cds, U66616 Human SWI/SNF complex 170 KD subunit (BAF170) mRNA, complete cds, U29607 Human methionine aminopeptidase mRNA, complete cds, D14520 Human mRNA for GC-Box binding protein BTEB2, complete cds, D14874 H. sapiens mRNA for adrenomedullin precursor, complete cds, D85429 H. sapiens gene for heat shock protein 40, complete cds, t M69181 Human nonmuscle myosin heavy chain-B (MYH10) mRNA, partial cds, U60205 Human methyl sterol oxidase (ERG25) mRNA, complete cds, X75342 H. sapiens SHB mRNA, t D45906 H. sapiens mRNA for LIMK-2, complete cds, X59434 Human rohu mRNA for rhodanese, M96803 Human general beta-spectrin (SFMBN1) mRNA, complete cds, D79994 Human mRNA for KIAA0172 gene, partial cds, D86965 Human mRNA for KIAA0210 gene, complete cds, Y13647 Stearoyl-Coenzymea Desaturase, X52541 Human mRNA for early growth response protein 1 (hEGR1), Z26317 H. sapiens mRNA for desmoglein 2, t M57763 Human ADP-ribosylation factor (hARF6) mRNA, complete cds, L38490 H. sapiens ADP-ribosylation factor mRNA, complete cds, D87438 Human mRNA for KIAA0251 gene, partial cds, M31627 Human X box binding protein-1 (XBP-1) mRNA, complete cds, X80692 H. sapiens ERK3 mRNA, U37122 Human adducin gamma subunit mRNA, complete cds, M83667 Human NF-IL-6beta protein mRNA, complete cds, J05211 Desmoplakin I, D42123 H. sapiens mRNA for ESP1/CRP2, complete cds, X90858 H. sapiens mRNA for uridine phosphorylase, X76717 H. sapiens MT-11 mRNA, Y08915 H. sapiens mRNA for alpha 4 protein, U30999 Human (memc) mRNA, 3'UTR, L77886 Human protein tyrosine phosphatase mRNA, complete cds, U14603 Human protein-tyrosine phosphatase (HU-PP-1) mRNA, partial sequence, U28480 Uncoupling Protein Ucp, X53586 Human mRNA for integrin alpha 6, M64347 Human novel growth factor receptor mRNA, 3' cds, U52100 Human XMP mRNA, complete cds, D21852 Human mRNA for KIAA0029 gene, partial cds. X05409 Human RNA for mitochondrial aldehyde dehydrogenase I ALDH I (EC 1.2.1.3), D87462 Human mRNA for KIAA0272 gene, partial cds, L40391 H. sapiens (clone s153) mRNA fragment, D87469 Human mRNA for KIAA0279 gene, partial cds, S73591 brain-expressed HHCPA78 homolog [human, HL-60 acute promyelocytic leukemia cells, L19267 H. sapiens 59 protein mRNA, 3' end, M81601 Human transcription elongation factor (SIT) mRNA, complete cds, X52611 Human mRNA for transcription factor AP-2, U28811 Human cysteine-rich fibroblast growth factor receptor (CFR-1) mRNA, complete cds, L31801 H. sapiens monocarboxylate transporter 1 (SLC16A1) mRNA, complete cds, M13929 Human c-myc-P64 mRNA, initiating from promoter P0, (HLmyc2.5) partial cds, L48546 H. sapiens tuberin (TSC2) gene, exons 38, 39, 40 and 41, L00058 Human (GH) germline c-myc proto-oncogene, exon 3 and 3' flank, U09587 Human glycyl-tRNA synthetase mRNA, complete cds, L37127 H. sapiens RNA polymerase II mRNA, complete cds, U52426 H. sapiens GOK (STIM1) mRNA, complete cds, U72066 H. sapiens CtBP interacting protein CtIP (CtIP) mRNA, complete cds, U83115 Human nonlens beta gamma-crystallin like protein (AIM1) mRNA, partial cds, M90656 Human gamma-glutamylcysteine synthetase (GCS) mRNA, complete cds, D90209 Human mRNA for DNA binding protein TAXREB67, D83777 Human mRNA for KIAA0193 gene, complete cds, U42031 Human 54 kD progesterone receptor-associated immunophilin FKBP54 mRNA, partial, M80244 Human E16 mRNA, complete cds, 134. D31883 Human mRNA for KIAA0059 gene, complete cds, J04444 Human cytochrome c-1 gene, complete cds, M38258 Human retinoic acid receptor gamma 1 mRNA, complete cds, M95787 Human 22 kD smooth muscle protein (SM22) mRNA, complete cds, U00968 Human SREBP-1 mRNA, complete cds, K03195 Human (HepG2) glucose transporter gene mRNA, complete cds, X92720 H. sapiens mRNA for phosphoenolpyruvate carboxykinase, X77366 H. sapiens HBZ17 mRNA, U53347 Human neutral amino acid transporter B mRNA, complete cds, X80695 H. sapiens OXA1Hs mRNA, J04102 Human erythroblastosis virus oncogene homolog 2 (ets-2) mRNA, complete cds, S75762 Oncogene Tls/Chop, Fusion Activated, U14550 Human sialyltransferase SThM (sthm) mRNA, complete cds, L09229 Human long-chain acyl-coenzyme A synthetase (FACL1) mRNA, complete cds, X76534 H. sapiens NMB mRNA, M55268 Human casein kinase II alpha' subunit mRNA, complete cds, M27396 Human asparagine synthetase mRNA, complete cds, U37519 Human aldehyde dehydrogenase (ALDH8) mRNA, complete cds, X69111 H. sapiens HLH 1R21 mRNA for helix-loop-helix protein, M77836 Human pyrroline 5-carboxylate reductase mRNA, complete cds, D32050 Human mRNA for alanyl-tRNA synthetase, complete cds, X01630 Human mRNA for argininosuccinate synthetase. This group of ultraviolet radiation-regulated polynucleotides is hereinafter referred to as the "repressed response group" of ultraviolet radiation-regulated polynucleotides.

In one embodiment thereof, the composition of matter is a gene array suitable for monitoring gene expression. In one embodiment, the gene array is a low density gene array. In another embodiment, the gene array is a high density gene array. Polynucleotides utilized in the construction of the low or high density gene array include genomic clones, cDNAs, oligonucleotides, and the like.

In accordance with another aspect of the invention, there are provided pharmaceutical compositions for modulating the response of a cell to ultraviolet radiation exposure. The pharmaceutical compositions of the invention comprise a compound in sufficient quantity to modulate the response of the cell to ultraviolet radiation exposure and a pharmaceutically acceptable carrier. The response of the cell to ultraviolet radiation comprises a pattern of expression comprising at least one of the following: a first response group, a second response group, and a third response group. In one embodiment, the first response group comprises altered expression of at least one nucleic acid molecule encoding a transcription factor protein, at least one nucleic acid molecule encoding a signal transducing protein, and at least one nucleic acid molecule encoding a mitochondrial protein. The second response group comprises altered expression of at least one nucleic acid molecule encoding a secreted growth factor, at least one nucleic acid molecule encoding a cytokine, and at least one nucleic acid molecule encoding a chemokine. The third response group comprises altered expression of at least one nucleic acid molecule encoding an actin-binding protein, at least one nucleic acid molecule encoding a desmosomal protein, at least one nucleic acid molecule encoding a tubulin protein, at least one nucleic acid molecule encoding a cornified envelope protein.

These groups are hereinafter referred to as the "primary first response group," the "primary second response group," and the "primary third response group," respectively.

In other embodiments thereof, the pharmaceutical compositions of the invention comprise a compound in sufficient quantity to modulate the response of the cell to ultraviolet radiation exposure, the response comprising a pattern of expression comprising at least one of the following: (1) the primary first response group; or (2) the primary second response group; or (3) the primary third response group. In other embodiments, the pattern comprises the primary first response group and the primary second response group. In another embodiment, the pattern comprises the primary first response group and the primary third response group. In yet another embodiment, the response comprises the primary second response group and the primary third response group. In still another embodiment, the response comprises the primary first response group, the primary second response group, and the primary third response group.

Additional embodiments of the invention provide pharmaceutical compositions comprising a compound in sufficient quantity to modulate the response of the cell to ultraviolet radiation exposure, comprising ultraviolet radiation energy at a wavelength in the range of about 220 nm to about 440 nm, or ultraviolet radiation energy at a wavelength from about 290 nm to about 320 nm, or ultraviolet radiation energy at a wavelength from about 320 to about 440 nm, or a total ultraviolet radiation energy exposure in the range from about 0.2 mJ/cm$^2$ to about 40 mJ/cm$^2$. Other embodiments thereof provide a pharmaceutical formulation to modulate the response of a cell that is a skin cell (epidermal or dermal) or the cell is selected from the group consisting of a keratinocyte, a Langerhans cell a melanocyte, and a fibroblast cell.

In yet another embodiment, the pharmaceutical compositions of the invention comprise a compound in sufficient quantity to modulate the response of the cell to ultraviolet radiation exposure and a pharmaceutically acceptable carrier, wherein the response comprises a pattern of expression comprising at least one of the following: a first response group, a second response group, and a third response group. The first response group comprises at least one polynucleotide that is at least 90% identical to a nucleic acid molecule selected from the group consisting of. M62831 Human transcription factor ETR101 mRNA, complete cds, X68277 H. sapiens CL 100 mRNA for protein tyrosine phosphatase, L04731 H. sapiens translocation T(4:11) of ALL-1 gene to chromosome 4, X56681 Human junD mRNA, U20734 Human transcription factor junB (junB) gene, 5' region and complete cds, L38951 H. sapiens importin beta subunit mRNA, complete cds, D87071 Human mRNA for KIAA0233 gene, complete cds, M72885 Human GOS2 gene, 5' flank and cds, M92843 H. sapiens zinc finger transcriptional regulator mRNA, complete cds, S81914 IEX-1=radiation-inducible immediate-early gene [human, placenta, mRNA Partial, U72649 Human BTG2 (BTG2) mRNA, complete cds, D86988 Human mRNA for KIAA0221 gene, complete cds, L19779 H. sapiens histone H2A.2 mRNA, complete cds, U62317 Chromosome 22q13 BAC Clone CIT987SK-384D8 complete sequence, X04412 Human mRNA for plasma gelsolin L27706 Human chaperonin protein (Tcp20) gene complete cds, X61123 Human BTG1 mRNA, M60974growth arrest and DNA-damage-inducible protein (gadd45) mRNA, complete cds, L19437 Human transaldolase mRNA containing transposable element, complete cds, X57985 H. sapiens genes for histones H2B1.1 and H2A, D90086 Human pyruvate dehydrogenase (EC 1.2.4.1) beta subunit gene, exons 1–10, M34182 Human testis-specific protein kinase gamma-subunit mRNA, complete cds, L16862 H. sapiens G protein-coupled receptor kinase (GRK6) mRNA, complete cds, D13705 Human mRNA for fatty acids omega-hydroxylase (cytochrome P-450HKV), complete cd, U37122 Human adducin gamma subunit mRNA, complete cds, D45906 H. sapiens mRNA for LIMK-2, complete cds, U07664 Human HB9 homeobox gene, exons 2 and 3 and complete cds, D87438 Human mRNA for KIAA0251 gene, partial cds, L37042 H. sapiens casein kinase I alpha isoform (CSNK1A1) mRNA, complete cds, D14043 Human mRNA for MGC-24, complete cds, D13988 Human rab GDI mRNA, complete cds, U28480 Uncoupling Protein Uc, D50840 H. sapiens mRNA for ceramide glucosyltransferase, complete cds, M55265 Human casein kinase II alpha subunit mRNA, complete cds, M96803 Human general beta-spectrin (SPTBN1) mRNA, complete cds, U89336 Human HLA class III region containing NOTCH4 gene, partial sequence, homeobox P, D87442 Human mRNA for KIAA0253 gene, partial cds, J03161 Human serum response factor (SRF) mRNA, complete cds, D8965 Human mRNA for KIAA0210 gene, complete cds, U17327 Human neuronal nitric oxide synthase (NOS1) mRNA, complete cds, D86966 Human mRNA for KIAA0211 gene, complete cds, D85527 H. sapiens mRNA for LIM domain, partial cds, U42031 Human 54 kD progesterone receptor-associated immunophilin FKBP54 mRNA, partial, X59434 Human rohu mRNA for rhodanese, M13929 Human c-myc-P64 mRNA, initiating from promoter P0, (HLmyc2.5) partial cds, J05211 Desmoplakin.

The second response group of this embodiment comprises at least one polynucleotide that is at least 90% identical to a nucleic acid molecule selected from the group consisting of: M57731 Human gro-beta mRNA, complete cds, S81914 EX-1=radiation-inducible immediate-early gene [human, placenta, mRNA Partial, 1, Y00787 Human mRNA for MDNCF (monocyte-derived neutrophil chemotactic factor), XS4489 Human gene for melanoma growth stimulatory activity (MGSA), M72885 Human GOS2 gene, 5' flank and cds, M62831 Human transcription factor ETR101mRNA, complete cds, M28130 Human interleukin 8 (IL8) gene, .complete cds, X57985 H. sapiens genes for histones H2B.1 and H2A, X53800 Human mRNA for macrophage inflammatory protein-2beta (MIP2beta), L19779 H. sapiens histone H2A.2 mRNA, complete cds, AP001294 H. sapiens IPL (IPL) mRNA, complete cds, X56681 Human junD mRNA, S75762 Oncogene Tls/Chop, Fusion Activate, M84739 Human autoantigen calreticulin mRNA, complete cds, M21302 Human small proline rich protein (sprII) mRNA, clone 174N, V00599 Tubulin, Bet, X70326 Macmarck, D10923 Human mRNA for HM74, D64142 Human mRNA for histone H1x, complete cds, D86974 Human mRNA for KIAA0220 gene, partial cds, M60974 Human growth arrest and DNA-damage-inducible protein (gadd45) mRNA, complete cds, X68277 H. sapiens CL 100 mRNA for protein tyrosine phosphatase, L13391 Human helix-loop-helix basic phosphoprotein (G0S8) gene, complete cds, M31627 Human X box binding protein-1 (XBP-1) mRNA, complete cds, U40369 Human spermidine/spermine N1-acetyltransferase (SSAT) gene, complete cds, X52560 Nuclear Factor Nf-I1, X61123 Human BTG1 mRNA, U20734 Human transcription factor junB (junB) gene, 5' region and complete cds, U35048 Human TSC-22 protein mRNA, complete cds, M69043 H. sapiens MAD-3 mRNA encoding IkB-like activity, complete cds, X51345 Human jun-B mRNA for JUN-B protein, S68616 Na+/H+ exchanger NHE-1 isoform [human, heart, mRNA, 4516 nt], X89750 H. sapiens mRNA for TGIF protein, X69111 H. sapiens HLH 1R21 mRNA for helix-loop-helix protein, U14603 Human protein-tyrosine phosphatase (HU-PP-1) mRNA, partial sequence, X52541 Human mRNA for early growth response protein 1 (hEGR1), D50683 H. sapiens mRNA for TGF-betaIIR alpha, complete cds, M92843 H. sapiens zinc finger transcriptional regulator mRNA, complete cds, X91247 H. sapiens mRNA for thioredoxin reductase, U05875 Human clone pSK1 interferon gamma receptor accessory factor-1 (AF-1) mRNA, comp, L19314 Human HRY gene, complete cds, M30703 Human amphiregulin (AR) gene, exon 6, clones lambda-ARH(6,12), U34252 Human gamma-aminobutyraldehyde dehydrogenase mRNA, complete cds, S78825 Id1, D85429 H. sapiens gene for heat shock protein 40, complete cds, U41766 Human metalloprotease/disintegrin/cysteine-rich protein precursor (MDC9) mRNA, U89336 Human HLA class III region containing NOTCH4 gene, partial sequence, homeobox PB, M69181 Human nonmuscle myosin heavy chain-B (MYH10) mRNA, partial cds, D15050 Human mRNA for transcription factor AREB6, complete cds, U28386 Human nuclear localization sequence receptor hSRP1alpha mRNA, complete cds, L77886 Human protein tyrosine phosphatase mRNA, complete cds, X64330 H. sapiens mRNA for ATP-citrate lyase, U37122 Human adducin gamma subunit mRNA, complete cds, X74008 H. sapiens mRNA for protein phosphatase 1 gamma, U60205 Human methyl sterol oxidase (ERG25) mRNA, complete cds, X76534 H. sapiens NMB mRNA, D87071 Human mRNA for KIAA0233 gene, complete cds, U90716 Human cell surface protein HCAR mRNA, complete cds, M91083 Human DNA-binding protein (HRC1) mRNA, complete cds, U29607 Human methionine aminopeptidase mRNA, complete cds, M76482 Human 130-kD pemphigus vulgaris antigen mRNA, complete cds, U72066 H. sapiens CtBP interacting protein CtIP (CtIP) mRNA, complete cds, K03195 Human (HepG2) glucose transporter gene mRNA, complete cds, X12953 Human rab2 mRNA, YPT1-related and member of ras family, M60483 Human protein phosphatase 2A catalytic subunit-alpha gene, complete cds, U72649 Human BTG2 (BTG2) mRNA, complete cds, D14520 Human mRNA for GC-Box binding protein BTEB2, complete cds, L08069 Human beat shock protein, E. coli DnaJ homolog mRNA, complete cds, D50840 H. sapiens mRNA for ceramide glucosyltransferase, complete cds, L31801 H. sapiens monocarboxylate transporter 1 (SLC16A1) mRNA, complete cds, S74017 Nrf2=NF-E2-like basic leucine zipper transcriptional activator [human, hemin-in, X87241 H. sapiens mRNA for hFat protein, X52425 Human IL-4-R mRNA for the interleukin 4 receptor, D79994 Human mRNA for KIAA0172 gene, partial cds, M58286 H. sapiens tumor necrosis factor receptor mRNA, complete cds, M13829 Human putative raf related protein (pks/a-raf) mRNA, partial cds, X78992 H. sapiens ERF-2 mRNA, U42031 Human 54 kD progesterone receptor-associated immunophilin FKBP54 mRNA, partial, U88629 Human RNA polymerase II elongation factor ELL2, complete cds, X52611 Human mRNA for transcription factor AP-2, U28749 Human high-mobility group phosphoprotein isoform I-C (HMGIC) mRNA, complete cds, L00058 Human (GH) germline c-myc proto-oncogene, exon 3 and 3' flank, L26336 Heat Shock Protein, 70 KD (Gb:Y00371, L08246 Human myeloid cell differentiation protein (MCL1) mRNA, S73591 brain-expressed HHCPA78 homolog [human, HL-60 acute promyelocytic, leukemia cells, J05211 Desmoplakin, L00352 Human low density lipoprotein receptor gene, exon 18, Y13647 Stearoyl-Coenzymea Desaturase, X77794 H. sapiens mRNA for cyclin G1, M90656 Human gamma-glutamylcysteine synthetase (GCS) mRNA, complete cds, M13929 Human c-myc-P64 mRNA, initiating from promoter P0, (HLmyc2.5) partial cds, D78129 H. sapiens mRNA for squalene epoxidase, partial cds, X80692 H. sapiens ERK3 mRNA, J00120 Proto-Oncogene C-Myc, Alt. Splice 3, Orf 114.

The third response group of this embodiment comprises at least one polynucleotide that is at least 90% identical to a nucleic acid molecule selected from the group consisting of: M20030 Human small proline rich protein (sprII) mRNA, clone 930, X53065, M13903 Human involucrin gene, exon 2, M22918 Myosin, Light Chain, Alkali, Smooth Muscle (Gb:U02629), Non-Muscle, Alt. Splice, L10343 Human elafin gene, complete cds, M63573 Human secreted cyclophilin-like protein (SCYLP) mRNA, complete cds, M21302 Human small proline rich protein (sprII) mRNA, clone 174N, Y00787 Human mRNA for MDNCF (monocyte-derived neutrophil chemotactic factor), X57985 H. sapiens genes for histones H2B.1 and H2A, L05188 H. sapiens small proline-rich protein 2 (SPRR2B) gene, complete cds, X70326 Macmarcks, X67325 H. sapiens p27 mRNA, L19779 H. sapiens histone H2A.2 mRNA, complete cds, S81914 IEX-1=radiation-inducible immediate-early gene [human, placenta, mRNA Partial 1, D45248 Human mRNA for proteasome activator hPA28 subunit beta, complete cds, Z22548 H. sapiens thiol-specific antioxidant protein mRNA, M22918 Myosin, Light Chain, Alkali, Smooth Muscle (Gb:U02629), Non-Muscle, Alt. Splice, X06956 Tubulin, Alpha 1, Isoform 44, V00594 Human mRNA for metallothionein from cadmium-treated cells, M80254 H. sapiens cyclophilin isoform (hCyP3) mRNA, complete cds, U04636 Human cyclooxygenase-2 (hCox-2) gene, complete cds, Z14244 H. sapiens coxVIIb mRNA for cytochrome c oxidase subunit VIIb, X99920 H. sapiens mRNA for S100 calcium-binding protein A13, U62800 Human cystatin M (CST6) mRNA, complete cds, L08069 Human heat shock protein, E. coli DnaJ homolog mRNA, complete cds, L20688 Human GDP-dissociation inhibitor protein (Ly-GDI) mRNA, complete cds, M13755 Human interferon-induced 17-kD/15-kD protein mRNA, complete cds, M60278 Human heparin-binding EGF-like growth factor mRNA, complete cds, AF001294 *H. sapiens* IPL (IPL) mRNA, complete cds, X54489 Human gene for melanoma growth stimulatory activity (MGSA), M21186 Human neutrophil cytochrome b light chain p22 phagocyte b-cytochrome mRNA, compl, D42040 Human mRNA for KIAA9001 gene, complete cds, V00599 Tubulin, Beta, U37690 Human RNA polymerase II subunit (hsRPB10) mRNA, complete cds, M21005 Human migration inhibitory factor-related protein 8 (MRP8) gene, complete cds, M37583 Human histone (H2A.Z) mRNA, complete cds, Z49989 *H. sapiens* mRNA for smoothelin, L24564 Human Rad mRNA, complete cds, D49824 Human HLA-B null allele mRNA, M59465 Human tumor necrosis factor alpha inducible protein A20 mRNA, complete cds, S54005 thymosin beta-10 [human, metastatic melanoma cell line, mRNA, 453 nt], Z49254 *H. sapiens* L23-related mRNA, M22919 Myosin, Light Chain, Alkali, Smooth Muscle (Gb:U02629), Smooth Muscle, Alt. Spli, U70660 Human copper transport protein HAH1 (HAH1) mRNA, complete cds, AF006084 *H. sapiens* Arp2/3 protein complex subunit p41-Arc (ARC41) mRNA, complete cds, X62083 *H. sapiens* mRNA for Drosophila female sterile homeotic (FSH) homolog, D86974 Human mRNA for KIAA0220 gene, partial cds, M72885 Human GOS2 gene, 5' flank and cds, S80437 fatty acid synthase {3' region} [human, breast and HepG2 cells, mRNA Partial, 22, X04654 Human mRNA for U1 RNA-associated 70K protein, t M26311 Human cystic fibrosis antigen mRNA, complete cds, X14850 Human H2A.X mRNA encoding histone H2A.X, M14328 Human alpha enolase mRNA, complete cds, U07919 Human aldehyde dehydrogenase 6 mRNA, complete cds, M28130 Human interleukin 8 (IL8) gene, complete cds, Z21507 *H. sapiens* EF-1delta gene encoding human elongation factor-1-delta, M92934 Human connective tissue growth factor, complete cds, M27436 Human tissue factor gene, complete cds, with a Alu repetitive sequence in the 3', X74874 *H. sapiens* gene for RNA pol II largest subunit, exon 1, X57351 Human 1-8D gene from interferon-inducible gene family, X52979 Human gene for small nuclear ribonucleoproteins SmB and SmB', U41515 Human deleted in split hand/split foot 1 (DSS1) mRNA, complete cds, D28235 Human PTGS2 gene for prostaglandin endoperoxide synthase-2, complete cds, Y00503 Human mRNA for keratin 19. M57731 Human gro-beta mRNA, complete cds, D50840 *H. sapiens* mRNA for ceramide glucosyltransferase, complete cds, U52101 Human YMP mRNA, complete cds. D13413 Human mRNA for tumor-associated 120 kD nuclear protein p120, partial cds(carbox, L42379 *H. sapiens* bone-derived growth factor (BPGF-1) mRNA, complete cds, X52426 *H. sapiens* mRNA for cytokeratin 13, J04456 Human 14 kD lectin mRNA, complete cds, S78771 NAT=CpG island-associated gene [human, mRNA, 1741 nt], M26730 Human mitochondrial ubiquinone-binding protein (QP) gene, exon 4, U26727 Human p16INK4/MTS1 mRNA, complete cds, X92896 *H. sapiens* mRNA for ITBA2 protein, Z69043 *H. sapiens* mRNA translocon-associated protein delta subunit precursor, L76568 *H. sapiens* excision and cross link repair protein (ERCC4) gene, complete genom, M12125 Human fibroblast muscle-type tropomyosin mRNA, complete cds, U09937 Human urokinase-type plasminogen receptor, exon 7, X15822 Human COX VIIa-L mRNA for liver-specific cytochrome c oxidase (EC 1.9.3.1.), M34516 Human omega light chain protein 14.1 (Ig lambda chain related) gene, exon 3, U53830 *H. sapiens* interferon regulatory factor 7A mRNA, complete cds, X82693 *H. sapiens* mRNA for E48 antigen, M58026 Human NB-1 mRNA, complete cds, M90657 Human tumor antigen (L6) mRNA, complete cds, X57579 *H. sapiens* activin beta-A subunit (exon 2), D38251 Human mRNA for RPB5 (XAP4), complete cds, D89667 *H. sapiens* mRNA for c-myc binding protein, complete cds, AB000584 *H. sapiens* mRNA for TGF-beta superfamily protein, complete cds, L76200 Human guanylate kinase (GUK1) mRNA, complete cds, J04794 Human aldehyde reductase mRNA, complete cds, X52882 Human t-complex polypeptide 1 gene, M79463 Human PML-2 mRNA, complete CDS, Y09022 *H. sapiens* mRNA for Not56like protein, M12529 Human apolipoprotein E mRNA, complete cds, X71129 *H. sapiens* mRNA for electron transfer flavoprotein beta subunit, X83416 *H. sapiens* PrP gene, exon 2, D89052 *H. sapiens* mRNA for proton-ATPase-like protein, complete cds, M60974 Human growth arrest and DNA-damage-inducible protein (gadd45) mRNA, complete cds, M16364 Human creatine kinase-B mRNA, complete cds, D38305 Human mRNA for Tob, complete cds, X87679 Major Histocompatibility Complex, Class I, E (Gb:M21533), Z29505 *H. sapiens* mRNA for nucleic acid binding protein sub2.3, K02574, U09813 Human mitochondrial ATP synthase subunit 9, P3 gone copy, mRNA, nuclear gene enc, X67951 *H. sapiens* mRNA for proliferation-associated gene (pag), J04611 Human lupus p70 (Ku) autoantigen protein mRNA, complete cds, U09578 *H. sapiens* MAPKAP kinase (3 pK) mRNA, complete cds, X53800 Human mRNA for macrophage inflammatory protein-2beta (MIP2beta), V00599 Tubulin, Beta 2, U69126 Human FUSE binding protein 2 (FBP2) mRNA, partial cds, X53416 Human mRNA for actin-binding protein (filamin) (ABP-280), U90546 Human butyrophilin (BTF4) mRNA, complete cds, M58459 Human ribosomal protein (RPS4Y) isoform mRNA, complete eds, M19961 Human cytochrome oxidase subunit Vb (coxVb) mRNA, complete cds, U65579 Human mitochondrial NADH dehydrogenase-ubiquinone Fe—S protein 8, 23 kD subunit, X77794 *H. sapiens* mRNA for cyclin G1, M29064 Human hnRNP B1 protein mRNA, D21853 Human mRNA for KIAA0111 gene, complete cds, X78687 *H. sapiens* G9 gene encoding sialidase, X15729 Human mRNA for nuclear p68 protein, X04828 Human mRNA for G(i) protein alpha-subunit (adenylate cyclase inhibiting GTP-bind, L27943 *H. sapiens* cytidine deaminase (CDA) mRNA, complete cds, L40391 *H. sapiens* (clone s153) mRNA fragment, D42123 *H. sapiens* mRNA for ESP1/CRP2, complete cds, X74104 *H. sapiens* mRNA for TRAP beta subunit, M84332 Human ADP-ribosylation factor 1 gene, exons 2–5, L37127 *H. sapiens* RNA polymerase II mRNA, complete cds, M92843 *H. sapiens* zinc finger transcriptional regulator mRNA, complete cds, U07664 Human HB9 homeobox gene, exons 2 and 3 and complete cds, L48546 *H. sapiens* tuberin (TSC2) gene, exons 38, 39, 40 and 41, X53586 Human mRNA for integrin alpha 6, t D21852 Human mRNA for KIAA0029 gene, partial cds, L11066 Human mRNA sequence, J04444 Human cytochrome c-1 gene, complete cds, M95787 Human 22 kD smooth muscle protein (SM22) mRNA, complete cds, L07517 Mucin 6, Gastric (Gb:L07517), X91247 *H. sapiens* mRNA for thioredoxin reductase, L11672 Human Kruppel related zinc finger protein (HTF10) mRNA, complete cds, U30999 Human (memc) mRNA, 3'UTR, U01337 Human Ser/Thr protein kinase (A-RAF-1) gene, complete cds, U28480 Uncoupling Protein Ucp, X12794 Human v-erbA related ear-2 gene, L22005 Human ubiquitin conjugating enzyme mRNA, partial cds, M12886 Human T-cell receptor active beta-chain mRNA, complete cds, Y08915 *H. sapiens* mRNA for alpha 4 protein, M24547 Amyloid Beta (A4) Precursor Protein, Alt. Splice 2, A4(751), X76717 *H. sapiens* MT-11 mRNA, M64347 Human novel growth factor receptor mRNA, 3' cds, X05409 Human RNA f6r mitochondrial aldehyde dehydrogenase I ALDH I (EC 1.2.1.3), D87469 Human mRNA for KIAA0279 gene, partial cds, M58603 Human nuclear factor kappa-B DNA binding subunit (NF-kappa-B) mRNA, complete cds. M76482 Human 130-kD pemphigus vulgaris antigen mRNA, complete cds, X06323 Human MRL3 mRNA for ribosomal protein L3 homolog (MRL3= mammalian ribosome L, X78992 *H. sapiens* ERF-2 mRNA, L41351 *H. sapiens* prostasin mRNA, complete cds, X75342 *H. sapiens* SHB mRNA, U83115 Human non-lens beta gamma-crystallin like protein (AIM1) mRNA, partial cds, U88629 Human RNA polymerase II elongation factor ELL2, complete cds, S78825 Id1, U28811 Human cysteine-rich fibroblast growth factor receptor (CFR-1) mRNA, complete cds, M58286 *H. sapiens* tumor necrosis factor receptor mRNA, complete cds, D78129 *H. sapiens* mRNA for squalene epoxidase, partial cds, D14874 *H. sapiens* mRNA for adrenomedullin precursor, complete cds, Z26317 *H. sapiens* mRNA for desmoglein 2, L19267 *H. sapiens* 59 protein mRNA, 3' end, J00120 Proto-Oncogene C-Myc, Alt. Splice 3, Orf 114, U33821 Human tax1-binding protein TXBP151 mRNA, complete cds, U52100 Human XMP mRNA, complete cds, L31801 *H. sapiens* monocarboxylate transporter 1 (SLC16A1) mRNA, complete cds, L00058 Human (GH) germline c-myc proto-oncogene, exon 3 and 3' flank, U52426 *H. sapiens* GOK (STIM1) mRNA, complete cds, M80244 Human E16 mRNA, complete cds, U56418 Human lysophosphatidic acid acyltransferase-beta mRNA, complete cds, L38490 *H. sapiens* ADP-ribosylation factor mRNA, complete cds, U14603 Human protein-tyrosine phosphatase (HU-PP-1) mRNA, partial sequence, L77886 Human protein tyrosine phosphatase mRNA, complete cds, M38258 Human retinoic acid receptor gamma 1 mRNA, complete cds, X89750 *H. sapiens* mRNA for TGIF protein, D85429 *H. sapiens* gene for heat shock protein 40, complete cds, J05211 Desmoplakin I, M31627 Human X box binding protein-1 (XBP-1) mRNA, complete cds, X80695 *H. sapiens* OXA1Hs mRNA, M54915 Human h-pim-1 protein (h-pim-1) mRNA, complete cds, D83777 Human mRNA for KIAA0193 gene, complete cds, D31883 Human mRNA for KIAA0059 gene, complete cds, U00968 Human SREBP-1 mRNA, complete cds, K03195 Human (HepG2) glucose transporter gene mRNA, complete cds, D86965 Human mRNA for KIAA0210 gene, complete cds, Z30643 *H. sapiens* mRNA for chloride channel (putative) 2139 bp, D14520 Human mRNA for GC-Box binding protein BTEB2, complete cds, D87462 Human mRNA for KIAA0272 gene, partial cds, X80692 *H. sapiens* ERK3 mRNA, X90858 *H. sapiens* mRNA for uridine phosphorylase, M57763 Human ADP-ribosylation factor (hARF6) mRNA, complete cds, X92720 *H. sapiens* mRNA for phosphoenolpyruvate carboxykinase, M81601 Human transcription elongation factor (SII) mRNA, complete cds, X52611 Human mRNA for transcription factor AP-2, U09587 Human glycyl-tRNA synthetase mRNA, complete cds, U14550 Human sialyltransferase STHM (sthm) mRNA, complete cds, D90209 Human mRNA for DNA binding protein TAXREB67, X77366 *H. sapiens* HBZ17 mRNA, X76534 *H. sapiens* NMB mRNA, U37519 Human aldehyde dehydrogenase (ALDH8) mRNA, complete cds, M83667 Human NF-IL6beta protein mRNA, complete cds, U53347 Human neutral amino acid transporter B mRNA, complete cds, L09229 Human long-chain acyl-coenzyme A synthetase (FACL1) mRNA, complete cds, S73591 brain-expressed HHCPA78 homolog [human, HL-60 acute promyelocytic leukemia cells, M13929 Human c-myc-P64 mRNA, initiating from promoter P0, (HLmyc2.5) partial cds, M55268 Human casein kinase II alpha' subunit mRNA, complete cds, M77836 Human pyrroline 5-carboxylate reductase mRNA, complete cds, HG2724HT2820_at S75762 Oncogene Tls/Chop, Fusion Activated, U72066 *H. sapiens* CtBP interacting protein CtIP (CtIP) mRNA, complete cds, U42031 Human 54 kD progesterone receptor-associated immunophilin FKBP54 mRNA, partial, M27396 Human asparagine synthetase mRNA, complete cds, X01630 Human mRNA for argininosuccinate synthetase, D32050 Human mRNA for alanyl-tRNA synthetase, complete cds, M90656 Human gamma-glutamylcysteine synthetase (GCS) mRNA, complete cds, J04102 Human erythroblastosis virus oncogene homolog 2 (ets-2) mRNA, complete cds, X69111 *H. sapiens* HLH 1R21 mRNA for helix-loop-helix protein.

These groups are hereinafter referred to as the "secondary first response group," the "secondary second response group," and the "secondary third response group," respectively.

In another aspect of the invention, pharmaceutical compositions of the invention comprise a compound in sufficient quantity to modulate the response of the cell to ultraviolet radiation exposure and a pharmaceutically acceptable carrier, wherein the response comprises the altered regulation of a protein encoded by a polynucleotide selected from the first response group, second response group, and the third response group. Furthermore, in this embodiment, the first response group comprises altered expression of at least one transcription factor protein, at least one signal transducing protein, and at least one mitochondrial protein. The second response group comprises altered expression of at least one secreted growth factor, at least one cytokine, and at least one chemokine. The third response group comprises altered expression of at least one actin-binding protein, at least one desmosomal protein, and at least one tubulin protein.

These groups are hereinafter referred to as the "tertiary first response group," the "tertiary second response group," and the "tertiary third response group," respectively. Thus, where the primary first, second, and third response groups relate to nucleic acid molecules, the tertiary first, second, and third response groups relate to the proteins encoded by nucleic acid molecules of the primary groups.

In other embodiments thereof, the pharmaceutical compositions of the invention comprise a compound in sufficient quantity to modulate the response of the cell to ultraviolet radiation exposure, the response comprising a pattern of expression comprising at least one of the following: (1) the tertiary first response group; or (2) the tertiary second response group; or (3) the tertiary third response group; or (4) the tertiary first response group and the tertiary second response group; or (5) the tertiary first response group and the tertiary third response group; or (6) the tertiary second response group and the tertiary third response group; or (7) the tertiary first response group and the tertiary second response group and the tertiary third response group.

Additional embodiments thereof provide pharmaceutical compositions comprising a compound in sufficient quantity to modulate the response of the cell to ultraviolet radiation exposure, comprising ultraviolet radiation energy at a wavelength in the range of about 220 nm to about 440 nm, or ultraviolet radiation energy at a wavelength of about 290 nm to about 320 nm, or ultraviolet radiation energy at a wavelength of about 320 to about 440 nm, or a total ultraviolet radiation energy exposure in the range of about 0.2 mJ/cm$^2$ to about 40 mJ/cm². Other embodiments of the invention provide a pharmaceutical formulation for modulating the expression of a response of a skin cell (epidermal or dermal) or a cell selected from the group consisting of a keratinocyte, a Langerhans cell a melanocyte, and a fibroblast cell, in response to ultraviolet radiation.

In yet another embodiment, the pharmaceutical compositions of the invention comprise a compound in sufficient quantity to modulate the response of the cell to ultraviolet radiation exposure, the response comprising at least one of the following: a first response group; a second response group, and a third response group. In this embodiment, the first response group comprises the altered expression of a plurality of protein molecules, each encoded by a polynucleotide that is at least 90% identical to a nucleic acid molecule selected from the group consisting of the secondary first response group. The second response group comprises the altered expression of a plurality of protein molecules, each encoded by a polynucleotide that is at least 90% identical to a nucleic acid molecule selected from the group consisting of the secondary second response group. The third response group comprises the altered expression of a plurality of protein molecules, each encoded by a polynucleotide that is at least 90% identical to a nucleic acid molecule selected from the group consisting of the secondary third response group. These first, second and third response groups are hereinafter referred to as the "quaternary first response group," the "quaternary second response group," and the "quaternary third response group." These groups are, in effect, the protein molecules encoded by the nucleic acid molecules of the secondary first, second and third response groups.

In other embodiments, the pharmaceutical compositions of the invention comprise a compound in sufficient quantity to modulate the response of the cell to ultraviolet radiation exposure, the response comprising: (1) the quaternary first response group; or (2) the quaternary second response group; or (3) the quaternary third response group; or (4) the quaternary first response group and the quaternary second response group; or (5) the quaternary first response group and the quaternary third response group; or (6) the quaternary second response group and the quaternary third response group; or (7) the quaternary first response group and the quaternary second response group and the quaternary third response group.

Additional embodiments thereof provide pharmaceutical compositions comprising a compound in sufficient quantity to modulate the response of the cell to ultraviolet radiation exposure, comprising: (1) ultraviolet radiation energy at a wavelength in the range of about 220 nm to about 440 nm; or (2) ultraviolet radiation energy at a wavelength of about 290 nm to about 320 nm; or (3) ultraviolet radiation energy at a wavelength of about 320 to about 440 mm; or (4) a total ultraviolet radiation energy exposure in the range of about 0.2 mJ/cm2 to about 40 mJ/cm². Other embodiments thereof provide a therapeutic composition to modulate the response of a skin cell (epidermal or dermal) or a cell selected from the group consisting of a keratinocyte, a Langerhans cell, a melanocyte, and a fibroblast cell, to ultraviolet radiation.

Another aspect of the invention provides a pharmaceutical composition for modulating a response of a cell to ultraviolet radiation exposure. This pharmaceutical composition comprises a compound in sufficient quantity to modulate the response of the cell to ultraviolet radiation exposure, the response being an altered pattern of expression comprising at least one of the following: the primary first response group, the primary second response group and the primary third response group; and a pharmaceutically acceptable carrier. In embodiments thereof, modulation of the cellular response is an inhibition of the ultraviolet radiation exposure-induced RNA expression or an inhibition of the ultraviolet radiation exposure-repressed RNA expression.

In yet another aspect, the invention provides a pharmaceutical composition for modulating a response of a cell to ultraviolet radiation exposure. This pharmaceutical composition comprises a compound in sufficient quantity to modulate the response of the cell to ultraviolet radiation exposure, the response being an altered pattern of expression comprising at least one of the following: a secondary first response group, a secondary second response group, and a secondary third response group.

Another aspect of the invention provides a pharmaceutical composition for modulating a response of a cell to ultraviolet radiation exposure. This pharmaceutical composition comprises a compound in sufficient quantity to modulate the response of the cell to ultraviolet radiation exposure, the response being an altered pattern of expression comprising at least one of the following: the tertiary first response group, the tertiary second response group and the tertiary third response group; and a pharmaceutically acceptable carrier. In embodiments thereof, modulation of the cellular response is an inhibition of the ultraviolet radiation exposure-induced protein expression or an inhibition of the ultraviolet radiation exposure-repressed protein expression.

Another aspect of the invention provides a pharmaceutical composition for modulating a response of a cell to ultraviolet radiation exposure. This pharmaceutical composition comprises a compound in sufficient quantity to modulate the response of the cell to ultraviolet radiation exposure, the response being an altered pattern of expression comprising at least one of the following: the quaternary first response group, the quaternary second response group and the quaternary third response group; and a pharmaceutically acceptable carrier. In embodiments thereof, modulation of the cellular response is an inhibition of the ultraviolet radiation exposure-induced protein expression or an inhibition of the ultraviolet radiation exposure-repressed protein expression. In embodiments thereof, modulation of the cellular response is an inhibition of the ultraviolet radiation exposure-induced protein expression or an inhibition of the ultraviolet radiation exposure-repressed protein expression.

Another aspect of the invention provides methods for detecting exposure of a cell to ultraviolet radiation. The method comprises measuring the levels of a plurality of RNA molecules in the cell, wherein a pattern of expression is established and the pattern is indicative of ultraviolet radiation exposure. In various embodiments thereof, this pattern of expression comprises a first response group, a second response, and/or a third response. In one embodiment thereof, the first response group is the primary first response group previously described above; the second response is the primary second response previously described above; and the third response is the primary third response previously described above. Other embodiments of this aspect of the invention include the following: (1) the pattern of expression is the primary first response group; or (2) the pattern of expression is the primary second response group; or (3) the pattern of expression is the primary third response group; or (4) the pattern of expression is the primary first response group and the primary second response group; or (5) the pattern of expression is the primary first response group and the primary third response group; or (6) the pattern of expression is the primary second response group and the primary third response group; or (7)

the pattern of expression is the primary first response group, the primary second response group, and the primary third response group.

Additional embodiments thereof provide methods in which the ultraviolet radiation exposure of the cell comprises: (1) ultraviolet radiation energy at a wavelength in the range of about 220 nm to about 440 nm; or (2) ultraviolet radiation energy at a wavelength of about 290 nm to about 320 nm; or (3) ultraviolet radiation energy at a wavelength of about 320 to about 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or a cell selected from the group consisting of a keratinocyte, a Langerhans cell, a melanocyte, and a fibroblast cell.

In another embodiment, the method for detecting exposure of a cell to ultraviolet radiation comprises measuring the levels of a plurality of RNA molecules in the cell for at least one time point, wherein a pattern of expression is established and the pattern is indicative of ultraviolet radiation exposure. In this embodiment, the pattern of expression comprises a first response group which is the secondary first response group previously described above; a second response which is the secondary second response previously described above; and a third response which is the primary third response previously described above.

In various embodiments thereof, this pattern of expression comprises a first response group, and/or a second response, and/or a third response. In this embodiment, the first response group is the secondary first response group previously described above; the second response is the secondary second response previously described above; and the third response is the secondary third response previously described above. Embodiments thereof include the following: (1) the pattern of expression is the secondary first response group; or (2) the pattern of expression is the secondary second response group; or (3) the pattern of expression is the secondary third response group; or (4) the pattern of expression is the secondary first response group and the secondary second response group; or (5) the pattern of expression is the secondary first response group and the secondary third response group; or (6) the pattern of expression is the secondary second response group and the secondary third response group; or (7) the pattern of expression is the secondary first response group, the secondary second response group, and the secondary third response group.

Additional embodiments of this aspect of the invention provide detection methods in which the ultraviolet radiation exposure of the cell comprises: (1) ultraviolet radiation energy at a wavelength in the range of 220 nm to 440 nm; or (2) ultraviolet radiation energy at a wavelength of about 290 nm to 320 nm; or (3) ultraviolet radiation energy at a wavelength of about 320 to 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or the cell is selected from the group consisting of a keratinocyte, a Langerhans cell, a melanocyte, and a fibroblast cell.

The invention also provides methods for detecting exposure of a cell to ultraviolet radiation in which the measurement of the level of the plurality of RNA molecules is done by expression array analysis. In this method, RNA is isolated from the cell at a time post-ultraviolet radiation exposure. A test expression array is created through nucleic acid hybridization between a labeled probe complementary to the RNA and an expression array substrate. The test expression array is analyzed to create a test expression array data set, which is then compared to the control expression array data. The levels of the plurality of RNA molecules in the cell is then analyzed to establish a response pattern of the cell the response pattern of a cell exposed to ultraviolet radiation comprising: (i) a first response group comprising altered expression of at least one nucleic acid molecule encoding a transcription factor protein, at least one nucleic acid molecule encoding a signal transducing protein, and at least one nucleic acid molecule encoding a mitochondrial protein; (ii) a second response comprising altered expression of at least one nucleic acid molecule encoding a secreted growth factor, at least one nucleic acid encoding a cytokine, and at least one nucleic acid encoding a chemokine; and/or (iii) a third response comprising altered expression of at least one nucleic acid molecule encoding an actin-binding protein, at least one nucleic acid molecule encoding a desmosomal protein, at least one nucleic acid molecule encoding a tubulin protein, and at least one nucleic acid molecule encoding a cornified envelope protein. If the test expression array data set is substantially similar to the response of a cell to ultraviolet radiation, then the cell was exposed to ultraviolet radiation.

Another aspect of the invention provides other methods for detecting exposure of a cell to ultraviolet radiation. These methods comprise measuring a plurality of protein molecules in the cell, wherein a pattern of expression is established and the pattern is indicative of ultraviolet radiation exposure. In various embodiments thereof, this pattern of expression comprises a first response group, a second response, and/or a third response. In one embodiment thereof, the first response group is the tertiary first response group previously described above; the second response is the tertiary second response previously described above; and the third response is the tertiary third response previously described above. Embodiments of this method include the following: (1) the pattern of expression is the tertiary first response group; or (2) the pattern of expression is the tertiary second response group; or (3) the pattern of expression is the tertiary third response group; or (4) the pattern of expression is the tertiary first response group and the tertiary second response group; or (5) the pattern of expression is the tertiary first response group and the tertiary third response group; or (6) the pattern of expression is the tertiary second response group and the tertiary third response group; or (7) the pattern of expression is the tertiary first response group, the tertiary second response group, and the tertiary third response group.

Additional embodiments thereof provide methods in which the cell is exposed to ultraviolet radiation comprising ultraviolet radiation energy at a wavelength in the range of about 220 nm to about 440 nm; ultraviolet radiation energy at a wavelength of about 290 nm to about 320 nm; ultraviolet radiation energy at a wavelength of about 320 to about 440 nm; or a total ultraviolet radiation energy exposure in the range of about 0.2 mJ/cm$^2$ to about 40 mJ/cm$^2$. Other embodiments of this aspect of the invention provide methods in which the cell exposed to ultraviolet radiation is a skin cell (epidermal or dermal) or a cell selected from the group consisting of a keratinocyte, a Langerhans cell, a melanocyte, and a fibroblast cell.

In another embodiment, the method for detecting exposure of a cell to ultraviolet radiation comprises measuring the levels of a plurality of protein molecules in the cell for at least one time point, wherein a pattern of expression is established and the pattern is indicative of ultraviolet radiation exposure. In this embodiment, the pattern of expression comprises a first response group which is the quaternary first response group previously described above; a second response which is the quaternary second response previously described above; and a third response which is the tertiary third response previously described above.

In other embodiments, the first response group is the quaternary first response group previously described above; the second response is the quaternary second response previously described above; and the third response is the quaternary third response previously described above. In yet another embodiment, the pattern of expression is the quaternary first response group; the pattern of expression is the quaternary second response group; the pattern of expression is quaternary third response group; the pattern of expression is the quaternary first response group and the quaternary second response group; the pattern of expression is the quaternary first response group and the quaternary third response group; the pattern of expression is the quaternary second response group and the quaternary third response group; or the pattern of expression is the quaternary first response group, the quaternary second response group, and the quaternary third response group.

Additional embodiments thereof provide methods in which the ultraviolet radiation exposure comprising ultraviolet radiation energy at a wavelength in the range of about 220 nm to about 440 nm; ultraviolet radiation energy at a wavelength of about 290 mn to about 320 nm; ultraviolet radiation energy at a wavelength of about 320 to about 440 nm; or a total ultraviolet radiation energy exposure in the range of about 0.2 mJ/cm$^2$ to about 40 mi/cm$^2$. Other embodiments thereof provide that the cell exposed to ultraviolet radiation is a skin cell (epidermal or dermal) or a cell selected from the group consisting of a keratinocyte, a Langerhans cell, a melanocyte, and a fibroblast cell. In one embodiment, the measurement of the level of the plurality of protein molecules is done by ELISA.

Another aspect of the invention provides a screening method for the detection of a compound that modulates a response of a cell to ultraviolet radiation exposure. The screening method comprises contacting a cell with a compound, exposing the cell to ultraviolet radiation to induce a response of the cell to ultraviolet radiation exposure, and measuring the levels of a plurality of RNA molecules in the cell after ultraviolet radiation exposure, wherein any change in the first, second, and/or third response indicates that the compound modulates the response of the cell to ultraviolet radiation exposure. In one embodiment thereof, the response comprises at least one of the following: a first response group that is the primary first response group, a second response that is the primary second response, and a third response that is the primary third response.

In other embodiments thereof, the response, or pattern of expression, comprises the following: (1) the pattern of expression is the primary first response group; or (2) the pattern of expression is the primary second response group; or (3) the pattern of expression is the primary third response group; or (4) the pattern of expression is the primary first response group and the primary second response group; or (5) the pattern of expression is the primary first response group and the primary third response group; or (6) the pattern of expression is the primary second response group and the primary third response group; or (7) the pattern of expression is the primary first response group, the primary second response group, and the primary third response group.

Additional embodiments thereof provide methods in which the ultraviolet radiation exposure of the cell comprises: (1) ultraviolet radiation energy at a wavelength in the range of about 220 nm to about 440 nm; or (2) ultraviolet radiation energy at a wavelength of about 290 nm to about 320 nm; or (3) ultraviolet radiation energy at a wavelength of about 320 to about 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or a cell selected from the group consisting of a keratinocyte, a Langerhans cell, a melanocyte, and a fibroblast cell In another embodiment, the screening method for the detection of a compound that modulates a response of a cell to ultraviolet radiation comprises contacting a cell with a compound, exposing the cell to ultraviolet radiation to induce a response of the cell to ultraviolet radiation exposure, and measuring the levels of a plurality of RNA molecules in the cell after ultraviolet radiation exposure, wherein any change in the first, second, and/or third response indicates that the compound modulates the response of the cell to ultraviolet radiation exposure. In this embodiment, the pattern of expression comprises a first response group that is the secondary first response group; a second response that is the secondary second response; and/or a third response that is the secondary third response.

In various embodiments thereof, this pattern of expression comprises a first response group, and/or a second response, and/or a third response. In this embodiment, the first response group is the secondary first response group previously described above; the second response is the secondary second response previously described above; and the third response is the secondary third response previously described above. Embodiments thereof include the following: (1) the pattern of expression is the secondary first response group; or (2) the pattern of expression is the secondary second response group; or (3) the pattern of expression is secondary third response group; or (4) the pattern of expression is the secondary first response group and the secondary second response group; or (5) the pattern of expression is the secondary first response group and the secondary third response group; or (6) the pattern of expression is the secondary second response group and the secondary third response group; or (7) the pattern of expression is the secondary first response group, the secondary second response group, and the secondary third response group.

Additional embodiments of this aspect of the invention provide detection methods in which the ultraviolet radiation exposure of the cell comprises: (1) ultraviolet radiation energy at a wavelength in the range of 220 nm to 440 nm; or (2) ultraviolet radiation energy at a wavelength of about 290 nm to 320 nm; or (3) ultraviolet radiation energy at a wavelength of about 320 to 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or the cell is selected from the group consisting of a keratinocyte, a Langerhans cell, a melanocyte, and a fibroblast cell.

The invention also provides methods for the detection of a compound that modulates a response of a cell to ultraviolet radiation in which the measurement of the level of the plurality of RNA molecules is done by expression array analysis. In this method, RNA is isolated from the cell at a time post-ultraviolet radiation exposure. A test expression array is created through nucleic acid hybridization between a labeled probe complementary to the RNA and an expression array substrate. The test expression array is analyzed to create a test expression array data set, which is then compared to the control expression array data set to identify a modulation response of the exposed cell. Modulation indicates that the compound modulates the response of the cell to ultraviolet radiation. The levels of the plurality of RNA molecules in the cell are then analyzed to establish a response pattern of the cell, the response pattern comprising at least one of the following: a secondary first response group, a secondary second response group, and a secondary third response group.

Another aspect of the invention provides other methods for the detection of a compound that modulates a response of a cell to ultraviolet radiation. These methods comprise measuring a plurality of protein molecules in the cell, wherein a pattern of expression is established and the pattern is indicative of ultraviolet radiation exposure. In various embodiments thereof, this pattern of expression comprises a first response group, a second response, and/or a third response. In one embodiment thereof, the first response group is the tertiary first response group previously described above; the second response is the tertiary second response previously described above; and the third response is the tertiary third response previously described above. Embodiments of this method include the following: (1) the pattern of expression is the tertiary first response group; or (2) the pattern of expression is the tertiary second response group; or (3) the pattern of expression is the tertiary third response group; or (4) the pattern of expression is the tertiary first response group and the tertiary second response group; or (5) the pattern of expression is the tertiary first response group and the tertiary third response group; or (6) the pattern of expression is the tertiary second response group and the tertiary third response group; or (7) the pattern of expression is the tertiary first response group, the tertiary second response group, and the tertiary third response group.

Additional embodiments thereof provide methods in which the cell is exposed to ultraviolet radiation comprising ultraviolet radiation energy at a wavelength in the range of about 220 nm to about 440 nm; ultraviolet radiation energy at a wavelength of about 290 nm to about 320 nm; ultraviolet radiation energy at a wavelength of about 320 to about 440 nm; or a total ultraviolet radiation energy exposure in the range of about 0.2 $mJ/cm^2$ to about 40 $mJ/cm^2$. Other embodiments of this aspect of the invention provide methods in which the cell exposed to ultraviolet radiation is a skin cell (epidermal or dermal) or a cell selected from the group consisting of a keratinocyte, a Langerhans cell a melanocyte, and a fibroblast cell.

In another embodiment, the method for the detection of a compound that modulates a response of a cell to ultraviolet radiation comprises measuring the levels of a plurality of protein molecules in the cell for at least one time point, wherein a pattern of expression is established and the pattern is indicative of ultraviolet radiation exposure. In this embodiment, the pattern of expression comprises a first response group which is the quaternary first response group previously described above; a second response which is the quaternary second response previously described above; and a third response which is the quaternary third response previously described above.

In other embodiments, the first response group is the quaternary first response group previously described above; the second response is the quaternary second response previously described above; and the third response is the quaternary third response previously described above. In yet another embodiment, the pattern of expression is the quaternary first response group; the pattern of expression is the quaternary second response group; the pattern of expression is quaternary third response group; the pattern of expression is the quaternary first response group and the quaternary second response group; the pattern of expression is the quaternary first response group and the quaternary third response group; the pattern of expression is the quaternary second response group and the quaternary third response group; or the pattern of expression is the quaternary first response group, the quaternary second response group, and the quaternary third response group.

Additional embodiments thereof provide methods in which the ultraviolet radiation exposure comprising ultraviolet radiation energy at a wavelength in the range of about 220 nm to about 440 nm; ultraviolet radiation energy at a wavelength of about 290 nm to about 320 nm; ultraviolet radiation energy at a wavelength of about 320 to about 440 nm; or a total ultraviolet radiation energy exposure in the range of about 0.2 $mJ/cm^2$ to about 40 $mJ/cm^2$. Other embodiments thereof provide that the cell exposed to ultraviolet radiation is a skin cell (epidermal or dermal) or a cell selected from the group consisting of a keratinocyte, a Langerhans cell, a melanocyte, and a fibroblast cell. In one embodiment, the measurement of the level of the plurality of protein molecules is done by ELISA.

Another aspect of the invention provides a screening method for the detection of a compound that simulates a response of a cell to ultraviolet radiation exposure. The method comprises contacting the cell with the compound, and measuring a level of at least one RNA molecule in the contacted cell, and determining that the level of at least one RNA molecule is substantially similar to that found in the response of the cell to ultraviolet radiation exposure, the response of the cell characterized by at least one of the following: a first response group that is the primary first response group, a second response that is the primary second response group, and a third response that is the primary third response group. A determination that the level of at least one RNA molecule is substantially similar to the altered expression found in the primary first response group, the primary second response group and/or the primary third response group indicates that the compound simulates the response of the cell to ultraviolet radiation exposure.

In other embodiments of the screening method for the detection of a compound that simulates a response of a cell to ultraviolet radiation exposure include the following: (1) the pattern of expression is the primary first response group; or (2) the pattern of expression is the primary second response group; or (3) the pattern of expression is the primary third response group; or (4) the pattern of expression is the primary first response group and the primary second response group; or (5) the pattern of expression is the primary first response group and the primary third response group; or (6) the pattern of expression is the primary second response group and the primary third response group; or (7) the pattern of expression is the primary first response group, the primary second response group, and the primary third response group.

Additional embodiments thereof provide methods in which the ultraviolet radiation exposure of the cell comprises: (1) ultraviolet radiation energy at a wavelength in the range of about 220 nm to about 440 nm; or (2) ultraviolet radiation energy at a wavelength of about 290 nm to about 320 nm; or (3) ultraviolet radiation energy at a wavelength of about 320 to about 440 nm; or (4) a total ultraviolet radiation energy exposure in the range of about 0.2 $mJ/cm^2$ to about 40 $mJ/cm^2$. Other embodiments thereof provide that the exposed cell is a skin cell (epidermal or dermal) or a cell selected from the group consisting of a keratinocyte, a Langerhans cell, a melanocyte, and a fibroblast cell.

In another embodiment, the screening method for the detection of a compound that simulates a response of a cell to ultraviolet radiation exposure, the method comprises contacting the cell with the compound, and measuring a level of at least one RNA molecule in the contacted cell, and determining that the level of at least one RNA molecule is substantially similar to that found in the response of the cell to ultraviolet radiation exposure, the response of the cell characterized by at least one of the following: a secondary first response group, a secondary second response group, and a secondary third response group.

In other embodiments thereof, this response comprises the following: (1) the pattern of expression is the secondary first response group; or (2) the pattern of expression is the secondary second response group; or (3) the pattern of expression is the secondary third response group; or (4) the pattern of expression is the secondary first response group and the secondary second response group; or (5) the pattern of expression is the secondary first response group and the secondary third response group; or (6) t pattern of expression is the secondary second response group and the secondary third response group; or (7) the pattern of expression is the secondary first response group, the secondary second response group, and the secondary third response group.

Additional embodiments of this aspect of the invention provide methods in which the ultraviolet radiation exposure of the cell comprises: (1) ultraviolet radiation energy at a wavelength in the range of 220 nm to 440 nm; or (2) ultraviolet radiation energy at a wavelength of about 290 nm to 320 nm; or (3) ultraviolet radiation energy at a wavelength of about 320 to 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or the cell is selected from the group consisting of a keratinocyte, a Langerhans cell, a melanocyte, and a fibroblast cell.

Another aspect of the invention provides a screening method for the detection of a compound that simulates the response of a cell to ultraviolet radiation exposure. The method comprises contacting the cell with the compound, and measuring a level of at least one protein molecule in the contacted cell, and determining that the level of at least one protein molecule is substantially similar to that found in the response of the cell to ultraviolet radiation exposure, the response of the cell characterized by at least one of the following: a first response group that is the tertiary first response group, a second response group that is the tertiary second response group, and a third response group that is the tertiary third response group. A determination that the level of at least one protein molecule is substantially similar to the altered expression found in the tertiary first response group, the tertiary second response group and/or the tertiary third response group indicates that the compound simulates the response of the cell to ultraviolet radiation exposure.

In another embodiment, the screening method for the detection of a compound that simulates a response of a cell to ultraviolet radiation exposure, the method comprises contacting the cell with the compound, and measuring a level of at least one protein molecule in the contacted cell, and determining that the level of at least one protein molecule is substantially similar to that found in the response of the cell to ultraviolet radiation exposure, the response of the cell characterized by at least one of the following: a tertiary first response group, a tertiary second response group, and a tertiary third response group.

In other embodiments thereof, this response comprises the following: (1) the pattern of expression is the tertiary first response group; or (2) the pattern of expression is the tertiary second response group; or (3) the pattern of expression is tertiary third response group; or (4) the pattern of expression is the tertiary first response group and the tertiary second response group; or (5) the pattern of expression is the tertiary first response group and the tertiary third response group; or (6) the pattern of expression is the tertiary second response group and the tertiary third response group; or (7) the pattern of expression is the tertiary first response group, the tertiary second response group, and the tertiary third response group.

Additional embodiments of this aspect of the invention provide methods in which the ultraviolet radiation exposure of the cell comprises: (1) ultraviolet radiation energy at a wavelength in the range of 220 nm to 440 nm: or (2) ultraviolet radiation energy at a wavelength of about 290 nm to 320 nm; or (3) ultraviolet radiation energy at a wavelength of about 320 to 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or the cell is selected from the group consisting of a keratinocyte, a Langerhans cell, a melanocyte, and a fibroblast cell.

Another aspect of the invention provides a screening method for the detection of a compound that simulates the response of a cell to ultraviolet radiation exposure. The method comprises contacting the cell with the compound, and measuring a level of at least one RNA molecule in the contacted cell, and determining that the level of at least one protein molecule is substantially similar to that found in the response of the cell to ultraviolet radiation exposure, the response of the cell characterized by at least one of the following: a first response group that is the quaternary first response group, a second response group that is the quaternary second response group, and a third response group that is the quaternary third response group. A determination that the level of at least one RNA molecule is substantially similar to the altered expression found in the primary first response group, the primary second response group and/or the primary third response group indicates that the compound simulates the response of the cell to ultraviolet radiation exposure.

In another embodiment, the screening method for the detection of a compound that simulates a response of a cell to ultraviolet radiation exposure, the method comprises contacting the cell with the compound, and measuring a level of at least one protein molecule in the contacted cell, and determining that the level of at least one protein molecule is substantially similar to that found in the response of the cell to ultraviolet radiation exposure, the response of the cell characterized by at least one of the following: a quaternary first response group, a quaternary second response group, and a quaternary third response group.

In other embodiments thereof, this response comprises the following: (1) the pattern of expression is the quaternary first response group; or (2) the pattern of expression is the quaternary second response group; or (3) the pattern of expression is quaternary third response group; or (4) the pattern of expression is the quaternary first response group and the quaternary second response group; or (5) the pattern of expression is the quaternary first response group and the quaternary third response group; or (6) the pattern of expression is the quaternary second response group and the quaternary third response group; or (7) the pattern of expression is the quaternary first response group, the quaternary second response group, and the quaternary third response group.

Additional embodiments of this aspect of the invention provide methods in which the ultraviolet radiation exposure of the cell comprises: (1) ultraviolet radiation energy at a wavelength in the range of 220 nm to 440 nm; or (2) ultraviolet radiation energy at a wavelength of about 290 nm to 320 nm; or (3) ultraviolet radiation energy at a wavelength of about 320 to 440 nm; or (4) a total ultraviolet radiation energy exposure in the range of about 0.2 mJ/cm$^2$ to about 40 mJ/cm$^2$. Other embodiments thereof provide that the exposed cell is a skin cell (epidermal or dermal) or the cell is selected from the group consisting of a keratinocyte, a Langerhans cell a melanocyte, and a fibroblast cell.

In an alternative aspect, the invention provides another method for detecting exposure of a cell to ultraviolet radiation. This method comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; a second response comprising an altered pattern of expression of at least one polynucleotide selected from the group consisting of a nucleic acid molecule encoding a secreted growth factor, a nucleic acid molecule encoding a cytokine, and a nucleic acid molecule encoding a chemokine; and a third response comprising an altered pattern of expression of at least one polynucleotide selected from the group consisting of a nucleic acid molecule encoding an actin-binding protein, a nucleic acid molecule encoding a desmosomal protein, a nucleic acid molecule encoding a tubulin protein, and at least one nucleic acid molecule encoding a cornified envelope protein.

In embodiments of the method thereof, the cell is a skin cell (epidermal or dermal) or the cell is selected from the group consisting of a keratinocyte, a Langerhans cell, a melanocyte, and a fibroblast cell Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also provides an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

The invention also provides another method for detecting exposure of a cell to ultraviolet radiation. This method comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 run; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

In yet another aspect of the invention, a method is provided for detecting exposure of a cell to ultraviolet radiation comprising measuring the levels of a plurality of RNA molecules in the cell by expression array analysis. This method comprises isolating RNA from the cell post ultraviolet radiation exposure, creating a test expression array through nucleic acid hybridization between a labeled probe complementary to the RNA and an expression array substrate. An analysis of the levels of the plurality of RNA molecules in the cell establishes an expression response pattern of the cell. Exposure of the cell to ultraviolet radiation is indicated by an altered pattern of expression comprising the following: (1) a first response comprising an altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; (2) a second response comprising an altered pattern of expression of at least one polynucleotide selected from the group consisting of a nucleic acid molecule encoding a secreted growth factor, a nucleic acid molecule encoding a cytokine, and (3) a nucleic acid molecule encoding a chemokine; and a third response comprising an altered pattern of expression of at least one polynucleotide selected from the group consisting of a nucleic acid molecule encoding an actin-binding protein, a nucleic acid molecule encoding a desmosomal protein, a nucleic acid molecule encoding a tubulin protein, and at least one nucleic acid molecule encoding a cornified envelope protein.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

In another embodiment, the method thereof comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In an alternative aspect, the invention provides another method for detecting exposure of a cell to ultraviolet radiation. This method comprises measuring the levels of a plurality of proteins in the cell for at least one time point, wherein an altered pattern of expression is established and is indicative of ultraviolet radiation exposure. This pattern comprises a first response comprising an altered pattern of expression of at least one protein selected from the group consisting of a transcription factor protein, a signal transducing protein, and a mitochondrial protein; a second response comprising an altered pattern of expression of at least one protein selected from the group consisting of a secreted growth factor, a cytokine, and a chemokine; and a third response comprising an altered pattern of expression of at least one protein selected from the group consisting of an actin-binding protein, a desmosomal protein, a tubulin protein, and a cornified envelope protein.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in protein level. Thus, in one particular embodiment, the expression level of a member of the first response group, and/or second response group, and/or third response group increases. In another embodiment thereof, the expression level of a member of the first response group, and/or second response group, and/or third response group decreases.

In another embodiment, the invention provides another method for detecting exposure of a cell to ultraviolet radiation. This method comprises measuring the levels of a plurality of protein molecules in the cell for at least one time point, wherein an altered pattern of expression is established and is indicative of ultraviolet radiation exposure. This pattern comprises a first response comprising an altered pattern of expression of at least one protein that is at least 90% identical to a polypeptide encoded by a polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In various embodiments related to a protein expression profile of a cell exposed to ultraviolet radiation, ELISA is used to measure the levels of the plurality of proteins in a cell presumptively exposed to ultraviolet radiation.

Another aspect of the invention relates to a screening method for the detection of a compound that modulates a response of a cell to ultraviolet radiation exposure. The method comprises contacting the cell with the compound and exposing the cell to ultraviolet radiation to induce the response, the response being an altered pattern of expression comprising the following: (1) a first response comprising the altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; (2) a second response comprising the altered pattern of expression of at least one polynucleotide selected from the group consisting of a nucleic acid molecule encoding a secreted growth factor, a nucleic acid molecule encoding a cytokine, and a nucleic acid molecule encoding a chemokine; and (3) a third response comprising for the altered pattern of expression of at least one polynucleotide selected from the group consisting of a nucleic acid molecule encoding an actin-binding protein, a nucleic acid molecule encoding a desmosomal protein, a nucleic acid molecule encoding a tubulin protein, and a nucleic acid molecule encoding a codified envelope protein. Next, the levels of a plurality of RNA molecules in the cell are measured for at least one time point after ultraviolet radiation exposure. A change in the altered pattern of expression of the first response, the second response, and/or the third response indicates that the compound modulates the response of the cell to ultraviolet radiation exposure.

In one embodiment of the method thereof, the cell is contacted with the compound in vitro.

In another embodiment of the method thereof, the cell is contacted with the compound in vivo. In other embodiments of the method thereof, the cell is a skin cell (epidermal or dermal) or the cell is selected from the group consisting of a keratinocyte, a Langerhans cell a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

Another aspect of the invention relates to a screening method for the detection of a compound that modulates a response of a cell to ultraviolet radiation exposure. The method comprises contacting the cell with the compound and exposing the cell to ultraviolet radiation to induce the response, the response being an altered pattern of expression. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group. The levels of a plurality of RNA molecules in the cell are measured for at least one time point after ultraviolet radiation exposure, and a change in the altered pattern of expression of the first response group, the second response group, and/or the third response group indicates that the compound modulates the response of the cell to ultraviolet radiation exposure.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the Lime period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In yet another aspect of the invention, a screening method is provided for the detection of a compound that modulates a response of a cell to ultraviolet radiation exposure. The method comprises contacting the cell with the compound and exposing the cell to ultraviolet radiation to induce the response, the response being an altered pattern of expression. This method comprises isolating RNA from the cell post ultraviolet radiation exposure, creating a test expression array through nucleic acid hybridization between a labeled probe complementary to the RNA and an expression array substrate, analyzing the test expression array to create a test expression array data set; and comparing the test expression array data set to the response of the cell exposed to ultraviolet radiation in the absence of the drug, the response being an altered pattern of expression comprising the following a primary first response group, a primary second response group, and a primary third response group. A change in the altered pattern of expression of the primary first response, the primary second response, and/or the primary third response indicates that the compound modulates the response of the cell to ultraviolet radiation exposure.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

Other embodiments of the method thereof are included in the invention. For example, in one embodiment, cell contact with the compound is topical contact. In another embodiment, the compound modulates the cellular response by inhibiting ultraviolet radiation-induced RNA expression. In another embodiment, the compound inhibits the ultraviolet radiation-repressed expression. In these latter two embodiments, ultraviolet radiation-induced expression is the "induced response group" and ultraviolet radiation-repressed expression is the "repressed response group."

Another aspect of the invention relates to a screening method for the detection of a compound that modulates a response of a cell to ultraviolet radiation exposure. The screening method comprises contacting the cell with the compound and exposing the cell to ultraviolet radiation to induce the response, the response being an altered pattern of expression comprising the following: (1) a tertiary first response group, (2) a tertiary second response group, and (3) a tertiary third response group; and measuring the levels of a plurality of RNA molecules in the cell for at least one time point after ultraviolet radiation exposure. A change in the altered pattern of expression of the tertiary first response, the tertiary second response, and/or the tertiary third response indicates that the compound modulates the response of the cell to ultraviolet radiation exposure.

In various embodiments of the screening method thereof, the cell is contacted with the compound in vitro or in vivo. In other embodiments of the screening method thereof, the cell is a skin cell (epidermal or dermal), or the cell is selected from the group consisting of a keratinocyte, a Langerhans cell a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the screening method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In various embodiments related to screening method thereof, ELISA is used to measure the levels of the plurality of proteins in a cell in determining the response of the cell to ultraviolet radiation in the presence and absence of the compound.

Another aspect of the invention relates to a screening method for the detection of a compound that modulates a response of a cell to ultraviolet radiation exposure. The screening method comprises contacting the cell with the compound and exposing the cell to ultraviolet radiation to induce the response, the response being an altered pattern of expression comprising the following: (1) a quaternary first response group, (2) a quaternary second response group, and (3) a quaternary third response group; and measuring the levels of a plurality of RNA molecules in the cell for at least one time point after ultraviolet radiation exposure. A change in the altered pattern of expression of the quaternary first response, the quaternary second response, and/or the quaternary third response indicates that the compound modulates the response of the cell to ultraviolet radiation exposure.

In various embodiments of the screening method thereof, the cell is contacted with the compound in vitro or in vivo. In other embodiments of the screening method thereof, the cell is a skin cell (epidermal or dermal) or the cell is selected from the group consisting of a keratinocyte, a Langerhans cell a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 $mJ/cm^2$ to about 40 $mJ/cm^2$.

Other embodiments of the screening method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In various embodiments related to screening method thereof, ELISA is used to measure the levels of the plurality of proteins in a cell in determining the response of the cell to ultraviolet radiation in the presence and absence of the compound.

Another aspect of the invention provides a screening method for the detection of a compound that simulates the response of a cell to ultraviolet radiation exposure. This screening method comprises contacting the cell with the compound; measuring a level of at least one RNA molecule in the contacted cell; and determining that the level of at least one RNA molecule in the cell after exposure to the compound is substantially similar to the level of the RNA found in the cell in response to ultraviolet radiation exposure, the response of the cell to ultraviolet radiation exposure being characterized by altered expression of the following: a primary first response group, a primary second response group, and a primary third response group. A determination that the level of expression of at least one RNA molecule is substantially similar to the altered expression found for the RNA molecule in the primary first response, the primary second response or the primary third response indicates that the compound simulates exposure of the cell to ultraviolet radiation.

Another aspect of the invention provides a screening method for the detection of a compound that simulates the response of a cell to ultraviolet radiation exposure. This screening method comprises contacting the cell with the compound; measuring a level of at least one RNA molecule in the contacted cell; and determining that the level of at least one RNA molecule in the cell after exposure to the compound is substantially similar to the level of the RNA found in the cell in response to ultraviolet radiation exposure, the response of the cell to ultraviolet radiation exposure being characterized by altered expression of the following: a secondary first response group, a secondary second response group, and a secondary third response group. A determination that the level of expression of at least one RNA molecule is substantially similar to the altered expression found for the RNA molecule in the secondary first response, the secondary second response or the secondary third response indicates that the compound simulates exposure of the cell to ultraviolet radiation.

Another aspect of the invention provides a screening method for the detection of a compound that simulates the response of a cell to ultraviolet radiation exposure. This screening method comprises contacting the cell with the compound; measuring a level of at least one Protein in the contacted cell; and determining that the level of at least one protein in the cell after exposure to the compound is substantially similar to the level of the protein found in the cell in response to ultraviolet radiation exposure, the response of the cell to ultraviolet radiation exposure being characterized by altered expression of the following: a tertiary first response group, a tertiary second response group, and a tertiary third response group. A determination that the level of expression of at least one protein is substantially similar to the altered expression found for the protein in the tertiary first response group, the tertiary second response group or the tertiary third response group indicates that the compound simulates exposure of the cell to ultraviolet radiation.

Another aspect of the invention provides a screening method for the detection of a compound that simulates the response of a cell to ultraviolet radiation exposure. This screening method comprises contacting the cell with the compound; measuring a level of at least one protein in the contacted cell; and determining that the level of at least one protein in the cell after exposure to the compound is substantially similar to the level of the protein found in the cell in response to ultraviolet radiation exposure, the response of the cell to ultraviolet radiation exposure being characterized by altered expression of the following: a quaternary first response group, a quaternary second response group, and a quaternary third response group. A determination that the level of expression of at least one protein is substantially similar to the altered expression found for the protein in the quaternary first response group, the quaternary second response group or the quaternary third response group indicates that the compound simulates exposure of the cell to ultraviolet radiation.

BRIEF DESCRIPTION OF THE FIGURES

FIG. 4 is a representation of immunohistological staining demonstrating that ultraviolet radiation exposure enhances the expression of involucrin in human skin organ culture and at 2, 8 and 16 hours after ultraviolet radiation. Suprabasal staining of the epidermis with the involucrin antibody is greatly augmented 16 hours after ultraviolet irradiation.

DETAILED DESCRIPTION OF THE PREFERRED EMBODIMENTS

Figure 1A:
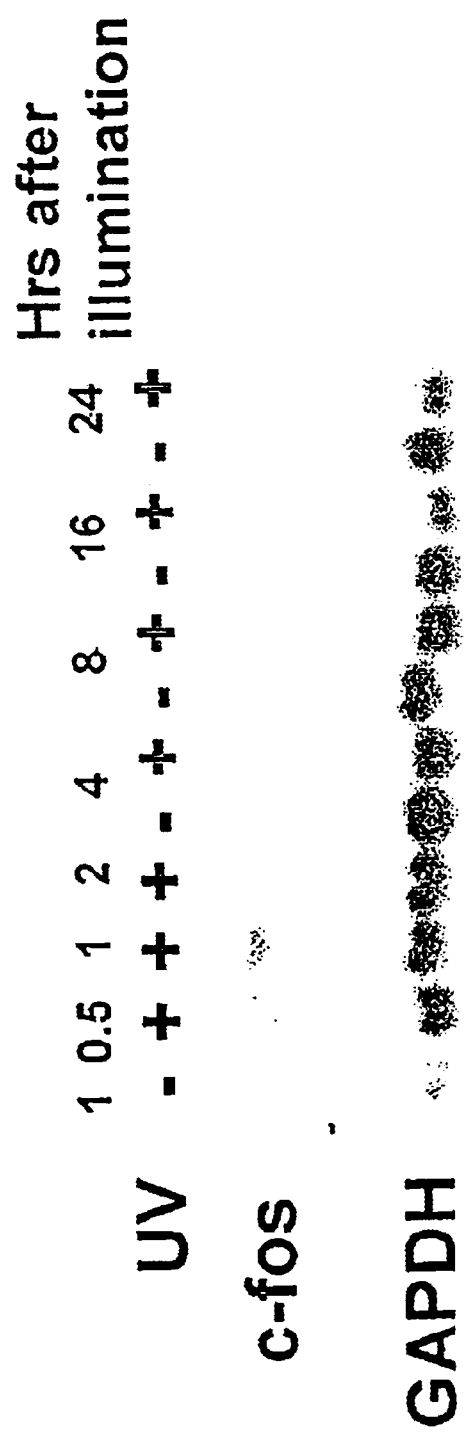
FIG. 1A is a representation of a Northern blot in which RNA isolated from exposed to ultraviolet radiation is screened to monitor the quality of the RNA's prior to use in experiments utilizing expression array hybridization. RNA samples were isolated from keratinocytes at 0.5, 1, 2, 4, 8, 16, 24 hours after ultraviolet irradiation. The glyceraldehyde-3-phosphate dehydrogenase (GAPDH) probe was used as a control, and the one hour untreated sample was used as a control for the 0.5, 1 and 2 hour treated samples.

The patent and scientific literature cited herein establishes the knowledge that is available to those with skill in the art. The issued U.S. patents, allowed applications, published foreign applications, and references cited herein are hereby incorporated by reference.

Aspects of the invention utilize techniques and methods common to the fields of molecular biology, cell biology and immunology. Useful laboratory references for these types of methodologies are readily available to those skilled in the art. See, for example, *Molecular Cloning. A Laboratory Manual,* 2nd. edition, edited by Sambrook, J., Fritsch, B. F. and Maniatis, T., (1989), Cold Spring Harbor Laboratory Press; *Current Protocols In Molecular Biology and Current Protocols in Immnunology,* Wiley Interscience, New York (19 ____); Harlow & Lane, *Antibodies: A Laboratory Manual,* Cold Spring Harbor Press, Cold Spring Harbor, N.Y. (1988). All nucleic acid sequences and the respective amino acid sequences encoded thereby identified above by the appropriate GenBank accession number are herein incorporated by reference. This information is also disclosed in the appropriate tables provided herein.

The invention provides a detailed analysis of the molecular events underlying the response of a cell to exposure to ultraviolet radiation by identifying a plurality of nucleic acid molecules and protein molecules, the expression of which is regulated in response to ultraviolet radiation exposure. These ultraviolet radiation-regulated nucleic acid and protein molecules are further characterized temporally in relation to the cellular response (a first response, a second response, and a third response) and in a quantitative fashion (induced or repressed) in relation to expression levels. These data are also presented in the following table format.

Table 1 presents a list of gene sequences that occur more than once on the gene array, which were used as a monitor of the fidelity of gene array hybridization.

TABLE 1

| | Genes Multiply Present on the Gene Array | | | | | | |
|---|---|---|---|---|---|---|---|
| Duplicate genes. | Fold regulation | | | | | | |
| Description | 0.5 hr | 1 hr | 2 hr | 4 hr | 8 hr | 16 hr | 24 hr |
| U20734_s_at U20734 Human transcription factor junB (junB) gene, 5' region and complete cds. | 1.9 | 3.2 | 3.9 | 3 | −1.8 | −1.9 | 1.9 |
| X51345_at X51345 Human jun-B mRNA for JUN-B protein. | 1.5 | 2.1 | 2 | | 2.7 | −2.4 | −1.3 | 2 |
| L00058_at L00058 Human (GH) germline c-myc proto-oncogene, exon 3 and 3' flank. | 1.7 | 1.6 | 1.1 | −1.7 | −4.3 | −1.7 | −3 |

TABLE 1-continued

Genes Multiply Present on the Gene Array

Duplicate genes.

| Description | Fold regulation | | | | | | |
|---|---|---|---|---|---|---|---|
| | 0.5 hr | 1 hr | 2 hr | 4 hr | 8 hr | 16 hr | 24 hr |
| M13929_s_at M13929 Human c-myc-P64 mRNA, initiating from promoter P0, (HLmyc2.5) partial cds. | −3.1 | −3 | −2.3 | −2.3 | −5 | −4.3 | −2.9 |
| HG3523-HT4899_s_at J00120 Proto-Oncogene C-Myc, Alt. Splice 3, Orf 114 | −1.2 | −1.9 | −1.4 | −3.9 | −5.8 | −3.4 | −1.3 |
| U04636_rna1_at U04636 Human cyclooxygenase-2 (hCox-2) gene, complete cds. | 1 | 1 | 1 | 1.5 | 2.4 | 4.5 | 3.9 |
| D28235_s_at D28235 Human PTGS2 gene for prostaglandin endoperoxide synthase-2, complete cds. | 1 | 1 | 1 | 1.6 | 2 | 2.5 | 2.6 |
| M21302_at M21302 Human small proline rich protein (sprll) mRNA, clone 174N. | −1.1 | −1.1 | 1 | 2.4 | 3.5 | 3.3 | 7.6 |
| L05188_f_at L05188 H. sapiens small proline-rich protein 2 (SPRR2B) gene, complete cds. | −1 | 1 | 1.6 | 1.2 | 1.9 | 3.1 | 7.1 |
| M20030_f_at M20030 Human small proline rich protein (sprll) mRNA, clone 930. | 1.3 | 2.1 | 1.5 | 1.1 | 1.6 | 5.9 | 21.1 |
| HG4322-HT4592_at V00599 Tubulin, Beta | 2 | 1.9 | 1.7 | 2.7 | 3 | 3.4 | 3.6 |
| HG1980-HT2023_at V00599 Tubulin, Beta 2 | 1 | 1.3 | 1.4 | 1 | 1.3 | 1.1 | 2.6 |
| HG2815-HT4023_s_at M22919 Myosin, Light Chain, Alkali, Smooth Muscle (Gb: U02629), Smooth Muscle, Alt. Spli | 1.1 | −1.2 | 1 | −1 | 1.1 | 2.5 | 3.7 |
| HG2815-HT2931_at M22918 Myosin, Light Chain, Alkali, Smooth Muscle (Gb: U02629), Non-Muscle, Alt. Splice | 1.1 | −1.1 | 1.1 | −1.1 | −1 | 9.9 | 6.6 |
| HG2815-HT2931_s_at M22918 Myosin, Light Chain, Alkali, Smooth Muscle (Gb: U02629), Non-Muscle, Alt. Splice | 1.5 | 1 | 1.1 | −1 | −1.3 | 5.2 | 3.7 | and
Table 2 presents a list of DNA metabolism and DNA repair genes that are ultraviolet radiation-regulated.

TABLE 2

Ultraviolet Radiation-Regulated DNA Metabolism And Repair Genes

| | | DNA repair proteins. | Fold regulation | | | | | | |
|---|---|---|---|---|---|---|---|---|---|
| NO. | Accession | Gene Description | 0.5 hr | 1 hr | 2 hr | 4 hr | 8 hr | 16 hr | 24 hr |
| 1 | X57985 | Histones H2B.1 and H2A. | 1 | 1 | 3.1 | 3.3 | 4.4 | 5.9 | 4.8 |
| 2 | L19779 | Histone H2A.2. | 1.6 | 2.3 | 3.1 | 3.3 | 3.4 | 5.1 | 4.6 |
| 3 | M72885 | GOS2 | 1.6 | 2.8 | 3.5 | 4.7 | 3.9 | 1.7 | 4 |
| 4 | M37583 | Histone (H2A.Z). | 1.2 | −1 | 1.1 | 1.4 | 1.2 | 3.4 | 3.4 |
| 5 | X77794 | Cyclin G1. | 2.2 | 1.4 | 1.5 | −2.4 | −4.7 | −1.3 | 3.2 |
| 6 | X14850 | Histone H2A.X. | 1.4 | 1.7 | 2 | 2 | 1.7 | 2.5 | 3.1 |
| 7 | L76568 | Excision and cross link repair protein ERCC4. | 1.8 | 1.7 | 1.5 | −1.2 | −1.4 | 2 | 2.5 |
| 8 | M60974 | Growth arrest and DNA-damage-inducible protein gadd45 | 1.6 | 1.5 | 2.6 | 3.1 | 1.6 | 1.5 | 2.5 |
| 9 | Y07604 | Nucleoside-diphosphate kinase. | 1.2 | 1.3 | 1.4 | 1.1 | 1.6 | 2.3 | 2.1 |
| 10 | U40369 | Spermidine/spermine N1-acetyltransferase | 1.9 | 1.7 | 1.8 | 2.5 | 1.3 | 2.3 | 2 |
| 11 | U26727 | p16INK4/MTS1 | 2 | 1.4 | 1 | −1 | 1.1 | 3 | 1.6 |
| 12 | L76200 | Guanylate kinase | 2.4 | 1.4 | 1.3 | 1.5 | 1.1 | 2.6 | 1.6 |
| 13 | D64142 | Histone H1x,. | 1.5 | 1.4 | 1.3 | 2.6 | 2.3 | 1.6 | 1.4 |
| 14 | X61123 | BTG1 | 1.2 | 1.2 | 2.7 | 2.8 | −1.4 | 1 | 2.3 |
| 15 | U72649 | BTG2 | 1.7 | 2.8 | 2.7 | −1.3 | −2.8 | −1.8 | 1.4 |
| 16 | D38305 | Tob | 1.6 | 1.4 | 1.6 | 2 | −1.2 | 1.2 | 2.7 |
| 17 | U28749 | High-mobility group phosphoprotein isoform I-C (HMGIC). | 1.3 | −1 | −2 | −2.7 | −3.2 | 1 | 1.2 |
| 18 | L19437 | Transaldolase. | 2.5 | 1.6 | 1.5 | 1.1 | −1 | 1.9 | 1 |
| 19 | L27943 | Cytidine deaminase (CDA). | 1.1 | 1.2 | −1.1 | −1.3 | −1.5 | 2.6 | −1.3 |
| 20 | X90858 | Uridine phosphorylase. | 1.3 | 1.1 | 1.1 | 1.6 | −1.2 | −3 | −2.5 | and

Table 3 presents a list of signal transducer and transcription factor proteins that are ultraviolet radiation regulated.

TABLE 3

Ultraviolet Radiation-Regulated Signal Transducers And Transcription Factors

| | | Signaling molecules. | Fold regulation | | | | | | | |
|---|---|---|---|---|---|---|---|---|---|---|
| NO | Accession # | Gene and its description | 0.5 hr | 1 hr | 2 hr | 4 hr | 8 hr | 16 hr | 24 hr | Function |
| 1 | D50840 | Ceramide glucosyltransferase | −1.5 | −2 | −2.9 | −1.6 | −2.8 | −2 | 6.8 | Enzyme |
| 2 | U04636 | Cyclooxygenase-2 (hCox-2) | 1 | 1 | 1 | 1.5 | 2.4 | 4.5 | 3.9 | Enzyme |
| 3 | D28235 | PTGS2 gene for prostaglandin endoperoxide synthase-2 | 1 | 1 | 1 | 1.6 | 2 | 2.5 | 2.6 | Enzyme |
| 4 | U56418 | Lysophosphatidic acid acyltransferase-β | −1.1 | −2.2 | −1 | −1.1 | −1.7 | −3.5 | −1.3 | Enzyme |
| 5 | HG2855 | Heat Shock Protein, 70 KD | 1.9 | 1.7 | 1.3 | −1.3 | −4.8 | −1.3 | 2.1 | HSP |
| 6 | L11066 | Human mRNA sequence. | 1.1 | 1.1 | 1.1 | −1.1 | 1.1 | −2.9 | 1 | HSP |
| 7 | D85429 | Heat shock protein 40 | −1 | −1 | 1 | 1 | −4.2 | −3.2 | −1.8 | HSP |
| 8 | D86965 | KIAA0210 gene | −2.6 | −2.6 | −1.8 | −1.2 | −1.1 | −3.3 | −2 | Immunophilin |
| 9 | Y08915 | α4 protein. | 1.5 | 1.7 | 1.4 | 1 | −1.3 | −1.4 | −2.6 | Immunophilin |
| 10 | U42031 | 54 kD progesterone receptor-associated immunophilin FKBP54 | −2.2 | −2.8 | −3 | −2.6 | −2.9 | −4.6 | −3.4 | Immunophilin |
| 11 | M26311 | Cystic fibrosis antigen | 1.8 | 1.5 | 1.4 | 1.1 | −1 | 1.7 | 3.9 | Kinase |
| 12 | U09578 | MAPKAP kinase (3pK) | 2.8 | 1.8 | 2 | 1.6 | −1 | 2.8 | 1 | Kinase |
| 13 | X78549 | Brk tyrosine kinase. | 1.5 | 1.2 | 2 | 1.8 | −1 | −2 | 1 | Kinase |
| 14 | M34182 | Testis-specific protein kinase γ subunit | −1.2 | −2.5 | −1.3 | 1.2 | −1 | −1.5 | −1.1 | Kinase |
| 15 | L37042 | Casein kinase I α (CSNK1A1) | −1.3 | −2 | −2.7 | −1 | −2.3 | −2.2 | −1.1 | Kinase |
| 16 | U01337 | Ser/Thr protein kinase (A-RAF-1) | 1.2 | −1.1 | −1 | −1 | −1.2 | −2.6 | −1.1 | Kinase |
| 17 | X12794 | v-erbA related ear-2 gene. | 1.2 | 1 | 1.3 | −1.6 | −1.9 | −2.8 | −1.1 | Kinase |
| 18 | M55265 | Casein kinase II α | −1.5 | −2.1 | −2.8 | −1.4 | −1.6 | −2.4 | −1.2 | Kinase |
| 19 | M54915 | H-pim-1 protein (h-pim-1) | −1 | −1.9 | −1.1 | 1.2 | −1.5 | −3.7 | −1.5 | Kinase |
| 20 | D45906 | LIMK-2 | −1.4 | −1.2 | −2.8 | −1.1 | −1.3 | −2 | −1.9 | Kinase |
| 21 | X80692 | ERK3 | 1.7 | 1.4 | 1.1 | −2.2 | −6.9 | −3.2 | −2.3 | Kinase |
| 22 | L19267 | 59 protein | −1.2 | −1.1 | −1.8 | −1.8 | −1.9 | −1.8 | −2.8 | Kinase |
| 23 | M55268 | Casein kinase II α | 1.3 | 1.1 | −1.2 | −1.1 | −1.7 | −2.6 | −4.7 | Kinase |
| 24 | M60483 | Protein phosphatase 2A (PP2A) | 1.2 | −1.6 | −1.1 | −1.4 | −2.7 | −1.9 | 1.2 | Phosphatase |
| 25 | X68277 | MKP1 protein tyrosine phosphatase (CL100). | 2.3 | 4.9 | 6.6 | 6.2 | −1.6 | −1 | 1 | Phosphatase |
| 26 | X74008 | Protein phosphatase 1 gamma (PP1G) | 1.3 | 1.2 | 1.1 | −1.1 | −2.8 | −2.3 | 1 | Phosphatase |
| 27 | U14603 | Protein-tyrosine phosphatase (HU-PP-1) | 1.1 | −1.3 | −1.5 | 1.1 | −2.5 | −2.2 | −2.6 | Phosphatase |
| 28 | L77886 | Protein tyrosine phosphatase | 1.3 | 1 | −1 | −1.2 | −2.6 | −2.3 | −2.6 | Phosphatase |
| 29 | U72066 | CtBP interacting protein CtIP (CtIP) | −1 | −1.3 | −1.6 | −1.2 | −2.8 | −4.5 | −3.2 | Rb-binding |
| 30 | U09937 | Urokinase-type plasminogen receptor | 1 | −1.2 | 1.1 | −1.1 | 1 | 1.2 | 3.2 | Receptor |
| 31 | D38305 | Tob | 1.6 | 1.4 | 1.6 | 2 | −1.2 | 1.2 | 2.7 | Receptor |
| 32 | D10923 | HM74. | 1 | 1 | 1 | 2.8 | 2.2 | 1.5 | 1.3 | Receptor |
| 33 | AF006041 | Fas-binding protein (DAXX) | −1.5 | −2.6 | −2.1 | 1.1 | 1 | −1.5 | 1.2 | Receptor |
| 34 | X52425 | IL-4-R interleukin 4 receptor. | 1.4 | 1.1 | −1 | −1.9 | −2.9 | −1.1 | 1.1 | Receptor |
| 35 | M12886 | T-cell receptor active β-chain | −1.7 | −1.7 | −1.7 | −1 | −1.3 | −2.7 | −1.2 | Receptor |
| 36 | L00352 | Low density lipoprotein receptor | 1.6 | 1.3 | 1 | −1.2 | −5.7 | −1.3 | −1.2 | Receptor |
| 37 | D50683 | TGF-βIIR α1 | 1.2 | −1.4 | −1.8 | 1.1 | −2.7 | −1.7 | −1.2 | Receptor |
| 38 | M58286 | Tumor necrosis factor recepto | −1.2 | −1.2 | −1.2 | −1.6 | −3.3 | −3.4 | −1.2 | Receptor |
| 39 | U05875 | pSK1 interferon gamma receptor accessory factor-1 (AF-1) | 1.3 | −1.1 | −1.3 | 1.3 | −3.3 | −2 | −1.3 | Receptor |
| 40 | X75342 | SHB | 1.1 | 1.1 | 1.3 | −1.5 | −1.5 | −2.5 | −1.9 | Receptor |
| 41 | M64347 | Novel growth factor receptor | 1.6 | 1.4 | 1.3 | 1.1 | −2.1 | −1.4 | −2.7 | Receptor |
| 42 | U28811 | Cysteine-rich fibroblast growth factor receptor (CFR-1) | −1 | −1.1 | −1.2 | −1 | −2 | −1.6 | −2.9 | Receptor |
| 43 | L24564 | Rad | 1 | 1 | 1 | 1 | 1 | 1 | 5.5 | Small, GTP binding |

TABLE 3-continued

Ultraviolet Radiation-Regulated Signal Transducers And Transcription Factors

| NO | Accession # | Gene and its description | 0.5 hr | 1 hr | 2 hr | 4 hr | 8 hr | 16 hr | 24 hr | Function |
|---|---|---|---|---|---|---|---|---|---|---|
| 44 | L20688 | GDP-dissociation inhibitor protein (Ly-GDI) | −1 | −1 | 1 | 1 | 1.6 | 3.8 | 3.9 | Small, GTP binding |
| 45 | L16862 | G protein-coupled receptor kinase (GRK6) | −1.4 | −2.8 | −1 | 1.1 | −1.2 | −1 | 1.5 | Small, GTP binding |
| 46 | M84332 | ADP-ribosylation factor | 1.3 | −1 | 1 | −1.1 | −2 | −2.6 | 1.4 | Small, GTP binding |
| 47 | D13988 | Rab GDI | −1.6 | −2.5 | −2.1 | −1.2 | −1 | −1.7 | −1.2 | Small, GTP binding |
| 48 | U68142 | RalGDS-like 2 (RGL2) | 2.4 | 2.2 | 2.6 | 1.3 | 1.1 | 1.1 | −1.4 | Small, GTP binding |
| 49 | X12953 | Rab2 YPT1-related member of ras family. | −1.4 | −2.2 | −1.6 | −1.6 | −2.5 | −2.3 | −1.4 | Small, GTP binding |
| 50 | X04828 | G(i) protein alpha-subunit (adenylate cyclase inhibiting) | 1.2 | 1 | 1.2 | −1 | −1 | 3.1 | −1.6 | Small, GTP binding |
| 51 | M13829 | Raf related protein (pks/a-raf) | 1 | 1 | 1 | −2.8 | −2.2 | 1 | −1.7 | Small, GTP binding |
| 52 | M57763 | ADP-ribosylation factor (hARF6) | −1.7 | −2 | −1.9 | −1 | −2.1 | −3.8 | −2.1 | Small, GTP binding |
| 53 | L38490 | ADP-ribosylation factor | 1.5 | 1.7 | 2.2 | −1.4 | −2 | −2.6 | −2.2 | Small, GTP binding |
| 54 | L48546 | Tuberin (TSC2) | −1.6 | −2.2 | −1.5 | 1 | 1.7 | 1.4 | −3 | Small, GTP binding |
| 55 | D42040 | KIAA9001 gene | 1.3 | 1.6 | 1.3 | −1 | 1.1 | 2.4 | 4.6 | Transcription Factor |
| 56 | X62083 | Drosophila female sterile homeotic (FSH) homolog. | 1.8 | 1.1 | 1 | 1.7 | −1.1 | 1.9 | 4 | Transcription Factor |
| 57 | X74874 | RNA pol II largest subunit | 1.7 | 1.4 | 1.5 | −1.2 | −1.3 | 1.7 | 3.7 | Transcription Factor |
| 58 | S78771 | NAT = CpG island-associated gene | 1.4 | 1.3 | 1.2 | 1.1 | −1 | 1.4 | 3.3 | Transcription Factor |
| 59 | X15729 | Nuclear p68 protein. | 1.6 | −1.1 | 1.2 | 1.1 | −1.5 | −1.1 | 2.6 | Transcription Factor |
| 60 | M79463 | PML-2 mRNA | 1.5 | 1.8 | 2.1 | −1 | −1 | 1.6 | 2.5 | Transcription Factor |
| 61 | U37690 | RNA polymerase II subunit (hsRPB10) | 1.6 | 1.3 | 1.3 | 1.2 | 1.1 | 4.7 | 2.3 | Transcription Factor |
| 62 | M62831 | Transcription factor ETR101 | 4.6 | 5.7 | 5.8 | 9.4 | −1.3 | 1 | 2 | Transcription Factor |
| 63 | X51345 | JunB | 1.5 | 2.1 | 2 | 2.7 | −2.4 | −1.3 | 2 | Transcription Factor |
| 64 | U20734 | JunB | 1.9 | 3.2 | 3.9 | 3 | −1.8 | −1.9 | 1.9 | Transcription Factor |
| 65 | D38251 | RPB5 (XAP4), | 2.2 | 1.4 | 1 | −1.1 | −1.1 | 2.6 | 1.7 | Transcription Factor |
| 66 | M69043 | MAD-3 encoding lkB-like activity. | 1.4 | 1.4 | 1.6 | 2.5 | −1.7 | 1.4 | 1.7 | Transcription Factor |
| 67 | D89667 | c-myc | 1.8 | 1.1 | 1.1 | 1.6 | 1.4 | 2.8 | 1.5 | Transcription Factor |
| 68 | J04611 | Lupus p70 (Ku) autoantigen | 1.8 | 1.2 | 1 | 1.7 | 1.2 | 2.5 | 1.4 | Transcription Factor |
| 69 | D15050 | Transcription factor AREB6 | −1.4 | −2 | −2 | −1.2 | −2.5 | −1.1 | 1.4 | Transcription Factor |
| 70 | U35048 | TSC-22 | 1.8 | 1.3 | 1.6 | 2.7 | −1.8 | −1.9 | 1.4 | Transcription Factor |
| 71 | M92843 | Zinc finger transcriptional regulator | 1.4 | 2.8 | 3.6 | 1.2 | −2.9 | −2.8 | 1.4 | Transcription Factor |
| 72 | U69126 | FUSE binding protein 2 (FBP2) | 1.6 | −0.02 | 1.6 | −1 | 1.7 | 2.5 | 1.2 | Transcription Factor |
| 73 | U07664 | HB9 homeobox gene | −1.8 | −2.5 | −1.6 | 1 | −1.2 | −2.8 | 1.2 | Transcription Factor |
| 74 | U13991 | TATA-binding protein associated factor 30 kD subunit (tafII30) | 2.9 | 1.18 | 2 | 1.6 | 1.4 | 1.7 | 1.1 | Transcription Factor |
| 75 | D86966 | KIAA0211 gene | −2.5 | −2.5 | −2.5 | −1 | 1.3 | −1.7 | 1 | Transcription Factor |
| 76 | X56681 | JunD | 2 | 3 | 4.6 | 3.2 | 2.9 | 1.2 | 1 | Transcription Factor |
| 77 | V01512 | c-fos | 2.3 | 3.2 | 2.8 | 1.2 | 1 | 1 | 1 | Transcription Factor |
| 78 | L13391 | Helix-loop-helix basic phosphoprotein (G0S8) | 1 | 1 | 1 | 3.2 | 1 | 1 | 1 | Transcription Factor |
| 79 | HG3494 | Nuclear Factor Nf-116 | 1.7 | 1.7 | 2 | 2.9 | −1.1 | −1.1 | 1 | Transcription Factor |
| 80 | L11672 | Kruppel related zinc finger protein (HTF10) | −1.4 | −1.3 | −1.5 | −1.7 | −1.6 | −2.5 | −1 | Transcription Factor |
| 81 | X78992 | ERF-2 | −1.2 | −1.2 | −1.7 | −1.3 | −3.9 | −3.3 | −1 | Transcription Factor |
| 82 | L19314 | HRY | 1.5 | 1.78 | 2.4 | 1.1 | −3.1 | −1.9 | −1.1 | Transcription Factor |
| 83 | L04731 | Translocation T(4:11) of ALL-1 gene to chromosome 4. | 3.2 | 3.1 | 3.8 | −1.2 | 1.1 | 1.5 | −1.2 | Transcription Factor |
| 84 | X89750 | TGIF | −1 | −1.3 | −1.4 | 1.5 | −2.5 | −3.8 | −1.2 | Transcription Factor |
| 85 | S74017 | Nrf2 = NF-E2-like basic leucine zipper transcriptional activator | 1.5 | 1.4 | 1.1 | −1.6 | −2.9 | −1.9 | −1.2 | Transcription Factor |
| 86 | U88629 | RNA polymerase II elongation factor ELL2, | −1.4 | −1.8 | −1.7 | −2.5 | −3.2 | −3.3 | −1.2 | Transcription Factor |
| 87 | J03161 | Serum response factor (SRF) | −1.6 | −2.7 | −2.6 | −1.3 | −2.3 | −1.3 | −1.2 | Transcription Factor |
| 88 | M58603 | NF-κB) | −1.2 | −1.3 | −1.2 | −1 | −1.5 | −2.9 | −1.3 | Transcription Factor |
| 89 | HG3523 | c-Myc | −1.2 | −1.9 | −1.4 | −3.9 | −5.8 | −3.4 | −1.3 | Transcription Factor |
| 90 | M91083 | DNA-binding protein (HRC1) | −1.4 | −1.3 | −1.7 | −1.3 | −2.6 | −1.8 | −1.4 | Transcription Factor |
| 91 | HG3342 | Id1 | 2 | 2.2 | 1.5 | 1.1 | −3.6 | −3 | −1.5 | Transcription Factor |
| 92 | U66616 | SWI/SNF complex 170 KD subunit (BAF170) | −3.1 | −2.1 | −1.6 | 1.7 | −1 | −1.3 | −1.7 | Transcription Factor |
| 93 | D14520 | GC-Box binding protein BTEB2, | −1.2 | −1.8 | −2.4 | −1.4 | −2.8 | −3.7 | −1.7 | Transcription Factor |

TABLE 3-continued

Ultraviolet Radiation-Regulated Signal Transducers And Transcription Factors

| | | Signaling molecules. | Fold regulation | | | | | | | |
|---|---|---|---|---|---|---|---|---|---|---|
| NO | Accession # | Gene and its description | 0.5 hr | 1 hr | 2 hr | 4 hr | 8 hr | 16 hr | 24 hr | Function |
| 94 | X52541 | Early growth response protein 1 (hEGR1). | 1.5 | 1.4 | 1 | 2.2 | −3.8 | −2.1 | −2.1 | Transcription Factor |
| 95 | M31627 | X box binding protein-1 (XBP-1) | −1.1 | −1.1 | 1 | 2.6 | 1.5 | −2.8 | −2.3 | Transcription Factor |
| 96 | M83667 | NF-IL6-β | 1.4 | 1.4 | 1.6 | 1.4 | −1.9 | −4.2 | −2.4 | Transcription Factor |
| 97 | D42123 | ESP1/CRP2 | 1.3 | 1 | 1.4 | 1.3 | 1.1 | 1.5 | −2.5 | Transcription Factor |
| 98 | M81601 | Transcription elongation factor (SII) | −1.1 | −1.3 | −1.4 | −1.1 | −1.7 | −3.3 | −2.8 | Transcription Factor |
| 99 | X52611 | AP-2. | −1.3 | −1.2 | −1.6 | −2.4 | −3.4 | −3.3 | −2.8 | Transcription Factor |
| 100 | M13929 | c-myc | −3.1 | −3 | −2.3 | −2.3 | −5 | −4.3 | −2.9 | Transcription Factor |
| 101 | L00058 | c-myc | 1.7 | 1.6 | 1.1 | −1.7 | −4.3 | −1.7 | −3 | Transcription Factor |
| 102 | L37127 | RNA polymerase II mRNA | 1 | 1 | 1 | 1.8 | −1.9 | 1.9 | −3.1 | Transcription Factor |
| 103 | D90209 | DNA binding protein TAXREB67. | 1.6 | 1.6 | 1.7 | 2.4 | 1.3 | −2.8 | −3.4 | Transcription Factor |
| 104 | M38258 | Retinoic acid receptor gamma | 1.3 | 1.2 | −1 | −1.7 | −1.3 | −1.3 | −3.6 | Transcription Factor |
| 105 | U00968 | SREBP-1 | 1.8 | 1.4 | 1.2 | −1.2 | −2.3 | −1.5 | −3.7 | Transcription Factor |
| 106 | X77366 | HBZ17 | 1.8 | 1.2 | −1.1 | −1 | −2.4 | −2.5 | −3.9 | Transcription Factor |
| 107 | J04102 | ets-2 | −1.8 | −1.8 | −1.8 | −1.7 | −2.2 | −5.5 | −4.1 | Transcription Factor |
| 108 | HG2724 | Oncogene Tls/Chop, | 1 | 1 | 1 | 5.1 | 1 | −3.4 | −4.2 | Transcription Factor |
| 109 | X69111 | HLH 1R21 helix-loop-helix protein. | 1.5 | 0.58 | 2 | 1.5 | −2.8 | −6 | −5.3 | Transcription Factor |
| 110 | M59465 | Tumor necrosis factor alpha inducible protein A20 | 1.2 | 1 | 1 | 1.1 | −1 | 1.4 | 5 | Zn finger |
| 111 | D85527 | LIM domain | −2.8 | −2.1 | −2.7 | −1.9 | −2.1 | −1.8 | 1 | Zn finger |
| 112 | U33821 | Tax1-binding protein TXBP151 | 1.4 | −1.1 | −1 | 1.2 | −1.6 | −3 | −1.7 | Zn finger | and

Table 4 presents a list of cytoskeletal and structural proteins that are ultraviolet radiation-regulated.

TABLE 4

Ultraviolet Radiation-Regulated Cytoskeletal and Structural Proteins

| | | Structural proteins. | Fold regulation | | | | | | | |
|---|---|---|---|---|---|---|---|---|---|---|
| No. | Accession | Gene and its description | 0.5 hr | 1 hr | 2 hr | 4 hr | 8 hr | 16 hr | 24 hr | Function |
| 1 | M20030 | Small proline rich protein (sprII). | 1.3 | 2.1 | 1.5 | 1.1 | 1.6 | 5.9 | 21.1 | differentiation |
| 2 | X53065 | Small proline rich protein SPRR2A | 1.1 | 1.3 | 1.3 | 1.5 | 1.7 | 2.9 | 21 | differentiation |
| 3 | M13903 | Involucrin | 1.2 | −1.2 | −2.3 | −1.1 | −1.1 | 5.8 | 13.5 | differentiation |
| 4 | L10343 | Elafin. | 1.2 | −1.1 | −1.1 | 1.5 | 1.2 | 3.4 | 10 | differentiation |
| 5 | M21302 | Small proline rich protein (sprII). | −1.1 | −1.1 | 1 | 2.4 | 3.5 | 3.3 | 7.6 | differentiation |
| 6 | L05188 | Small proline-rich protein 2 (SPRR2B). | −1 | 1 | 1.6 | 1.2 | 1.9 | 3.1 | 7.1 | differentiation |
| 7 | HG2815 | Myosin, Light Chain Smooth Muscle. | 1.1 | −1.1 | 1.1 | −1.1 | −1 | 9.9 | 6.6 | cytoskeletal |
| 8 | HG1612 | Macmarcks | 1.4 | 1.3 | 1.7 | 2.6 | 2.7 | 3.5 | 6.5 | cytoskeletal |
| 9 | X52426 | Keratin 13. | −1.1 | −1.1 | 1.2 | −1.1 | −1.2 | −1.5 | 6.2 | cytoskeletal |
| 10 | Z49989 | Smoothelin. | 1.5 | 1.2 | 1.1 | 1.2 | 1.9 | 1.8 | 4.9 | cytoskeletal |
| 11 | HG2815 | Myosin, Light Chain, Smooth Muscle. | 1.5 | 1 | 1.1 | −1 | −1.3 | 5.2 | 3.7 | cytoskeletal |
| 12 | HG2815 | Myosin, Light Chain, Smooth Muscle. | 1.1 | −1.2 | 1 | −1 | 1.1 | 2.5 | 3.7 | cytoskeletal |
| 13 | X99920 | X99920 S100 calcium-binding protein A13. | 1.9 | 1.7 | 1.6 | 1 | 1 | 4.3 | 3.6 | differentiation |
| 14 | HG4322 | Tubulin β | 2 | 1.9 | 1.7 | 2.7 | 3 | 3.4 | 3.6 | cytoskeletal |
| 15 | S54005 | Thymosin β-10. | 1.5 | 1 | 1.2 | 1.1 | −1 | 3 | 3.4 | cytoskeletal |
| 16 | X83416 | PrP prion protein. | 1.2 | 1.2 | 1.9 | −1.4 | −1.1 | 1.1 | 2.9 | structural |
| 17 | HG1980 | Tubulin, β 2 | 1 | 1.3 | 1.4 | 1 | 1.3 | 1.1 | 2.6 | cytoskeletal |
| 18 | HG2259 | Tubulin, α 1. | 2.2 | 1.3 | 1.9 | −1.2 | −1 | 6.4 | 2.5 | cytoskeletal |
| 19 | X57579 | Activin β-A subunit. | −1.7 | −1.5 | −2.1 | 1.2 | −1.7 | 1.8 | 2.5 | cytoskeletal |
| 20 | AF006084 | Arp2/3 protein complex subunit p41-Arc (ARC41). | 1.8 | 1.1 | −1.2 | 1.3 | 1.2 | 4 | 2.1 | cytoskeletal |

TABLE 4-continued

Ultraviolet Radiation-Regulated Cytoskeletal and Structural Proteins

| | | Structural proteins. | Fold regulation | | | | | | | |
|---|---|---|---|---|---|---|---|---|---|---|
| No. | Accession | Gene and its description | 0.5 hr | 1 hr | 2 hr | 4 hr | 8 hr | 16 hr | 24 hr | Function |
| 21 | Y00503 | Keratin 19. | 1.5 | 1.2 | 1.2 | −1 | −1.3 | 2.9 | 2.1 | cytoskeletal |
| 22 | M12125 | Fibroblast muscle-type tropomyosin. | 1.3 | 1 | 1.3 | 1.1 | 1.2 | 2.5 | 2 | cytoskeletal |
| 23 | X82693 | Desmoglein III, E48 antigen. | 1.3 | 1.3 | 1.1 | −1.4 | −2 | 3 | 1.4 | differentiation |
| 24 | M19309 | Slow skeletal muscle troponin T | 2.6 | 2 | 2 | 1.4 | 1.1 | 2.4 | 1.4 | cytoskeletal |
| 25 | X53416 | Filamin (ABP-280). | 1.6 | 1.5 | 1.5 | 1 | −1 | 2.7 | 1 | Cytoskeletal |
| 26 | X04412 | Plasma gelsolin. | 3 | 1.9 | 1.2 | 1 | −1.5 | 2 | −1.3 | cytoskeletal |
| 27 | M76482 | 130-kD pemphigus vulgaris antigen.. | −1 | −1.3 | −1.4 | −1.5 | −2.5 | −2.9 | −1.3 | cytoskeletal |
| 28 | M69181 | Nonmuscle myosin heavy chain-B (MYH10). | −1 | −1.1 | −1 | −2.6 | −1.1 | −1.3 | −1.8 | cytoskeletal |
| 29 | M96803 | β-spectrin (SPTBN1). | −1.7 | −2.6 | −2.2 | −1.5 | −1.5 | −2.3 | −1.9 | cytoskeletal |
| 30 | Z26317 | Desmoglein 2. | −1.4 | −1.3 | 1 | −1.3 | −2 | −2.5 | −2.1 | cytoskeletal |
| 31 | U37122 | Adducin γ subunit. | −1.3 | −2.5 | −1.5 | −1.1 | −2.7 | −1.3 | −2.3 | cytoskeletal |
| 32 | HG174 | Desmoplakin I | −1.8 | −2.9 | −3.8 | −2.6 | −4.1 | −2.6 | −2.4 | cytoskeletal |
| 33 | X53586 | Integrin α 6. | 1.8 | 1.4 | 1.4 | −1.4 | −2 | 1 | −2.7 | cytoskeletal |
| 34 | U83115 | Non-lens beta gamma-crystallin like protein (AIM1). | 1.1 | 1 | 1 | −1.2 | −1.7 | −1.1 | −3.3 | cytoskeletal |
| 35 | D31883r | KIAA0059 gene product, actin binding | 1.5 | 1.3 | 1 | −1.1 | −1.6 | −1.7 | −3.5 | cytoskeletal |
| 36 | M95787 | 22 kD smooth muscle transgelin (SM22). | 1.6 | 1 | 1 | −1.6 | −2.4 | 1.2 | −3.7 | cytoskeletal | and

Table 5 presents a list of secreted peptides that are ultraviolet radiation regulated.

TABLE 5

Ultraviolet Radiation-Regulated Secreted Peptides

| | | Growth factors, cytokines and chemokines. | Fold regulation | | | | | | |
|---|---|---|---|---|---|---|---|---|---|
| No | Accession | Gene and its description | 0.5 hr | 1 hr | 2 hr | 4 hr | 8 hr | 16 hr | 24 hr |
| 1 | M57731 | Gro-β | 1 | 1 | 2.1 | 19.6 | 8.7 | 1.9 | 3 |
| 2 | Y00787 | Interleukin-8 (IL-8) | 1 | 1 | 1 | 6.7 | 5.9 | 4 | 6.8 |
| 3 | X54489 | Melanocyte growth stimulatory activity (MGSA, Gro-α). | 1 | 1 | 1 | 3.9 | 5.7 | 2.7 | 4.4 |
| 4 | X53800 | Macrophage inflammatory protein-2β (MIP2β). | 1 | 1 | 1 | 3.4 | 3.8 | 1 | 2.7 |
| 6 | M60278 | Heparin-binding EGF-like growth factor (HB-EGF) | −1.2 | −1.2 | −1.2 | 1 | 2.3 | 3.2 | 4.2 |
| 8 | M63573 | Secreted cyclophilin-like protein (SCYLP) | 2.7 | 2.7 | 1.8 | 1 | 1.3 | 7.1 | 4.5 |
| 9 | L42379 | Bone-derived growth factor (BPGF-1) | 1.2 | 1.2 | −1.3 | 1 | 1 | 2.9 | 1.9 |
| 10 | J04456 | 14 kD lectin | 1.3 | 1.3 | 1 | 1.2 | 1 | 2.5 | 2.2 |
| 11 | M92934 | Connective tissue growth factor (CTGF) | 1 | 1 | 1 | 1 | 1 | 1.1 | 4.3 |
| 12 | AB000584 | TGF-β superfamily protein | 1 | 1 | 1 | 1 | 1 | 1.1 | 3.1 |
| 14 | M12529 | Apolipoprotein E | 1.7 | 1.7 | −1 | 1.7 | −1.1 | 2.9 | 1.2 |
| 16 | D14874 | Adrenomedullin precursor | 1.6 | 1.6 | 1.6 | −1 | −2.4 | −2.8 | −1.8 |
| 17 | M30703 | Amphiregulin (AR) | 1.2 | 1.2 | −1 | 1.6 | −3.8 | −2 | 1.7 |
| 7 | X94563 | dbi/acbp | −3.4 | −3.4 | −1.5 | 1.6 | 2 | −1 | 1.1 | and
Table 6 presents a list of mitochondrial proteins that are ultraviolet radiation-regulated.

TABLE 6

Ultraviolet Radiation-Regulated Mitochondrial Proteins

| | Mitochondrial proteins | Fold regulation | | | | | | |
|---|---|---|---|---|---|---|---|---|
| Accession | Gene and description | 0.5 hr | 1 hr | 2 hr | 4 hr | 8 hr | 16 hr | 24 hr |
| J04444 | Cytochrome c-1. | 4.3 | 2.9 | 1.6 | 1.6 | 1.3 | 1.7 | −3.6 |
| Z49254 | Mitochondrial ribosome L23 subunit-related. | 3.1 | 2.1 | 2.7 | 1.2 | 1.2 | 4.2 | 2.1 |
| U65579 | Mitochondrial NADH dehydrogenase-ubiquinone Fe—S protein 8, 23 kD subunit | 2.8 | 2 | 2 | 1.4 | 1 | 3 | −1 |
| M19961 | Cytochrome c oxidase subunit Vb (coxVb). | 2.6 | 1.7 | 1 | 1.2 | 1.3 | 3.1 | −1 |
| M21186 | Neutrophil cytochrome b light chain. | 2 | 1.6 | 1.2 | 1.3 | 1.3 | 4.5 | 2.6 |
| Z14244 | CoxVIIb mRNA for cytochrome c oxidase subunit VIIb. | 1.9 | 1.2 | 1.7 | 1.5 | −1.6 | 4.1 | 4.2 |
| M26730 | Mitochondrial ubiquinone-binding protein (QP) gene, exon 4. | 1.8 | 1.7 | 2 | −1 | 1.2 | 2.8 | 1.8 |
| X15822 | COX VIIa-L mRNA for liver-specific cytochrome c oxidase (EC 1.9.3.1.). | 1.8 | 1.4 | 1.9 | 1.1 | 1 | 2.6 | 1.8 |
| U09813 | Mitochondrial ATP synthase subunit 9 | 1.5 | 1 | 1.1 | 1 | −1.2 | 2.6 | 1.3 |
| X05409). | Mitochondrial aldehyde dehydrogenase I ALDH I (EC 1.2.1.3). | 1.4 | 1.2 | 1 | 1.2 | −1.3 | −1.3 | −2.8 |
| Y07604 | Nucleoside-diphosphate kinase. | 1.2 | 1.3 | 1.4 | 1.1 | 1.6 | 2.3 | 2.1 |
| X80695 | cytochrome oxidase assembly protein OXA1Hs | 1.2 | 1.2 | 1.4 | −1.4 | −1 | −1 | −4.1 |
| X71129 | Electron transter flavoprotein beta subunit. | 1.2 | 1.1 | −1.5 | 1.9 | −1.4 | 2.9 | 1.2 |
| J03824 | Uroporphyrinogen III synthase | 1.1 | 1 | 1.2 | 2.5 | 1.1 | 1.5 | 1 |
| X89267 | Uroporphyrinogen decarboxylase | −1.8 | −2.7 | −1.6 | 1.3 | 1.7 | −1.2 | −1 |
| HG3492 | Thermogenic uncoupling protein Ucp | −1.8 | −2.7 | −1.8 | −1.5 | −1.3 | −1.1 | −2.6 |
| X59434 | Rhodanese. | −3 | −2.6 | −2.7 | −1.1 | −1.2 | −1 | −1.9 |

TABLE 7

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | #### | comment |
|---|---|---|---|---|---|---|---|---|---|---|---|---|---|
| | | | | | | First Response Gene Set | | | | | | | |
| 4.6 | 5.7 | 5.8 | 16.1 | 9.4 | -1 | 8.1 | 1 | 2 | 3 | M62831_at M62831 Human transcription factor ETR101 mRNA, complete cds. | TF | 27.2 | Immediate early |
| 2.3 | 4.9 | 6.6 | 13.8 | 6.2 | -2 | 4.6 | -1 | 1 | 0 | X68277_at X68277 H. sapiens CL 100 mRNA for protein tyrosine phosphatase. | signaling | 18.4 | |
| 3.2 | 3.1 | 3.8 | 10.1 | -1.2 | 1.1 | -0.1 | 1.5 | -1 | 0.3 | L04731_at L04731 H. sapiens translocation T(4;11) of ALL-1 gene to chromosome 4. | signaling | 10.3 | Tritorax-like |
| 2 | 3 | 4.6 | 9.6 | 3.2 | 2.9 | 6.1 | 1.2 | 1 | 2.2 | X56681_s_at X56681 Human junD mRNA. | TF | 17.9 | Immediate early |
| 1.9 | 3.2 | 3.9 | 9 | 3 | -2 | 1.2 | -2 | 1.9 | 0 | U20734_s_at U20734 Human transcription factor junB (junB) gene, 5' region and complete cds. | TF | 10.2 | Immediate early |
| 3.5 | 3.1 | 1.8 | 8.4 | 1.3 | -1 | 0.2 | -1 | -2 | -3 | L38951_at L38951 H. sapiens importin beta subunit mRNA, complete cds. | RNA processing | 5.6 | |
| 4.5 | 2.8 | 1 | 8.3 | -2.6 | -1 | -3.9 | 2.5 | -1 | 1.3 | D87071_at D87071 Human mRNA for KIAA0233 gene, complete cds. | ??? | 5.7 | No homology with anything, large prot. |
| 1.6 | 2.8 | 3.5 | 7.9 | 4.7 | 3.9 | 8.6 | 1.7 | 4 | 5.7 | M72885_rna1_s_at M72885 Human GOS2 gene, 5' flank and cds. | Cell cycle | 22.2 | |
| 1.4 | 2.8 | 3.6 | 7.8 | 1.2 | -3 | -1.7 | -3 | 1.4 | -1.4 | M92843_s_at M92843 H. sapiens zinc finger transcriptional regulator mRNA, complete cds. | TF | 4.7 | |
| 2.2 | 2.6 | 2.5 | 7.3 | 15 | 1.6 | 16.9 | 3.6 | 5.9 | 9.5 | S81914_at S81914 IEX-1 = radiation-inducible immediate-early gene [human, placenta, mRNA Partial, 1 | Apoptosis | 33.7 | Apoptosis inhibitor, NFkB-regulated |
| 1.7 | 2.8 | 2.7 | 7.2 | -1.3 | -3 | -4.1 | -2 | 1.4 | -0.4 | U72649_at U72649 Human BTG2 (BTG2) mRNA, complete cds. | Cell cycle | 2.7 | antiproliferative p53-dependent |
| 2 | 2.8 | 2.2 | 7 | 1.1 | -1 | 0.1 | 1.5 | 1.8 | 3.3 | D86988_at D86988 Human mRNA for KIAA0221 gene, complete cds. | RNA processing | 10.4 | mRNA decay trans-acting factor!! |
| 1.6 | 2.3 | 3.1 | 7 | 3.3 | 3.4 | 6.7 | 5.1 | 4.6 | 9.7 | L19779_at L19779 H. sapiens histone H2A.2 mRNA, complete cds. | Cell cycle | 23.4 | |
| 3.1 | 2.1 | 1.7 | 6.9 | 1 | -1 | -0.2 | 1.4 | 1 | 2.4 | U62317_rna3_at U62317 Chromosome 22q13 BAC Clone CIT987SK-384D8 complete sequence. | ??? | 9.1 | Choline phosphorylase-like |
| 3 | 1.9 | 1.2 | 6.1 | 1 | -2 | -0.5 | 2 | -1 | 0.7 | X04412_at X04412 Human mRNA for plasma gelsolin. | cytoskel. | 6.3 | |
| 2.5 | 1.7 | 1.7 | 5.9 | 1.5 | -1 | 0.3 | 2.2 | 1.2 | 3.4 | L27706_at L27706 Human chaperonin protein (Tcp2O) gene complete cds. | Chaperone | 9.6 | |
| 1.2 | 1.8 | 2.7 | 5.7 | 2.8 | -1 | 1.4 | 1 | 2.3 | 3.3 | X61123_at X61123 Human BTG1 mRNA. | GF/cyt | 10.4 | |
| 1.6 | 1.5 | 2.6 | 5.7 | 3.1 | 1.6 | 4.7 | 1.5 | 2.5 | 4 | M60974_s_at M60974 Human growth arrest and DNA-damage-inducible protein (gadd45) mRNA, complete cds | DNA rep. | 14.4 | |
| 2.5 | 1.6 | 1.5 | 5.6 | 1.1 | -1 | 0.1 | 1.9 | 1 | 2.9 | L19437_at L19437 Human transaldolase mRNA containing transposable element, complete cds. | DNA rep. | 8.6 | glucolysis, pentose phosphate |
| 1 | 1 | 3.1 | 5.1 | 3.1 | 4.4 | 7.5 | 5.9 | 4.8 | 10.7 | X57985_rna2_at X57985 H. sapiens genes for histones H2B.1 and H2A. | Cell cycle | 23.3 | |
| 2.5 | -1 | -1 | 0.5 | 1.7 | -1 | 0.3 | -2 | -1 | -2.7 | D90086_at D90086 Human pyruvate dehydrogenase (EC 1.2.4.1) beta subunit gene, exons 1-10. | Energy | -1.9 | |

TABLE 7-continued

Ultraviolet Radiation-Regulated First, Second And Third Response Gene Sets

| 0.5 hr | 1 hr | 2 hr | #### | 4 hr | 8 hr | #### | 16 hr | 24 hr | #### | Description | Function | #### | comment |
|---|---|---|---|---|---|---|---|---|---|---|---|---|---|
| −1.2 | −3 | −1 | −5 | 1.2 | −1 | 0.2 | −2 | −1 | −2.6 | M34182_at M34182 Human testis-specific protein kinase gamma-subunit mRNA, complete cds. | signaling | −7.4 | |
| −1.4 | −3 | −1 | −5.2 | 1.1 | −1 | −0.1 | −1 | 1.5 | 0.5 | L16862_at L16862 H. sapiens G protein-coupled receptor kinase (GRK6) mRNA, complete cds. | signaling | −4.8 | |
| −2.6 | −2 | −1 | −5.3 | −1.2 | −1 | −2.2 | −1 | 1 | −0.3 | D13705_s_at D13705 Human mRNA for fatty acids omega-hydroxylase (cytochrome P-450HKV), complete cds | detox | −7.8 | |
| −1.3 | −2 | −2 | −5.3 | −1.1 | −3 | −3.8 | −1 | −2 | −3.6 | U37122_at U37122 Human adducin gamma subunit mRNA, complete cds. | cytoskel. | −12.7 | |
| −1.4 | −1 | −3 | −5.4 | −1.1 | −1 | −2.4 | −2 | −2 | −3.9 | D45906_at D45906 H. sapiens mRNA for LIMK-2, complete cds. | signaling | −11.7 | |
| −1.8 | −3 | −2 | −5.9 | 1 | −1 | −0.2 | −3 | 1.2 | −1.6 | U07664_at U07664 Human HB9 homeobox gene, exons 2 and 3 and complete cds. | TF | −7.7 | |
| −1.4 | −2 | −3 | −6 | −1 | −2 | −2.6 | −2 | −2 | −4 | D87438_at D87438 Human mRNA for KIAA0251 gene, partial cds. | ??? | −12.6 | |
| −1.3 | −2 | −2 | −6 | −1 | −2 | −3.3 | −2 | −1 | −3.3 | L37042_at L37042 H. sapiens casein kinase I alpha isoform (CSNK1A1) mRNA, complete cds. | signaling | −12.6 | |
| −1.1 | −2 | −2 | −6 | 1.3 | −2 | −0.2 | −2 | −2 | −3.4 | D14043_at D14043 Human mRNA for MGC-24, complete cds. | ??? | −9.6 | agglutinin binding |
| −1.6 | −3 | −2 | −6.2 | −1.2 | −2 | −2.2 | −2 | −2 | −2.9 | D13988_at D13988 Human rab GDI mRNA, complete cds. | signaling | −11.3 | |
| −1.8 | −3 | −2 | −6.3 | −1.5 | −1 | −2.8 | −1 | −3 | −3.7 | HG3492-HT3686_at U28480 Uncoupling Protein Ucp | Mit. | −12.8 | thermogenic |
| −1.5 | −2 | −3 | −6.4 | −1.6 | −3 | −4.4 | −2 | 6.8 | 4.8 | D50840_at D50840 H. sapiens mRNA for ceramide glucosyltransferase, complete cds. | signaling | −6 | |
| −1.5 | −2 | −3 | −6.4 | −1.4 | −2 | −3 | −1 | −1 | −3.6 | M55265_at M55265 Human casein kinase II alpha subunit mRNA, complete cds. | signaling | −13 | |
| −1.7 | −3 | −2 | −6.5 | −1.5 | −1 | −3 | −1 | −2 | −4.2 | M96803_at M96803 Human general beta-spectrin (SPTBN1) mRNA, complete cds. | cytoskel. | −13.7 | |
| −2.2 | −2 | −2 | −6.6 | −2.6 | −1 | −3.7 | −2 | −1 | −1.3 | U89336_cds4_at U89336 Human HLA class III region containing NOTCH4 gene, partial sequence, homeobox PB | integral membrane protein | −11.6 | |
| −1.8 | −3 | −2 | −6.9 | −1.1 | −1 | −2.2 | −1 | −1 | −2.5 | D87442_at D87442 Human mRNA for KIAA0253 gene, partial cds. | ??? | −11.6 | No homology with anything, large prot. |
| −1.6 | −3 | −3 | −6.9 | −1.3 | −2 | −3.6 | −1 | −1 | −2.5 | J03161_at J03161 Human serum response factor (SRF) mRNA, complete cds. | signaling | −13 | |
| −2.6 | −3 | −2 | −7 | −1.2 | −2 | −2.3 | −3 | −2 | −5.3 | D86965_at D86965 Human mRNA for KIAA0210 gene, complete cds. | signaling | −14.6 | |
| −2.8 | −3 | −3 | −7.2 | −1 | −1 | −2.4 | −2 | 1 | −0.5 | U17327_at U17327 Human neuronal nitric oxide synthase (NOS1) mRNA, complete cds. | NO | −10.1 | |
| −2.5 | −3 | −3 | −7.5 | −1 | 1.3 | 0.3 | −2 | 1 | −0.7 | D86966_at D86966 Human mRNA for KIAA0211 gene, complete cds. | TF | −7.9 | ZFY |
| −2.8 | −2 | −3 | −7.6 | −1.9 | −2 | −4 | −2 | 1 | −0.8 | D85527_at D85527 H. sapiens mRNA for LIM domain, partial cds. | signaling | −12.4 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| −2.2 | −3 | −3 | −8 | −2.6 | −3 | −5.5 | −5 | −3 | −8 | U42031_at U42031 Human 54 kD progesterone receptor-associated immunophilin FKBP54 mRNA, partial | signaling | −21.5 | |
| −3 | −3 | −3 | −8.3 | −1.1 | −1 | −2.3 | −1 | −2 | −2.9 | X59434_at X59434 Human rohu mRNA for rhodanese. | Mit. | −13.5 | |
| −3.1 | −3 | −2 | −8.4 | −2.3 | −5 | −7.3 | −4 | −3 | −7.2 | M13929_s_at M13929 Human c-myc-P64 mRNA, initiating from promoter P0, (HLmyc2.5) partial cds. | TF | −22.9 | |
| −1.8 | −3 | −4 | −8.5 | −2.6 | −4 | −6.7 | −3 | −2 | −5 | HG174-HT174_at J05211 Desmoplakin I Second Response Gene Set | cytoskel. | −20.2 | |
| 1 | 1.2 | 2.1 | 4.3 | 20 | 8.7 | 28.3 | 1.9 | 3 | 4.9 | M57731_s_at M57731 Human gro-beta mRNA, complete cds. | GF/cyt | 37.5 | |
| 2.2 | 2.6 | 2.5 | 7.3 | 15 | 1.6 | 16.9 | 3.6 | 5.9 | 9.5 | S81914_at S81914 IEX-1 = radiation-inducible immediate-early gene [human, placenta, mRNA Partial, 1 | Apoptosis | 33.7 | Apoptosis inhibitor, NFkB-regulated |
| 1 | 1 | 1 | 3 | 6.7 | 5.9 | 12.6 | 4 | 6.8 | 10.8 | Y00787_s_at Y00787 Human mRNA for MDNCF (monocyte-derived neutrophil chemotactic factor). | GF/cyt | 26.4 | |
| 1 | 1 | 1 | 3 | 3.9 | 5.7 | 9.6 | 2.7 | 4.4 | 7.1 | X54489_rna1_at X54489 Human gene for melanoma growth stimulatory activity (MGSA). | GF/cyt | 19.7 | |
| 1.6 | 2.8 | 3.5 | 7.9 | 4.7 | 3.9 | 8.6 | 1.7 | 4 | 5.7 | M72885_ma1_s_at M72885 Human GOS2 gene, 5' flank and cds. | Cell cycle | 22.2 | |
| 4.6 | 5.7 | 5.8 | 16.1 | 9.4 | −1 | 8.1 | 1 | 2 | 3 | M62831_at M62831 Human transcription factor ETR101 mRNA, complete cds. | TF | 27.2 | Immediate early |
| 1 | 1 | 1 | 3 | 4 | 3.7 | 7.7 | 2.4 | 3.1 | 5.5 | M28130_ma1_s_at M28130 Human interleukin 8 (IL8) gene, complete cds. | GF/cyt | 16.2 | |
| 1 | 1 | 3.1 | 5.1 | 3.1 | 4.4 | 7.5 | 5.9 | 4.8 | 10.7 | X57985_rna2_at X57985 H. sapiens genes for histones H2B.1 and H2A. | Cell cycle | 23.3 | |
| 1 | 1 | 1 | 3 | 3.4 | 3.8 | 7.2 | 1 | 2.7 | 3.7 | X53800_s_at X53800 Human mRNA for macrophage inflammatory protein-2beta (MIP2beta). | GF/cyt | 13.9 | |
| 1.6 | 2.3 | 3.1 | 7 | 3.3 | 3.4 | 6.7 | 5.1 | 4.6 | 9.7 | L19779_at L19779 H. sapiens histone H2A.2 mRNA, complete cds. | Cell cycle | 23.4 | |
| 1.3 | 1.5 | 1.5 | 4.3 | 3.9 | 2.7 | 6.6 | 3.5 | 3.7 | 7.2 | AF001294_at AF001294 H. sapiens IPL (IPL) mRNA, complete cds. | Apoptosis | 18.1 | imprinted, possibly in apoptosis, PH dom. |
| 2 | 3 | 4.6 | 9.6 | 3.2 | 2.9 | 6.1 | 1.2 | 1 | 2.2 | X56681_s_at X56681 Human JunD mRNA. | TF | 17.9 | Immediate early |
| 1 | 1 | 1 | 3 | 5.1 | 1 | 6.1 | −3 | −4 | −7.6 | HG2724-HT2820_at S75762 Oncogene Tls/Chop, Fusion Activated | signaling | 1.5 | |
| 1 | 1.3 | −1 | 1.3 | 1.2 | 4.8 | 6 | 1 | 1.3 | 2.3 | M84739_at M84739 Human autoantigen calreticulin mRNA, complete cds. | ER/vesicles/lysosome | 9.6 | Ca binding protein, ER |
| −1.1 | −1.1 | 1 | −1.2 | 2.4 | 3.5 | 5.9 | 3.3 | 7.6 | 10.9 | M21302_at M21302 Human small proline rich protein (sprII) mRNA, clone 174N. | differentiation | 15.6 | |
| 2 | 1.9 | 1.7 | 5.6 | 2.7 | 3 | 5.7 | 3.4 | 3.6 | 7 | HG4322-HT4592_at V00599 Tubulin, Beta | cytoskel. | 18.3 | |
| 1.4 | 1.3 | 1.7 | 4.4 | 2.6 | 2.7 | 5.3 | 3.5 | 6.5 | 10 | HG1612-HT1612_at X70326 Macmarcks | cytoskel. | 19.7 | |
| 1 | 1 | 1 | 3 | 2.8 | 2.2 | 5 | 1.5 | 1.3 | 2.8 | D10923_at D10923 Human mRNA for HM74. | signaling | 10.8 | |
| 1.5 | 1.4 | 1.3 | 4.2 | 2.6 | 2.3 | 4.9 | 1.6 | 1.4 | 3 | D64142_at D64142 Human mRNA for histone H1x, complete cds. | Cell cycle | 12.1 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| -1.2 | 1 | 1.2 | 1 | 2 | 2.8 | 4.8 | 3.7 | 2.1 | 5.8 | D86974_at D86974 Human mRNA for KIAA0220 gene, partial cds. | ??? | 11.6 | |
| 1.6 | 1.5 | 2.6 | 5.7 | 3.1 | 1.6 | 4.7 | 1.5 | 2.5 | 4 | M60974_s_at M60974 Human growth arrest and DNA-damage-inducible protein (gadd45) mRNA, complete cds | DNA rep. | 14.4 | |
| 2.3 | 4.9 | 6.6 | 13.8 | 6.2 | -2 | 4.6 | -1 | 1 | 0 | X68277_at X68277 H. sapiens CL 100 mRNA for protein tyrosine phosphatase. | Signaling | 18.4 | |
| 1 | 1 | 1 | 3 | 3.2 | 1 | 4.2 | 1 | 1 | 2 | L13391_at L13391 Human helix-loop-helix basic phosphoprotein (G0S8) gene, complete cds. | TF | 9.2 | |
| -1.1 | -1.1 | 1 | -1.2 | 2.6 | 1.5 | 4.1 | -3 | -2 | -5.1 | M31627_at M31627 Human X box binding protein-1 (XBP-1) mRNA, complete cds. | TF | -2.2 | |
| 1.9 | 1.7 | 1.8 | 5.4 | 2.5 | 1.3 | 3.8 | 2.3 | 2 | 4.3 | U40369_rna1_at U40369 Human spermidine/spermine N1-acetyltransferase (SSAT) gene, complete cds. | DNA rep. | 13.5 | |
| 1.7 | 1.7 | 2 | 5.4 | 2.9 | -1 | 1.8 | -1 | 1 | -0.1 | HG3494-HT3688_at X52560 Nuclear Factor Nf-116 | TF | 7.1 | |
| 1.2 | 1.8 | 2.7 | 5.7 | 2.8 | -1 | 1.4 | 1 | 2.3 | 3.3 | X61123_at X61123 Human BTG1 mRNA. | GF/cyt | 10.4 | |
| 1.9 | 3.2 | 3.9 | 9 | 3 | -2 | 1.2 | -2 | 1.9 | 0 | U20734_s_at U20734 Human transcription factor junB (junB) gene, 5' region and complete cds. | TF | 10.2 | Immediate early |
| 1.8 | 1.3 | 1.6 | 4.7 | 2.7 | -2 | 0.9 | -2 | 1.4 | -0.5 | U35048_at U35048 Human TSC-22 protein mRNA, complete cds. | TF | 5.1 | |
| 1.4 | 1.4 | 1.6 | 4.4 | 2.5 | -2 | 0.8 | 1.4 | 1.7 | 3.1 | M69043_at M69043 H. sapiens MAD-3 mRNA encoding IkB-like activity, complete cds. | TF | 8.3 | |
| 1.5 | 2.1 | 2 | 5.6 | 2.7 | -2 | 0.3 | -1 | 2 | 0.7 | X51345_at X51345 Human jun-B mRNA for JUN-B protein. | TF | 6.6 | Immediate early |
| -1.1 | -1 | -1 | -3.5 | 1.6 | -3 | -0.9 | 1.8 | 1 | 2.8 | S68616_at S68616 Na+/H+ exchanger NHE-1 isoform [human, heart, mRNA, 4516 nt]. | Integral membrane protein | -1.6 | integral membrane protein |
| -1 | -1.3 | -1 | -3.7 | 1.5 | -3 | -1 | -4 | -1 | -5 | X89750_at X89750 H. sapiens mRNA for TGIF protein. | TF | -9.7 | homeobox |
| 1.5 | 0.6 | 2 | 4.08 | 1.5 | -3 | -1.3 | -6 | -5 | -11.3 | X69111_at X69111 H. sapiens HLH 1R21 mRNA for helix-loop-helix protein. | TF | -8.52 | |
| 1.1 | -1.3 | -2 | -1.7 | 1.1 | -3 | -1.4 | -2 | -3 | -4.8 | U14603_at U14603 Human protein-tyrosine phosphatase (HU-PP-1) mRNA, partial sequence. | Signaling | -7.9 | |
| 1.5 | 1.4 | 1 | 3.9 | 2.2 | -4 | -1.6 | -2 | -2 | -4.2 | X52541_at X52541 Human mRNA for early growth response protein 1 (hEGR1). | Signaling | -1.9 | GAP |
| 1.2 | -1.4 | -2 | -2 | 1.1 | -3 | -1.6 | -3 | -1 | -2.9 | D50683_at D50683 H. sapiens mRNA for TGF-betaIIR alpha, complete cds. | Signaling | -6.5 | |
| 1.4 | 2.8 | 3.6 | 7.8 | 1.2 | -3 | -1.7 | -3 | 1.4 | -1.4 | M92843_s_at M92843 H. sapiens zinc finger transcriptional regulator mRNA, complete cds. | TF | 4.7 | |
| -1 | -1 | -1 | -3 | 1 | -3 | -1.9 | -3 | -1 | -3.5 | X91247_at X91247 H. sapiens mRNA for thioredoxin reductase. | Detox | -8.4 | |
| 1.3 | -1.1 | -1 | -1.1 | 1.3 | -3 | -2 | -2 | -1 | -3.3 | U05875_at U05875 Human clone pSK1 interferon gamma receptor accessory factor-1 (AF-1) mRNA, compl | Signaling | -6.4 | IFN-inducibl |

TABLE 7-continued

Ultraviolet Radiation-Regulated First, Second And Third Response Gene Sets

| 0.5 hr | 1 hr | 2 hr | #### | 4 hr | 8 hr | #### | 16 hr | 24 hr | #### | Description | Function | #### | comment |
|---|---|---|---|---|---|---|---|---|---|---|---|---|---|
| 1.5 | 1.8 | 2.4 | 5.68 | 1.1 | -3 | -2 | -2 | -1 | -3 | L19314_at L19314 Human HRY gene, complete cds. | TF | 0.68 | |
| 1.2 | -1.3 | -1 | -1.1 | 1.6 | -4 | -2.2 | -2 | 1.7 | -0.3 | M30703_s_at M30703 Human amphiregulin (AR) gene, exon 6, clones lambda-ARH(6,12). | GF/cyt | -3.6 | |
| 1.6 | 1.5 | 1.5 | 4.6 | 1.5 | -4 | -2.3 | 1 | -2 | -0.7 | U34252_at U34252 Human gamma-aminobutyraldehyde dehydrogenase mRNA, complete cds. | Energy | 1.6 | aldehyde dehydrog. detox |
| 2 | 2.2 | 1.5 | 5.7 | 1.1 | -4 | -2.5 | -3 | -2 | -4.5 | HG3342-HT3519_s_at S78825 Id1 | TF | -1.3 | |
| -1 | -1 | -1 | -1 | 1 | -4 | -3.2 | -3 | -2 | -5 | D85429_at D85429 H. sapiens gene for heat shock protein 40, complete cds. | Signaling | -9.2 | |
| 1.6 | 1 | 1 | 3.6 | -1 | -3 | -3.6 | -1 | 1.2 | 0.2 | U41766_s_at U41766 Human metalloprotease/disintegrin/cysteine-rich protein precursor (MDC9) mRNA, c | Protease | 0.2 | |
| -2.2 | -2.2 | -2 | -6.6 | -2.6 | -1 | -3.7 | -2 | 1 | -1.3 | U89336_cd4_at U89336 Human HLA class III region containing NOTCH4 gene, partial sequence, homeobox PB | Integral membrane protein | -11.6 | |
| -1 | -1.1 | -1 | -3.1 | -2.6 | -1 | -3.7 | -1 | -2 | -3.1 | M69181_at M69181 Human nonmuscle myosin heavy chain-B (MYH10) mRNA, partial cds. | Cytoskel. | -9.9 | |
| -1.4 | -2 | -2 | -5.4 | -1.2 | -3 | -3.7 | -1 | 1.4 | 0.3 | D15050_at D15050 Human mRNA for transcription factor AREB6, complete cds. | TF | -8.8 | |
| 1.7 | 1 | 1.1 | 3.8 | -1.2 | -3 | -3.7 | 1 | 1.2 | 2.2 | U28386_at U28386 Human nuclear localization sequence receptor hSRP1alpha mRNA, complete cds. | Nucler transport | 2.3 | |
| 1.3 | 1 | 1 | 1.3 | -1.2 | -3 | -3.8 | -2 | -3 | -4.9 | L77886_at L77886 Human protein tyrosine phosphatase mRNA, complete cds. | Signaling | -7.4 | |
| 1.2 | -1 | -1 | -0.9 | -1.1 | -3 | -3.8 | 1.2 | -1 | 0.2 | X64330_at X64330 H. sapiens mRNA for ATP-citrate lyase. | Lipid metabolism | -4.5 | lipid synthesis |
| -1.3 | -2.5 | -2 | -5.3 | -1.1 | -3 | -3.8 | -1 | -2 | -3.6 | U37122_at U37122 Human adducin gamma subunit mRNA, complete cds. | Cytoskel. | -12.7 | |
| 1.3 | 1.2 | 1.1 | 3.6 | -1.1 | -3 | -3.9 | -2 | 1 | -1.3 | X74008_at X74008 H. sapiens mRNA for protein phosphatase 1 gamma. | Signaling | -1.6 | |
| 1.1 | -1 | 1 | 1.1 | -1.1 | -3 | -3.9 | 1.2 | -2 | -0.7 | U60205_at U60205 Human methyl sterol oxidase (ERG25) mRNA, complete cds. | Lipid metabolism | -3.5 | lipid metabolism |
| 1 | 1 | 1 | 3 | -1 | -3 | -3.9 | -2 | -5 | -6.4 | X76534_at X76534 H. sapiens NMB mRNA. | Integral membrane protein | -7.3 | antimetastatic transmembrane glycoprot. |
| 4.5 | 2.8 | 1 | 8.3 | -2.6 | -1 | -3.9 | 2.5 | -1 | 1.3 | D87071_at D87071 Human mRNA for KIAA0233 gene, complete cds. | ??? | 5.7 | No homology with anything, large prot. |
| 1.3 | 1 | 1 | 3.3 | -1.3 | -3 | -3.9 | -1 | -1 | -2.7 | U90716_at U90716 Human cell surface protein HCAR mRNA, complete cds. | Cell surface/ Adhesion | -3.3 | virus receptors |
| -1.4 | -1.3 | -2 | -4.4 | -1.3 | -3 | -3.9 | -2 | -1 | -3.2 | M91083_at M91083 Human DNA-binding protein (HRC1) mRNA, complete cds. | TF | -11.5 | |
| -1.6 | -2 | -2 | -5.7 | -1.3 | -3 | -3.9 | -2 | -2 | -3.5 | U29607_at U29607 Human methionine aminopeptidase mRNA, complete cds. | Translation | -13.1 | Inhibitor |
| -1 | -1.3 | -1 | -3.7 | -1.5 | -3 | -4 | -3 | -1 | -4.2 | M76482_at M76482 Human 130-kD pemphigus vulgaris antigen mRNA, complete cds. | Cytoskel. | -11.9 | |
| -1 | -1.3 | -2 | -3.9 | -1.2 | -3 | -4 | -5 | -3 | -7.7 | U72066_at U72066 H. sapiens CBP interacting protein CtIP (CtIP) mRNA, complete cds. | Signaling | -15.6 | Rb-binding |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.3 | 1.3 | 1.2 | 3.8 | -1.2 | -3 | -4 | -2 | -4 | -5.2 | K03195_at K03195 Human (HepG2) glucose transporter gene mRNA, complete cds. | Energy | -5.4 | |
| -1.4 | -2.2 | -2 | -5.2 | -1.6 | -3 | -4.1 | -2 | -1 | -3.7 | X12953_at X12953 Human rab2 mRNA, YPT1-related and member of ras family. | Signaling | -13 | |
| 1.2 | -1.6 | -1 | -1.5 | -1.4 | -3 | -4.1 | -2 | 1.2 | -0.7 | M60483_rna1_s_at M60483 Human protein phosphatase 2A catalytic subunit-alpha gene, complete cds. | Signaling | -6.3 | |
| 1.7 | 2.8 | 2.7 | 7.2 | -1.3 | -3 | -4.1 | -2 | 1.4 | -0.4 | U72649_at U72649 Human BTG2 (BTG2) mRNA, complete cds. | Cell cycle | 2.7 | antiproliferative p53-dependent |
| -1.2 | -1.8 | -2 | -5.4 | -1.4 | -3 | -4.2 | -4 | -2 | -5.4 | D14520_at D14520 Human mRNA for GC-Box binding protein BTEB2, complete cds. | TF | -15 | |
| 1.3 | -1 | -1 | -0.9 | -1.7 | -3 | -4.3 | 1.8 | 5.9 | 7.7 | L08069_at L08069 Human heat shock protein, E. coli DnaJ homolog mRNA, complete cds. | DNA rep. | 2.5 | |
| -1.5 | -2 | -3 | -6.4 | -1.6 | -3 | -4.4 | -2 | 6.8 | 4.8 | D50840_at D50840 H. sapiens mRNA for ceramide glucosyltransferase, complete cds. | Signaling | -6 | |
| -1.4 | -1.9 | -2 | -5.5 | -1.4 | -3 | -4.4 | -2 | -3 | -4.7 | L31801_at L31801 H. sapiens monocarboxylate transporter 1 (SLC16A1) mRNA, complete cds. | Transporter | -14.6 | Lactate and pyruvate |
| 1.5 | 1.4 | 1.1 | 4 | -1.6 | -3 | -4.5 | -2 | -1 | -3.1 | S74017_at S74017 Nrf2 = NF-E2-like basic leucine zipper transcriptional activator [human, hemin-ind | TF | -3.6 | |
| 1.7 | 1 | 1 | 3.7 | -1.3 | -3 | -4.5 | -2 | 1 | -0.8 | X87241_at X87241 H. sapiens mRNA for hFat protein. | Cell surface/ adhesion | -1.6 | |
| 1.4 | 1.1 | -1 | 1.5 | -1.9 | -3 | -4.8 | -1 | 1.1 | 0 | X52425_at X52425 Human IL-4-R mRNA for the interleukin 4 receptor. | Signaling | -3.3 | |
| -1.1 | -1.8 | -2 | -5 | -1.6 | -3 | -4.8 | -2 | -2 | -4 | D79994_at D79994 Human mRNA for KIAA0172 gene, partial cds. | ??? | -13.8 | ankyrin-related |
| -1.2 | -1.2 | -1 | -3.6 | -1.6 | -3 | -4.9 | -3 | -1 | -4.6 | M58286_s_at M58286 H. sapiens tumor necrosis factor receptor mRNA, complete cds. | Signaling | -13.1 | |
| 1 | 1 | 1 | 3 | -2.8 | -2 | -5 | 1 | -2 | -0.7 | M13829_s_at M13829 Human putative raf related protein (pks/a-raf) mRNA, partial cds. | Signaling | -2.7 | |
| -1.2 -2.2 | -1.2 -2.8 | -2 -3 | -4.1 -8 | -1.3 -2.6 | -4 -3 | -5.2 -5.5 | -3 -5 | -1 -3 | -4.3 -8 | X78992_at X78992 H. sapiens ERF-2 mRNA. U42031_at U42031 Human 54 kD progesterone receptor-associated immunophilin FKBP54 mRNA, partial | TF Signaling | -13.6 -21.5 | |
| -1.4 | -1.8 | -2 | -4.9 | -2.5 | -3 | -5.7 | -3 | -1 | -4.5 | U88629_at U88629 Human RNA polymerase II elongation factor ELL2, complete cds. | TF | -15.1 | |
| -1.3 | -1.2 | -2 | -4.1 | -2.4 | -3 | -5.8 | -3 | -3 | -6.1 | X52611_s_at X52611 Human mRNA for transcription factor AP-2. | TF | -16 | |
| 1.3 | -1 | -2 | -1.7 | -2.7 | -3 | -5.9 | 1 | 1.2 | 2.2 | U28749_at U28749 Human high-mobility group phosphoprotein isoform I-C (HMGIC) mRNA, complete cds. | DNA rep. | -5.4 | |
| 1.7 | 1.6 | 1.1 | 4.4 | -1.7 | -4 | -6 | -2 | -3 | -4.7 | L00058_at L00058 Human (GH) germline c-myc proto-oncogene, exon 3 and 3' flank. | TF | -6.3 | |
| 1.9 | 1.7 | 1.3 | 4.9 | -1.3 | -5 | -6.1 | -1 | 2.1 | 0.8 | HG2855-HT2995_at L26336 Heat Shock Protein, 70 KD (Gb: Y00371) | signaling | -0.4 | |
| 1.6 | 1.2 | -1 | 1.5 | -1.5 | -5 | -6.4 | -2 | -1 | -3.5 | L08246_at L08246 Human myeloid cell differentiation protein (MCL1) mRNA. | Apoptosis | -8.4 | Bcl2-like |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.2 | 1.2 | 1.4 | 3.8 | −1.5 | −5 | −6.4 | −4 | −3 | −6.9 | S73591_at S73591 brain-expressed HHCPA78 homolog [human, HL-60 acute promyelocytic leukemia cells | detox | −9.5 | Thioredoxin interacting |
| −1.8 | −2.9 | −4 | −8.5 | −2.6 | −4 | −6.7 | −3 | −2 | −5 | HG174-HT174_at J05211 Desmoplakin I | cytoskel. | −20.2 | |
| 1.6 | 1.3 | 1 | 3.9 | −1.2 | −6 | −6.9 | −1 | −1 | −2.5 | L00352_at L00352 Human low density lipoprotein receptor gene, exon 18. | signaling | −5.5 | |
| −1.5 | −1.6 | −2 | −4.6 | −3.1 | −4 | −7.1 | −2 | −2 | −3.9 | HG3930-HT4200_at Y13647 Stearoyl-Coenzymea Desaturase | lipid metabolism | −15.6 | lipogenic |
| 2.2 | 1.4 | 1.5 | 5.1 | −2.4 | −5 | −7.1 | −1 | 3.2 | 1.9 | X77794_at X77794 H. sapiens mRNA for cyclin G1. | Cell cycle | −0.1 | |
| −1.3 | −1.8 | −2 | −5.5 | −1.7 | −5 | −7.1 | −6 | −3 | −9.4 | M90656_at M90656 Human gamma-glutamylcysteine synthetase (gCS) mRNA, complete cds. | detox | −22 | glutathione biosynthesis |
| −3.1 | −3 | −2 | −8.4 | −2.3 | −5 | −7.3 | −4 | −3 | −7.2 | M13929_s_at M13929 Human c-myc-P64 mRNA, initiating from promoter P0, (HLmyc2.5) partial cds. | TF | −22.9 | |
| 1 | −1.3 | −1 | −1.5 | −2 | −6 | −8.3 | −3 | −1 | −4.6 | D78129_at D78129 H. sapiens mRNA for squalene epoxidase, partial cds. | lipid metabolism | −14.4 | lipogenic, cholesterol synth. |
| 1.7 | 1.4 | 1.1 | 4.2 | −2.2 | −7 | −9.1 | −3 | −2 | −5.5 | X80692_at X80692 H. sapiens ERK3 mRNA. | signaling | −10.4 | |
| −1.2 | −1.9 | −1 | −4.5 | −3.9 | −6 | −9.7 | −3 | −1 | −4.7 | HG3523-HT4899_s_at J00120 Proto-Oncogene C-Myc, Alt. Splice 3, Orf 114 | TF | −18.9 | |

Third Response Gene Set

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.3 | 2.1 | 1.5 | 4.9 | 1.1 | 1.6 | 2.7 | 5.9 | 21 | 27 | M20030_f_at M20030 Human small proline rich protein (spr1) mRNA, clone 930. | differentiation | 34.6 | |
| 1.1 | 1.3 | 1.3 | 3.7 | 1.5 | 1.7 | 3.2 | 2.9 | 21 | 23.9 | X53065_f_at X53065 | differentiation | 30.8 | |
| 1.2 | −1.2 | −2 | −2.3 | −1.1 | −1 | −2.2 | 5.8 | 14 | 19.3 | M13903_at M13903 Human involucrin gene, exon 2. | differentiation | 14.8 | |
| 1.1 | −1.1 | 1.1 | 1.1 | −1.1 | −1 | −2.1 | 9.9 | 6.6 | 16.5 | HG2815-HT2931_at M22918 Myosin, Light Chain, Alkali, Smooth Muscle (Gb: U02629), Non-Muscle, Alt. Splice | cytoskel. | 15.5 | |
| 1.2 | −1.1 | 1 | −1 | 1.5 | 1.2 | 2.7 | 3.4 | 10 | 13.4 | L10343_at L10343 Huma elafin gene, complete cds. | differentiation | 15.1 | |
| 2.7 | 2 | 1.8 | 6.5 | 1 | 1.3 | 2.3 | 7.1 | 4.5 | 11.6 | M63573_at M63573 Human secreted cyclophilin-like protein (SCYLP) mRNA, complete cds. | GF/cyt | 20.4 | |
| −1.1 | −1.1 | 1 | −1.2 | 2.4 | 3.5 | 5.9 | 3.3 | 7.6 | 10.9 | M21302_at M21302 Human small proline rich protein (sprII) mRNA, clone 174N. | differentiation | 15.6 | |
| 1 | 1 | 1 | 3 | 6.7 | 5.9 | 12.6 | 4 | 6.8 | 10.8 | Y00787_s_at Y00787 Human mRNA for MDNCF (monocyte-derived neutrophil chemotactic factor). | GF/cyt | 26.4 | |
| 1 | 1 | 3.1 | 5.1 | 3.1 | 4.4 | 7.5 | 5.9 | 4.8 | 10.7 | X57985_rna2_at X57985 H. sapiens genes for histones H2B.1 and H2A. | Cell cycle | 23.3 | |
| −1 | 1 | 1.6 | 1.6 | 1.2 | 1.9 | 3.1 | 3.1 | 7.1 | 10.2 | L05188_f_at L05188 H. sapiens small proline-rich protein 2 (SPRR2B) gene, complete cds. | differentiation | 14.9 | |
| 1.4 | 1.3 | 1.7 | 4.4 | 2.6 | 2.7 | 5.3 | 3.5 | 6.5 | 10 | HG1612-HT1612_at X70326 Macmarcks | cytoskel. | 19.7 | |
| 3.1 | 2 | 1.7 | 6.8 | 1.7 | 1.2 | 2.9 | 6.1 | 3.9 | 10 | X67325_at X67325 H. sapiens p27 mRNA. | IFN-inducible | 19.7 | |
| 1.6 | 2.3 | 3.1 | 7 | 3.3 | 3.4 | 6.7 | 5.1 | 4.6 | 9.7 | L19779_at L19779 H. sapiens histone H2A.2 mRNA, complete cds. | Cell cycle | 23.4 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 2.2 | 2.6 | 2.5 | 7.3 | 15 | 1.6 | 16.9 | 3.6 | 5.9 | 9.5 | S81914_at S81914 IEX-1 = radiation-inducible immediate-early gene [human, placenta, mRNA Partial, 1 | Apoptosis | 33.7 | Apoptosis inhibitor, NFkB-regulated |
| 2.1 | 1.3 | 1.2 | 4.6 | 1.5 | 1.5 | 3 | 6.5 | 3 | 9.5 | D45248_at D45248 Human mRNA for proteasome activator hPA28 subunit beta, complete cds. | IFN-inducible | 17.1 | |
| 2.6 | 2.4 | 2.4 | 7.4 | 1.1 | 1.1 | 2.2 | 7.5 | 2 | 9.5 | Z22548_at Z22548 H. sapiens thiol-specific antioxidant protein mRNA. | detox | 19.1 | |
| 1.5 | 1 | 1.1 | 3.6 | -1 | 1 | -2.3 | 5.2 | 3.7 | 8.9 | HG2815-HT2931_s_at M22918 Myosin, Light Chain, Alkali, Smooth Muscle (Gb: U02629), Non-Muscle, Alt. Splice | cytoskel. | 10.2 | |
| 2.2 | 1.3 | 1.9 | 5.4 | -1.2 | -1 | -2.2 | 6.4 | 2.5 | 8.9 | HG2259-HT2348_s_at X06956 Tubulin, Alpha 1, Isoform 44 | cytoskel. | 12.1 | |
| -2.1 | -1.1 | -1 | -4.3 | -1.2 | 1.5 | 0.3 | 4.9 | 3.7 | 8.6 | V00594_at V00594 Human mRNA for metallothionein from cadmium-treated cells. | detox | 4.6 | |
| -1.2 | -1.2 | -1 | -3.6 | 2 | 1.7 | 3.7 | 2.5 | 5.9 | 8.4 | M80254_at M80254 H. sapiens cyclophilin isoform (hCyP3) mRNA, complete cds. | ??? | 8.5 | prolyl isomerase |
| 1 | 1 | 1 | 3 | 1.5 | 2.4 | 3.9 | 4.5 | 3.9 | 8.4 | U04636_rna1_at U04636 Human cyclooxygenase-2 (hCox-2) gene, complete cds. | signaling | 15.3 | |
| 1.9 | 1.2 | 1.7 | 4.8 | 1.5 | -2 | -0.1 | 4.1 | 4.2 | 8.3 | Z14244_at Z14244 H. sapiens coxVIIb mRNA for cytochrome c oxidase subunit VIIb | Mit. | 13 | |
| 1.9 | 1.7 | 1.6 | 5.2 | 1 | 1 | 2 | 4.3 | 3.6 | 7.9 | X99920_at X99920 H. sapiens mRNA for S100 calcium-binding protein A13. | differentiation | 15.1 | |
| 1 | 1 | 1 | 3 | 1.3 | 1.4 | 2.7 | 2 | 5.8 | 7.8 | U62800_at U62800 Human cystatin M (CST6) mRNA, complete cds. | protease inhibitor | 13.5 | protease inhibitor |
| 1.3 | -1 | -1 | -0.9 | -1.7 | -3 | -4.3 | 1.8 | 5.9 | 7.7 | L08069_at L08069 Human heat shock protein, E. coli DnaJ homolog mRNA, complete cds. | DNA rep. | 2.5 | |
| -1 | -1 | 1.4 | -1 | 1 | 1.6 | 2.6 | 3.8 | 3.9 | 7.7 | L20688_at L20688 Human GDP-dissociation inhibitor protein (Ly-GDI) mRNA, complete cds. | signaling | 9.3 | |
| 1.4 | 1.3 | 1.4 | 4.1 | 1.4 | 1.5 | 2.9 | 5.1 | 2.6 | 7.7 | M13755_at M13755 Human interferon-induced 17-kD/15-kB protein mRNA, complete cds. | IFN-inducible | 14.7 | |
| -1.2 | -1.2 | -1 | -3.6 | 1 | 2.3 | 3.3 | 3.2 | 4.2 | 7.4 | M60278_at M60278 Human heparin-binding EGF-like growth factor mRNA, complete cds. | GF/cyt | 7.1 | |
| 1.3 | 1.5 | 1.5 | 4.3 | 3.9 | 2.7 | 6.6 | 3.5 | 3.7 | 7.2 | AF001294_at AF001294 H. sapiens IPL (IPL) mRNA, complete cds. | Apoptosis | 18.1 | imprinted, possibly in apoptosis, PH dom. |
| 1 | 1 | 1 | 3 | 3.9 | 5.7 | 9.6 | 2.7 | 4.4 | 7.1 | X54489_rna1_at X54489 Human gene for melanoma growth stimulatory activity (MGSA). | GF/cyt | 19.7 | |
| 2 | 1.6 | 1.2 | 4.8 | 1.3 | 1.3 | 2.6 | 4.5 | 2.6 | 7.1 | M21186_at M21186 Human neutrophil cytochrome b light chain p22 phagocyte b-cytochrome mRNA, compl | Mit. | 14.5 | |
| 1.3 | 1.6 | 1.3 | 4.2 | -1 | 1.1 | 0.1 | 2.4 | 4.6 | 7 | D42040_s_at D42040 Human mRNA for KIAA9001 gene, complete cds. | signaling | 11.3 | RING3 domain |
| 2 | 1.9 | 1.7 | 5.6 | 2.7 | 3 | 5.7 | 3.4 | 3.6 | 7 | HG4322-HT4592_at V00599 Tubulin, Beta | cytoskel. | 18.3 | |
| 1.6 | 1.3 | 1.3 | 4.2 | 1.2 | 1.1 | 2.3 | 4.7 | 2.3 | 7 | U37690_at U37690 Human RNA polymerase II subunit (hsRPB10) mRNA, complete cds. | TF | 13.5 | |

TABLE 7-continued

Ultraviolet Radiation-Regulated First, Second And Third Response Gene Sets

| 0.5 hr | 1 hr | 2 hr | #### | 4 hr | 8 hr | #### | 16 hr | 24 hr | #### | Description | Function | #### | comment |
|---|---|---|---|---|---|---|---|---|---|---|---|---|---|
| 2.3 | 1.4 | 1.2 | 4.9 | 1.5 | -1 | 0.5 | 3.3 | 3.6 | 6.9 | M21005_at M21005 Human migration inhibitory factor-related protein 8 (MRP8) gene, complete cds. | GF/cyt | 12.3 | |
| 1.2 | -1 | 1.1 | 1.3 | 1.4 | 1.2 | 2.6 | 3.4 | 3.4 | 6.8 | M37583_at M37583 Human histone (H2A.Z) mRNA, complete cds. | Cell cycle | 10.7 | |
| 1.5 | 1.2 | 1.1 | 3.8 | 1.2 | 1.9 | 3.1 | 1.8 | 4.9 | 6.7 | Z49989_at Z49989 H. sapiens mRNA for smoothelin. | cytoskel. | 13.6 | actin binding |
| 1 | 1 | 1 | 3 | 1 | 1 | 2 | 1 | 5.5 | 6.5 | L24564_at L24564 Human Rad mRNA, complete cds. | signaling | 11.5 | |
| 1.6 | 1.2 | 1.3 | 4.1 | -1 | 1 | 0 | 3.2 | 3.3 | 6.5 | D49824_s_at D49824 Human HLA-B null allele mRNA. | integral membrane protein | 10.6 | |
| 1.2 | 1 | 1 | 3.2 | 1.1 | -1 | 0.1 | 1.4 | 5 | 6.4 | M59465_at M59465 Human tumor necrosis factor alpha inducible protein A20 mRNA, complete cds. | signaling | 9.7 | |
| 1.5 | 1 | 1.2 | 3.7 | 1.1 | -1 | 0.1 | 3 | 3.4 | 6.4 | S54005_s_at S54005 thymosin beta-10 [human, metastatic melanoma cell line, mRNA, 453 nt]. | cytoskel. | 10.2 | inhibition of actin polym. |
| 3.1 | 2.1 | 2.7 | 7.9 | 1.2 | 1.2 | 2.4 | 4.2 | 2.1 | 6.3 | Z49254_at Z49254 H. sapiens L23-related mRNA. | Mit. | 16.6 | |
| 1.1 | -1.2 | 1 | 0.9 | -1 | 1.1 | 0.1 | 2.5 | 3.7 | 6.2 | HG2815-HT4023_s_at M22919 Myosin, Light Chain, Alkali, Smooth Muscle (Gb: U02629), Smooth Muscle, Alt. Spli | cytoskel. | 7.2 | |
| 1.3 | 1.3 | 1.3 | 3.9 | 1 | 1.4 | 2.4 | 4.1 | 2.1 | 6.2 | U70660_at U70660 Human copper transport protein HAH1 (HAH1) mRNA, complete cds. | detox | 12.5 | Antioxidant defense |
| 1.8 | 1.1 | -1 | 1.7 | 1.3 | 1.2 | 2.5 | 4 | 2.1 | 6.1 | AF006084_at AF006084 H. sapiens Arp2/3 protein complex subunit p41-Arc (ARC41) mRNA, complete cds. | cytoskel. | 10.3 | |
| 1.8 | 1.1 | 1 | 3.9 | 1.7 | -1 | 0.6 | 1.9 | 4 | 5.9 | X62083_s_at X62083 H. sapiens mRNA for Drosophila female sterile homeotic (FSH) homolog. | signaling | 10.4 | |
| -1.2 | 1 | 1.2 | 1 | 2 | 2.8 | 4.8 | 3.7 | 2.1 | 5.8 | D86974_at D86974 Human mRNA for KIAA0220 gene, partial cds. | ??? | 11.6 | |
| 1.6 | 2.8 | 3.5 | 7.9 | 4.7 | 3.9 | 8.6 | 1.7 | 4 | 5.7 | M72885_rna1_s_at M72885 Human GOS2 gene, 5' flank and cds. | Cell cycle | 22.2 | |
| 1.2 | 1.1 | 1 | 3.3 | 1 | -1 | 0 | 3 | 2.7 | 5.7 | S80437_s_at S80437 fatty acid synthase (3' region) [human, breast and HepG2 cells, mRNA Partial, 22 | lipid metabolism | 9 | lipid synthesis |
| 2.1 | 1.4 | 1.3 | 4.8 | 1.2 | 1.1 | 0.1 | 3.2 | 2.5 | 5.7 | X04654_s_at X04654 Human mRNA for U1 RNA-associated 70K protein. | RNA processing | 10.6 | RNA binding |
| 1.8 | 1.5 | 1.4 | 4.7 | 1.1 | -1 | 0.1 | 1.7 | 3.9 | 5.6 | M26311_s_at M26311 Human cystic fibrosis antigen mRNA, complete cds. | signaling | 10.4 | protein kinase inhibitor |
| 1.4 | 1.7 | 2 | 5.1 | 2 | 1.7 | 3.7 | 2.5 | 3.1 | 5.6 | X14850_s_at X14850 Human H2A.X mRNA encoding histone H2A.X. | Cell cycle | 14.4 | |
| 1.7 | 1.3 | 1.5 | 4.5 | -1.2 | 1.1 | -0.1 | 3 | 2.6 | 5.6 | M14328_s_at M14328 Human alpha enolase mRNA, complete cds. | Energy | 10 | energy recruitment, ATP synth. |
| 1.1 | -1.5 | -1 | -1.7 | -1.3 | -1 | -2.4 | 1.9 | 3.6 | 5.5 | U07919_at U07919 Human aldehyde dehydrogenase 6 mRNA, complete cds. | detox | 1.4 | |
| 1 | 1 | 1 | 3 | 4 | 3.7 | 7.7 | 2.4 | 3.1 | 5.5 | M28130_rna1_s_at M28130 Human interleukin 8 (IL8) gene, complete cds. | GF/cyt | 16.2 | |
| 5.2 | 2.4 | 4.7 | 12.3 | 2 | 1.6 | 3.6 | 3.6 | 1.9 | 5.5 | Z21507_at Z21507 H. sapiens EF-1delta gene encoding human elongation factor-1-delta | Translation | 21.4 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1 | 1 | 1 | 3 | 1 | 1 | 2 | 1.1 | 4.3 | 5.4 | M92934_at M92934 Human connective tissue growth factor, complete cds. | GF/cyt | 10.4 | |
| −1 | −1.3 | −2 | −3.9 | 1.2 | −2 | −1.2 | 1.5 | 3.9 | 5.4 | M27436_s_at M27436 Human tissue factor gene, complete cds, with a Alu repetitive sequence in the 3′ | integral membrane protein | 0.3 | interacts with the serine protease |
| 1.7 | 1.4 | 1.5 | 4.6 | −1.2 | −1 | −2.5 | 1.7 | 3.7 | 5.4 | X74874_rna1_s_at X74874 H. sapiens gene for RNA pol II largest subunit, exon 1. | TF | 7.5 | |
| 1.1 | −1.1 | −1 | −1 | −1.3 | −1 | −2.3 | 2.6 | 2.8 | 5.4 | X57351_at X57351 Human 1-8D gene from interferon-inducible gene family. | IFN-inducible | 2.1 | |
| 1.6 | 1.2 | 1.2 | 4 | 1 | −1 | −0.2 | 2.6 | 2.7 | 5.3 | X52979_rna1_s_at X52979 Human gene for small nuclear ribonucleoproteins SmB and SmB′. | RNA processing | 9.1 | |
| 1.4 | 1.1 | 1.3 | 3.8 | 1.3 | 1.2 | 2.5 | 3.9 | 1.4 | 5.3 | U41515_at U41515 Human deleted in split hand/split foot 1 (DSS1) mRNA, complete cds. | ??? | 11.6 | |
| 1 | 1 | 1 | 3 | 1.6 | 2 | 3.6 | 2.5 | 2.6 | 5.1 | D28235_s_at D28235 Human PTGS2 gene for prostaglandin endoperoxide synthase-2, complete cds. | signaling | 11.7 | |
| 1.5 | 1.2 | 1.2 | 3.9 | −1 | −1 | −2.3 | 2.9 | 2.1 | 5 | Y00503_at Y00503 Human mRNA for keratin 19. | cytoskel. | 6.6 | |
| 1 | 1.2 | 2.1 | 4.3 | 20 | 8.7 | 28.3 | 1.9 | 3 | 4.9 | M57731_s_at M57731 Human gro-beta mRNA, complete cds. | GF/cyt | 37.5 | |
| −1.5 | −2 | −3 | −6.4 | −1.6 | −3 | −4.4 | −2 | 6.8 | 4.8 | D50840_at D50840 H. sapiens mRNA for ceramide glucosyltransferase, complete cds. | signaling | −6 | |
| 1 | −1 | −1 | −1.2 | 1 | 1.1 | 2.1 | 1.7 | 3.1 | 4.8 | U52101_at U52101 Human YMP mRNA, complete cds. | integral membrane protein | 5.7 | membrane glycoprotein |
| 1.7 | 1.6 | 1.8 | 5.1 | −1.1 | 1 | −0.1 | 2.9 | 1.9 | 4.8 | D13413_rna1_s_at D13413 Human mRNA for tumor-associated 120 kD nuclear protein p120, partial cds(carbox | RNA processing | 9.8 | |
| 1.2 | −1.1 | −1 | −1.2 | 1 | 1 | 2 | 2.9 | 1.9 | 4.8 | L42379_at L42379 H. sapiens bone-derived growth factor (BPGF-1) mRNA, complete cds. | GF/cyt | 5.6 | |
| −1.1 | −1.1 | 1.2 | −1 | −1.1 | −1 | −2.3 | −2 | 6.2 | 4.7 | X52426_s_at X52426 H. sapiens mRNA for cytokeratin 13. | cytoskel. | 1.4 | |
| 1.3 | 1.1 | 1 | 3.4 | 1.2 | 1 | 2.2 | 2.5 | 2.2 | 4.7 | J04456_at J04456 Human 14 kD lectin mRNA, complete cds. | GF/cyt | 10.3 | |
| 1.4 | 1.3 | 1.2 | 3.9 | 1.1 | −1 | 0.1 | 1.4 | 3.3 | 4.7 | S78771_s_at S78771 NAT = CpG island-associated gene [human, mRNA, 1741 nt]. | signaling | 8.7 | |
| 1.8 | 1.7 | 2 | 5.5 | −1 | 1.2 | 0.2 | 2.8 | 1.8 | 4.6 | M26730_s_at M26730 Human mitochondrial ubiquinone-binding protein (QP) gene, exon 4. | Mit. | 10.3 | |
| 2 | 1.4 | 1 | 4.4 | −1 | 1.1 | 0.1 | 3 | 1.6 | 4.6 | U26727_at U26727 Human p16INK4/MTS1 mRNA, complete cds. | Cell cycle | 9.1 | Tumor suppressor, Cdk4/6 interacting |
| 1.4 | −1.9 | −2 | −2.3 | −1 | −1 | −2.1 | 3.2 | 1.4 | 4.6 | X92896_at X92896 H. sapiens mRNA for ITBA2 protein. | ??? | 0.2 | |
| 1.3 | 1.4 | 1.4 | 4.1 | 1 | 1 | 2 | 1.8 | 2.7 | 4.5 | Z69043_s_at Z69043 H. sapiens mRNA transloconassociated protein delta subunit precursor. | ER/vesicles/lysosome | 10.6 | ER, transloconassociated protein |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.8 | 1.7 | 1.5 | 5 | −1.2 | −1 | −2.6 | 2 | 2.5 | 4.5 | L76568_xpt3_f_at L76568 H. sapiens excision and cross link repair protein (ERCC4) gene, complete genom | DNA rep. | 6.9 | |
| 1.3 | 1 | 1.3 | 3.6 | 1.1 | 1.2 | 2.3 | 2.5 | 2 | 4.5 | M12125_at M12125 Human fibroblast muscle-type tropomyosin mRNA, complete cds. | cytoskel. | 10.4 | |
| 1 | −1.2 | 1.1 | 0.9 | −1.1 | 1 | −0.1 | 1.2 | 3.2 | 4.4 | U09937_rna1_s_at U09937 Human urokinase-type plasminogen receptor, exon 7. | signaling | 5.2 | |
| 1.8 | 1.4 | 1.9 | 5.1 | 1.1 | 1 | 2.1 | 2.6 | 1.8 | 4.4 | X15822_at X15822 Human COX VIIa-L mRNA for liver-specific cytochrome c oxidase (EC 1.9.3.1). | Mit. | 11.6 | |
| 1 | 1 | 1.1 | 3.1 | 1 | 2.1 | 3.1 | 2.8 | 1.6 | 4.4 | M34516_at M34516 Human omega light chain protein 14.1 (Ig lambda chain related) gene, exon 3. | Cell surface/adhesion | 10.6 | |
| 1.1 | 1.4 | 1.1 | 3.6 | 2 | 2 | 4 | 2.9 | 1.5 | 4.4 | U53830_at U53830 H. sapiens interferon regulatory factor 7A mRNA, complete cds. | IFN-inducible | 12 | |
| 1.3 | 1.3 | 1.1 | 3.7 | −1.4 | −2 | −3.4 | 3 | 1.4 | 4.4 | X82693_at X82693 H. sapiens mRNA for E48 antigen | differentiation | 4.7 | Desmoglein III, PV target |
| 1.4 | 1.5 | 1.5 | 4.4 | −1.1 | −1 | −2.1 | 3.2 | 1.1 | 4.3 | M58026_at M58026 Human NB-1 mRNA, complete cds. | ??? | 6.6 | calmodulin-like |
| 1 | 1 | 1 | 3 | 1.4 | −2 | −0.6 | 1 | 3.3 | 4.3 | M90657_at M90657 Human tumor antigen (L6) mRNA, complete cds. | Cell surface/adhesion | 6.7 | Glucoproteins, cell surface |
| −1.7 | −1.5 | −2 | −5.3 | 1.2 | −2 | −0.5 | 1.8 | 2.5 | 4.3 | X57579_s_at X57579 H. sapiens activin beta-A subunit (exon 2). | cytoskel. | −1.5 | |
| 2.2 | 1.4 | 1 | 4.6 | −1.1 | −1 | −2.2 | 2.6 | 1.7 | 4.3 | D38251_at D38251 Human mRNA for RPB5 (XAP4), complete cds. | TF | 6.7 | |
| 1.8 | 1.1 | 1.1 | 4 | 1.6 | 1.4 | 3 | 2.8 | 1.5 | 4.3 | D89667_at D89667 H. sapiens mRNA for c-myc binding protein, complete cds. | signaling | 11.3 | |
| 1 | 1 | 1 | 3 | 1 | 1 | 2 | 1.1 | 3.1 | 4.2 | AB000584_at AB000584 H. sapiens mRNA for TGF-beta superfamily protein, complete cds. | GF/cyt | 9.2 | |
| 2.4 | 1.4 | 1.3 | 5.1 | 1.5 | 1.1 | 2.6 | 2.6 | 1.6 | 4.2 | L76200_at L76200 Human guanylate kinase (GUK1) mRNA, complete cds. | DNA rep. | 11.9 | |
| 1.2 | 1 | 1 | 3.2 | 1.5 | 1.2 | 2.7 | 3.1 | 1.1 | 4.2 | J04794_at J04794 Human aldehyde reductase mRNA, complete cds. | detox | 10.1 | |
| 1.4 | 1.1 | 1.1 | 3.6 | 1.4 | −1 | 0.2 | 1.3 | 2.8 | 4.1 | X52882_at X52882 Human t-complex polypeptide 1 gene. | Cell surface/adhesion | 7.9 | |
| 1.5 | 1.8 | 2.1 | 5.4 | −1 | 1 | −2 | 1.6 | 2.5 | 4.1 | M79463_s_at M79463 Human PML-2 mRNA, complete cds. | TF | 7.5 | |
| 1 | −1.1 | −1 | −1.2 | 1.7 | 2 | 3.7 | 1.6 | 2.5 | 4.1 | Y09022_at Y09022 H. sapiens mRNA for Not56-like protein. | ER/vesicles/lysosome | 6.6 | tenuous function!! |
| 1.7 | 1.3 | −1 | 2 | 1.7 | −1 | 0.6 | 2.9 | 1.2 | 4.1 | M12529_at M12529 Human apolipoprotein E mRNA, complete cds. | GF/cyt | 6.7 | |
| 1.2 | 1.1 | −2 | 0.8 | 1.9 | −1 | 0.5 | 2.9 | 1.2 | 4.1 | X71129_at X71129 H. sapiens mRNA for electron transfer flavoprotein beta subunit. | Mit. | 5.4 | |
| 1.2 | 1.2 | 1.9 | 4.3 | −1.4 | 1 | −2.5 | 1.1 | 2.9 | 4 | X83416_s_at X83416 H. sapiens PrP gene, exon 2. | cytoskel. | 5.8 | prion protein |
| −1 | −2.6 | −1 | −4.7 | 1.4 | 2 | 3.4 | 1.4 | 2.6 | 4 | D89052_at D89052 H. sapiens mRNA for proton-ATPase-like protein, complete cds. | Energy | 2.7 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.6 | 1.5 | 2.6 | 5.7 | 3.1 | 1.6 | 4.7 | 1.5 | 2.5 | 4 | M60974_s_at M60974 Human growth arrest and DNA-damage-inducible protein (gadd45) mRNA, complete cds | DNA rep. | 14.4 | |
| 1 | 1 | 1 | 3 | 1 | 1 | 2 | 3 | 1 | 4 | M16364_s_at M16364 Human creatine kinase-B mRNA, complete cds. | Energy | 9 | energy recruitment, ATP synth. |
| 1.6 | 1.4 | 1.6 | 4.6 | 2 | -1 | 0.8 | 1.2 | 2.7 | 3.9 | D38305_at D38305 Human mRNA for Tob, complete cds. | signaling | 9.3 | |
| 1.4 | 1.5 | 1.3 | 4.2 | 1 | -1 | 0 | 1.2 | 2.7 | 3.9 | HG2917-HT3061_f_at X87679 Major Histocompatibility Complex, Class I, E (Gb: M21533) | Cell surface/adhesion | 8.1 | |
| 1.4 | 1.3 | 1.4 | 4.1 | -1.1 | -1 | -2.2 | 1.2 | 2.7 | 3.9 | Z29505_at Z29505 H. sapiens mRNA for nucleic acid binding protein sub2.3 | RNA processing | 5.8 | |
| 1.1 | 1 | -1 | 1 | 1.2 | 1.1 | 2.3 | 1.3 | 2.6 | 3.9 | K02574_at K02574 | ??? | 7.2 | |
| 1.5 | 1 | 1.1 | 3.6 | 1 | -1 | -0.2 | 2.6 | 1.3 | 3.9 | U09813_at U09813 Human mitochondrial ATP synthase subunit 9, P3 gene copy, mRNA, nuclear gene enc | Mit. | 7.3 | |
| 1.5 | 1.5 | 1.3 | 4.3 | -1.1 | -1 | -2.1 | 2.6 | 1.3 | 3.9 | X67951_at X67951 H. sapiens mRNA for proliferation-associated gene (pag). | detox | 6.1 | antioxidant protein |
| 1.8 | 1.2 | 1 | 4 | 1.7 | 1.2 | 2.9 | 2.5 | 1.4 | 3.9 | J04611_at J04611 Human lupus p70 (Ku) autoantigen protein mRNA, complete cds. | TF | 10.8 | |
| 2.8 | 1.8 | 2 | 6.6 | 1.6 | -1 | 0.6 | 2.8 | 1 | 3.8 | U09578_at U09578 H. sapiens MAPKAP kinase (3pK) mRNA, complete cds. | signaling | 11 | |
| 1 | 1 | 1 | 3 | 3.4 | 3.8 | 7.2 | 1 | 2.7 | 3.7 | X53800_at X53800 Human mRNA for macrophage inflammatory protein-2beta (MIP2beta). | GF/cyt | 13.9 | |
| 1 | 1.3 | 1.4 | 3.7 | 1 | 1.3 | 2.3 | 1.1 | 2.6 | 3.7 | HG1980-HT2023_at V00599 Tubulin, Beta 2 | cytoskel. | 9.7 | |
| 1.6 | -0 | 1.6 | 3.18 | -1 | 1.7 | 0.7 | 2.5 | 1.2 | 3.7 | U69126_s_at U69126 Human FUSE binding protein 2 (FBP2) mRNA, partial cds. | TF | 7.58 | |
| 1.6 | 1.5 | 1.5 | 4.6 | 1 | -1 | 0 | 2.7 | 1 | 3.7 | X53416_at X53416 Human mRNA for actin-binding protein (filamin) (ABP-280). | cytoskel. | 8.3 | |
| 1 | 1 | 1 | 3 | 1 | 1 | 2 | 1 | 2.6 | 3.6 | U90546_r_at U90546 Human butyrophilin (BTF4) mRNA, complete cds. | integral membrane protein | 8.6 | membrane glycoprotein |
| 2.6 | 1.9 | 1.8 | 6.3 | 1.3 | 1.1 | 2.4 | 4.2 | -1 | 3.2 | M58459_at M58459 Human ribosomal protein (RPS4Y) isoform mRNA, complete cds. | Translation | 11.9 | |
| 2.6 | 1.7 | 1 | 5.3 | 1.2 | 1.3 | 2.5 | 3.1 | -1 | 2.1 | M19961_at M19961 Human cytochrome c oxidase subunit Vb (coxVb) mRNA, complete cds. | Mit. | 9.9 | |
| 2.8 | 2 | 2 | 6.8 | 1.4 | 1 | 2.4 | 3 | -1 | 2 | U65579_at U65579 Human mitochondrial NADH dehydrogenase-ubiquinone Fe—S protein 8, 23 kD subunit | Mit. | 11.2 | |
| 2.2 | 1.4 | 1.5 | 5.1 | -2.4 | -5 | -7.1 | -1 | 3.2 | 1.9 | X77794_at X77794 H. sapiens mRNA for cyclin 61. | Cell cycle | -0.1 | |
| 1.8 | 1.5 | 1.2 | 4.5 | 1.4 | -1 | 0.3 | 2.7 | -1 | 1.7 | M29064_at M29064 Human hnRNP B1 protein mRNA. | RNA processing | 6.5 | |
| 1.3 | 1 | -1 | 1.2 | 1 | 1 | -0.2 | -1 | 2.7 | 1.6 | D21853_at D21853 Human mRNA for KIAA0111 gene, complete cds. | Translation | 2.6 | translation initiation |
| -1.1 | -1.4 | -1 | -3.9 | 1.4 | 1.7 | 3.1 | -1 | 2.7 | 1.5 | X78687_at X78687 H. sapiens G9 gene encoding sialidase. | Cell surface/adhesion | 0.7 | Glucoproteins, cell surface |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.6 | -1.1 | 1.2 | 1.7 | 1.1 | -2 | -0.4 | -1 | 2.6 | 1.5 | X15729_s_at X15729 Human mRNA for nuclear p68 protein. | TF | 2.8 | |
| 1.2 | 1 | 1.2 | 3.4 | -1 | -1 | -2 | 3.1 | -1.6 | 1.5 | X04828_at X04828 Human mRNA for G(i) protein alpha-subunit (adenylate cyclase inhibiting GTP-bind | signaling | 2.9 | |
| 1.1 | 1.2 | -1 | 1.2 | -1.3 | -2 | -2.8 | 2.6 | -1.3 | 1.3 | L27943_at L27943 H. sapiens cytidine deaminase (CDA) mRNA, complete cds. | DNA rep. | -0.3 | |
| 1.4 | -1.5 | -2 | -1.9 | 1.1 | -1 | -0.3 | 1.9 | -2.8 | -0.9 | L40391_at L40391 H. sapiens (clone s153) mRNA fragment. | ??? | -3.1 | |
| 1.3 | 1 | 1.4 | 3.7 | 1.3 | 1.1 | 2.4 | 1.5 | -2.5 | -1 | D42123_at D42123 H. sapiens mRNA for ESP1/CRP2, complete cds. | signaling | 5.1 | cytoskel. LIM domain |
| 1 | 1.1 | -1 | 1.1 | 1.1 | -1 | 0 | -3 | 1.4 | -1.2 | X74104_at X74104 H. sapiens mRNA for TRAP beta subunit. | ER/vesicles/lysosome | -0.1 | ER, translocon-associated protein |
| 1.3 | -1 | 1 | 1.3 | -1.1 | -2 | -3.1 | -3 | 1.4 | -1.2 | M84332_at M8432 Human ADP-ribosylation factor 1 gene, exons 2–5. | signaling | -3 | |
| 1 | 1 | 1 | 3 | 1.8 | -2 | -0.1 | 1.9 | -3.1 | -1.2 | L37127_at L37127 H. sapiens RNA polymerase II mRNA, complete cds. | TF | 1.7 | |
| 1.4 | 2.8 | 3.6 | 7.8 | 1.2 | -3 | -1.7 | -3 | 1.4 | -1.4 | M92843_s_at M92843 H. sapiens zinc finger transcriptional regulator mRNA, complete cds. | TF | 4.7 | |
| -1.8 | -2.5 | -2 | -5.9 | 1 | -1 | -0.2 | -3 | 1.2 | -1.6 | U07664_at U07664 Human HB9 homeobox gene, exons 2 and 3 and complete cds. | TF | -7.7 | |
| -1.6 | -2.2 | -2 | -5.3 | 1 | 1.7 | 2.7 | 1.4 | -3 | -1.6 | L48546_at L48546 H. sapiens tuberin (TSC2) gene, exons 38, 39, 40 and 41. | signaling | -4.2 | GAP |
| 1.8 | 1.4 | 1.4 | 4.6 | -1.4 | -2 | -3.4 | 1 | -2.7 | -1.7 | X53586_rna1_at X53586 Human mRNA for Integrin alpha 6. | cytoskel. | -0.5 | ECM |
| 1.5 | 1 | -1 | 1.2 | 1.4 | 1.1 | 2.5 | 1 | -2.8 | -1.8 | D21852_at D21852 Human mRNA for KIAA0029 gene, partial cds. | ??? | 1.9 | |
| 1.1 | 1.1 | 1.1 | 3.3 | -1.1 | 1.1 | 0 | -3 | 1 | -1.9 | L11066_at L11066 Human mRNA sequence. | signaling | 1.4 | HSP-associated |
| 4.3 | 2.9 | 1.6 | 8.8 | 1.6 | 1.3 | 2.9 | 1.7 | -3.6 | -1.9 | J04444_at J04444 Human cytochrome c-1 gene, complete cds. | Mit. | 9.8 | |
| 1.6 | 1 | 1 | 3.6 | -1.7 | -2 | -4 | 1.2 | -3.7 | -2.5 | M95787_at M95787 Human 22 kD smooth muscle protein (SM22) mRNA, complete cds. | cytoskel. | -2.9 | transgelin |
| -5.6 | -4.5 | -1 | -11.4 | 1.3 | 1 | 2.3 | -5 | 1 | -3.5 | HG880-HT880_at L07517 Mucin 6, Gastric (Gb: L07517) | ??? | -12.6 | |
| -1 | -1 | -1 | -3 | 1 | -3 | -1.9 | -3 | -1 | -3.5 | X91247_at X91247 H. sapiens mRNA for thioredoxin reductase. | detox | -8.4 | |
| -1.4 | -1.3 | -2 | -4.2 | -1.7 | -2 | -3.3 | -1 | -1 | -3.5 | L11672_at L11672 Human Kruppel related zinc finger protein (HTF10) mRNA, complete cds. | TF | -11 | |
| 1.1 | -1.1 | -2 | -1.8 | 1.1 | -1 | -0.1 | -1 | -2.6 | -3.6 | U30999_at U30999 Human (meme) mRNA, 3UTR. | ??? | -5.5 | |
| 1.2 | -1.1 | -1 | -0.9 | -1 | -1 | -2.2 | -3 | -1.1 | -3.7 | U01337_at U01337 Human Ser/Thr protein kinase (A-RAF-1) gene, complete cds. | signaling | -6.8 | |
| -1.8 | -2.7 | -2 | -6.3 | -1.5 | -1 | -2.8 | -1 | -2.6 | -3.7 | HG3492-HT3686_at U28480 Uncoupling Protein Ucp | Mit. | -12.8 | thermogenic |
| 1.2 | 1 | 1.3 | 3.5 | -1.6 | -2 | -3.5 | -3 | -1.1 | -3.9 | X12794_at X12794 Human v-erbA related ear-2 gene. | signaling | -3.9 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.1 | 1.2 | −2 | 0.6 | 1.1 | −2 | −0.8 | −3 | −1.1 | −3.9 | L22005_at L22005 Human ubiquitin conjugating enzyme mRNA, partial cds. | protease | −4.1 | protease |
| −1.7 | −1.7 | −2 | −5.1 | −1 | −1 | −2.3 | −3 | −1.2 | −3.9 | M12886_at M12886 Human T-cell receptor active beta-chain mRNA, complete cds. | signaling | −11.3 | |
| 1.5 | 1.7 | 1.4 | 4.6 | 1 | −1 | −0.3 | −1 | −2.6 | −4 | Y08915_at Y08915 H. sapiens mRNA for alpha 4 protein. | signaling | 0.3 | |
| 1.3 | 1.1 | 1.1 | 3.5 | −1.4 | −2 | −3.2 | −3 | −1.3 | −4.1 | HG3638-HT3849_s_at M24547 Amyloid Beta (A4) Precursor Protein, Alt. Splice 2, A4(751) | ECM | −3.8 | ECM |
| 1 | 1 | −1 | 0.9 | −1.3 | −1 | −2.4 | −2 | −2.5 | −4.1 | X76717_at X76717 H. sapiens MT-11 mRNA. | detox | −5.6 | |
| 1.6 | 1.4 | 1.3 | 4.3 | 1.1 | −2 | −1 | −1 | −2.7 | −4.1 | M64347_at M64347 Human novel growth factor receptor mRNA, 3′ cds. | signaling | −0.8 | |
| 1.4 | 1.2 | 1 | 3.6 | 1.2 | −1 | −0.1 | −1 | −2.8 | −4.1 | X05409_at X05409 Human RNA for mitochondrial aldehyde dehydrogenase I ALDH I (EC 1.2.1.3). | Mit. | −0.6 | |
| −1.1 | −1.4 | −2 | −4.1 | 1.3 | −1 | −0.1 | −1 | −2.8 | −4.1 | D87469_at D87469 Human mRNA for KIAA0279 gene, partial cds. | Cell surface/adhesion | −8.3 | seven-pass transmembrane cadherin |
| −1.2 | −1.3 | −1 | −3.7 | −1 | −2 | −2.5 | −3 | −1.3 | −4.2 | M58603_at M58603 Human nuclear factor kappa-B DNA binding subunit (NF-kappa-B) mRNA, complete cds | TF | −10.4 | |
| −1 | −1.3 | −1 | −3.7 | −1.5 | −3 | −4 | −3 | −1.3 | −4.2 | M76482_at M76482 Human 130-kD pemphigus vulgaris antigen mRNA, complete cds. | cytoskel. | −11.9 | |
| 1.3 | −1 | −1 | −1 | 1.4 | −1 | 0.4 | −3 | −1.6 | −4.2 | X06323_at X06323 Human MRL3 mRNA for ribosomal protein L3 homolog (MRL3 = mammalian ribosome L | Translation | −4.8 | |
| −1.2 | −1.2 | −2 | −4.1 | −1.3 | −4 | −5.2 | −3 | −1 | −4.3 | X78992_at X78992 H. sapiens ERF-2 mRNA. | TF | −13.6 | |
| 1.8 | 1 | −1 | 1.7 | 1 | −2 | −1 | −3 | −1.2 | −4.3 | L41351_at L41351 H. sapiens prostasin mRNA, complete cds. | protease | −3.6 | secreted protease |
| 1.1 | 1.1 | 1.3 | 3.5 | −1.5 | −2 | −3 | −3 | −1.9 | −4.4 | X75342_at X75342 H. sapiens SHB mRNA. | signaling | −3.9 | SH2 prot. |
| 1.1 | 1 | 1 | 3.1 | −1.2 | −2 | −2.9 | −1 | −3.3 | −4.4 | U83115_at U83115 Human non-lens beta gamma-crystallin like protein (AIM1) mRNA, partial cds. | cytoskel. | −4.2 | |
| −1.4 | −1.8 | −2 | −4.9 | −2.5 | −3 | −5.7 | −3 | −1.2 | −4.5 | U88629_at U88629 Human RNA polymerase II elongation factor ELL2, complete cds. | TF | −15.1 | |
| 2 | 2.2 | 1.5 | 5.7 | 1.1 | −4 | −2.5 | −3 | −1.5 | −4.5 | HG3342-HT3519_s_at S78825 Id1 | TF | −1.3 | |
| −1 | −1.1 | −1 | −3.3 | −1 | −2 | −3 | −2 | −2.9 | −4.5 | U28811_at U28811 Human cysteine-rich fibroblast growth factor receptor (CFR-1) mRNA, complete cds | signaling | −10.8 | |
| −1.2 | −1.2 | −1 | −3.6 | −1.6 | −3 | −4.9 | −3 | −1.2 | −4.6 | M58286_s_at M58286 H. sapiens tumor necrosis factor receptor mRNA, complete cds. | signaling | −13.1 | |
| 1 | −1.3 | −1 | −1.5 | −2 | −6 | −8.3 | −3 | −1.4 | −4.6 | D78129_at D78129 H. sapiens mRNA for squalene epoxidase, partial cds. | lipid metabolism | −14.4 | lipogenic, cholesterol synth. |
| 1.6 | 1.6 | 1.6 | 4.6 | −1 | −2 | −3.4 | −3 | −1.8 | −4.6 | D14874_at D14874 H. sapiens mRNA for adrenomedullin precursor, complete cds. | GF/cyt | −3.2 | |
| −1.4 | −1.3 | 1 | −1.7 | −1.3 | −2 | −3.3 | −3 | −2.1 | −4.6 | Z26317_at Z26317 H. sapiens mRNA for desmoglein 2. | cytoskel. | −9.6 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| -1.2 | -1.1 | -2 | -4.1 | -1.8 | -2 | -3.7 | -2 | -2.8 | -4.6 | L19267_at L19267 H. sapiens 59 protein mRNA, 3' end. | signaling | -12.4 | myotonic dystrophy |
| -1.2 | -1.9 | -1 | -4.5 | -3.9 | -6 | -9.7 | -3 | -1.3 | -4.7 | HG3523-HT4899_s_at J00120 Proto-Oncogene C-Myc, Alt. Splice 3, Orf 114 | TF | -18.9 | |
| 1.4 | -1.1 | 1 | -0.7 | 1.2 | -2 | -0.4 | -3 | -1.7 | -4.7 | U33821_at U33821 Human taxi1-binding protein TXBP151 mRNA, complete cds. | signaling | -5.8 | |
| 1.2 | 1 | -1 | 1 | -1 | -2 | -2.8 | -2 | -2.7 | -4.7 | U52100_at U52100 Human XMP mRNA, complete cds. | Cell surface/adhesion | -6.5 | membrane glycoprotein |
| -1.4 | -1.9 | -2 | -5.5 | -1.4 | -3 | -4.4 | -2 | -2.9 | -4.7 | L31801_at L31801 H. sapiens monocarboxylate transporter 1 (SLC16A1) mRNA, complete cds. | transporter | -14.6 | Lactate and pyruvate |
| 1.7 | 1.6 | 1.1 | 4.4 | -1.7 | -4 | -6 | -2 | -3 | -4.7 | L00058_at L00058 Human (GH) germline c-myc proto-oncogene, exon 3 and 3' flank. | TF | -6.3 | |
| -1 | 1.2 | -1 | -1.2 | -1.1 | -2 | -3.3 | -2 | -3.2 | -4.7 | U52426_at U52426 H. sapiens GOK (STIM1) mRNA, complete cds. | ??? | -9.2 | secreted protein |
| 1.6 | 1.2 | 1.2 | 4 | -1.1 | -2 | -2.8 | -1 | -3.5 | -4.7 | M80244_at M80244 Human E16 mRNA, complete cds. | Translation | -3.5 | aa transporter |
| -1.1 | -2.2 | -1 | -4.3 | -1.1 | -2 | -2.8 | -4 | -1.3 | -4.8 | U56418_at U56418 Human lysophosphatidic acid acyltransferase-beta mRNA, complete cds. | signaling | -11.9 | |
| 1.5 | 1.7 | 2.2 | 5.4 | -1.4 | -2 | -3.4 | -3 | -2.2 | -4.8 | L38490_s_at L38490 H. sapiens ADP-ribosylation factor mRNA, complete cds. | signaling | -2.8 | |
| 1.1 | -1.3 | -2 | -1.7 | 1.1 | -3 | -1.4 | -2 | -2.6 | -4.8 | U14603_at U14603 Human protein-tyrosine phosphatase (HU-PP-1) mRNA, partial sequence. | signaling | -7.9 | |
| 1.3 | 1 | -1 | 1.3 | -1.2 | -3 | -3.8 | -2 | -2.6 | -4.9 | L77886_at L77886 Human protein tyrosine phosphatase mRNA, complete cds. | | -7.4 | |
| 1.3 | 1.2 | -1 | 1.5 | -1.7 | -1 | -3 | -1 | -3.6 | -4.9 | M38258_at M38258 Human retinoic acid receptor gamma 1 mRNA, complete cds. | TF | -6.4 | |
| -1 | -1.3 | -1 | -3.7 | 1.5 | -3 | -1 | -4 | -1.2 | -5 | X89750_at X89750 H. sapiens mRNA for TGIF protein. | TF | -9.7 | homeobox |
| -1 | -1 | 1 | -1 | 1 | -4 | -3.2 | -3 | -1.8 | -5 | D85429_at D85429 H. sapiens gene for heat shock protein 40, complete cds. | signaling | -9.2 | |
| -1.8 | -2.9 | -4 | -8.5 | -2.6 | -4 | -6.7 | -3 | -2.4 | -5.1 | HG174-HT174_at J05211 Desmoplakin I | cytoskel. | -20.2 | |
| -1.1 | -1.1 | 1 | -1.2 | 2.6 | 1.5 | 4.1 | -3 | -2.3 | -5.1 | M31627_at M31627 Human X box binding protein-1 (XBP-1) mRNA, complete cds. | TF | -2.2 | |
| 1.2 | 1.2 | 1.4 | 3.8 | -1.4 | -1 | -2.4 | -1 | -4.1 | -5.1 | X80695_at X80695 H. sapiens OXA1Hs mRNA. | Mit. | -3.7 | cytochrome oxydase assembly |
| -1 | -1.9 | -1 | -4 | 1.2 | 1 | -0.3 | -4 | -1.5 | -5.2 | M54915_s_at M54915 Human h-pim-1 protein (h-pim-1) mRNA, complete cds. | signaling | -9.5 | ST kinase |
| -1 | -1 | -1 | -3.4 | 1 | 1 | 2 | -2 | -3.4 | -5.2 | D83777_at D83777 Human mRNA for KIAA0193 gene, complete cds. | ??? | -6.6 | |
| 1.5 | 1.3 | 1 | 3.8 | -1.1 | -2 | -2.7 | -2 | -3.5 | -5.2 | D31883_at D31883 Human mRNA for KIAA0059 gene, complete cds. | cytoskel. | -4.1 | actin binding |
| 1.8 | 1.4 | 1.2 | 4.4 | -1.2 | -2 | -3.5 | -2 | -3.7 | -5.2 | U00968_at U00968 Human SREBP-1 mRNA, complete cds. | TF | -4.3 | |
| 1.3 | 1.3 | 1.2 | 3.8 | -1.2 | -3 | -4 | -2 | -3.7 | -5.2 | K03195_at K03195 Human (HepG2) glucose transporter gene mRNA, complete cds. | Energy | -5.4 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| −2.6 | −2.6 | −2 | −7 | −1.2 | −1 | −2.3 | −3 | −2 | −5.3 | D86965_at D86965 Human mRNA for KIAA0210 gene, complete cds. | signaling | −14.6 | |
| −1.7 | −1.3 | −1 | −4 | −1.1 | −2 | −3.5 | −4 | −1.4 | −5.4 | Z30643_at Z30643 H. sapiens mRNA for chloride channel (putative) 2139 bp. | Channel | −12.9 | Channel |
| −1.2 | −1.8 | −2 | −5.4 | −1.4 | −3 | −4.2 | −4 | −1.7 | −5.4 | D14520_at D14520 Human mRNA for GC-Box binding protein BTEB2, complete cds. | TF | −15 | |
| 1.6 | 1.2 | 1.8 | 4.6 | 1.2 | −1 | −0.2 | −3 | −2.8 | −5.4 | D87462_at D87462 Human mRNA for KIAA0272 gene, partial cds. | ??? | −1 | BRCA1-associated |
| 1.7 | 1.4 | 1.1 | 4.2 | −2.2 | −7 | −9.1 | −3 | −2.3 | −5.5 | X80692_at X80692 H. sapiens ERK3 mRNA. | signaling | −10.4 | |
| 1.3 | 1.1 | 1.1 | 3.5 | 1.6 | −1 | 0.4 | −3 | −2.5 | −5.5 | X90858_at X90858 H. sapiens mRNA for uridine phosphorylase. | DNA rep. | −1.6 | |
| −1.7 | −2 | −2 | −5.6 | −1 | −2 | −3.1 | −4 | −2.1 | −5.9 | M57763_at M57763 Human ADP-ribosylation factor (hARF6) mRNA, complete cds. | signaling | −14.6 | |
| 1.4 | 1.3 | 1.5 | 4.2 | 1.4 | −1 | 0.1 | −2 | −3.8 | −5.9 | X92720_at X92720 H. sapiens mRNA for phosphoenolpyruvate carboxykinase. | Energy | −1.6 | gluconegenesys!! |
| −1.1 | −1.3 | −1 | −3.8 | −1.1 | −2 | −2.8 | −3 | −2.8 | −6.1 | M81601_at M81601 Human transcription elongation factor (SII) mRNA, complete cds. | TF | −12.7 | |
| −1.3 | −1.2 | −2 | −4.1 | −2.4 | −3 | −5.8 | −3 | −2.8 | −6.1 | X52611_s_at X52611 Human mRNA for transcription factor AP-2. | TF | −16 | |
| 1.3 | 1.2 | −1 | 1.5 | −1.4 | −2 | −3 | −3 | −3 | −6.1 | U09587_at U09587 Human glycyl-tRNA synthetase mRNA, complete cds. | Translation | −7.6 | |
| 1.8 | 1 | 1 | 3.8 | 1.3 | −1 | −0.1 | −2 | −4.4 | −6.1 | U14550_at U14550 Human sialyltransferase SThM (sthm) mRNA, complete cds. | Cell surface/adhesion | −2.4 | Glucoproteins, cell surface |
| 1.6 | 1.6 | 1.7 | 4.9 | 2.4 | 1.3 | 3.7 | −3 | −3.4 | −6.2 | D90209_at D90209 Human mRNA for DNA binding protein TAXREB67. | TF | 2.4 | |
| 1.8 | 1.2 | −1 | 1.9 | −1 | −2 | −3.4 | −3 | −3.9 | −6.4 | X77366_at X77366 H. sapiens HBZ17 mRNA. | TF | −7.9 | antimetastatic |
| 1 | 1 | 1 | 3 | −1 | −3 | −3.9 | −2 | −4.7 | −6.4 | X76534_at X76534 H. sapiens NMB mRNA. | integral membrane protein | −7.3 | transmembrane glycoprot. |
| −1.7 | −1 | −1 | −4 | −1.3 | −2 | −3.7 | −1 | −5.2 | −6.5 | U37519_at U37519 Human aldehyde dehydrogenase (ALDH8) mRNA, complete cds. | detox | −14.2 | |
| 1.4 | 1.4 | 1.6 | 4.4 | 1.4 | −2 | −0.5 | −4 | −2.4 | −6.6 | M83667_rna1_s_at M83667 Human NF-IL6-beta protein mRNA, complete cds. | TF | −2.7 | |
| 1 | 1 | −2 | 0.5 | −1.1 | −1 | −2.4 | −3 | −3.9 | −6.6 | U53347_at U53347 Human neutral amino acid transporter B mRNA, complete cds. | AA metabolism | −8.5 | AA metabolism |
| −1.3 | −1.4 | −2 | −4.2 | −1.4 | −2 | −3.7 | −2 | −4.6 | −6.6 | L09229_s_at L09229 Human long-chain acyl-coenzyme A synthetase (FACL1) mRNA, complete cds. | lipid metabolism | −14.5 | fatty acid synth. |
| 1.2 | 1.2 | 1.4 | 3.8 | −1.5 | −5 | −6.4 | −4 | −2.8 | −6.9 | S73591_at S73591 brain-expressed HHCPA78 homolog [human, HL-60 acute promyelocytic leukemia cells | detox | −9.5 | Thioredoxin interacting |
| −3.1 | −3 | −2 | −8.4 | −2.3 | −5 | −7.3 | −4 | −2.9 | −7.2 | M13929_s_at M13929 Human c-myc-P64 mRNA, initiating from promoter P0, (HLmyc2.5) partial cds. | TF | −22.9 | |
| 1.3 | 1.1 | −1 | 1.2 | −1.1 | −2 | −2.8 | −3 | −4.7 | −7.3 | M55268_at M55268 Human casein kinase II alpha' subunit mRNA, complete cds. | signaling | −8.9 | |

TABLE 7-continued

Ultraviolet Radiation-Regulated First, Second And Third Response Gene Sets

| 0.5 hr | 1 hr | 2 hr | ##### | 4 hr | 8 hr | ##### | 16 hr | 24 hr | ##### | Description | Function | ##### | comment |
|---|---|---|---|---|---|---|---|---|---|---|---|---|---|
| 1.2 | 1.1 | 1 | 3.3 | 1.2 | 1.7 | 2.9 | −2 | −5.4 | −7.3 | M77836_at M77836 Human pyrroline 5-carboxylate reductase mRNA, complete cds. | Urea cycle | −1.1 | Urea cycle |
| 1.3 | 1.2 | −1 | 1.5 | −1.4 | −2 | −3 | −3 | −3 | −6.1 | U09587_at U09587 Human glycyl-tRNA synthetase mRNA, complete cds. | Translation | −7.6 | |
| 1 | 1 | 1 | 3 | 5.1 | 1 | 6.1 | −3 | −4.2 | −7.6 | HG2724-HT2820_at S75762 Oncogene Tls/Chop, Fusion Activated | signaling | 1.5 | |
| −1 | −1.3 | −2 | −3.9 | −1.2 | −3 | −4 | −5 | −3.2 | −7.7 | U72066_at U72066 H. sapiens CIBP interacting protein CtIP (CtIP) mRNA, complete cds. | signaling | −15.6 | Rb-binding |
| −2.2 | −2.8 | −3 | −8 | −2.6 | −3 | −5.5 | −5 | −3.4 | −8 | U42031_at U42031 Human 54 kD progesterone receptor-associated immunophilin FKBP54 mRNA, partial | signaling | −21.5 | |
| 1.2 | 1 | −1 | 1.2 | −1.1 | −2 | −2.7 | −3 | −4.8 | −8.1 | M27396_s_at M27396 Human asparagine synthetase mRNA, complete cds. | Translation | −9.6 | |
| 1.2 | 1.2 | 1.1 | 3.5 | −1 | −2 | −2.6 | −2 | −6 | −8.1 | X01630_at X01630 Human mRNA for argininosuccinate synthetase. | Urea cycle | −7.2 | Urea cycle |
| 1 | −1.2 | −1 | −1.4 | 1.1 | −1 | 0.1 | −3 | −5.8 | −9.2 | D32050_at D32050 Human mRNA for alanyl-tRNA synthetase, complete cds. | Translation | −10.5 | |
| −1.3 | −1.8 | −2 | −5.5 | −1.7 | −5 | −7.1 | −6 | −3.3 | −9.4 | M90656_at M90656 Human gamma-glutamylcysteine synthetase (GCS) mRNA, complete cds. | detox | −22 | glutathione biosynthesis |
| −1.8 | −1.8 | −2 | −5.4 | −1.7 | −2 | −3.9 | −6 | −4.1 | −9.6 | J04102_at J04102 Human erythroblastosis virus oncogene homolog 2 (ets-2) mRNA, complete cds. | TF | −18.9 | |
| 1.5 | 0.58 | 2 | 4.08 | 1.5 | −3 | −1.3 | −6 | −5.3 | −11.3 | X69111_at X69111 H. sapiens HLH 1R21 mRNA for helix-loop-helix protein. | TF | −8.52 | |

TABLE 8

Ultraviolet Radiation-Regulated Induced Genes Set

Induced Gene Set

M20030_f_at M20030 Human small proline rich protein (sprll) mRNA, clone 930.
X53065_f_at X53065
M13903_at M13903 Human involucrin gene, exon 2.
L10343_at L10343 Huma elaf in gene, complete cds.
M21302_at M21302 Human small proline rich protein (sprll) mRNA, clone 174N.
L05188_f_at L05188 H. sapiens small proline-rich protein 2 (SPRR2B) gene, complete cds.
Y00787_s_at Y00787 Human mRNA for MDNCF (monocyte-derived neutrophil chemotactic factor).
D50840_at D50840 H. sapiens mRNA for ceramide glucosyltransferase, complete cds.
HG2815-HT2931_at M22918 Myosin, Light Chain, Alkali, Smooth Muscle (Gb:U02629), Non-Muscle, Alt. Splice
HG1612-HT1612_at X70326 Macmarcks
X52426_s_at X52426 H. sapiens mRNA for cytokeratin 13.
S81914_at S81914 IEX-1 = radiation-inducible immediate-early gene [human, placenta, mRNA Partial, 1
M80254_at M80254 H. sapiens cyclophilin isoform (hCyP3) mRNA, complete cds.
L08069_at L08069 Human heat shock protein, E. coil DnaJ homolog mRNA, complete cds.
U62800_at U62800 Human cystatin M (CST6) mRNA, complete cds.
L24564_at L24564 Human Rad mRNA, complete cds.
M59465_at M59465 Human tumor necrosis factor alpha inducible protein A20 mHNA, complete cds.
Z49989_at Z49989 H. sapiens mRNA for smoothelin.
X57985_ma2_at X57985 H. sapiens genes for histones H2B.1 and H2A.
L19779_at L19779 H. sapiens histone H2A.2 mRNA, complete cds.
D42040_s_at D42040 Human mRNA for KIAA9001 gene, complete cds.
M63573_at M63573 Human secreted cyclophilin-like protein (SCYLP) mRNA, complete cds.
X54489_rna1_at X54489 Human gene for melanoma growth stimulatory activity (MGSA).
M92934_at M92934 Human connective tissue growth factor, complete cds.
Z14244_at Z14244 H. sapiens coxVIIb mRNA for cytochrome c oxidase subunit VIIb.
M60278at M60278 Human heparin-binding EGF-like growth factor mRNA, complete cds.
M72885_rna1_s_at M72885 Human GOS2 gene, 5 flank and cds.
X62083_s_at X62083 H. sapiens mRNA for Drosophila female sterile homeotic (FSH) homolog.
X67325_at X67325 H. sapiens p27 mRNA.
U04636_rna1_at U04636 Human cyclooxygenase-2 (hCox-2) gene, complete cds.
M26311_s_at M26311 Human cystic fibrosis antigen mRNA, complete cds.
L20688_at L20688 Human GDP-dissociation inhibitor protein (Ly-GDI) mRNA, complete cds.
M27436_s_at M27436 Human tissue factor gene, complete cds, with a Alu repetitive sequence in the 3
AF001294_at AF001294 H. sapiens IPL (IPL) mRNA, complete cds.
HG2815-HT2931_s_at M22918 Myosin, Light Chain, Alkali, Smooth Muscle (Gb:U02629), Non-Muscle, Alt. Splice
X74874_rna1_s_at X74874 H. sapiens gene for RNA pol II largest subunit, exon 1.
HG2815-HT4023_s_at M22919 Myosin, Light Chain, Alkali, Smooth Muscle (Gb:U02629), Smmoth Muscle, Alt. Spli
V00594_V00594 Human mRNA for metallothionein from cadmium-reated cells.
HG4322-HT4592_at V00599 Tublin, Beta
X99920_at X99920 H. sapiens mRNA for S100 calcium-binding protein A13.
M21005_at M21005 Human migration inhibitory factor-related protein 8 (MRP8) gene, complete cds.
U07919_at U07919 Human aldehyde dehydrogenase 6 mRNA, complete cds
M37583_at M37583 Human histone (H2A.Z) mRNA, complete cds.

TABLE 8-continued

Ultraviolet Radiation-Regulated Induced Genes Set

Induced Gene Set

S54005_s_at S54005 thymosin beta-b [human, metastatic melanoma cell line, mRNA, 453 nt]
D49824_s_at D49824 Human HLA-B null allele mRNA.
S78771_s_at S78771 NAT = CpG island-associated gene [human, mRNA, 1741 nt].
M90657_at M90657 Human tumor antigen (L6) mRNA, complete cds.
U09937_rna1_s at U09937 Human urokinase-type plasminogen receptor, exon 7.
X77794_at X77794 H. sapiens mRNA for cyclin G1.
M28130_rna1_s_at M28130 Human interleulon 8 (IL8) gene, complete cds
X14850_at X14850 Human H2A.X mRNA encoding histone H2A.X.
AB000584_at AB000584 H. sapiens mRNA for TGF-beta superfamily protein, complete cds.
U52101_at U52101 Human YMP mRNA, complete cds.
M57731_s_at M57731 Human gro-beta mRNA, complete cds.
D45248_at D45248 Human mRNA for proteasome activator hPA28 subunit beta, complete cds.
X83416_s_at X83416 H. sapiens PrP gene, exon 2.
X52882_at X52882 Human t-complex polypeptide 1 gene.
X57351_at X57351 Human 1-8D gene from interferon-inducible gene family.
X53800_s_at X53800 Human mRNA for macrophage inflammatory protein-2beta (MIP2beta).
Z69043_s_at Z69043 H. sapiens mRNA translocon-associated protein delta subunit precursor.
D38305_at D38305 Human mRNA for Tob, complete cds.
X52979_rna1_s_at X52979 Human gene for small nuclear ribonucleoproteins SmB and SmB'.
S80437_s_at S80437 fatty acid synthase {3' region} [human, breast and HepG2 cells, mRNA Partial, 22
HG2917-HT3061_f_at X87679 Major Histocompatibility Complex, Glass I, E (Gb:M21533)
Z29505_at 729505 H. sapiens mRNA for nucleic acid binding protein sub2.3.
D21853_at D21853 Human mRNA for KIAA0111 gene, complete cds.
X78687_at X78687 H. sapiens G9 gene-encoding sialidase.
M13755_at M13755 Human interferon-induced 17-kD/15-kD protein mRNA, complete cds.
M21186_at M21186 Human neutrophil cytochrome b light chain p22 phagocyte b-cytochrome mRNA, compl
D28235_s_at D28235 Human PTGS2 gene for prostaglandin endoperoxide synthase-2, complete cds.
M14328_s_at M14328 Human alpha enolase mRNA, complete cds.
HG1980-HT2023_at V00599 Tubulin, Beta 2
U90546_s_at U90546 Human butyrophilin (BTF4) mRNA, complete cds.
K02574_at K02574
X15729_s_at X15729 Human mRNA for nuclear p68 protein.
D89052_at D89052 H. sapiens mRNA for proton-ATPase-like protein, complete cds.
M60974_s_at M60974 Human growth arrest and DNA-damage-inducible protein (gadd45) mRNA, complete cds
HG2259-HT2348_s_at X06956 Tubulin, Alpha 1, Isoform 44
X04654_s_at X04654 Human mRNA for U1 RNA-associated 70K protein.
M79463_s_at M79463 Human PML-2 mRNA, complete CDS.
L76568_xpt3_f_at L76568 H. sapiens excision and cross link repair protein (ERGC4) gene, complete genom
Y09022_at Y09022 H. sapiens mRNA for Not56-like protein.
X57579_s_at X57579 H. sapiens activin beta-A subunit (exon 2).
U37690_at U37690 Human RNA polymerase II subunit (hsRPB10) mRNA, complete cds.
X61123_at X61123 Human BRG1 mRNA.
J04456_at J04456 Human 14 kD lectin mRNA, complete cds.
Z49254_at Z49254 H. sapiens L23-related mRNA.
U70660_at U70660 Human copper transport protein HAH1 (HAH1) mRNA, complete cds.
D86974_at D86974 Human mRNA for KIAA0220 gene, partial cds.
AF006084_at AF006084 H. sapiens Arp2/3 protein complex subunit p41-Arc (ARC41) mRNA, complete cds.
Y00503_at Y00503 Human mRNA for keratin 19.

TABLE 8-continued

Ultraviolet Radiation-Regulated Induced Genes Set

Induced Gene Set

M62831_at M62831 Human transcription factor ETR101 mRNA, complete cds.
Z22548_at Z22548 H. sapiens thiol-specific antioxidant protein mRNA.
U40369_rna1_at U40369 Human spermidine/spermine N1-acetyltransferase (SSAT) gene, complete cds.
M12125_at M12125 Human fibroblast muscle-type tropomyosin mRNA, complete cds.
X51315_at X51345 Human jun-B mHNA for JUN-B protein.
Z21507_at Z21507 H. sapiens EF-1delta gene encoding human elongation factor-1-delta.
U20734_s_at U20734 Human transcription factor junB (junB) gene, 5, region and complete cds.
D13413_rna1_s at D13413 Human mRNA for tumor-associated 120 kD nuclear protein p120, partial cds(carbox
L42379_at L42379 H. sapiens bone-derived growth factor (BPGF-1) mRNA, complete cds.
X15822_at X15822 Human COX VIIa-L mRNA for liver-specific cytochrome c oxidase (EC 1.9.3.1.).
D86988_at D86988 Human mRNA for KIAA0221 gene, complete cds.
M26730_s_at M26730 Human mitochondrial ubiquinone-binding protein (QF) gene, exon 4.
M69043_at M69043 H. sapiens MAD-3 mRNA encoding IkB-like activity, complete cds.
D38251_s_at D38251 Human mRNA for RPB5 (XAP4), complete cds.
L76200_at L76200 Human guanylate kinase (GUK1) mRNA, complete cds.
M34516_at M34516 Human omega light chain protein 14.1 (Ig lambda chain related) gene, exon 3.
U26727_at U26727 Human p16INK4/MTS1 mRNA, complete cds.
U53830_at U53830 H. sapiens interferon regulatory factor 7A mRNA, complete cds.
M22960_at M22960 Human protective protein mRNA, complete cds.
D89667_at D89667 H. sapiens mRNA for c-myc binding protein, complete cds.
M19309_s_at M19309 Human slow skeletal muscle troponin T mRNA, clone H22h.
D64142_at D64142 Human mRNA for histone Hix, complete cds.
U41515 at U41515 Human deleted in split hand/split foot 1 (DSS1) mRNA, complete cds.
J04611_at J04611 Human lupus p70 (Ku) autoantigen protein mRNA, complete cds.
U35048_at U35048 Human TSC-22 protein mRNA, complete cds.
X82693_at X82693 H. sapiens mRNA for E48 antigen.
M92843_s_at M92843 H. sapiens zinc finger transcriptional regulator mRNA, complete cds.
U72649_at U72649 Human BTG2 (BTG2) mRNA, complete cds.
X92896_at X92896 H. sapiens mRNA for ITBA2 protein.
D10923_at D10923 Human mRNA for HM74.
M84739_at M84739 Human autoantigen cafreticulin mRNA, complete cds.
U09813_at U09813 Human mitochondrial ATP synthase subunit 9, P3 gene copy, mRNA, nuclear gene enc
X67951_at X67951 H. sapiens mRNA for proliferation-ssociated gene (pag).
L27706_at L27706 Human chaperonin protein (Tcp20) gene complete cds.
U69126_s_at U69126 Human FUSE binding protein 2 (FBP2) mRNA, partial cds.
M12529 at M12529 Human apolipoprotein E mRNA, complete cds.
X71129_at X71129 H. sapiens mRNA for electron transfer flavoprotein beta subunit.
U13991_at U13991 Human TATA-binding protein associated factor 30 kD subunit (tafII30) mRNA, comp
J04794_at J04794 Human aldehyde reductase mRNA, complete cds.
U51586_at U51586 Human siah binding protein 1 (SiahBP1) mRNA, partial cds.
M58026_at M58026 Human NB-1 mRNA, complete cds.
X68277_at X68277 H. sapiens CL 100 mRNA for protein tyrosine phosphatase.
X56681_s_at X56681 Human juno mRNA.
V01512_rna1_at V01512 Human cellular oncogene c-fos (complete sequence).

TABLE 8-continued

Ultraviolet Radiation-Regulated Induced Genes Set

Induced Gene Set

U09578_at U09578 H. sapiens MAPKAP kinase (3pK) mRNA, complete cds.
L13391_at L13391 Human helix-loop-helix basic phosphoprotein (G0S8) gene, complete cds.
U62317_rna3_at U62317 Chromosome 22q13 BAG Clone CIT987SK-38408 complete sequence.
M16364_s_at M16364 Human creatine kinase-B mRNA, complete cds.
L19437_at L19437 Human transaldolase mRNA containing transposable element, complete cds.
X53416_at X53416 Human mRNA for actin-binding protein (filamin) (ABP-280).
HG3494-HT3688_at X52560 Nuclear Factor Nf-ll6
M58459_at M58459 Human ribosomal protein (RPS4Y) isoform mRNA, complete cds.
U65579_at U65579 Human mitochondrial NADH dehydrogenase-biguinone Fe-S protein 8, 23 kD subunit
M19961_at M19961 Human cytochrome c oxidase subunit Vb (coxVb) mRNA, complete cds.
M29064_at M29064 Human hnRNP B1 protein mRNA.
D90086_at D90086 Human pyruvate dehydrogenase (EC 1.2.4.1) beta subunit gene, exons 1–10.
L04731_at L04731 H. sapiens translocation T(4:11) of ALL-1 gene to chromosome 4.
D87071_at D87071 Human mRNA for KIAA0233 gene, complete cds.
X04412_at X04412 Human mRNA for plasma gelsolin.
L27943_at L27943 H. sapiens cytidine deaminase (CDA) mRNA, complete cds
U68142_at U68142 Human RaIGDS-like 2 (RGL2) mRNA, partial cds.
U63825_at U63825 Human hepatitis delta antigen interacting protein A (dipA) mRNA, complete cds.
X04828_at X04828 Human mRNA for G(i) protein alpha-subunit (adenylate cyclase inhibiting GTP-bind
L38951_at L38951 H. sapiens importin beta subunit mRNA, complete cds.
M31627_at M31627 Human X box binding protein-1 (XBP-1) mRNA, complete cds.
J04444_at J04444 Human cytochrome c-1 ene, complete cds.
HG2724-HT2820_at S75762 Oncogene Tls/Chop, Fusion Activated and Table 9 presents a list of genes the expression of which are repressed in response to ultraviolet radiation exposure.

TABLE 9

Ultraviolet Radiation-Regulated Repressed Gene Set

Repressed Gene Set

D50840_at D50840 H. sapiens mRNA for ceramide glucosyltransferase, complete cds.
L08069_at L08069 Human heat shock protein, E. coli DnaJ homolog mRNA, complete cds.
X77794_at X77794 H. sapiens mRNA for cyclin G1.
D89052_at D89052 H. sapiens mRNA for proton-ATPase-like protein, complete cds.
HG2855-HT2995_at L26336 Heat Shock Protein, 70 KD (Gb:Y00371)
M30703_s_at M30703 Human amphiregulin (AR) gene, exon 6, clones lambda-ARH (6, 12).
L16862_at L16862 H. sapiens G protein-coupled receptor kinase (GRK6) mRNA, complete cds
M92843_s_at M92843 H. sapiens zinc finger transcriptional regulator mRNA, complete cds.
U72649_at U72649 Human BTG2 (BTG2) mRNA, complete cds.
X74104_at X74104 H. sapiens mRNA tor TRAP beta subunit.
M84332_at M84332 Human ADP-ribosylation factor 1 gene, exons 2–5.
D15050_at D15050 Human mRNA for transcription factor AREB6, complete cds.
U28386_at U28386 Human nuclear localization sequence receptor hSRP1alpha mRNA, complete cds.

TABLE 9-continued

Ultraviolet Radiation-Regulated Repressed Gene Set

Repressed Gene Set

U41766_s_at U41766 Human metalloprotease/
disintegrinlcysteine-rich protein precursor (M009) mRNA, c
AF006041_at AF006041 H. sapiens Fas-binding protein
(DAXX) mRNA, partial cds.
U28749_s_at U28749 Human high-mobility group
phosphoprotein isoform I-C (HMGIC) mRNA, complete cds.
M60483_rnal_s at M60483 Human protein phosphatase
2A catalytic subunit-alpha gene, complete cds.
U07664_at U07664 Human HB9 homeobox gene, exons 2 and 3 and
complete cds.
X52425_at X52425 Human IL-4-R mRNA for the interleukin
4 receptor.
X94563_xpt2_rat X94563 H. sapiens dbi/acbp
gene exon 1 & 2.
L11066_at L11066 Human mRNA sequence.
X74008_at X74008 H. sapens mRNA for protein phosphatase
1 gamma.
X87241_at X87241 H. sapiens mRNA for hFat protein.
S68616_at S68616 Na+/H+ exchanger NHE-1 isoform
[human, heart, mRNA, 4516 nt].
D13705_s_at D13705 Human mRNA for fatty acids
omega-hydroxylase (cytochrome P-450HKV), complete cds
D86966_at D86966 Human mRNA for KIAA0211 gene,
complete cds.
U17327_at U17327 Human neuronal nitric oxide synthase
(NOS1) mRNA, complete cds.
U89336_cds4 at U89336 Human HLA class III region containing
NOTCH4 gene, partial sequence, homeobox PB
D85527_at D85527 H. sapiens mRNA for LIM domain,
partial cds.
HG880-HT880_at L07517 Mucin 6, Gastric (Gb:L07517)
X64330_at X64330 H. sapiens mRNA for
ATP-citrate lyase.
X89267_at X89267 H. sapiens DNA for uroporphyrinogen
decarboxylase gene.
X91247_at X91247 H. sapiens mRNA for thioredoxin
reductase.
L11672_at L11672 Human Kruppel related zinc finger
protein (HTF10) mRNA, complete cds.
X78992_at X78992 H. sapiens ERF-2 mRNA.
L19314_at L19314 Human HRY gene, complete cds.
X12794_at X12794 Human v-erbA related ear-2 gene.
L22005_at L22005 Human ubiquitin conjugating enzyme
mRNA, partial cds.
U01337_at U01337 Human Ser, Thr protein kinase (A-RAF-1)
gene, complete cds.
M34182_at M34182 Human testis-specific protein kinase
gamma-subunit mRNA, complete cds.
L08246_at L08246 Human myeloid cell differentiation
protein (MCL1) mRNA.
L37042_at L37042 H. sapiens casein kinase I alpha
isoform (CSNK1A1) mRNA, complete cds.
D87071_at D87071 Human mRNA for KIAA0233 gene, complete cds.
S74017_at S74017 Nrf2 = NF-E2-like basic leucine zipper
transctiptional activator [human, hemin-ind
L41351_at L41351 H. sapiens prostasin mRNA, complete cds.
L00352_at L00352 Human low density lipoprotein receptor
gene, exon 18.
D50683_at D50683 H. sapiens mRNA for TGF-betallR
alpha, complete cds.
X89750_at X89750 H. sapiens mRNA for TGIF protein.
D13988_at D13988 Human rab GDI mRNA, complete cds.
M12886_at M12886 Human T-cell receptor active beta-chain
mRNA, complete cds.
M55265_at M55265 Human casein kinase II alpha subunit
mRNA, complete cds.
J03161_at J03161 Human serum response factor (SRF) mRNA,
complete cds.
M58286_s_at M58286 H. sapiens tumor necrosis
factor receptor mRNA, complete cds.
U88629_at U88629 Human RNA polymerase II elongation factor
ELL2, complete cds.
U90716_at U90716 Human cell surface protein HCAR mRNA,
complete cds.
HG3638-HT3849_s_at M24547 Amyloid Beta (A4)
Precursor Protein, Alt. Splice 2, A4(751)
U05875_at U05875 Human clone pSK1 interferon gamma
receptor accessory factor-1 (AF-1) mRNA, compl
M58603_at M58603 Human nuclear factor kappa-B DNA binding
subunit (NE-kappa-B) mRNA, complete cds
D87442_at D87442 Human mRNA for KIAA0253 gene, partial cds.
M76482_at M76482 Human 130-kD pemphigus vulgaris antigen
mRNA, complete cds.
U56418_at U56418 Human lysophosphatidic acid acyltransferase-
beta mRNA, complete cds.
HG3523-HT4899_s_at J00120 Proto-Oncogene C-Myc,
Alt. Splice 3, Orf 114
U88898_at U88898 Human endogenous retroviral H
protease/integrase-derived ORF1 mRNA, complete cds
M91083_at M91083 Human DNA-binding protein (HRC1) mRNA,
complete cds.
Z30643_at Z30643 H. sapiens mRNA for chloride channel
(putative) 2139 bp.
X12953_at X12953 Human rab2 mRNA, YPT1-related and member
of ras family.
D78129_at D78129 H. sapiens mRNA for squalene epoxidase,
partial cds.
HG3342-HT3519_s_at S78825 ld1
M54915_s_at M54915 Human h-pim-1 protein (h-pim-1)
mRNA, complete cds.
X06323_at X06323 Human MRL3 mRNA for ribosomal protein L3
homolog ( MRL3 = mammalian ribosome L
D14043_at D14043 Human mRNA for MGC-24, complete cds.
U34252_at U34252 Human gamma-aminobutyraldehyde
dehydrogenase m RNA, complete cds.
M13829_s_at M13829 Human putative rat related
protein (pks/a-raf) mRNA, partial cds.
U33821_at U33821 Human taxi-binding protein TXBP151 mRNA,
complete cds.
U66616_at U66616 Human SWI/SNE complex 170 KD subunit
(BAE170) mRNA, complete cds
U29607_at U29607 Human methionine aminopeptidase mRNA,
complete cds.
D14520_at D14520 Human mRNA for GC-Box binding protein
BTEB2, complete cds.
D14874_at D14874 H. sapiens mRNA for adrenomedullin
precursor, complete cds.
D85429_at D85429 H. sapiens gene for heat shock
protein 40, complete cds.
M69181_at M69181 Human nonmuscle myosin heavy chain-B
(MYH10) mRNA, partial cds.
U60205_at U60205 Human methyl sterol oxidase (ERG25)
mRNA, complete cds.
X75342_at X75342 H. sapiens SHB mRNA.
D45906_at D45906 H. sapiens mRNA for LIMK-2,
complete cds.
X59434_at X59434 Human rohu mRNA for rhodanese.
M96803_at M96803 Human general beta-spectrin (SPTBN1)
mRNA, complete cds.
D79994_at D79994 Human mRNA for KIAA0172 gene, partial cds.
D86965_at D86965 Human mRNA for KIAA0210 gene, complete cds.
HG3930-HT4200_at Y13647 Stearoyl-Coenzymea Desaturase
X52541_at X52541 Human mRNA for early growth response
protein 1 (hEGR1).
Z26317_at Z26317 H. sapiens mRNA for desmoglein 2.
M57763_at M57763 Human ADP-ribosylation factor (hARF6)
mRNA, complete cds.
L38490_s_at L38490 H. sapiens ADP-ribosylation
factor mRNA, complete cds.
D87438_at D87438 Human mRNA for KIAA0251 gene, partial cds.
M31627_at M31627 Human X box binding protein-1 (XBP-1)
mRNA, complete cds.
X80692_at X80692 H. sapiens ERK3 mRNA.
U37122_at U37122 Human adducin gamma subunit mRNA,
complete cds.
M83667_rnal_s_at M83667 Human
NF-IL6-beta protein mRNA, complete cds.
HG174-HT174_at J05211 Desmoplakin I
D42123_at D42123 H. sapiens mRNA for ESP1/CRP2,
complete cds.

TABLE 9-continued

Ultraviolet Radiation-Regulated Repressed Gene Set

Repressed Gene Set

X90858_at X90858 H. sapiens mRNA for uridine
phosphorylase.
X76717_at X76717 H. sapiens MT-1l mRNA.
Y08915_at Y08915 H. sapiens mRNA for alpha 4 protein.
U30999_at U30999 Human (memc) mRNA, 3'UTR.
L77886_at L77886 Human protein tyrosine phosphatase mRNA,
complete cds.
U14603_at U14603 Human protein-tyrosine phosphatase
(HU-PP-1) mRNA, partial sequence.
HG3492-HT3686_at U28480 Uncoupling Protein Ucp
X53586_rna1_at X53586 Human mRNA for integrin
alpha 6.
M64347_at M64347 Human novel growth factor receptor mRNA,
3 cds.
U52100_at U52100 Human XMP mRNA, complete cds.
D21852_at D21852 Human mRNA for KIAA0029 gene,
partial cds.
X05409_at X05409 Human RNA for mitochondrial aldehyde
dehydrogenase I ALDH I (EC 1.2.1.3).
D87462_at D87462 Human mRNA for KIAA0272 gene,
partial cds.
L40391_at L40391 H. sapiens (clone s153)
mRNA fragment.
D87469_at D87469 Human mRNA for KIAA0279 gene,
partial cds.
S73591_at S73591 brain-expressed HHCPA78 homolog
[human, HL-60 acute promyalocytic leukemia cells
L19267_at L19267 H. sapiens 59 protein mRNA,
3' end.
M81601_at M81601 Human transcription elongation factor
(SII) mRNA, complete cds.
X52611_s_at X52611 Human mRNA for transcription
factor AP-2.
U28811_at U28811 Human cysteine-rich fibroblast growth
factor receptor (CFR-1) mRNA, complete cds
L31801_at L31801 H. sapiens monocarboxylate transporter
1 (SLC16A1) mRNA, complete cds.
M13929_s_at M13929 Human c-myc-P64 mRNA,
initiating from promoter P0, (HLmyc2.5) partial cds
L48546_at L48546 H. sapiens tuberin (TSC2) gene,
exons 38,39,40 and 41.
L00058_at L00058 Human (GH) germline c-myc proto-oncogene,
exon 3 and 3' flank.
U09587_at U09587 Human glycyl-tRNA synthetase mRNA,
complete cds.
L37127_at L37127 H. sapiens RNA polymerase II mRNA,
complete cds.
U52426_at U52426 H. sapiens GOK (STIM1) mRNA,
complete cds.
U72066_at U72066 H. sapiens CtBP interacting protein
CtIP (CtIP) mRNA, complete cds.
U83115_at U83115 Human non-lens beta gamma-crystallin
like protein (AIM1) mRNA, partial cds.
M90656_at M90656 Human gamma-glutamylcysteine synthetase
(GCS) mRNA, complete cds.
D90209_at D90209 Human mRNA for DNA binding protein
TAXREB67.
D83777_at D83777 Human mRNA for KIAA0193 gene, complete cds.
U42031_at U42031 Human 54 kD progesterone receptor-associated
immunophilin FKBP54 mRNA, partial
M80244_at M80244 Human E16 mRNA, complete cds.
D31883_at D31883 Human mRNA for KIAA0059 gene,
complete cds.
J04444_at J04444 Human cytochrome c-1 gene, complete cds.
M38258_at M38258 Human retinoic acid receptor gamma 1 mRNA,
complete cds.
M95787_at M95787 Human 22kD smooth muscle protein (SM22)
mRNA, complete cds.
U00968_at U00968 Human SHEBP-1 mRNA, complete cds.
K03195_at K03195 Human (HepG2) glucose transporter gene
mRNA, complete cds.
X92720_at X92720 H. sapiens mRNA for phosphoenolpyruvate
carboxykinase.
X77366_at X77366 H. sapiens HBZ17 mRNA.

TABLE 9-continued

Ultraviolet Radiation-Regulated Repressed Gene Set

Repressed Gene Set

U53347_at U53347 Human neutral amino acid transporter B mRNA,
complete cds.
X80695_at X80695 H. sapiens OXA1Hs mRNA.
J04102_at J04102 Human erythroblastosis virus oncogene
homolog 2 (ets-2) mRNA, complete cds.
HG2724-HT2824_at S75762 Oncogene Tis/Chop, Fusion Activated
U14550_at U14550 Human sialyltransferase SThM (sthm) mRNA,
complete cds.
L09229_s_at L09229 Human long-chain acyl-coenzyme A
synthetase (FACL1) mRNA, complete cds.
X76534_at X76534 H. sapiens NMB mRNA.
M55268_at M55268 Human casein kinase II alpha' subunit
mRNA, complete cds.
M27396_s_at M27396 Human asparagine synthetase
mRNA, complete cds.
U37519_at U37519 Human aldehyde dehydrogenase (ALDH8) mRNA,
complete cds.
X69111_at X69111 H. sapiens HLH 1R21 mRNA for
helix-loop-helix protein.
M77836_at M77836 Human pyrroline 5-carboxylate reductase
mRNA, complete cds.
D32050_at D32050 Human mRNA for alanyl-tRNA synthetase,
complete cds.
X01630_at X01630 Human mRNA for argininosuccinate synthetase.

I. Compositions of the Invention

The present invention exploits the discovery of a pattern of RNA and protein expression in a cell exposed to ultraviolet radiation. Compositions of matter of the invention include a plurality of specific nucleic acid and protein molecules identified by the invention as ultraviolet radiation-regulated. In one aspect, the compositions of the invention are directed to nucleic acid molecules that are at least 90%, 91%, 92%, 93%, 94%, 95%, 96%, 97%, 98%, 99% or 100% identical at the nucleotide sequence level to the complete list group of ultraviolet radiation-regulated nucleic acid molecules (Table 7). In another aspect, the compositions of the invention are directed to nucleic acid molecules that are at least 90%, 91%, 92%, 93%, 94%, 95%, 96%, 97%, 98%, 99% or 100% identical at the nucleotide sequence level to the complementary sequences of the complete list group (Table 7).

As used herein, the terms "nucleic acid" or "nucleic acid molecule" refer to a deoxyribonucleotide or ribonucleotide polymer in either single-or double-stranded form, and unless otherwise limited, would encompass analogs of natural nucleotides that can function in a similar manner as the naturally occurring nucleotide. An "oligonucleotide" is a single-stranded nucleic acid of 12 bases plus N bases, wherein N is a whole integer from 0 to 500. Nucleic acids may be isolated and purified, cloned, or synthesized using any techniques known in the art. They may also include non-naturally occurring nucleotide analogs, such as those which are modified to improve hybridization.

As known to those skilled in the art, the "percentage of sequence identity" or "sequence identity" may be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see above) is calculated using default gap weights.

Optimal alignment of sequences for comparison may be conducted by the local homology algorithm of Smith and Waterman (*Adv. Appl. Math.* (1981) 2:482); by the homology alignment algorithm of Needleman and Wunsch (*J. Mol. Biol.* (1970) 48:443); by the search for similarity method of Pearson and Lipman (*Proc. Natl. Acad. Sci.* (*USA*) (1988) 85:2444); by computerized implementations of these algorithms (including, but not limited to, CLUSTAL in the PC/Gene program by Intelligenetics (Mountain View, Calif.) GAP, BESTFIT, FASTA, and TFASTA in the Wisconsin Genetics Software Package, Genetics Computer Group (GCG) (Madison, Wis.); or by inspection. In particular, methods for aligning sequences using the CLUSTAL program are well described by Higgins and Sharp (*Gene* (1988) 73:237–244), (*CABIOS* (1989) 5:151–153), and both the BLAST and the PSI-BLAST programs (Altschul et al. (1997), *Nucleic Acids Res.* 25:3389–3402).

In one aspect, the invention provides a composition of matter comprising a plurality of nucleic acid molecules, the expression of which is altered by exposure to ultraviolet radiation. Nucleic acid molecules of the composition are selected from at least one of the following groups: the primary first response group, the primary second response group, and the primary third response group. Alternatively, in another embodiment, the composition comprises a plurality of nucleic acid molecules defined to be at least one, or at least two, or at least three, or at least four, or at least five, or at least six, or at least seven, or at least eight, or at least nine, or at least ten nucleic acid molecules selected from the complete list group described hereinabove.

In an alternative embodiment, the composition of matter comprises a plurality of nucleic acid molecules, each one being at least 90%, at least 91%, at least 92%, at least 93%, at least 94%, at least 95%, at least 96%, at least 97%, at least 98%, at least 99%, or 100% identical on a sequence level to a polynucleotide selected from at least one of the following: the secondary first response group, the secondary second response group, and the secondary third response group. Alternatively, in another embodiment, the composition of matter comprises a plurality of nucleic acid molecules, each one being at least 90%, at least 91%, at least 92%, at least 93%, at least 94%, at least 95%, at least 96%, at least 97%, at least 98%, at least 99% or 100% identical on a sequence level to a member of the group of polynucleotides consisting of least one, or at least two, or at least three, or at least four, or at least five, or at least six, or at least seven, or at least eight, or at least nine, or at least ten nucleic acid molecules selected from the complete list group described hereinabove.

The compositions of matter of the invention are useful for the production of DNA- or oligonucleotide arrays, referred to collectively herein as a "gene array." Gene arrays comprise a plurality of different "probe" or "target" nucleic acids (or other compounds) attached to one or more substrates or surfaces (e.g., solid, membrane, or gel). Gene arrays may be constructed in a low or high density format. A high density gene array provides a rapid, essentially simultaneous, evaluation of a number of hybridizations in a single test. In a preferred embodiment, the plurality of nucleic acid molecules (or other moieties) are attached to a single contiguous surface or to a multiplicity of surfaces juxtaposed to each other in an array format. In this way, a large number of different hybridization reactions can be run essentially "in parallel." The method of performing hybridization reactions in array based formats are well known to those of skill in the art (see, e.g., Pastinen (1997) *Genome Res.* 7:606(614; Jackson (1996) *Nature Biotechnol.* 14:1685; Chee (1995) *Science* 274:610; WO 96/17958; and Pinkel et al. (1998) *Nature Genetics* 20;207–211, which are incorporated herein by reference).

Different embodiments of the invention are directed to low and high density nucleic acid and oligonucleotide arrays. Depending on the intended application, arrays may be constructed using oligonucleotides, cDNAs, genomic clones, etc.; such a determination is well within the knowledge of one skilled in the art. Typically, oligonucleotide arrays are utilized in a high density format. Thus, the invention includes oligo expression arrays in which the specific oligo nucleotides are selected from the nucleic acid molecules identified herein as regulated in response to ultraviolet radiation exposure. Genomic clones, cDNAs and other polynucleotides greater than about 500 base pairs are easily utilized in a low density setting, but to obtain a high density array with these polynucleotides it is most easily accomplished by robotic application to a substrate. U.S. Pat. No. 5,143,854 and PCT Patent Publication Nos. WO 90/15070 and WO 92/10092 teach the use of light-directed combinatorial synthesis of high density oligonucleotide arrays, and the synthesis of high density arrays is also described in U.S. Pat. Nos. 5,744,305, 5,800,992 and 5,445,934.

Many methods for immobilizing nucleic acids on a variety of substrates are known in the art. A wide variety of organic and inorganic polymers, as well as other materials, both natural and synthetic, can be employed as the material for the solid surface of a gene array. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include, but are not limited to, paper, ceramics, metals, metalloids, semiconductive materials, and the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

The gene arrays of the invention may also be prepared commercially. For example, a service provided by Affymetrix, Inc. (Santa Clara, Calif.), producer of the GeneChip®, utilizes a proprietary synthesis system to create on a glass substrate a nucleic acid expression array. Construction of the Affymetrix array involves a multitude of gene sequences, each gene being represented on the probe array by multiple probe pairs, biased toward the 3' end of the gene. In addition, each probe pair consists of a perfect match and a mismatch oligonucleotide. With the exception of a homo-mismatch at the center base position, the mismatch oligonucleotide is identical in sequence to the perfect match, a pairing strategy which helps identify and subtract non-specific hybridization and background signal.

In a particularly preferred embodiment, the composition of matter comprises nucleic acid molecules that are oligonucleotides selected to have a length of about 12 bases plus N bases, wherein N is a whole integer from 0 to 500. In another particularly preferred embodiment, the composition of matter comprises oligonucleotides that are about 21 bases in length, and in a most preferred embodiment, the composition of matter is characterized as a gene array. The specific sequences of the oligonucleotides are selected from the nucleic acid sequences of the complete list group (Table 7) previously described herein, or from the secondary first response group, the secondary second response group, the secondary third response group, the induced group and/or the repressed group, all previously described herein and found in Tables 8 and 9, respectively.

In yet another embodiment, the composition of matter comprises a plurality of nucleic acid molecules, each one at least 90%, or 91%, or 92%, or 93%, or 94%, or 95%, or 96%, or 97%, or 98%, or 99% or 100% identical to the complementary nucleotide sequence of a member of the group of polynucleotides consisting of the secondary first response group, the secondary second response group, the secondary third response group, the induced group, and/or the repressed group. The term "complementary nucleotide sequence" as used herein refers to a nucleic acid base sequence that can form a double-stranded structure by matching base pairs; for example, the complementary sequence to G-T-A-C is C-A-TG The term "base pair matching" refers to the hydrogen bonding that occurs between certain nucleotides (adenine and thymine, guanine and cytosine) from opposite strands of a double stranded nucleic acid (such as DNA or RNA).

Another aspect of the invention provides pharmaceutical compositions for modulating the response of a cell to ultraviolet radiation exposure. The pharmaceutical compositions of the invention comprise a compound in sufficient quantity to modulate the response of the cell to exposure to ultraviolet radiation and a pharmaceutically acceptable carrier, the response being at least one of the following: the primary first response group, and the primary second response group, and the primary third response group. In various embodiments thereof, the response is the primary first response group, or the primary second response group, or the primary third response group, or the primary first response group and the primary second response group, or the primary first response group and the primary third response group, or the primary second response group and the primary third response group, or the primary first response group, the primary second response group, and the primary third response group.

The ultraviolet radiation to which the cell is exposed can comprise ultraviolet radiation energy at a wavelength in the range of about 220 nm to about 440 nm. Preferably, the cell is exposed to ultraviolet radiation energy at a wavelength of about 290 nm to about 320 nm at a wavelength of about 320 to about 440 nm, or to a total ultraviolet radiation energy exposure in the range of about 0.2 mJ/cm$^2$ to about 40 mJ/cm$^2$ The response of the cell thereto is at least one of the primary first response group, the primary second response group and/or the primary third response group. The cell that provides the response(s) is a skin cell (epidermal or dermal) or a cell selected from the group consisting of a keratinocyte, a Langerhans cell, a melanocyte, and a fibroblast cell.

The term "about" is used herein to mean "approximately," or "roughly," or "around," or "in the region of." When the term "about" is used in conjunction with a numerical range, it modifies that range by extending the boundaries above and below the numerical values set forth. In general, the term "about" is used herein to modify a numerical value above and below the stated value by a variance of 20 percent. Thus, the phrase "about 320 nm" is construed to mean that a 20% variance in value is placed on the numeral; for example, "about 320 nm" refers to all values between 320 nm minus (0.2)(320) and 320 nm plus (0.2)(320).

Exposure of a cell to a specific wavelength of ultraviolet radiation to induce the response of the cell to ultraviolet radiation exposure is easily accomplished by those familiar with the art. Sources of ultraviolet radiation may be obtained commercially that have a defined output for a limited range or a specific wavelength of ultraviolet radiation For example, the Stratagene 2000 illuminator specially equipped with FG15T light bulb is used which produces maximum output in the ultraviolet-B radiation wavelength range. In addition, one skilled in the art has the requisite knowledge to determine the total amount of ultraviolet radiation energy delivered to a cell in exposing it to ultraviolet radiation. For example, a luminometer UVB-500C from the National Biological Corp. (Twinsburg, Ohio) is useful for measuring the total amount of ultraviolet radiation energy a cell receives upon exposure to ultraviolet radiation.

The invention also provides pharmaceutical compositions for modulating the response of a cell to ultraviolet radiation exposure. This pharmaceutical composition comprises a compound in sufficient quantity to modulate the response of the cell to ultraviolet radiation exposure and a pharmaceutically acceptable carrier, wherein the response is characterized by a pattern of expression comprising the secondary first response group, the secondary second response group, and/or the secondary third response group.

In another embodiment thereof, the pharmaceutical composition is a compound in sufficient quantity to modulate the response of the cell to ultraviolet radiation exposure and a pharmaceutically acceptable carrier. In this embodiment the response is the altered expression of at least one, or at least two, or at least three, or at least four, or at least five, or at least six, or at least seven, or at least eight, or at least nine, or at least ten nucleic acid molecules, each of which is at least 90%, at least 91%, at least 92%, at least 93%, at least 94%, at least 95%, at least 96%, at least 97%, at least 98%, at least 99% or 100% identical at the nucleotide sequence level to a polynucleotide sequence from the secondary first response group, the secondary second response group, and/or the secondary third response group.

In other specific embodiments thereof, the invention provides pharmaceutical compositions that modulate the response of a cell to ultraviolet radiation. In this embodiment, the response is characterized by either a pattern of expression that is induced or repressed by exposure to ultraviolet radiation. More specifically, in these embodiments, the response is the induced response group (Table 8) or the repressed response group (Table 9).

The term "cell" as used herein is meant to include any skin cell (e.g., epidermal or dermal) or precursors thereof, in a culture, tissue, or organism. In specific cases, the cell is a keratinocyte, a melanocyte, a Langerhans cell, or a fibroblast cell.

By "a plurality of RNA molecules" is meant an RNA sample of high complexity; the term "complexity" being used here according to standard meaning of the term as established by Britten et al. (*Meth. Enzymol.* (1974) 29:363).

The level of an RNA molecule or a plurality of RNA molecules may be measured by any means known in the art. Methods of detecting and/or quantifying the transcript(s) of one or more gene(s) or EST(s) of this invention (e.g., mRNA or cDNA made therefrom) using nucleic acid hybridization techniques are known to those of skill in the art. For example, one method for evaluating the presence, absence, or quantity of gene or EST reverse-transcribed cDNA involves a Southern blot transfer and subsequent quantitation using nucleic acid hybridization technology. Alternatively, in a Northern blot, mRNA is directly quantitated. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target mRNA.

The probes used herein for detection of the gene(s) and/or EST(s) of this invention can be full length or less than the full length of the gene or EST. Shorter probes are empirically tested for specificity. Preferably, nucleic acid probes are 20 bases or longer in length. (See, Sambrook et al., supra, for methods of selecting nucleic acid probe sequences for use in nucleic acid hybridization). Visualization of the hybridized portions allows the qualitative determination of the presence or absence of gene(s) and/or EST(s) of this invention.

Another aspect of the invention provides a pharmaceutical composition for modulating the response of a cell to ultraviolet radiation exposure comprising a compound in sufficient quantity to modulate the response of the cell to ultraviolet radiation, wherein the response is a pattern of expression comprising a tertiary first response group, and/or a tertiary second response group, and/or a tertiary third response, and an acceptable pharmaceutical carrier. The pattern of expression may be the tertiary first response group, the tertiary second response group, and/or the tertiary third response group. In an alternative embodiment thereof, the response is the quaternary first response group, the quaternary second response group, and/or the quaternary third response group. The response may be modulation of at least one, at least two, at least three, at least four, at least five, at least six, at least seven, at least eight, at least nine, or at least ten protein molecules encoded by the polynucleotides selected from the induced group or selected from the repressed group.

It will be understood that, when administered to a human patient, the total daily usage of the pharmaceutical compositions of the present invention will be decided by the attending physician within the scope of sound medical judgment. The specific therapeutically effective dose level for any particular patient will depend upon a variety of factors including: the type and degree of the response to be achieved; the specific composition of another agent, if any, employed; the age, body weight, general health, sex and diet of the patient; the time of administration, route of administration, and rate of excretion of the composition; the duration of the treatment; drugs (such as a chemotherapeutic agent) used in combination or coincidental with the specific composition of the invention; and like factors well known in the medical arts. Suitable formulations, known in the art, can be found in *Remington's Pharmaceutical Sciences* ((latest edition), Mack Publishing Company (Easton, Pa.)).

Moreover, the pharmaceutical compositions may be administered in a convenient manner such as by the topical, intradermal, subcutaneous, intravenous, intraperitoneal intramuscular, or oral routes. The pharmaceutical compositions are administered in an amount which is effective for treatment and/or prophylaxis of the specific indication. By way of example, specific indications for the application of the pharmaceutical compositions include, but are not limited to, wrinkling of the skin, discoloration of the skin, benign keratinocytic tumors (keratoacanthoma and seborrheic keratosis), premalignant actinic keratosis (solar keratosis), malignant epidermal tumors such as basal cell carcinoma and squamous cell carcinomas, and malignant melanoma (which is classified into four types: (1) superficial spreading melanoma, (2) lentigo maligna melanoma, (3) acral-lentiginous melanoma, and (4) nodular melanoma).

Another aspect of the invention provides a pharmaceutical composition for modulating a response of a cell to ultraviolet radiation exposure, comprising a compound in sufficient quantity to modulate the response of the cell to ultraviolet radiation exposure, the response being an altered pattern of expression comprising at least one of the following: the primary first response group, the primary second response group and the primary third response group; and a pharmaceutically acceptable carrier. In embodiments thereof, modulation of the cellular response is an inhibition of the ultraviolet radiation exposure-induced RNA expression or an inhibition of the ultraviolet radiation exposure-repressed RNA expression.

In yet another aspect, the invention provides a pharmaceutical composition for modulating a response of a cell to ultraviolet radiation exposure, comprising a compound in sufficient quantity to modulate the response of the cell to ultraviolet radiation exposure, the response being an altered pattern of expression comprising at least one of the following: a secondary first response group, a secondary second response group and a secondary third response group.

Another aspect of the invention provides a pharmaceutical composition for modulating a response of a cell to ultraviolet radiation exposure, comprising a compound in sufficient quantity to modulate the response of the cell to ultraviolet radiation exposure, the response being an altered pattern of expression comprising at least one of the following: the tertiary first response group, the tertiary second response group and the tertiary third response group; and a pharmaceutically acceptable carrier. In embodiments thereof, modulation of the cellular response is an inhibition of the ultraviolet radiation exposure-induced protein expression or an inhibition of the ultraviolet radiation exposure-repressed protein expression.

Another aspect of the invention provides a pharmaceutical composition for modulating a response of a cell to ultraviolet radiation exposure, comprising a compound in sufficient quantity to modulate the response of the cell to ultraviolet radiation exposure, the response being an altered pattern of expression comprising at least one of the following: the quaternary first response group, the quaternary second response group and the quaternary, third response group; and a pharmaceutically acceptable carrier. In embodiments thereof, modulation of the cellular response is an inhibition of the ultraviolet radiation exposure-induced protein expression or an inhibition of the ultraviolet radiation exposure-repressed protein expression. In embodiments thereof, modulation of the cellular response is an inhibition of the ultraviolet radiation exposure-induced protein expression or an inhibition of the ultraviolet radiation exposure-repressed protein expression.

In a further aspect invention provides a pharmaceutical composition for modulating the response of a cell to ultraviolet radiation exposure, the response being an altered pattern of expression determined by gene expression array analysis. The pharmaceutical composition comprises a compound in sufficient quantity to modulate the response of the cell to ultraviolet radiation exposure; and a pharmaceutically acceptable carrier.

II. Methods of the Invention

A. Method to Identify Cellular Ultraviolet Radiation Exposure

Another aspect o the invention provides methods for detecting exposure of a cell to ultraviolet radiation comprising measuring the levels of a plurality of RNA or protein molecules in the cell, wherein the response, i.e., a pattern of altered expression, of the cell to ultraviolet radiation exposure is established and indicates that the cell was exposed to ultraviolet radiation. In various embodiments thereof, the response of the cell comprises at least one of a first response group, a second response, and/or a third response.

As used herein and as understood by those skilled in the art, the term "altered expression" may refer to an increase or decrease in the expression level of one or more nucleic acids, preferably one or more RNA molecules. The term "altered expression" may also refer to a relative increase or decrease in the expression level of one or more protein molecules. Also, it will be understood by one skilled in the art that an increase or decrease in an expression level may be effected by synthesis rate, i.e., transcription rate for RNA and translation rate for protein, or a change in the stability of either the RNA or protein molecules affected. Thus, all of the "responses" described herein by a cell exposed to ultraviolet radiation represent "altered expression" relative to nucleic acid molecules (e.g., RNAs) or proteins expressed in a cell that was not exposed to ultraviolet radiation.

The invention describes various responses of the cell to ultraviolet radiation exposure. Through the use of gene array expression analysis, the invention provides a categorization and listing of genes and proteins the expression of which is altered in a cell exposed to ultraviolet radiation. As disclosed in more detail in Example 1, below, of the 7,080 gene entries examined by gene array expression analysis, some 3,000 were scored as present in keratinocytes at at least one time point post-ultraviolet radiation exposure, and approximately 1,400 of these are present at all time points during the response of the keratinocyte to ultraviolet radiation exposure. Among the entries, 308 were differentially regulated at least two-and a half-fold at at least one time point. Of these 308 gene sequences, specific attention was paid to genes represented by multiple probes on the gene (for example, gene sequences for jun-B, c-Myc, Cox-2). Although the actual values of "fold regulation" varied, very similar patterns of regulation were found for these multiple probe sets, which provided confidence in the fidelity of the hybridizations (Table 1). Of the 308 genes found to be regulated at some point by 2.5 fold or more, 9 gene sequences were both induced and suppressed 2.5 fold or more at different time points, while the remaining 299 gene sequences are approximately divided equally (152 versus 147) between the induced and repressed group, respectively.

Using a clustering algorithm, seven time points after ultraviolet radiation exposure (FIG. 2) were grouped according to the temporal occurrence of the altered expression for each mn sequence. The most closely related temporally were the 0.5, 1 and 2 hour time points, which formed the first wave of regulated genes and proteins. Also very similar were the 16 and 24 hour time points, forming the third wave of regulated genes and proteins. The four and eight hour time points were more similar to each other than to the other time points analyzed and, therefore, these were grouped together to form the second wave of regulated genes and proteins. Thus, in addition to identifying the genes and proteins, the expression of which are altered by ultraviolet radiation exposure, the invention also provides a temporal grouping of the responses in the first 24 hours after ultraviolet radiation exposure: the first response (from about 0.5 to about two hours), the second response (from about four to about eight hours), and the third response (from about 16 to about 24 hours). These first, second, and third responses have been variously defined as detailed hereinabove.

In one embodiment, the invention provides a method to detect exposure of a cell to ultraviolet radiation wherein the response comprises at least one of the following: a primary first response group, a primary second response group, and a primary third response group. The cell exposed to ultraviolet radiation may be a skin cell (epidermal or dermal) or a cell selected from the group consisting of a keratinocyte, a Langerhans cell, a melanocyte, or a fibroblast cell. The cell is exposed to ultraviolet radiation comprising: ultraviolet radiation energy at a wavelength in the range of about 220 nm to about 440 nm, ultraviolet radiation energy at a wavelength in the range of about 290 nm to about 320 nm, or ultraviolet radiation energy at a wavelength in the range of about 320 to about 440 nm, or a total ultraviolet radiation energy exposure in the range of about 0.2 mJ/cm$^2$ to about 40 mJ/cm$^2$.

The method may further comprise a response characterized by: the primary first response occurring from about 0.5 hours to about two hours post-exposure to ultraviolet radiation, the primary second response occurring from about four hours to about eight hours post-exposure to ultraviolet radiation, and/or the primary third response occurring from about 16 hours to about 24 hours post-exposure to ultraviolet radiation. The response comprises an increase or decrease in expression level relative the expression in a control cell not exposed to ultraviolet radiation. For these embodiments, the response is either the induced group response or the repressed group response.

In yet another embodiment, the invention provides a method for detecting exposure of a cell to ultraviolet radiation comprising measuring the levels of a plurality of RNA molecules in the cell, wherein the response, i.e., a pattern of expression, is established and the pattern indicates that the cell was exposed to ultraviolet radiation. In this embodiment, the response is the altered expression of at least one of the following: the secondary first response group, the secondary second response group, and the secondary third response group.

In some embodiments thereof, the response comprises the modulated expression of at least one, or at least two, or at least three, or at least four, or at least five, or at least six, or at least seven, or at least eight, or at least nine, or at least ten nucleic acid molecules, each of which is at least 90%, at least 91%, at least 92%, at least 93%, at least 94%, at least 95%, at least 96%, at least 97%, at least 98%, at least 99% or 100% identical at the nucleotide sequence level to a polynucleotide sequence from the secondary first response group, the secondary second response group, and/or the secondary third response group.

The invention also provides a method to detect exposure of a cell to ultraviolet radiation comprising measuring the levels of a plurality of RNA molecules in the cell by expression array analysis. Expression array analysis comprises isolating RNA from the cell post-ultraviolet radiation exposure, creating a test expression array through nucleic acid hybridization between a labeled probe that is complementary to the RNA, and an expression array substrate, analyzing the test expression array to create a test expression array data set, and comparing the test expression array data set to a control expression array data set to identity alterations in the expression level. The levels of the plurality of RNA molecules are then analyzed to establish a response pattern of the cell, wherein exposure of the cell to ultraviolet radiation is indicated by the response pattern comprising at least one of the primary first response group, the primary second response group, and/or the primary third response group.

In this method, the cellular response is sometimes characterized by the first response occurring from about 05 to about two hours post-exposure to ultraviolet radiation, the second response occurring from about four to about eight hours post-exposure to ultraviolet radiation, and the third response occurring from about 16 to about 24 hours post-exposure to ultraviolet radiation. The response comprises an increase in expression level or a decrease in expression level.

Another aspect of the invention provides methods for detecting exposure of a cell to ultraviolet radiation. The method comprises measuring a plurality of protein molecules in the cell for at least one time point, wherein a pattern of protein expression is established and the pattern is indicative of ultraviolet radiation exposure. In various embodiments thereof, this pattern of expression comprises a first response, a second response, and/or a third response. In one embodiment thereof, the first response is the tertiary first response previously described above; the second response is the tertiary second response previously described above; and the third response is the tertiary third response previously described above. The expression pattern is the tertiary first response, the tertiary second response group, or the tertiary third response group; the tertiary first response group and the tertiary second response group; the tertiary first response group and the tertiary third response group; the tertiary second response group and the tertiary a third response group; or the tertiary first response group, the tertiary second response group, and the tertiary third response group.

In another embodiment, the method for detecting exposure of a cell to ultraviolet radiation comprises measuring the levels of a plurality of protein molecules in the cell for at least one time point, wherein a pattern of expression is established and the pattern is indicative of ultraviolet radiation exposure. In various embodiments thereof, the first response is the quaternary first response previously described above; the second response is the quaternary second response previously described above; and the third response is the tertiary third response previously described above. The pattern of expression is the quaternary first response group, the quaternary second response group, or the quaternary third response group; the quaternary first response group and the quaternary second response group; the quaternary first response group and the quaternary third response group; the quaternary second response group and the quaternary third response group; or the quaternary first response group, the quaternary second response group, and the quaternary third response group.

Preferably, the levels of a plurality of protein molecules are measured by enzyme-linked immunosorbent assays (ELISAs). In other embodiments of the invention, the polypeptides encoded by the gene sequences identified by the invention as ultraviolet radiation-regulated may be detected and quantified by any of a number of methods well known to those skilled in the art These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), immunofluorescence assays, Western blotting, and the like.

As known by those skilled in the art, an ELISA assay (e.g., Coligan, et al. (1991) *Curr. Protocols Immunol.* 1(2):Chapter 6) includes preparing an antibody (preferably a monoclonal antibody) specific to a target protein. In addition, a reporter antibody is prepared against the monoclonal antibody. To the reporter antibody is attached a detectable reagent such as radioactive isotope, fluorescent tag or enzyme (e.g., horseradish peroxidase). A sample is removed from a host and incubated on a solid support (e.g. a polystyrene dish) that binds the proteins in the sample. Any free protein binding sites on the dish are then covered by incubating with a non-specific protein like bovine serum albumen. Next, the monoclonal antibodies attach to any target proteins attached to the polystyrene dish. All unbound monoclonal antibody is washed away with buffer. The reporter antibody is then placed in the dish resulting in binding of the reporter antibody to any monoclonal antibody bound to the target protein. Unattached reporter antibody is then washed out of the dish The detectable reagent is then detected to identify the protein of interest bound by the antibody specific for the target protein. For example, when horseradish peroxidase is used as a detectable label, peroxidase substrate is added to the dish, and the amount of color developed in a given time period is a measurement of the amount of target protein present in a given volume of sample when compared against a standard curve.

Other assays useful for the measurement of protein levels include: radioimmunoassays, competitive-binding assays, Western blot analysis, and "sandwich" assays. In one representative sandwich assay, the target protein is passed over a solid support and binds to target-specific antibody attached to the solid support. A second antibody is then bound to the target protein. A third antibody which is labeled and specific to the second antibody is then passed over the solid support and binds to the second antibody and an amount target protein can then be indirectly quantified. In a competition assay, antibodies specific to the target protein are attached to a solid support and labeled target protein and a sample derived from the host are passed over the solid support. The amount of label detected, for example, by liquid scintillation chromatography can be correlated to a quantity of target protein in the sample.

The term "quantifying" when used in the context of quantifying transcription levels of a gene can refer to absolute or relative quantification. Absolute quantification may be accomplished by inclusion of known concentration(s) of one or more target nucleic acids and referencing the hybridization intensity of unknown nucleic acids with the known target nucleic acids (e.g., through generation of a standard curve). Alternatively, relative quantification can be accomplished by comparison of hybridization signals between two or more genes, or between two or more treatments, to quantify the changes in hybridization intensity and, by implication, the changes in the transcription level. A similar approach may be taken with protein quantification.

In a further aspect, the invention provides a method for detecting exposure of a cell to ultraviolet radiation by screening for a response of the cell to ultraviolet radiation exposure, the response being an altered pattern of expression determined by gene expression array analysis. The method comprises: (1) measuring the levels of a plurality of RNA molecules in the cell for at least one time point after ultraviolet radiation exposure to establish a test pattern of expression; and (2) comparing the test pattern of expression to the response of a cell to ultraviolet radiation exposure. If the pattern of expression for the cell is substantially similar to the response of the cell to ultraviolet radiation, the cell was exposed to ultraviolet radiation.

In a further aspect, the invention provides a method for detecting exposure of a cell to ultraviolet radiation by screening for a response of the cell to ultraviolet radiation exposure, the response being an altered pattern of expression determined by gene expression array analysis. The method comprises: (1) measuring the levels of a plurality of proteins in the cell for at least one time point after ultraviolet radiation exposure to establish a test pattern of expression; and (2) comparing the test pattern of expression to the response of a cell to ultraviolet radiation exposure. If the pattern of expression for the cell is substantially similar to the response of the cell to ultraviolet radiation, the cell was exposed to ultraviolet radiation.

B. Screening Methods for the Identification of Compounds that Modulate a Response of a Cell to Ultraviolet Radiation Exposure The invention includes a screening method for the detection of a compound that modulates a response of a cell to ultraviolet radiation exposure. This screening method comprises contacting a cell with a compound, exposing the cell to ultraviolet radiation to induce a response of the cell to ultraviolet radiation exposure, and measuring the levels of a plurality of RNA molecules in the cell after ultraviolet radiation exposure. Any change in the first, second, and/or third response to ultraviolet radiation indicates that the compound modulates the response of the cell to ultraviolet radiation exposure. Measurement of the levels of a plurality of RNA molecules may be done at one or several time points post-ultraviolet radiation exposure.

The term "compound" includes both organic molecules and inorganic molecules. The term compound also encompasses proteins, nucleic acid molecules, carbohydrates, lipids, and combinations thereof.

As one skilled in the art recognizes, there are many ways in which a cell may be "contacted" with a compound. Contact may be in vivo or in vitro. For example, the compound may be placed in a carrier liquid medium, such as phosphate buffered saline (PBS) or tissue culture media, and when cells are incubated in this media, the compound contacts or touches the cell. Alternatively, contact may be through a cream or a gel which is applied topically.

The cell contacted with the compound is a cell in a culture, a cell in an isolated tissue, or a cell in an organism, such as a skin cell (epidermal or dermal). Alternatively, a cell may be selected from the group consisting of a keratinocyte, a Langerhans cell a melanocyte, and a fibroblast cell. The cell is exposed to ultraviolet radiation consisting of ultraviolet radiation energy at a wavelength in the range of about 220 nm to about 440 nm, ultraviolet radiation energy at a wavelength of about 290 nm to about 320 nm, ultraviolet radiation energy at a wavelength of about 320 to about 440 nm, or a total ultraviolet radiation energy exposure in the range of about 0.2 mJ/cm$^2$ to about 40 mJ/cm$^2$.

The response of the cell is characterized by at least one of the following: a primary first response occurring from about 0.5 hours to about two hours post-exposure to ultraviolet radiation; a primary second response occurring from about four to about eight hours post-exposure to ultraviolet radiation; and a primary third response occurring from about 16 to about 24 hours post-exposure to ultraviolet radiation. The pattern of expression comprises an increase or decrease in expression level. For these embodiments, the response comprises either the induced response or the repressed response, or both the induced and the repressed response.

Preferably, the screening method provides a compound that modulates the response of a cell to ultraviolet radiation in which the response is the altered expression of at least one, or at least two, or at least three, or at least four, or at least five, or at least six, or at least seven, or at least eight, or at least nine, or at least ten nucleic acid molecules, each of which is at least 90%, or at least 91%, or at least 92%, or at least 93%, or at least 94%, or at least 95%, or at least 96%, or at least 97%, or at least 98%, or at least 99% or 100% identical at the nucleotide sequence level to a polynucleotide sequence from at least the secondary first response group, the secondary second response group, and/or the secondary third response group.

Preferably, the screening method measures the levels of the plurality of RNAs by an expression array analysis. This analysis includes isolating RNA from the cell for at least one time point post-ultraviolet radiation exposure, creating a test expression array through nucleic acid hybridization between the labeled probe that is complementary to the isolated RNA and an expression array substrate, and analyzing the test expression array to create a test expression array data set. The test and control data sets are then compared to identify a modulation of the response of the cell exposed to ultraviolet radiation. The modulation indicates that the compound modulates the response of a cell exposed to ultraviolet radiation. The types of cells exposed to the radiation, as well as the ultraviolet radiation energy level of the radiation, are the same as those described above.

In some embodiments, the cellular response is characterized by the secondary first response occurring from about 0.5 hours to about two hours post-exposure to ultraviolet radiation, the secondary second response occurring from about four hours to about eight hours post-exposure to ultraviolet radiation, and the secondary third response occurring from about 16 hours to about 24 hours post-exposure to ultraviolet radiation. Other various embodiments of the method described above include methods wherein "altered expression" comprises an increase in expression level; or wherein "altered expression" comprises a decrease in expression level.

In an alternative aspect, the invention provides another method for detecting exposure of a cell to ultraviolet radiation. This method comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; a second response comprising an altered pattern of expression of at least one polynucleotide selected from the group consisting of a nucleic acid molecule encoding a secreted growth factor, a nucleic acid molecule encoding a cytokine, and a nucleic acid molecule encoding a chemokine; and a third response comprising an altered pattern of expression of at least one polynucleotide selected from the group consisting of a nucleic acid molecule encoding an actin-binding protein, a nucleic acid molecule encoding a desmosomal protein, and a nucleic acid molecule encoding a tubulin protein.

In embodiments of the method thereof, the cell is a cell in a culture, tissue, or organism such as skin cell (epidermal or dermal). For example, the cell is a keratinocyte, a Langerhans cell, a melanocyte, or a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also provides an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

The invention also provides another method for detecting exposure of a cell to ultraviolet radiation. This method comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

In yet another aspect of the invention, a method is provided for detecting exposure of a cell to ultraviolet radiation comprising measuring the levels of a plurality of RNA molecules in the cell by expression array analysis. This method comprises isolating RNA from the cell post ultraviolet radiation exposure, creating a test expression array through nucleic acid hybridization between a labeled probe complementary to the RNA and an expression array substrate. An analysis of the levels of the plurality of RNA molecules in the cell establishes an expression response pattern of the cell. Exposure of the cell to ultraviolet radiation is indicated by an altered pattern of expression comprising the following: (1) a first response comprising an altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; (2) a second response comprising an altered pattern of expression of at least one polynucleotide selected from the group consisting of a nucleic acid molecule encoding a secreted growth factor, a nucleic acid molecule encoding a cytokine, and a nucleic acid molecule encoding a chemokine; and (3) a third response comprising an altered pattern of expression of at least one polynucleotide selected from the group consisting of a nucleic acid molecule encoding an actin-binding protein, a nucleic acid molecule encoding a desmosomal protein, and a nucleic acid molecule encoding a tubulin protein.

In embodiments of the method thereof, the cell is a cell in a culture, tissue, or organism such as skin cell (epidermal or dermal). For example, the cell is a keratinocyte, a Langerhans cell, a melanocyte, or a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response.

In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

In another embodiment, the method thereof comprises measuring the levels of a plurality of RNA molecules in the cell for at least one time point, wherein an altered pattern of expression is established and is indicative of ultraviolet radiation exposure. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In an alternative aspect, the invention provides another method for detecting exposure of a cell to ultraviolet radiation. This method comprises measuring the levels of a plurality of proteins in the cell for at least one time point, wherein an altered pattern of expression is established and is indicative of ultraviolet radiation exposure. This pattern comprises a first response comprising an altered pattern of expression of at least one protein selected from the group consisting of a transcription factor protein, a signal transducing protein, and a mitochondrial protein; a second response comprising an altered pattern of expression of at least one protein selected from the group consisting of a secreted growth factor, a cytokine, and a chemokine; and a third response comprising an altered pattern of expression of at least one protein selected from the group consisting of an actin-binding protein, a desmosomal protein, a tubulin protein, and a cornified envelope protein.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in protein level. Thus, in one particular embodiment, the expression level of a member of the first response group, and/or second response group, and/or third response group increases. In another embodiment thereof, the expression level of a member of the first response group, and/or second response group, and/or third response group decreases.

In another embodiment, the invention provides another method for detecting exposure of a cell to ultraviolet radiation. This method comprises measuring the levels of a plurality of protein molecules in the cell for at least one time point, wherein an altered pattern of expression is established and is indicative of ultraviolet radiation exposure. This pattern comprises a first response comprising an altered pattern of expression of at least one protein that is at least 90% identical to a polypeptide encoded by a polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group.

In various embodiments related to creation of a protein expression profile of a cell exposed to ultraviolet radiation, ELISA is used to measure the levels of the plurality of proteins expressed in the presumptively exposed cell.

Another aspect of the invention relates to a screening method for the detection of a compound that modulates a response of a cell to ultraviolet radiation exposure. The method comprises contacting the cell with the compound and exposing the cell to ultraviolet radiation to induce the response, the response being an altered pattern of expression comprising the following: (1) a first response comprising the altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein; (2) a second response comprising the altered pattern of expression of at least one polynucleotide selected from the group consisting of a nucleic acid molecule encoding a secreted growth factor, a nucleic acid molecule encoding a cytokine, and a nucleic acid molecule encoding a chemokine; and (3) a third response comprising the altered pattern of expression of at least one polynucleotide selected from the group consisting of a nucleic acid molecule encoding an actin-binding protein, a nucleic acid molecule encoding a desmosomal protein, a nucleic acid molecule encoding a tubulin protein, a nucleic acid molecule encoding a cornified envelope protein; and measuring the levels of a plurality of RNA molecules in the cell for at least one time point after ultraviolet radiation exposure. A change in the altered pattern of expression of the first response, the second response, and/or the third response indicates that the compound modulates the response of the cell to ultraviolet radiation exposure.

In one embodiment of the method thereof, the cell is contacted with the compound in vitro.

In another embodiment of the method thereof, the cell is contacted with the compound in vivo. In other embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

The invention also comprises an embodiment of the method thereof wherein altered expression comprises an increase or decrease in RNA level. Thus, in one particular embodiment, the expression level of a member of the first response group, and/or second response group, and/or third response group increases. In another embodiment thereof, the expression level of a member of the first response group, and/or second response group, and/or third response group decreases.

Another aspect of the invention relates to a screening method for the detection of a compound that modulates a response of a cell to ultraviolet radiation exposure. The method comprises contacting the cell with the compound and exposing the cell to ultraviolet radiation to induce the response, the response being an altered pattern of expression. This pattern comprises a first response comprising an altered pattern of expression of at least one polynucleotide selected from the group consisting of the secondary first response group; a second response comprising an altered pattern of expression of at least one polynucleotide selected from the group consisting of the secondary second response group; and a third response comprising an altered pattern of expression of at least one polynucleotide selected from the group consisting of the secondary third response group. The levels of a plurality of RNA molecules in the cell are measured for at least one time point after ultraviolet radiation exposure, and a change in the altered pattern of expression of the first response group, the second response group, and/or the third response group indicates that the compound modulates the response of the cell to ultraviolet radiation exposure.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In yet another aspect of the invention, a screening method for the detection of a compound that modulates a response of a cell to ultraviolet radiation exposure. The method comprises contacting the cell with the compound and exposing the cell to ultraviolet radiation to induce the response; the response being an altered pattern of expression. This method comprises isolating RNA from the cell post ultraviolet radiation exposure; creating a test expression array through nucleic acid hybridization between a labeled probe complimentary to the RNA and an expression array substrate; analyzing the test expression array to create a test expression array data set; and comparing the test expression array data set to the response of the cell exposed to ultraviolet radiation in the absence of the drug, the response being an altered pattern of expression comprising the following a primary first response group, a primary second response group, and a primary third response group. A change in the altered pattern of expression of the primary first response, the primary second response, and/or the primary third response indicates that the compound modulates the response of the cell to ultraviolet radiation exposure.

In embodiments of the method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

Other embodiments of the method thereof are included in the invention. For example, in one embodiment, cell contact with the compound is topical contact, or in another embodiment, the compound modulates the cellular response by inhibiting ultraviolet radiation-induced RNA expression, or in another embodiment, the compound inhibits the ultraviolet radiation-repressed expression. In these latter two embodiments, ultraviolet radiation-induced expression is the "induced response group" and ultraviolet radiation-repressed expression is the "repressed response group."

Another aspect of the invention relates to a screening method for the detection of a compound that modulates a response of a cell to ultraviolet radiation exposure. The screening method comprises contacting the cell with the compound and exposing the cell to ultraviolet radiation to induce the response, the response being an altered pattern of expression comprising the following: (1) a tertiary first response group, (2) a tertiary second response group, and (3) a tertiary third response group; and measuring the levels of a plurality of RNA molecules in the cell for at least one time point after ultraviolet radiation exposure. A change in the altered pattern of expression of the tertiary first response, the tertiary second response, and/or the tertiary third response indicates that the compound modulates the response of the cell to ultraviolet radiation exposure.

In various embodiments of the screening method thereof, the cell is contacted with the compound in vitro or in vivo. In other embodiments of the screening method thereof, the cell is a skin cell (epidermal or dermal) or the cell is selected from the group consisting of a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the screening method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In various embodiments related to screening method thereof, ELISA is used to measure the levels of the plurality of proteins in a cell in determining the response of the cell to ultraviolet radiation in the presence and absence of the compound.

Another aspect of the invention relates to a screening method for the detection of a compound that modulates a response of a cell to ultraviolet radiation exposure. The screening method comprises contacting the cell with the compound and exposing the cell to ultraviolet radiation to induce the response, the response being an altered pattern of expression comprising the following: (1) a quaternary first response group; (2) a quaternary second response group; and (3) a quaternary third response group; and measuring the levels of a plurality of RNA molecules in the cell for at least one time point after ultraviolet radiation exposure. A change in the altered pattern of expression of the quaternary first response, the quaternary second response, and/or the quaternary third response indicates that the compound modulates the response of the cell to ultraviolet radiation exposure.

In various embodiments of the screening method, the cell is contacted with the compound in vitro or in vivo. The cell is a cell in a culture, tissue, or organism, such as skin cell (epidermal or dermal). The cell may be a keratinocyte, a Langerhans cell, a melanocyte, and a fibroblast cell. Embodiments of the method also vary by the wavelength of ultraviolet radiation and/or the total amount of ultraviolet radiation to which the cell is exposed. For example, in various embodiments, the ultraviolet radiation exposure comprises ultraviolet radiation energy at a wavelength in the range of about 220 nm to about 440 nm; or the ultraviolet radiation exposure comprises ultraviolet radiation energy at a wavelength of about 290 nm to about 320 nm; or the ultraviolet radiation exposure comprises ultraviolet radiation energy at a wavelength in the range of about 320 nm to about 440 nm; or the ultraviolet radiation exposure comprises a total ultraviolet radiation energy exposure in the range of about 0.2 mJ/cm$^2$ to about 40 mJ/cm$^2$.

Other embodiments of the screening method thereof vary according to the time period post-ultraviolet radiation exposure defining the first response, second response, and third response. In one embodiment, the first response is from about 0.5 hours to about two hours post-exposure to ultraviolet radiation. In another embodiment, the second response is from about four hours to about eight hours post-exposure to ultraviolet radiation. In another embodiment, the third response is from about 16 hours to about 24 hours post-exposure to ultraviolet radiation. In another embodiment, the first response is from about 0.5 hours to about two hours post-exposure to ultraviolet radiation, the second response is from about four hours to about eight hours post-exposure to ultraviolet radiation, and the third response is from about 16 hours to about 24 hours post-exposure to ultraviolet radiation.

In various embodiments related to screening method thereof, ELISA is used to measure the levels of the plurality of proteins in a cell in determining the response of the cell to ultraviolet radiation in the presence and absence of the compound.

Another aspect of the invention provides a screening method for the detection of a compound that simulates the response of a cell to ultraviolet radiation exposure, comprising: contacting the cell with the compound; measuring a level of at least one RNA molecule in the contacted cell; and determining that the level of at least one RNA molecule in the cell after exposure to the compound is substantially similar to the level of the RNA found in the cell in response to ultraviolet radiation exposure, the response of the cell to ultraviolet radiation exposure being characterized by altered expression of the following: a primary first response group, a prima second response group, and a primary third response group. A determination that the level of expression of at least one RNA molecule is substantially similar to the altered expression found for the RNA molecule in the primary first response, the primary second response, or the primary third response indicates that the compound simulates exposure of the cell to ultraviolet radiation.

Another aspect of the invention provides a screening method for the detection of a compound that simulates the response of a cell to ultraviolet radiation exposure, comprising: contacting the cell with the compound; measuring a level of at least one RNA molecule in the contacted cell; and determining that the level of at least one RNA molecule in the cell after exposure to the compound is substantially similar to the level of the RNA found in the cell in response to ultraviolet radiation exposure, the response of the cell to ultraviolet radiation exposure being characterized by altered expression of the following: a secondary first response group, a secondary second response group, and a secondary third response group. A determination that the level of expression of at least one RNA molecule is substantially similar to the altered expression found for the RNA molecule in the secondary first response, the secondary second response, or the secondary third response indicates that the compound simulates exposure of the cell to ultraviolet radiation.

Another aspect of the invention provides a screening method for the detection of a compound that simulates the response of a cell to ultraviolet radiation exposure, comprising: contacting the cell with the compound; measuring a level of at least one protein in the contacted cell; and determining that the level of at least one protein in the cell after exposure to the compound is substantially similar to the level of the protein found in the cell in response to ultraviolet radiation exposure, the response of the cell to ultraviolet radiation exposure being characterized by altered expression of the following: a tertiary first response group, a tertiary second response group, and a tertiary third response group. A determination that the level of expression of at least one protein is substantially similar to the altered expression found for the protein in the tertiary first response group, the tertiary second response group, or the tertiary third response group indicates that the compound simulates exposure of the cell to ultraviolet radiation.

Another aspect of the invention provides a screening method for the detection of a compound that simulates the response of a cell to ultraviolet radiation exposure, comprising: contacting the cell with the compound; measuring a level of at least one protein in the contacted cell; and determining that the level of at least one protein in the cell after exposure to the compound is substantially similar to the level of the protein found in the cell in response to ultraviolet radiation exposure, the response of the cell to ultraviolet radiation exposure being characterized by altered expression of the following: a quaternary first response group, a quaternary second response group, and a quaternary third response group. A determination that the level of expression of at least one protein is substantially similar to the altered expression found for the protein in the quaternary first response group, the quaternary second response group, or the quaternary third response group indicates that the compound simulates exposure of the cell to ultraviolet radiation.

In a further aspect, the invention provides a screening method for the detection of a compound that modulates a response of a cell to ultraviolet radiation exposure, the response being an altered pattern of expression determined by gene expression array analysis. The method comprises contacting the cell with the compound; exposing the cell to ultraviolet radiation to induce the response; and measuring the levels of a plurality of RNA molecules in the cell for at least one time point after ultraviolet radiation exposure by gene array expression analysis. A change in the response of the cell to ultraviolet radiation exposure indicates that the compound modulates the response of the cell to ultraviolet radiation exposure.

In a further aspect, the invention provides a screening method for the detection of a compound that modulates a response of a cell to ultraviolet radiation exposure, the response being an altered pattern of expression determined by gene expression array analysis. The method comprises contacting the cell with the compound; exposing the cell to ultraviolet radiation to induce the response; and measuring the levels of a plurality of proteins in the cell for at least one time point after ultraviolet radiation exposure by gene array expression analysis. A change in the response of the cell to ultraviolet radiation exposure indicates that the compound modulates the response of the cell to ultraviolet radiation exposure.

C. Therapeutic Methods

The invention provides therapeutic methods for the treatment or prevention of premature aging of the skin and of skin cancers and other disorders of an individual. The ultraviolet radiation-regulated nucleic acid molecules and proteins, according to the invention, may be used in the design of such therapeutics for an individual. As used herein, the term "individual" refers to a mammal, and more preferably refers to a human.

In one embodiment of the invention, therapeutic treatment is accomplished through known gene therapy techniques. Gene delivery vehicles suitable for gene therapy applications are well known to those skilled in the art. For example, a gene delivery vehicle may preferably be a viral vector and, more preferably, a retroviral, an adenoviral, an adeno-associated viral (AAV), a herpes viral, or an alphavirus vector. The viral vector can also be an astrovirus, a coronavirus, a orthomyxovirus, a papovavirus, a paramyxovirus, a parvovirus, a picornavirus, a poxvirus, or a togavirus viral vector (Jolly (1994) *Cancer Gene Ther.* 1:51–64; Kimura (1994) *Hum. Gene Ther.* 5:845–852; Connelly (1995) *Hum Gene Ther.* 6:185–193; and Kaplitt (1994) *Nat. Genet.* 6:148–153).

Delivery of the gene therapy constructs of this invention into cells is not limited to the above-mentioned viral vectors. Other delivery methods and media may be employed such as, for example, nucleic acid expression vectors, polycationic condensed DNA linked or unlinked to killed adenovirus alone (e.g., see Curiel (1992) *Hum Gene Ther:* 3:147–154); ligand linked DNA (e.g., see, Wu (1989) *J. Biol. Chem.* 264:16985–16987); deposition of photopolymerized hydrogel materials, hand-held gene transfer particle gun (e.g., U.S. Pat. No. 5,149,655); ionizing radiation (e.g., U.S. Pat. No. 5,206,152 and PCT Patent Publication No. WO 92/11033); or nucleic charge neutralization or fusion with cell membranes. Additional approaches are described in Philip ((1994) *Mol. Cell. Biol.* 14:2411–2418) and in Woffendin ((1994) *Proc. Natl. Acad. Sci. (USA)* 91:1581–1585).

Briefly, the sequence of interest can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, as described in Wu et al (*J. Biol. Chem.* (1987) 262:4429–4432), insulin as described in Hucked (*Biochem Pharmacol.* (1990) 40:253–263), galactose as described in Plank (*Bioconjugate Chem.* (1992) 3:533–539), lactose, or transferrin. Naked DNA may also be employed. Exemplary naked DNA introduction methods are described in PCT Patent Publication No. WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm Liposomes that can act as gene delivery vehicles are described in U.S. Pat. No. 5,422,120, PCT Patent Publication Nos. WO 95/13796, WO 94/23697, and WO 91/144445, and EP Patent No. 524,968.

Potential target cells for gene therapy include skin cells (epidermal and dermal) and, more specifically, keratinocytes, Langerhans cells, melanocytes, and/or fibroblast cells. Gene therapy methods specific for epidermal cells and fibroblasts are known in the art (see Ohsawa et al. (2000) *J. Dermatol.* 27(4):244–251; Ina et al. (2000) *Acta. Derm. Venereol.* 80(1):10–13; Bevan et al. (1999) *Biotechnol. Genet. Eng. Rev.* 16:231–256; and Pellegrini et al. (1998) *Med. Biol. Eng. Comput.* 36(6):778–790).

The invention provides herein the identification of many nucleic acid and protein molecules regulated by ultraviolet radiation exposure. Any one or more of these molecules may be targeted for use in gene therapy protocols.

Among the nucleic acids regulated by ultraviolet exposure are genes which may be grouped into several distinct and clearly demarcated functional categories: 1) induced DNA metabolism and repair genes; 2) signal transducing proteins and transcription factors induced and/or suppressed at all experimental time points; 3) secreted growth factors, chemokines and cytokines at the intermediate time points; 4) induced and surpressed structural proteins; and 5) mitochondrial proteins, which are among the first induced in response to ultraviolet radiation exposure. In addition, ultraviolet radiation regulates genes for proteins involved in the translation machinery, RNA processing, lipid, amino acid and urea metabolism, integral membrane and cell surface proteins, proteases and their inhibitors, and proteins that could not be classified into those categories, as well as several unidentified ESTs.

1) Proteins Involved in DNA Metabolism and Repair

One of the most notorious effects of ultraviolet radiation is DNA damage and the resulting mutagenesis as a result thereof. In mammalian cells, different DNA damaging agents activate different repair processes (e.g., Wang, et al (1998) *Cur. Opin. Cell. Biol.* 10(3):416); and Wang et al. (1998) *Curr. Opin. Cell. Biol.* 10:240–7)). Ultraviolet radiation-caused DNA lesions are repaired primarily by the nucleotide excision repair system (NER) (Lowndes, et al. (2000) *Curr. Opin. Genet. Dev.* 10:17–25; Batty et al. (2000) *Gene* 241:193–204). Ultraviolet radiation induces the expression of ERCC4, a protein essential for repair of DNA interstrand cross-links (Table 2). Several other repair enzymes are present in keratinocytes, but not further induced by ultraviolet radiation, including excision repair protein ERCC1, mismatch repair protein hmlh1, as well as XP-C, XP-Q, XP-E and XRCC1. Ultraviolet radiation also induces genes for several enzymes that produce building blocks for DNA synthesis, including guanylate kinase, nucleosidediphosphate kinase, cytidine deaminase and transaldolase. Similarly, ultraviolet radiation-induces the expression of the histones H2A.2, H2B.1, H2A.X, H1x, and H2A.Z, which may play a role in protecting nascent DNA from damage. Most of the DNA repair proteins are present in sufficient amounts in keratinocytes even before the ultraviolet radiation treatment, but cells produce more of the dNTPs and histones to build and protect the newly repaired DNA after ultraviolet radiation exposure.

Ultraviolet radiation regulates the expression of DNA damage-inducible proteins gadd45, cyclin G1 and BTG2. These proteins play a role in cell cycle arrest, which allows keratinocytes to repair their DNA, together with spermidine/spermine ni-acetyltransferase, and several growth controlling oncogenes (Jin, et al. (2000) *J. Biol. Chem.* 275:16602–16608; Cortes, et al. (2000) *Mol. Carcinog.* 27:57–64; van Lookeren Campagne, et al. (1998) *J. Neurosci. Res.* 53:279–296; and Alhonen et al. (1999) *Mol. Pharmacol.* 55:693–698). As expected, the regulation of these proteins is often complex. For example, cyclin G1 expression is suppressed at four and eight hours, but induced at 24 hours after ultraviolet radiation exposure (Table 2). Presumably, these proteins coordinate the DNA repair process with the cell cycle.

2) Signal Transducers and Transcription Factors

Signaling proteins regulated by ultraviolet radiation in keratinocytes have very complex patterns of regulation. Some signaling proteins are induced, others are suppressed, some are first induced and then suppressed, and for some just the opposite is the case. Reflecting the variety of processes affected by ultraviolet radiation, they may be grouped into several categories.

Cell surface receptors (Table 3), with the exception of the urokinase-type plasminogen receptor, are suppressed by ultraviolet radiation. These include IL-4-R, TNFαR, TGF-βIIR. T-cell receptor active β-chain, LDL receptor, the v-erbA related ear-2 receptor, cysteine-rich fibroblast growth factor receptor (CFR-1) and novel growth factor receptor. Receptor associated proteins are also generally suppressed. These include Fas-binding protein (DAXX), HM74, pSK1 interferon gamma receptor accessory factor-1, and SHB, which is an SH2 containing protein. An EGFR associated protein, BTG1 (Tob), is induced by ultraviolet radiation, while a close relative (BTG2 Job2, TIS21, PC3) is suppressed, although both are anti proliferative. In contrast, ligands to various receptors, growth factors and cytokines, are induced four and eight hours after illumination (see below).

Importantly, ultraviolet radiation regulates about a dozen of the small GTP-binding proteins and their associated factors (Table 3). Rad, a member of ras family, LyGDI, RGL2 and G(i) protein α subunit are induced by ultraviolet radiation at various time points, while ADP-ribosylation factors HARF1 and hARF6, Rab GDI, rab2 YPTI-related member of ras family (all involved in vesicular transport) and tuberin TSC2, which is a GAP factor, are all suppressed at various time points. Ultraviolet radiation also suppresses, at various time points, several less easily classified signaling proteins, including the progesterone receptor-associated immunophilin FKBP54 and α-4, a rapamycin-sensitive pathway protein, as well as two heat shock proteins, heat shock protein 40 and heat shock protein 70, and an HSP-associated protein (Table 3).

Most intracellular signaling processes involve protein phosphorylation and, therefore, protein kinases and phosphatases are among the regulated genes (Table 3). The dual specificity phosphatase CL100, which is the human homolog of murine MKPI that plays a role in shutting down the ultraviolet radiation-mediated signal transduction, is also induced by ultraviolet radiation (Hirsch et al. (1997) *J. Biol. Chem.* 272:4568–4575). Ultraviolet radiation induces at various time points three RING3 family proteins, MAPKAP kinase (3pK) and cystic fibrosis antigen, which is a protein kinase inhibitor. On the other hand, the following kinases are suppressed at various time points: G protein-coupled receptor kinase GRK6, Ser/Thr protein kinase (A-Raf-1), casein kinases CKI-α and CKII-α, ERK3, LIMK-2, testis-specific protein kinase α-subunit, H-pim1 and a raf related protein pks/a-raf. Also suppressed are the phosphatases PP2A,-Cα, PP1γ and PTP1.

Among the genes induced at early time points are several transcription factors (Table 3). The most highly induced in the first two hours are immediate early genes junB, junD, and c-fos, ETR101, A20 and GOS24 (a/k/a TTP, Nup475, Zfp36 and TIS11 (Hexiner SP, Forsdyke DRI)). Their induction is short-lived and by four hours most and, by 16 hours, all are either expressed to background levels, or even suppressed. junB, junD, and c-fos are genes encoding the AP1 family of proteins. These are accountable for inducing many of the known ultraviolet radiation-activated genes, such as matrix metalloproteases. AP1 proteins are activated by ultraviolet radiation in epidermis in vivo and may be responsible for the sun damage in humans. Their function is inhibited by retinoids. The skin-specific isoform of the retinoic acid receptor, RARγ is suppressed by ultraviolet radiation. Four transcription factors are first induced and then suppressed by ultraviolet radiation, Nup475 (a/k/a TTP, Zfp36 and TIS11), HRY, XBP-1 and in EGR 1 (a/k/a Krox-24), another immediate early gene.

The motif of increasing one and suppressing another member of an antagonistically coupled transcription pair, similar to AP1-RARγ, NFκB-IκB and C/EBPp-CHOP, is of note in the induction of MMI an inhibitor of c-Myc and strong and persistent suppression of c-Myc itself. This is consistent with the role of c-Myc in deregulating cell growth, promoting genomic instability, sensitizing to apoptosis, and inhibiting gadd34, gadd45 and gadd153, DNA damage induced growth arrest proteins (Amundson et al. (1998) *Oncogene*, 17:2149–54); Felsher et al. (1999) *Proc. Natl. Acad. Sci.* (*USA*), 96:3940–4; Pelengaris, et al. (2000) *Curr. Opin. Genet. Dev.*, 10:100–5). Epidermis-targeted over-expression of c-Myc causes benign but pre-malignant and extensive epidermal proliferation, which is not beneficial in the context of ultraviolet radiation induced DNA damage.

Ultraviolet radiation suppresses NFκB, while inducing the IκB-like protein. This is particularly interesting because NFκB transcription factor is activated by ultraviolet radiation. The suppression of its synthesis and induction of its inhibitor may serve to attenuate the initial ultraviolet radiation signal. This is similar to the induction of MKP1, a dual specificity kinase that attenuates the JNK pathway. Similarly, C/EBPβ is induced, while its inhibitors CHOP (GADD153) and C/EBPε are suppressed.

At the late time points, prominently induced are three of the components of RNA pol 11, namely the largest subunit, RP135 and RPB10, as well as taf1130 a TATA-box binding protein associated factor, priming the cells for enhanced transcription. On the other hand, transcription elongation factors ELL2 and SII are suppressed by ultraviolet radiation. Ultraviolet radiation also induces ALL-1 and PML-2, two transcription factors made oncogenic by translocations. Conversely, two homeobox proteins, TGIF and HB9 are suppressed.

Several additional transcription factors are suppressed by ultraviolet radiation, including ets-2, BTEB2, SRF, ZFY, ERF-2, HLH-1R21, HTF10, AREB6 and others. AP2, a transcription factor responsible for synthesis of keratinocyte basal cell markers, is suppressed by the ultraviolet radiation. Apparently, when responding to ultraviolet radiation, the keratinocytes abandon the basal cell phenotype and instead switch to an activated phenotype, more similar to wound-healing or psoriatic keratinocytes.

3) Secreted Polypeptides Growth Factors, Cytokines and Chemokines

In the intermediate response the most prominent group of regulated genes are secreted proteins, growth factors, cytokines and chemokines (Table 5). In particular, members of the IL-8 family are induced: IL-8, gro-a, gro-0, and MIP2-0 (Geiser et al. (1993) *J. Biol. Chem.* 268:15419–24; Kemeny et al. (1995) *Int. Arch. Allergy Immunol.* 106:351–6). These peptides are chemotactic and activating for neutrophils, basophils and macrophages and, presumably, play a role inviting inflammatory cells into ultraviolet radiation damaged tissue. Importantly, they also activate melanocytes, which may initiate tanning in response to ultraviolet radiation.

Heparin binding growth factor (HB-EGF) is induced, while amphiregulin (AR) is suppressed. Both are activators of the EGF receptor and, presumably, autocrine factors for keratinocyte activation. Additional secreted proteins, such as 14 kD lectin, apo-E and CTGF are also induced Also induced is SCYLP, a peptidyl-prolyl isomerase, which may play a role in maturation of collagens and other proline-rich extracellular matrix proteins implicated in photoaging.

The secreted peptides serve to alert the surrounding tissue that damage has occurred. The effects are paracrine, activating melanocytes, endothelial cells, neutrophils and fibroblasts, as well as autocrine, alerting keratinocytes themselves.

Several of the ultraviolet radiation-induced genes, including IL-8, have previously been shown to be inducible by interferon-γ (Fujisawa et al. (1997) *J. Interferon Cytokine Res.* 17:347–353; Aragane et al. (1997) *Proc. Natl. Acad. Sci.* (*USA*) 94:11490–11495). These genes are induced at later time points after ultraviolet irradiation and include p27, 17-kD/15-kD protein, IRF 7A, 1-81 gene, bPA28-β, interferon gamma receptor accessory factor-1 and STAT 5. These results may indicate a nexus between ultraviolet radiation and interferon-7 signaling.

4) Structural Proteins

Among the structural proteins regulated by ultraviolet radiation, prominent are cytoskeletal proteins, in particular actin binding proteins (ABPs), desmosomal components, and three tubulin subunits, as well as components of the cornified envelope, markers of keratinocyte differentiation (Table 4).

Actin affects the shape of the plasma membrane, allows cellular motility and maintains cell shape and polarity. To accomplish these tasks actin collaborates with approximately 60 different ABPs. The various ABPs work cooperatively or competitively with one another to aid in actin activity (Kreis and Vale, *Guidebook to the Cytoskeletal and Motor Proteins,* 2nd ed., New York: Oxford University Press (1999)). The ABPs induced early by ultraviolet irradiation are the genes encoding gelsolin and troponin. Gelsolin nucleates actin polymerization, but at high $Ca^{2+}$ concentrations it severs actin filaments, and is then released to allow the free actin ends to polymerize. Accordingly, gelsolin causes cytoplasmic streaming of large cells, a process that maintains an even distribution of metabolites throughout the cytoplasm and changes the cell shape. Mouse cells lacking gelsolin exhibit a deficiency in cell motility (Barkalow et al. (1996) *J. Cell. Biol.* 134:389–399; Witke et al. (1995) *Cell* 81:41–51). Liquefaction of the cell cortex by severing proteins also allows for the proper membrane contact and fusion of membrane-bound vesicles within the cell. Troponin, which is also activated by $Ca^{2+}$ binding, is one of the proteins that cause the shortening of muscle fibers in muscle cells.

ABP genes induced at the later time points include MacMARCKS, myosin light chain, Arp 2/3, filamin, tropomyosin, thymosin and smoothelin. MacMARCKS, induced four hours after illumination, is a homolog of MARCKS, which binds and cross links filamentous actin. MacMARCKS regulates actin structure during cell movement, phagocytosis, membrane trafficking and cell-cell adhesion. The myosin light chain can regulate the ATPase activity of myosin's heavy chain and is thus able to control the interaction of the myosin head with actin filaments. The entire myosin I protein moves vesicles along the actin filament, while myosin 11 slides the actin filaments past one another. The protein complex Arp2/3 nucleates actin filament formation, cross-links filaments into networks, and protects filament ends from depolymerization. Filamin cross-links actin filaments and causes them to form a gel. Tropomyosin binds along the length of actin filaments, increasing their strength and changing their affinity for other proteins. Thymosin binds to actin monomers, inhibits actin polymerization, and may play a role in preventing apoptosis (Niu et al. (2000) *Cell. Adhes. Commun.* 7:311–320).

In contrast to the induced genes, the gene encoding B-spectrin is suppressed by ultraviolet radiation in the early stages after illumination. B-spectrin is a component of spectrin, which provides rigidity and stability to the cell membrane by controlling the distribution of integral membrane proteins, and binds actin to hold it in place. Adducin expression is suppressed by ultraviolet radiation. Adducin caps and bundles actin and forms contacts between spectrin and actin.

The overall picture of the regulation of the cytoskeletal proteins by ultraviolet radiation shows an initial de-polymerization, softening of the actin cytoskeleton in the first two hours, which is followed by a re-polymerization of the actin filaments and reconstitution of the cytoskeletal network (Maekawa et al. (1996) *Clin. Exp. Immunol.* 105:389–396; Malorni, et al. (1994) *J. Photochem. Photobiol.* 26:265–270). Ultraviolet radiation also suppresses the expression of transgelin, a LIM protein and myosin heavy chain. In addition, tubulins Al, B and B2 and keratins K13 and K19 are induced, all at the later time points after illumination. K17 is already expressed at high levels in cultured keratinocytes, and further induction by ultraviolet radiation was not observed. Ultraviolet radiation, under the conditions used herein, does not appear to significantly regulate any other keratin.

The most strongly induced genes overall are keratinocyte differentiation markers, components of the cornified envelope. These include four of the small proline rich proteins SPRR1, 2A, 2B and 21, as well as involucrin, desmoglein III and S100 calcium-binding proteins A13 and A12. Only the small proline rich proteins were shown to be induced by ultraviolet radiation previously (Kartasova et al. (1988) *Mol. Cell. Biol.* 8:2195–2203; Gibbs et al. (1990) *Nucleic Acids Res.* 18:4401–4407). Of the epidermal differentiation markers, only the cornified envelope components are induced, while keratins and filaggrin are not. These proteins are all encoded in the epidermal marker locus on human chromosome 1, and are induced at later time points, i.e., 16 and 24 hours post-illumination. None of the differentiation markers appear to be suppressed by ultraviolet radiation. Apparently, one of the epidermal responses to ultraviolet radiation is enhancement of the stratum corneum production, which augments the dead, protective layer of skin.

5) Mitochondrial Proteins

Among the genes that are strongly induced immediately after ultraviolet radiation exposure are several mitochondrial proteins (Table 6). Specifically, cytochrome c-1 is induced in the first hour. At the 24 hour time point, its synthesis returns to the background levels, and is even suppressed. Cytochrome c oxidase subunits Vb, Vila-L, Vilb, and cytochrome b light chain are also induced early after the illumination. In contrast, OXA1 Hs, a cytochrome oxidase assembly protein, is suppressed. Several other mitochondrial proteins, including mitochondrial NADH dehydrogenase, mitochondrial ubiquinone-binding protein, mitochondrial ATP synthase, a mitochondrial ribosomal protein, and an electron transfer flavoprotein, are strongly induced. It appears that cells, upon illumination, sense a need for additional energy and induce mitochondrial proteins to address this need.

A further indication that ultraviolet radiation illumination leads to a requirement for additional energy comes from the fact that ultraviolet radiation induces several of the energy producing enzymes. These include α-enolase, creatine kinase-B, pyruvate dehydrogenase and a proton-ATPase-like protein. Conversely, gluconeogenic enzymes, phosphoenolpyruvate carboxykinase and gamma-aminobutyraldehyde dehydrogenase, as well as transporters for lactate and pyruvate and for glucose are suppressed. Moreover, enzymes for lipid synthesis are suppressed, including ATP-citrate lyase, squalene epoxidase, acyl-coenzyme A synthetase, stearoyl-cocnzyme-A desaturase and methyl sterol oxidase. Additionally, fatty acids omega-hydroxylase, cytochrome P-450HKV, is also suppressed at the earliest time point. Strong inhibition of lipid neogenesis seems in discrepancy with the induction of the cornified envelope proteins because both the lipid and the proteinaceous components contribute to the formation of stratum corneum.

The response of keratinocyte mitochondrial genes to ultraviolet radiation is quite different from the response of the mitochondrial genes in lymphoma cells to ionizing radiation (Voehringer, et al. (2000) *Proc. Natl. Acad. Sci. (USA)* 97:2680–2685). Comparing two cell lines that differ only in their responses to ionizing radiation, Voehringer et al. found that the resistant cell line expressed high levels of mitochondrial proteins fructose- 1,6-biphosphatase, VDAC, fatty acid binding proteins and uncoupling proteins. These are increased even further by the ionizing radiation treatment. While the highly expressed proteins seem to protect the resistant cells from apoptosis, the sensitive cells lacking these proteins are not protected and die. In the assays described herein, these proteins do not change significantly in response to ultraviolet radiation in keratinocytes. The keratinocytes, based on the ultraviolet radiation dose, may either survive or apoptose and increasing these proteins would predispose them to survive, which is a potentially dangerous response.

Mitochondrial proteins suppressed by ultraviolet radiation include aldehyde dehydrogenase 1, rhodanese (thiosulfate: cyanide sulfurtransferase), and UCP, a thermogenic uncoupling protein. These proteins are not immediately involved in energy production. Uroporphyrinogen synthetase is induced by LIV, while uroporphyrinogen decarboxylase, the enzyme degrading uroporphyrinogen, is suppressed, indicating that the mitochondria may require elevated levels of uroporphyrinogen and perhaps other Fe-binding proteins.

The changes in mitochondrial proteins are very important in epidermal response to ultraviolet radiation and probably have several functions. These include a burst of respiration proteins to provide additional energy needed to cope with the ultraviolet radiation-caused damage, and an increase of enzymes that remove reactive oxygen species as a detoxifying process. In addition, given the mitochondrial role in controlling apoptosis, irradiated keratinocytes may prepare their mitochondria to initiate apoptosis.

Ultraviolet radiation elicits induction of several antioxidant-detoxifying proteins. Specifically, metallothionein and copper transport protein HAH1, two thiol-specific antioxidant proteins, as well as aldehyde reductase and aldehyde dehydrogenase 6 are induced (Hanada et al. (1998) *J. Invest. Dermatol.* 111:582–585). On the other hand, isoforms of MT, metallothionein 1 L and aldehyde dehydrogenase, ALDI-18 are specifically suppressed. HHCPA78 homolog, a thioredoxin interacting protein, is suppressed with thioredoxin reductase and gamma-glutamylcysteine synthetase.

The following examples illustrate the preferred modes of making and practicing the present invention but are not meant to limit the scope of the invention since alternative methods may be utilized to obtain similar results.

EXAMPLES

Example 1

Identification of Gene and Protein Sequences Regulated by Exposure to Ultraviolet-B Radiation A. Keratinocyte Culture and Ultraviolet-B Radiation Cultures of epidermal keratinocytes from human foreskin were initiated using 3T3 feeder layers as described (Simon, et al. (1984) *Cell* 36:827–834) and then stored frozen in liquid $N_2$. Once thawed, the keratinocytes were grown without feeder cells in defined serum-free keratinocyte growth medium (KGM) supplemented with 0.05 g/l bovine pituitary extract, 5 ng/ml epidermal growth factor, and 1% penicillin/streptomycin (KGM from Gibco-BRL (Rockville, Md.). The keratinocytes were maintained at 37° C., in 5% $CO_2$. The medium was replaced every two days. The cells were expanded through three passages for the experiments. They were trypsinized with 0.025% trypsin, which was neutralized with 0.5 mg/ml trypsin inhibitor. Serum was avoided because it can promote keratinocyte differentiation. For all experiments, third-passage keratinocytes were used one day after reaching confluence.

For ultraviolet-B radiation, the Stratagene 2000 illuminator specially equipped with FG15T light bulb was used (Strategene, LaJolla, Calif.). This light produces maximum output in the ultraviolet-B radiation wavelength range. The medium was removed from the cell cultures, and keratinocytes were irradiated in open dishes with eight $mJ/cm^2$. Immediately after the ultraviolet-B radiation exposure, the same medium was replaced to the cultures. Control cells were subjected to the identical procedure but were only sham irradiated.

The protocol was chosen for two reasons: first, confluent keratinocytes more closely resemble skin than subconfluent ones; and second, nearly identical conditions from culture to culture were reliably and reproducibly achieved. The dose of ultraviolet-B radiation exposure was optimized by treating keratinocyte cultures with increasing amounts of radiation, replacing the medium and determining the cell viability 24 hours after the treatment. A dose of ultraviolet-B radiation was chosen so that at least 10%, but less that 20%, of cells were killed by ultraviolet-B radiation exposure; specifically, 8 $J/M^2$ was determined to be optimal.

Keratinocyte cultures were irradiated with a single 8 $J/M^2$ dose of ultraviolet-B radiation and the cells were harvested 0.5, 1, 2, 4, 8, 16, and 24 hours later. As controls, mock-irradiated cells were harvested 1, 4, 8, 16, and 24 hours after the treatment. The one hour mock-irradiated culture was then used as control for the 0.5, 1 and 2 hour time points, while all the later time points had cognate controls.

B. Isolation of Total RNA and Probe Synthesis

Cells were harvested by scraping the culture dish. Kits from Qiagen (Chatsworth, Calif.) were used to prepare the RNA according to the manufacturer's protocols. Qiashredders were used to homogenize cell lysates with centrifugation at 1800 g for two minutes. RNA was extracted using RNeasy Midi Kit. DNA was removed with on-column DNAse digestion using Qiagen RNAses-free DNAse Set.

After the RNAs were prepared, but before they were used for gene array hybridization, the RNAs were tested in Northern blot hybridizations with a probe corresponding to the c-fos gene.

For Northern blotting, 10 $\mu g$ RNA was loaded on a 1.0% agarose-formaldehyde gel and run at 100 V for three to four hours. The RNA was transferred overnight to a nylon membrane (Amersham Life Science, Piscataway, N.J.) and cross-linked with the Stratalinker (Stratagene, LaJolla, Calif.). The probes for c-fos and IL-6 were synthesized using reverse transcription-PCR from keratinocyte RNA and the RT-PCR kit from Ambion (Austin, Tex.). Additional probes were derived from cDNA clones obtained from the American Type Culture Collection (ATCC, Manassas, Va.). Each clone was sequenced from both 5' and 3' ends to confirm its identity. The $^{32}p$ labeled probes were generated using [$^{32}P$] dCTP (3000 Ci/mmol Dupont (NEN, Boston, Mass.) and the Multiprime DNA labeling system (Amersham Pharmacia Biotech, Piscataway, N.J.) and purified using D-Salt Excellulose Plastic Desalting Columns (Pierce, Rockford, Ill.).

Hybridizations were performed using ExpressHyb solution (Clontech, Palo Alto, Calif.) at 68° C. for one hour. Membranes were washed with 2×SSC, 0.05% SDS solution, with continuous shaking three times for 30 minutes at room temperature, and with 0.1×SSC, 0.1% SDS at 50° C. for 40 minutes. The membrane was exposed to Kodak Toronto, Canada) BIOMAX MS film at −80° C., and radiographs were scanned and analyzed with MultiImagine Light Cabinet AlphaImagine 2000 documentation and analysis system (Alpha Innotech Corporation, San Leandro, Calif.). The RNA levels were normalized to glyceraldehyde-3-phosphate dehydrogenase (GAPDH) mRNA.

Figure 1B:
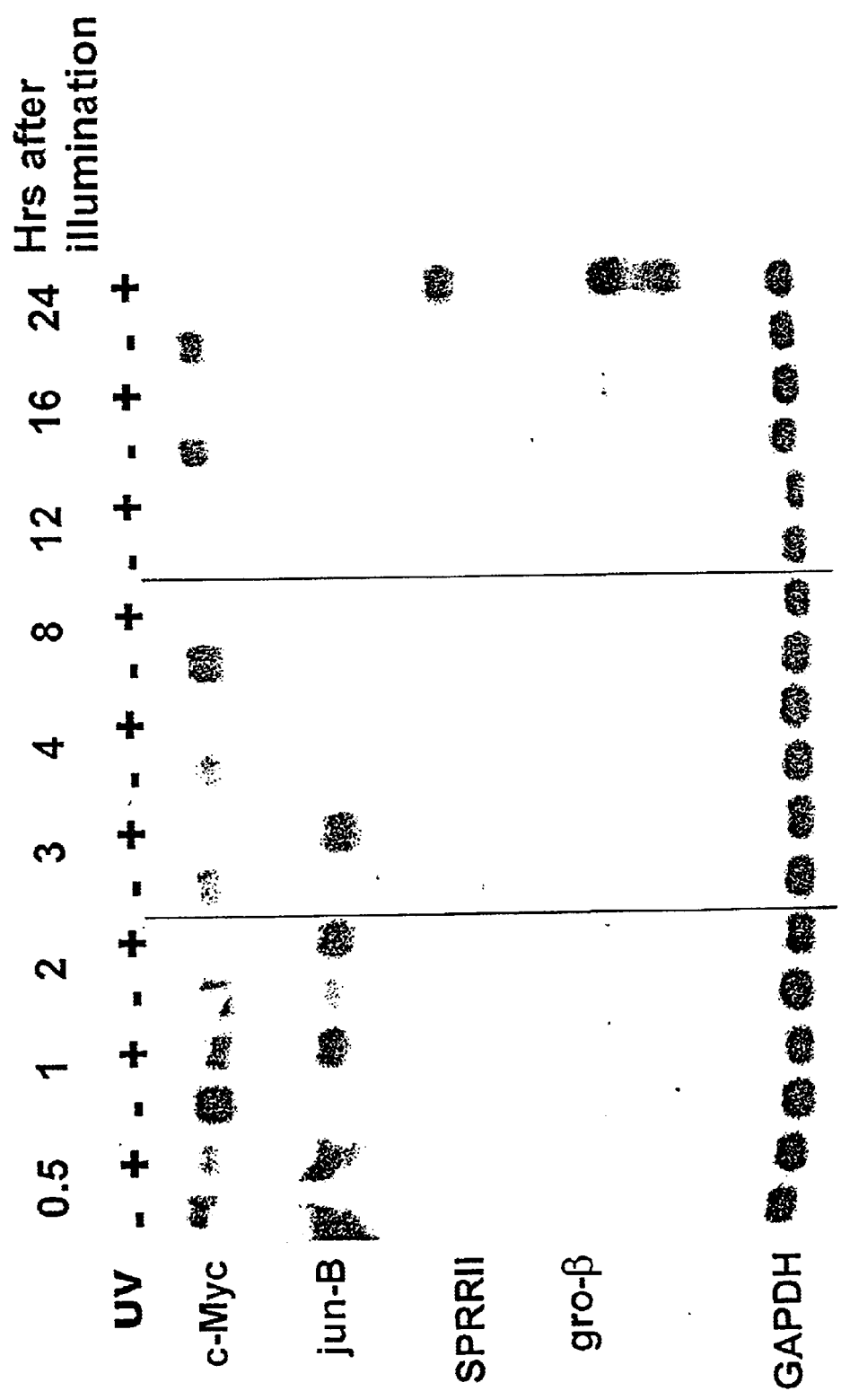
FIG. 1B is a representation of a Northern blot. The RNA samples were isolated from irradiated keratinocytes and harvested at 0.5, 1, 2, 4, 8, 16, 24 hours after ultraviolet irradiation. These RNA samples were hybridized to probes specific for c-Myc, jun-B, SPRRII, and gro-β RNAs, four RNA molecules that are ultraviolet radiation-regulated. Data obtained by Northern blot analysis closely correlate with the results obtained using expression array analysis. The GAPDH probe was used as a control to monitor the amount of RNA loaded in each lane.

As shown in FIG. 1A, appropriate induction of expression of c-fos gene was observed, which provided justification for using the RNA samples in expression array hybridization studies. Subsequently, to confirm the results from the arrays, Northern blots were used to examine the expression of the regulated genes (FIG 1B). A strong correlation between the array data and the blots for the genes shown was found.

For the synthesis of probe for use with the gene array, eight micrograms of total RNA were reverse transcribed, amplified and labeled as previously described (Mahadevappa et al. (1999) *J.A. Nature Biotechnol.* 17:1134–1136). As a result of the sequence of the primers used for reverse transcription, the resultant cDNA product contained an RNA polymerase promoter for use in the synthesis of cRNA probe to screen the gene array.

C. Gene Array Hybridization

Labeled cRNA was hybridized to the HU6800 array (Affymetrix Inc., Santa Clara, Calif.) under conditions recommended by the manufacturer. Arrays were washed, stained with anti-biotin streptavidin-phycoerythourin labeled antibody and scanned using the GeneChip system (Hewlett-Packard, Miami, Fla.). GeneChip 3.0 software to determine the expression of each gene. Intensity values were scaled by calculating the overall signal for each array type.

Differential expression was determined by calculating the ratio between signal intensity value from ultraviolet radiation exposed cells and control cells. To eliminate genes exhibiting potential false positive differential expression, only those genes that possessed a signal intensity of greater than 100 in any pair-wise comparison were selected.

For data interpretation, the Cluster and Tree View software (available at http://rana.standford.edu/software) were used. First, the data were imported into the cluster and tree view software in tab-delimited format. A data set containing the expression patterns of 311 regulated genes was clustered in two ways, based on the similarity of gene expression over the time course of 24 hours and based on the similarity between different time points The clusters were observed using Tree View program D. Northern Blot Analyses For Northern blotting, 10 μg RNA was loaded on a 1.0% agarose-formaldehyde gel and run at 100 V for three to four hours. The RNA was overnight transferred to a nylon membrane (Amersham Life Science, Piscataway, N.J.) and cross-linked with a ultraviolet-C radiation Stratalinker (Stratagene, LaJolla, Calif.). The probes for c-fos and IL-6 were synthesized using reverse transcription-PCR from keratinocyte RNA and the RT-PCR kit from Ambion, Austin, Tex. Additional probes were derived from cDNA clones obtained from ATCC. Each clone was sequenced from both 5' and 3' ends to confirm its identity. The $^{32}$P labeled probes were generated using [$^{32}$P] dCTP (3000 Ci/mmol Dupont NEN and the Multiprime DNA labeling system (Amersham Pharmacia Biotech, Piscataway, N.J.) and purified using D-Salt Excellulose Plastic Desalting Columns (Pierce, Rockford, Ill.).

Hybridizations were performed using ExpressHyb solution (Clontech, Palo Alto, Calif.) at 69° C. for one hour. Membranes were washed with 2×SSC, 0.05% SDS solution, with continuous shaking three times for 30 minutes at room temperature and with 0.1×SSC, 0.1% SDS at 50° C. for 40 minutes. The membrane was exposed to Kodak (Toronto, Canada) BIOMAX MS film at −80° C., and radiographs were scanned and analyzed with MultiImagine Light Cabinet AlphaImagine 2000 documentation and analysis system (Alpha Innotech Corp., San Leandro, Calif.). The RNA levels were normalized to GAPDH mRNA.

E. Western Blot Analyses

For preparation of the whole cell lysates, cells were washed with cold phosphate buffered saline (PBS) and lysed in IPP buffer containing 50 mM HEPES, pH 7.5, 150 mM NaCL, 1 mM EDTA, 1 mM EGTA, 10% glycerol, 1% triton X-100, 25 mM NaF, 10 mM ZnCl2, 1 mM PMSF and 10 mg/ml leupeptin. The lysates were centrifuged at 1000×g, for three minutes at 4° C. The protein concentration of each sample was determined with Bio-Rad Protein assay reagent. 50 μg of protein was loaded and separated on 10% or 20% SDS-polyacrylamide gel, transferred to Immobilon-P (polyvinylidene difluoride) membrane using a semi-dry transfer cell (BioRad, Hercules, Calif.) and blocked in 5% BSA in TBST (50 mM Tris, pH 7.5, 150 mM NaCl, 0.05% Tween 20). The membrane was incubated with primary antibody overnight at 4° C. in 2.0% BSA in TBST, and then washed extensively with TBST, and incubated with 1:5000 anti-rabbit or anti-mouse horseradish peroxidase (HRP)-conjugated secondary antibodies (Amersham Pharmacia Biotech, Piscataway, N.J.). Proteins were visualized with the ECL detection kit (Amersham Pharmacia Biotech, Piscataway, N.J.). The equivalent loading of proteins in each well was ascertained using Ponceau staining of the membrane.

The primary antibody specific for Cox-2 protein was purchased from Transduction Labs (Lexington, Ky.), for GRO-beta from Leinco Technologies (St. Louis, Mo.), for Jun-D from Abcam (Cambridge, UK), for IL-8, C-MYC, MCL-1 and Cytochrome C from Research Diagnostics (Flanders, N.J.). The primary antibodies specific for Amphiregulin Ab-2, HDJ-2, Involucrin and AB-1 antibodies were purchased from NeoMarkers (Fremont, Calif.).

Figure 3A:
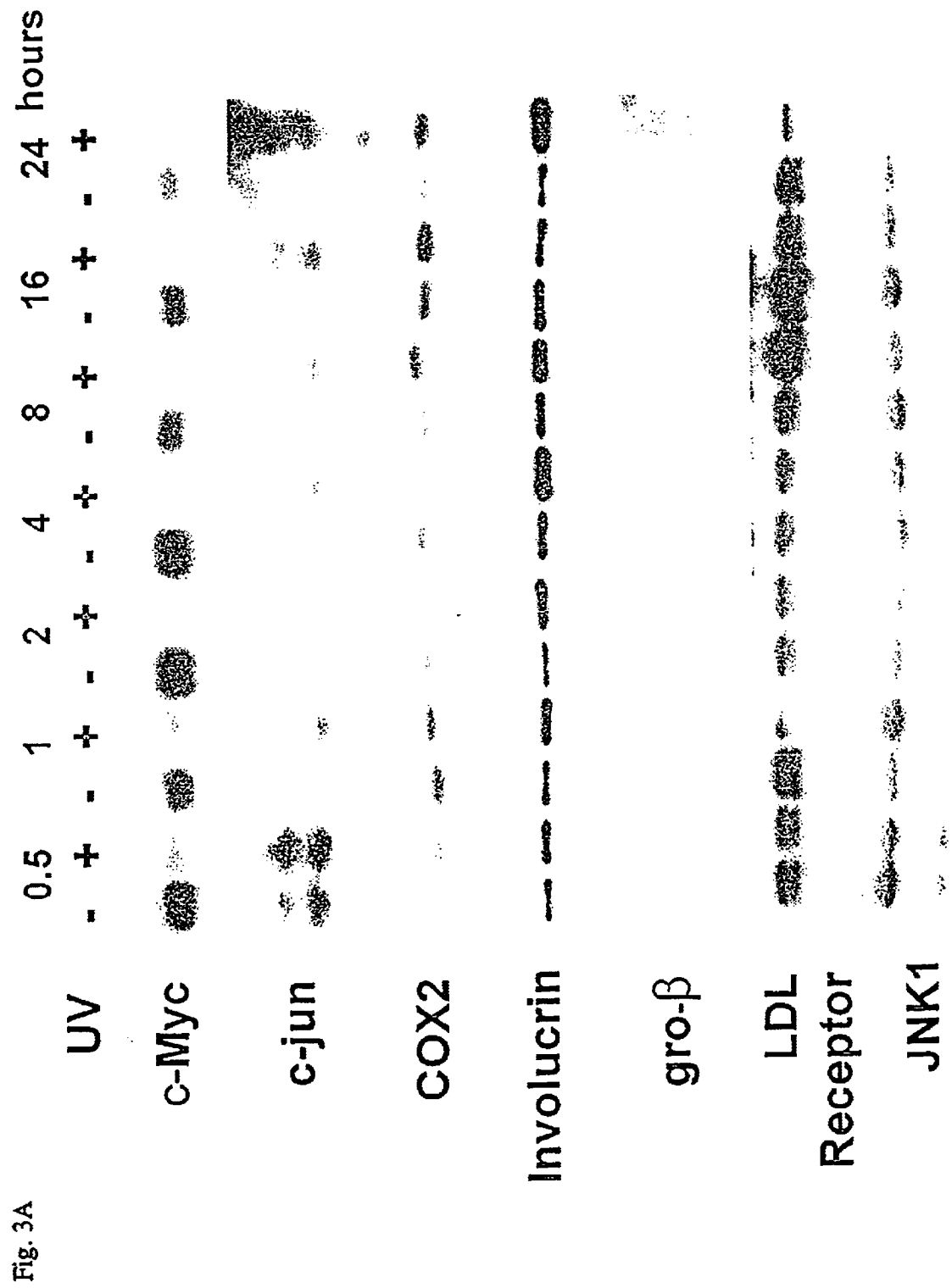
FIG. 3A is a representation of a Western blot demonstrating that the ultraviolet radiation-induced changes in protein levels parallel the changes in mRNA levels. Protein extracts were prepared from irradiated keratinocytes and harvested at 0.5, 1, 2, 4, 8, 16, and 24 hours after ultraviolet irradiation. These samples were screened with antibodies specific for c-Myc, c-jun, COX-2, involucrin, gro-β, and LDL receptor proteins. Antibody specific for JNK1 protein was used as a control for gel loading.
Figure 3B:
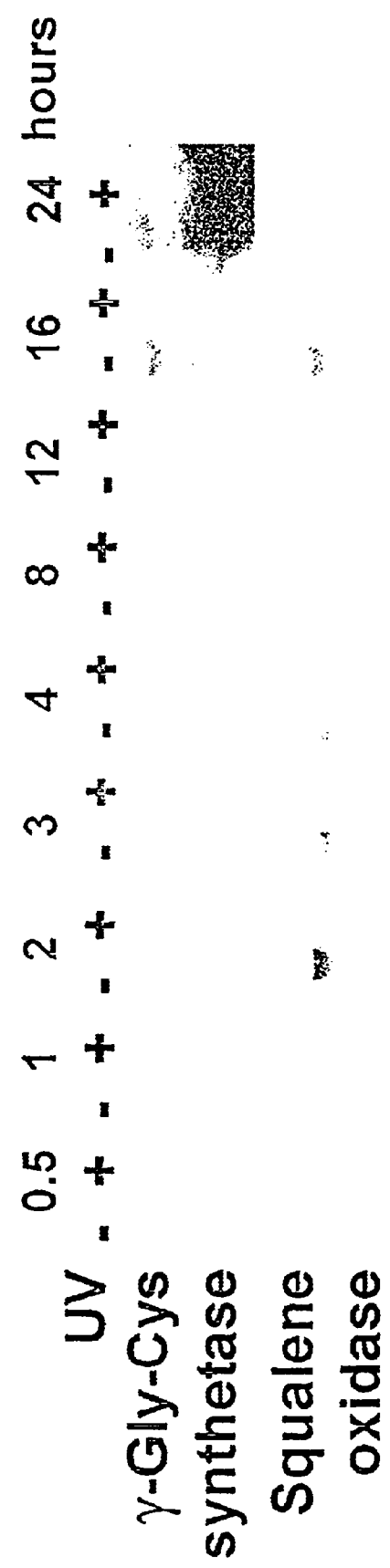
FIG. 3B is a representation of a Western blot demonstrating that the ultraviolet radiation-induced changes in protein levels parallel the changes in mRNA levels. Protein extracts were prepared from irradiated keratinocytes and harvested at 0.5, 1, 2, 3, 4, 8, 12, 16, and 24 hours after ultraviolet irradiation. These samples were screened with antibodies specific for γ-Gly-Cys synthetase and squalene oxidase.

As demonstrated in FIG. 3, protein extracts were prepared from irradiated keratinocytes and harvested at 0.5, 1, 2, 4, 8, 16, 24 hours after ultraviolet irradiation. These samples were screened with antibodies specific for the proteins c-Myc, c-jun, COX-2, involucrin, gro-β, and the LDL receptor. Antibody specific for JNK1 protein was used as a control for gel loading. As demonstrated in FIG. 3, the expression levels for ultraviolet radiation-regulated proteins as identified by Western blot analysis closely correlates with the results of the expression analaysis provided herein.

Confirmation that the ultraviolet radiation-regulated genes identified in the keratinocyte culture model system correlate with the in vivo response to ultraviolet radiation was obtained by examining the protein expression level in a skin organ culture system. Organ culture explants of normal human skin were maintained in culture as previously described (Fisher, G. J., et al., (1996) Nature 379, 335–339; and Varani, J., et al., (1993) American Journal of Pathology 142, 189–198). Briefly, pieces of normal human skin were obtained immediately after surgery, cut into pieces approximately 5 mm3, and incubated in keratinocyte basal medium (KBM) (Keratinocyte-SFM, Gibco-BRL, Gaithersburg, Md.) in a humidified incubator at 37° C. for 24 hours. Approximately 5 pieces of tissue were used per well (24well culture dish) and enough medium was added to the well to just cover the explants. For ultraviolet radiation exposure, the media was removed from the well, and the explants were exposed to 100 mJ/cm2 ultraviolet-B radiation. After exposure, the explanted tissue was re-immersed in culture media.

In order to determine the level of protein expression between control non-ultraviolet radiation exposed and ultraviolet radiation exposed samples, the protein in the explanted tissue samples was visualized in situ by immunofluorescent staining. Briefly, at the desired time point after ultraviolet radiation exposure, the explanted tissue samples were mounted in tissue Tec OCT compound (Sakura Finetek, Japan), frozen, and cut into sections 4 to 6 µm thick. The samples mounted on slides and fixed with methanol/ acetone for 10 min. The sectioned samples were incubated overnight with mouse anti-involucrin antibody (NeoMarkers, lab Vision Corporation, Frernont, Calif.) at 4° C., treated with peroxidase-conjugated anti-mouse IgG secondary antibody (Vecstatin ABC-nouse IgG kit from Vector Laboratories, Burlingame, Calif.) at room temperature for 1 hour, incubated with ABC complex (Vector Laboratories, Burlingame, Calif.) at room temperature for 1 hour and treated with 3,3'-Diaminobenzidine-tetrahydrochloride (Dojindo Corp., Japan) and 0.01% H2O2 in Tris pH 7.6 for 2 minutes. The sections were observed and photographed under the light microscope (Microphot-FXA, Nikon, Japan).

As demonstrated in FIG. 4, immunohistological staining demonstrates that ultraviolet radiation exposure enhances the expression of involucrin in human skin organ culture at 2, 8 and 16 hours after ultraviolet radiation. Note that the suprabasal staining of the epidermis with the involucrin antibody is greatly augmented 16 hours after ultraviolet irradiation.

F. Array Data Analysis

Of the 7,080 entries, some 3,000 are scored as present in keratinocytes at at least one time point, and approximately 1,400 are present at all time points. Among the entries, 308 are differentially regulated at least two-and one-half-fold at at least one time point. Judging 2.5-fold regulation to be significant, attention was focused on these 308 genes. Specific attention was paid to genes represented by multiple probes on the array, such as Jun-D, Tob, Cox-2 etc. Very similar patterns of regulation were observed for these multiple probe sets, which provided further confidence in the fidelity of the resulting hybridizations (Table 1). Of the 308 genes, nine are both induced and suppressed 2.5 fold or more at different time points. The remainder divides about equally (152 versus 147) between the induced and suppressed groups.

Figure 2:
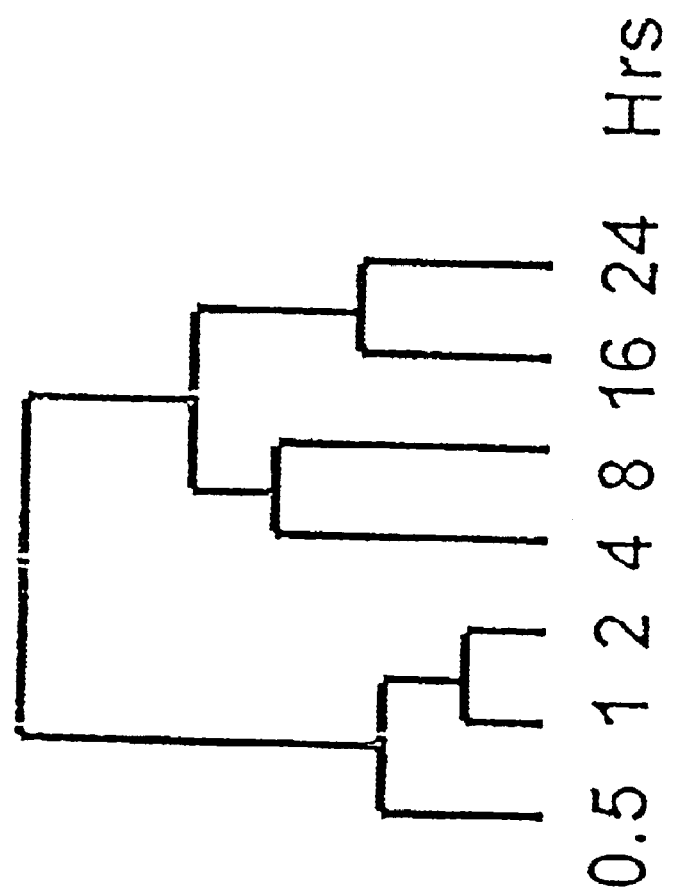
FIG. 2 is a graphic representation of a representative data set analysis showing three waves of regulated expression events post-ultraviolet radiation exposure. The clustering algorithm was used to group the time points. Those time points closest to one another with respect to the height of the terminal branches are most closely related to each other. For example, the terminal brances for the one and two hour time points are the shortest and most similar to each other than all other branches in the graph, therefore, these two time points are clustered together.

Using a clustering algorithm, data from seven time points were grouped into three waves after ultraviolet radiation exposure (FIG. 2). Only a small portion of the genes analyzed is presented in this figure. The most closely related were the 0.5, one and two hour time points. These form the early wave of regulated genes. Also very similar were the 16 and 24 hour time points, forming the late wave. The four and eight hour time points were more similar to each other than to the other time points and these formed the middle wave. Thus, the modification in gene expression in the first 24 hours after ultraviolet radiation exposure can conveniently be grouped into three "waves" of changes, the early or fist response, from about 0.5 to about two hours, the intermediate or second response, from about four to about eight hours, and the late or third response, from about 16 to about 24 hours.

Most of the regulated genes can be grouped by their function into several distinct and clearly demarcated functional categories, including: (1) induced DNA metabolism and repair genes induced, (2) signal transducing proteins and transcription factors (the two largest categories, which contain both induced and suppressed members at all experimental time points); (3) structural proteins (most cytoskeletal, containing both induced and suppressed members); (4) secreted growth factors, chemokines and cytokines (most strongly induced at intermediate time points); and (5) mitochondrial proteins (a significant category of proteins that are among the first induced). In addition, it was found that ultraviolet radiation regulates genes for proteins involved in the translation machinery, RNA processing, lipid, amino acid and urea metabolism, integral membrane, and cell surface proteins, proteases and their inhibitors, and proteins that could not be classified into those categories, as well as several unidentified ESTs.

Example 2

Identification of Gene and Protein Sequences Regulated by Exposure to Ultraviolet-A Radiation A. Keratinocyte Culture and Ultraviolet-A Radiation Cultures of epidermal keratinocytes from human foreskin are initiated using 3T3 feeder layers as described (Simon, et al., (1984) *Cell* 36:827–834) and then stored frozen in liquid $N_2$. Once thawed, the keratinocytes are grown without feeder cells in defined serum-free keratinocyte growth medium (KGM) supplemented with 0.05 g/l bovine pituitary extract, 5 ng/ml epidermal growth factor, and 1% penicillin/ streptomycin (KGM from Gibco-BRL, Rockville, Md.). The keratinocytes are maintained at 37° C., in 5% $CO_2$. The medium is replaced every two days. The cells are expanded through three passages for the experiments. They are trypsinized with 0.025% trypsin, which is neutralized with 0.5 mg/ml trypsin inhibitor. Serum is avoided because it can promote keratinocyte differentiation. For all experiments, third-passage keratinocytes are used one day after reaching confluence.

For ultraviolet-A radiation, an illuminator specially equipped to produce light output in the ultraviolet-A radiation wavelength range is used. For example, a Mutzhas Supersun 5000-type solar simulator (Mutzhas, Munich, Germany) is used by filtering for the emission of ultraviolet-A radiation (315 nm to 390 nm). The medium is removed from the cell cultures, and keratinocytes are irradiated in open dishes. Immediately after the ultraviolet-A radiation exposure, the same medium is replaced to the cultures. Control cells are subjected to the identical procedure but are only sham-irradiated.

The protocol is chosen for two reasons: first, confluent keratinocytes more closely resemble skin than sub confluent ones; and second, nearly identical conditions from culture to culture are reliably and reproducibly achieved. The dose of ultraviolet-A radiation exposure is optimized by treating keratinocyte cultures with increasing amounts of radiation, replacing the medium and determining the cell viability 24 hours after the treatment. A dose of ultraviolet-A radiation is chosen so that at least 10%, but less that 20% of cells are killed by ultraviolet-A radiation exposure.

Keratinocyte cultures are irradiated with a a single dose of ultraviolet-A radiation and harvested the cells 0.5, 1, 2, 4, 8, 16, and 24 hours later. The specific wavelength of ultraviolet-A radiation is from about 315 nm to about 390 nm. As controls, mock-irradiated cells are harvested 1, 4, 8, 16, and 24 hours after the treatment. The one hour mock-irradiated culture is then used as control for the 0.5, 1 and 2 hour time points, while all the later time points have cognate controls.

B. Isolation of Total RNA and Probe Synthesis

Cells are harvested by scraping the culture dish. Kits from Qiagen, (Chatsworth, Calif.) are used to prepare the RNA according to the manufacturer's protocols. Qiashredders are used to homogenize cell lysates with centrifugation at 1800 g for 2 minutes. RNA is extracted using RNeasy Midi Kit. DNA is removed with on-column DNAse digestion using Qiagen RNAses-free DNAse Set.

After the total RNAs are prepared, but before they are used for gene array hybridization, the RNAs are tested in Northern blot hybridizations with a probe corresponding to the c-fos gene.

For Northern blotting, 10 µg RNA is loaded on a 1.0% agarose-formaldehyde gel and run at 100 V for 3–4 hours. The RNA is transferred overnight to a nylon membrane (Amersham Life Science, Piscataway, N.J.) and cross-linked using a Stratalinker (Stratagene, La Jolla, Calif.). The probes for c-fos and IL-6 are synthesized using reverse transcription-PCR from keratinocyte RNA and the RT-PCR kit from Ambion (Austin, Tex.). Additional probes are derived from cDNA clones obtained from the American Type Culture Collection (ATCC, Manassas, Va.). Each clone is sequenced from both 5' and 3' ends to confirm its identity. The $^{32}$P labeled probes are generated using [$^{32}$P] dCTP (3000 Ci/mmol) (Dupont NEN, Boston, Mass.) and the Multiprime DNA labeling system (Amersham Pharmacia Biotech, Piscataway, N.J.) and purified using D-Salt Excellulose Plastic Desalting Columns (Pierce, Rockford, Ill.).

Hybridizations are performed using ExpressHyb solution (Clontech, Palo Alto, Calif.) at 68° C. for 1 hour. Membranes are ished with 2×SSC, 0.05% SDS solution, with continuous shaking thouree times for 30 minutes at room temperature and with 0.1×SSC, 0.1% SDS at 50° C. for 40 minutes. The membrane is exposed to Kodak (Toronto, Canada) BIOMAX MS film at −80° C., and radiographs are scanned and analyzed with MultiImagine Light Cabinet AlphaImagine 2000 documentation and analysis system (Alpha Innotech Corporation, San Leandro, Calif.). The RNA levels are normalize to glyceraldehyde-3-phosphate dehydrogenase (GAPDH) mRNA.

For the synthesis of probe for use with the gene array, eight micrograms of total RNA are reverse transcribed, amplified and labeled as previously described (Mahadevappa et al. (1999) *J.A. Nature Biotechnol.* 17:1134–1136). As a result of the sequence of the primers used for reverse transcription, the resultant cDNA product contains an RNA polymerase promoter for use in the synthesis of cRNA probe to screen the gene array.

C. Gene Array Hybridization

Labeled cRNA is hybridized to the HU6800 array (Affymetrix Inc., Santa Clara, Calif.) under conditions recommended by the manufacturer. Arrays are ished, stained with anti-biotin streptavidin-phycoerythourin labeled antibody and scanned using the GeneChip system (Hewlett-Packard, Miami, Fla.). GeneChip 3.0 software to determine the expression of each gene. Intensity values are scaled by calculating the overall signal for each array type.

Differential expression is determined by calculating the ratio between signal intensity value from ultraviolet radiation exposed cells and control cells. To eliminate genes exhibiting potential false positive differential expression, only those genes that possessed a signal intensity of greater than 100 in any pair-wise comparison are selected.

For data interpretation, the Cluster and Tree View software (available at http://rana.standford.edu/software) are used. Fast, the data are imported into the cluster and tree view software in tab-delimited format. A data set containing the expression patterns of 311 regulated genes is clustered in two ways, based on the similarity of gene expression over the time course of 24 hours and based on the similarity between different time points. The clusters are observed using Tree View program.

Equivalents

Those skilled in the art will recognize, or be able to ascertain, using no more than routine experimentation, many equivalents to the specific embodiments of the invention described herein. Such equivalents are intended to be encompasssed by the following claims.

What is claimed is:

1. A method for detecting exposure of a cell to ultraviolet radiation, comprising measuring the levels of a plurality of RNA molecules in the cell for at least one time point after ultraviolet radiation exposure to establish a pattern of expression, the response of the cell to ultraviolet radiation exposure comprising at least one of the following:

(a) a first response comprising altered expression of at least one nucleic acid molecule encoding a transcription factor protein, at least one nucleic acid molecule encoding a signal transducing protein, and at least one nucleic acid molecule encoding a mitochondrial protein;

(b) a second response comprising altered expression of at least one nucleic acid molecule encoding a secreted growth factor, at least one nucleic acid molecule encoding a cytokine, and at least one nucleic acid molecule encoding a chemokine; and (c) a third response comprising altered expression of at least one nucleic acid molecule encoding an actin-binding protein, at least one nucleic acid molecule encoding a desmosomal protein, and at least one nucleic acid molecule encoding a tubulin protein; and wherein if the pattern of expression for the cell is substantially similar to the response of the cell to ultraviolet radiation, the cell was exposed to ultraviolet radiation.

2. The method according to claim 1, wherein the pattern consists of the first response.

3. The method according to claim 1, wherein the pattern consists of the second response.

4. The method according to claim 1, wherein the pattern consists of the third response.

5. The method according to claim 1, wherein the pattern consists of the first response and the second response.

6. The method according to claim 1, wherein the pattern consists of the first response and the third response.

7. The method according to claim 1, wherein the pattern consists of the second response and the third response.

8. The method according to claim 1, wherein the pattern consists of the first response, the second response, and the third response.

9. The method according to claim 1, wherein the cell is selected from the group consisting of a keratinocyte, a Langerhans cell, a melanocyte, and a fibroblast cell.

10. The method according to claim 1, wherein the ultraviolet radiation exposure comprises energy at a wavelength in the range of about 220 nm to about 440 nm.

11. The method according to claim 10, wherein the ultraviolet radiation exposure comprises energy at a wavelength of about 290 nm to about 320 nm.

12. The method according to claim 10, wherein the ultraviolet radiation exposure comprises energy at a wavelength of about 320 to about 440 nm.

13. The method according to claim 10, wherein the ultraviolet radiation exposure comprises a total energy exposure in the range of about 0.2 mJ/cm$^2$ to about 40 mJ/cm$^2$.

14. The method according to claim 1, wherein the pattern further comprises the first response being from about 0.5 hours to about two hours post-exposure to ultraviolet radiation.

15. The method according to claim 1, wherein the pattern further comprises the second response being from about four hours to about eight hours post-exposure to ultraviolet radiation.

16. The method according to claim 1, wherein the pattern further comprises the third response being from about sixteen hours to about twenty-four hours post-exposure to ultraviolet radiation.

17. The method according to claim 1, wherein the pattern is further characterized by:
(a) the first response occurring from about 0.5 to about two hours post exposure to ultraviolet radiation;
(b) the second response occurring from about four to about eight hours post exposure to ultraviolet radiation; and
(c) the third response occurring from about sixteen to about twenty-four hours postexposure to ultraviolet radiation.

18. The method according to claim 1, wherein altered expression comprises an increase or decrease in RNA level.

19. The method according to claim 1, wherein:
(a) the first response further comprises altered expression of at least three nucleic acid molecules, each one being at least 90% identical to a polynucleotide selected from the group consisting of:
  (i) M62831 Human transcription factor ETR101 mRNA, complete cds,
  (ii) X68277 H. sapiens CL 100 mRNA for protein tyrosine phosphatase,
  (iii) L04731 H. sapiens translocation T(4:11) of ALL-1 gene to chromosome 4,
  (iv) X56681 Human junD mRNA,
  (v) U20734 Human transcription factor junB (junB) gene, 5' region and complete cds,
  (vi) L38951 H. sapiens importin beta subunit mRNA, complete cds,
  (vii) D87071 Human mRNA for KIAA0233 gene, complete cds,
  (viii) M72885 Human GOS2 gene, 5' flank and cds,
  (ix) M92843 H. sapiens zinc finger transcriptional regulator mRNA, complete cds,
  (x) S81914 IEX-1=radiation-inducible immediate-early gene [human, placenta, mRNA Partial,
  (xi) U72649 Human BTG2 (BTG2) mRNA, complete cds,
  (xii) D86988 Human mRNA for KIAA0221 gene, complete cds,
  (xiii) L19779 H. sapiens histone H2A.2 mRNA, complete cds,
  (xiv) U62317 Chromosome 22q13 BAC Clone CIT987SK-384D8 complete sequence,
  (xv) X04412 Human mRNA for plasma gelsolin,
  (xvi) L27706 Human chaperonin protein (Tcp20) gene complete cds,
  (xvii) X61123 Human BTG1 mRNA,
  (xviii) M60974 growth arrest and DNA-damage-inducible protein (gadd45) mRNA, complete cds,
  (xix) L19437 Human transaldolase mRNA containing transposable element, complete cds,
  (xx) X57985 H. sapiens genes for histones H2B.1 and H2A,
  (xxi) D90086 Human pyruvate dehydrogenase (EC 1.2.4.1) beta subunit gene, exons 1–10,
  (xxii) M34182 Human testis-specific protein kinase gamma-subunit mRNA, complete cds,
  (xxiii) L16862 H. sapiens G protein-coupled receptor kinase (GRK6) mRNA, complete cds,
  (xxiv) D13705 Human mRNA for fatty acids omega-hydroxylase (cytochrome P-450HKV), complete cds,
  (xxv) U37122 Human adducin gamma subunit mRNA, complete cds,
  (xxvi) D45906 H. sapiens mRNA for LIMK-2, complete cds,
  (xxvii) U07664 Human HB9 homeobox gene, exons 2 and 3 and complete cds,
  (xxviii) D87438 Human mRNA for KIAA0251 gene, partial cds,
  (xxix) L37042 H. sapiens casein kinase I alpha isoform (CSNK1A1) mRNA, complete cds,
  (xxx) D14043 Human mRNA for MGC-24, complete cds,
  (xxxi) D13988 Human rab GDI mRNA, complete cds,
  (xxxii) U28480 Uncoupling Protein Uc,
  (xxxiii) D50840 H. sapiens mRNA for ceramide glucosyltransferase, complete cds,
  (xxxiv) M55265 Human casein kinase II alpha subunit mRNA, complete cds,
  (xxxv) M96803 Human general beta-spectrin (SPTBN1) mRNA, complete cds,
  (xxxvi) U89336 Human HLA class III region containing NOTCH4 gene, partial sequence, homeobox P,
  (xxxvii) D87442 Human mRNA for KIAA0253 gene, partial cds,
  (xxxviii) J03161 Human serum response factor (SRF) mRNA, complete cds,
  (xxxix) D86965 Human mRNA for KIAA0210 gene, complete cds,
  (xl) U17327 Human neuronal nitric oxide synthase (NOS1) mRNA, complete cds,
  (xli) D86966 Human mRNA for KIAA0211 gene, complete cds,
  (xlii) D85527 H. sapiens mRNA for LIM domain, partial cds,
  (xliii) U42031 Human 54 kDa progesterone receptor-associated immunophilin FKBP54 mRNA, partial,
  (xliv) X59434 Human rohu mRNA for rhodanese,
  (xlv) M13929 Human c-myc-P64 mRNA, initiating from promoter P0, (HLmyc2.5) partial cds, and
  (xlvi) J05211 Desmoplakin;
(b) the second response further comprises altered expression of at least three nucleic acid molecules, each one being at least 90% identical to a polynucleotide selected from the group consisting of:
  (i) M57731 Human gro-beta mRNA, complete cds,
  (ii) S81914 IEX-1=radiation-inducible immediate-early gene [human, placenta, mRNA Partial, 1,
  (iii) Y00787 Human mRNA for MDNCF (monocyte-derived neutrophil chemotactic factor),
  (iv) X54489 Human gene for melanoma growth stimulatory activity (MGSA),
  (v) M72885 Human GOS2 gene, 5' flank and cds,
  (vi) M62831 Human transcription factor ETR101 mRNA, complete cds,
  (vii) M28130 Human interleukin 8 (IL-8) gene, complete cds,
  (viii) X57985 H. sapiens genes for histones H2B.1 and H2A, (ix) X53800 Human mRNA for macrophage inflammatory protein-2beta (MIP2beta),
(x) L19779 *H. sapiens* histone H2A.2 mRNA, complete cds,
(xi) AF001294 *H. sapiens* IPL (IPL) mRNA, complete cds,
(xii) X56681 Human junD mRNA,
(xiii) S75762 Oncogene Tls/Chop, Fusion Activate,
(xiv) M84739 Human autoantigen calreticulin mRNA, complete cds,
(xv) M21302 Human small proline rich protein (sprII) mRNA, clone 174N,
(xvi) V00599 Tubulin, Bet,
(xvii) X70326 Macmarck,
(xviii) D10923 Human mRNA for HM74,
(xix) D64142 Human mRNA for histone H1x, complete cds.
(xx) D86974 Human mRNA for KIAA0220 gene, partial cds,
(xxi) M60974 Human growth arrest and DNA-damage-inducible protein (gadd45) mRNA, complete cds,
(xxii) X68277 *H. sapiens* CL 100 mRNA for protein tyrosine phosphatase,
(xxiii) L13391 Human helix-loop-helix basic phosphoprotein (GOS8) gene, complete cds,
(xxiv) M31627 Human X box binding protein-1 (XBP-1) mRNA, complete cds,
(xxv) U40369 Human spermidine/spermine N1-acetyltransferase (SSAT) gene, complete cds,
(xxvi) X52560 Nuclear Factor Nf-II,
(xxvii) X61123 Human BTG1 mRNA,
(xxviii) U20734 Human transcription factor junB (junB) gene, 5' region and complete cds,
(xxix) U35048 Human TSC-22 protein mRNA, complete cds,
(xxx) M69043 *H. sapiens* MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 *H. sapiens* mRNA for TGIF protein,
(xxxiv) X69111 *H. sapiens* HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 *H sapiens* mRNA for TGF-betaIIR alpha, complete cds,
(xxxviii) M92843 *H. sapiens* zinc finger transcriptional regulator mRNA, complete cds,
(xxxix) X91247 *H. sapiens* mRNA for thioredoxin reductase,
(xl) U05875 Human clone pSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 *H. sapiens* gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1alpha mRNA, complete cds,
(li) L77886 Human protein tyrosine phosphatase mRNA, complete cds,
(lii) X64330 *H. sapiens* mRNA for ATP-citrate lyase,
(liii) U37122 Human adducin gamma subunit mRNA, complete cds,
(liv) X74008 *H. sapiens* mRNA for protein phosphatase 1 gamma,
(lv) U60205 Human methyl sterol oxidase (ERG25) mRNA, complete cds,
(lvi) X76534 *H. sapiens* NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 *H. sapiens* CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, *E coli* DnaJ homologue mRNA, complete cds,
(lxix) D50840 *H. sapiens* mRNA for ceramide glucosyltransferase, complete cds,
(lxx) L31801 *H. sapiens* monocarboxylate transporter 1 (SLC16A1) mRNA, complete cds,
(lxxi) S74017 Nrf2=NF-E2-like basic leucine zipper transcriptional activator [human, hemin-in,
(lxxii) X87241 *H. sapiens* mRNA for hFat protein,
(lxxiii) X52425 Human IL-4-R mRNA for the interleukin 4 receptor,
(lxxiv) D79994 Human mRNA for KIAA0172 gene, partial cds,
(lxxv) M58286 *H. sapiens* tumor necrosis factor receptor mRNA, complete cds,
(lxxvi) M13829 Human putative raf related protein (pks/a-raf) mRNA, partial cds,
(lxxvii) X78992 *H. sapiens* ERF-2 mRNA,
(lxxviii) U42031 Human 54 kDa progesterone receptor-associated immunophilin FKBP54 mRNA, partial,
(lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GH) germline c-myc proto-oncogene, exon 3 and 3' flank, (lxxxiii) L26336 Heat Shock Protein, 70 Kda (Gb:Y00371),
(lxxxiv) L08246 Human myeloid cell differentiation protein (MCL1) mRNA,
(lxxxv) S73591 brain-expressed HHCPA78 homolog [human, HL-60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 *H. sapiens* mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HLmyc2.5) partial cds,
(xcii) D78129 *H. sapiens* mRNA for squalene epoxidase, partial cds,
(xciii) X80692 *H. sapiens* ERK3 mRNA, and
(xciv) J00120 Proto-Oncogene C-Myc, Alt. Splice 3, Orf, 114; and (c) the third response further comprises altered expression of at least three nucleic acid molecules, each one being at least 90% identical to a polynucleotide selected from the group consisting of:
(i) M20030 Human small proline rich protein (sprII) mRNA, clone 930,
(ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 *H. sapiens* genes for histones H2B.1 and H2A,
(x) L05188 *H. sapiens* small proline-rich protein 2 (SPRR2B) gene, complete cds,
(xi) X70326 Macmarcks,
(xii) X67325 *H. sapiens* p27 mRNA,
(xiii) L19779 *H. sapiens* histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 *H. sapiens* thiol-specific antioxidant protein mRNA,
(xvii) M22918 Myosin, Light Chain, Alkali, Smooth Muscle (Gb:U02629), Non-Muscle, Alt. Splice,
(xviii) X06956 Tubulin, Alpha 1, Isoform 44,
(xix) V00594 Human mRNA for metallothionein from cadmium-treated cells,
(xx) M80254 *H. sapiens* cyclophilin isoform (hCyP3) mRNA, complete cds,
(xxi) U04636 Human cyclooxygenase-2 (Cox-2) gene, complete cds,
(xxii) Z14244 *H. sapiens* coxVIIb mRNA for cytochrome c oxidase subunit VIIb,
(xxiii) X99920 *H. sapiens* mRNA for S100 calcium-binding protein A13,
(xxiv) U62800 Human cystatin M (CST6) mRNA, complete cds,
(xxv) L08069 Human heat shock protein, *E. coli* DnaJ homologue mRNA, complete cds,
(xxvi) L20688 Human GDP4-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cds,
(xxix) AF001294 *H. sapiens* IPL (IPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl,
(xxxii) D42040 Human mRNA for KIAA9001 gene, complete cds,
(xxxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 *H. sapiens* mRNA for smoothelin,
(xxxviii) L24564 Human Rad mRNA, complete cds,
(xxxix) D49824 Human HLA-B null allele mRNA,
(xl) S59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 *H. sapiens* L23-related mRNA,
(xliii) M22919 Myosin, Light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 *H. sapiens* Arp2/3 protein complex subunit p41-Arc (ARC41) mRNA, complete cds,
(xlvi) X62083 *H. sapiens* mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} [human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X,
(liii) M14328 Human alpha enolase mRNA, complete cds,
(liv) U07919 Human aldehyde dehydrogenase 6 mRNA, complete cds,
(lv) M28130 Human interleukin 8 (IL8) gene, complete cds,
(lvi) Z21507 *H. sapiens* EF-1delta gene encoding human elongation factor-1-delta,
(lvii) M92934 Human connective tissue growth factor, complete cds.
(lviii) M27436 Human tissue factor gene, complete cds, with a Alu repetitive sequence in the 3',
(lix) X74874 *H. sapiens* gene for RNA pol II largest subunit, exon 1,
(lx) X57351 Human 1-8D gene from interferon-inducible gene family,
(lxi) X52979 Human gene for small nuclear ribonucleoproteins SmB and SmB',
(lxii) U41515 Human deleted in split hand/split foot 1 (DSS1) mRNA, complete cds, (lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 H. sapiens mRNA for ceramide glucosyltransferase, complete cds,
(lxvii) U52101 Human YMP mRNA, complete cds.
(lxviii) D13413 Human mRNA for tumor-associated 120 kDa nuclear protein p120, partial cds(carbox,
(lxix) L42379 H. sapiens bone-derived growth factor (BPGF-1) mRNA, complete cds,
(lxx) X52426 H. sapiens mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 H. sapiens mRNA for ITBA2 protein,
(lxxvi) Z69043 H. sapiens mRNA translocon-associated protein delta subunit precursor,
(lxxvii) L76568 H. sapiens excision and cross link repair protein (ERCC4) gene, complete genom,
(lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver specific cytochrome c oxidase (EC 1.9.3.1.),
(lxxxi) M34516 Human omega light chain protein 14.1 (Ig lambda chain related) gene, exon 3,
(lxxxii) U53830 H. sapiens interferon regulatory factor 7A mRNA, complete cds,
(lxxxiii) X82693 H. sapiens mRNA for E48 antigen,
(lxxxiv) M58026 Human NB-1 mRNA, complete cds,
(lxxxv) M90657 Human tumor antigen (L6) mRNA, complete cds,
(lxxxvi) X57579 H. sapiens activin beta-A subunit (exon 2),
(lxxxvii) D38251 Human mRNA for RPB5 (XAP4), complete cds,
(lxxxviii) D89667 H. sapiens mRNA for c-myc binding protein, complete cds,
(lxxxix) AB000584 H. sapiens mRNA for TGF-beta superfamily protein, complete cds,
(xc) L76200 Human guanylate kinase (GUK1) mRNA, complete cds,
(xci) J04794 Human aldehyde reductase mRNA, complete cds,
(xcii) X52882 Human t-complex polypeptide 1 gene,
(xciii) M79463 Human PML-2 mRNA, complete CDS,
(xciv) Y09022 H. sapiens mRNA for Not56-like protein,
(xcv) M12529 Human apolipoprotein E mRNA, complete cds,
(xcvi) X71129 H. sapiens mRNA for electron transfer flavoprotein beta subunit,
(xcvii) X83416 H. sapiens PrP gene, exon 2,
(xcviii) D89052 H. sapiens mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb;M21533),
(ciii) Z29505 H. sapiens mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 H. sapiens mRNA for proliferation-associated gene (pag),
(cvii) J04611 Human lupus p70 (Ku) autoantigen protein mRNA, complete cds,
(cviii) U09578 H. sapiens MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 kDa subunit,
(cxvii) X77794 H. sapiens mRNA for cyclin G1,
(cxviii) M29064 Human hnRNP B1 protein mRNA,
(cxix) D21853 Human mRNA for KIAA0111 gene, complete cds,
(cxx) X78687 H. sapiens G9 gene encoding sialidase,
(cxxi) X15729 Human mRNA for nuclear p68 protein,
(cxxii) X04828 Human mRNA for G(i) protein alpha-subunit (adenylate cyclase inhibiting GTP-bind,
(cxxiii) L27943 H. sapiens cytidine deaminase (CDA) mRNA, complete cds,
(cxxiv) L40391 H. sapiens (clone s 153) mRNA fragment,
(cxxv) D42123 H. sapiens mRNA for ESP1/CRP2, complete cds,
(cxxvi) X74104 H. sapiens mRNA for TRAP beta subunit,
(cxxvii) M84332 Human ADP-ribosylation factor 1 gene, exons 2–5,
(cxxviii) L37127 H. sapiens RNA polymerase II mRNA, complete cds,
(cxxix) M92843 H. sapiens zinc finger transcriptional regulator mRNA, complete cds,
(cxxx) U07664 Human HB9 homeobox gene, exons 2 and 3 and complete cds,
(cxxxi) L48546 H. sapiens tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds,
(cxxxiv) L11066 Human mRNA sequence,
(cxxxv) J04444 Human cytochrome c-1 gene, complete cds,
(cxxxvi) M95787 Human 22 kDa smooth muscle protein (SM22) mRNA, complete cds,
(cxxxvii) L07517 Mucin 6, Gastric (Gb:L07517),
(cxxxviii) X91247 H. sapiens mRNA for thioredoxin reductase, (cxxxix) L11672 Human Kruppel related zinc finger protein (HTF10) mRNA, complete cds,
(cxl) U30999 Human (memc) mRNA, 3'UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 *H. sapiens* mRNA for alpha 4 protein,
(cxlvii) M24547 Amyloid Beta (A4) Precursor Protein, Alt. Splice 2, A4(751),
(cxlviii) X76717 *H. sapiens* MT-11 mRNA,
(cxlix) M64347 Human novel growth factor receptor mRNA, 3' cds,
(cl) X05409 Human RNA for mitochondrial aldehyde dehydrogenase I ALDH I (EC 1.2.1.3),
(cli) D87469 Human mRNA for KIAA0279 gene, partial cds,
(clii) M58603 Human nuclear factor kappa-B DNA binding subunit (NF-kappa-B) mRNA, complete cds,
(cliii) M76482 Human 130-kD pemphigus vulgaris antigen mRNA, complete cds,
(cliv) X06323 Human MRL3 mRNA for ribosomal protein L3 homologue (MRL3=mammalian ribosome L,
(clv) X78992 *H. sapiens* ERF-2 mRNA,
(clvi) L41351 *H. sapiens* prostasin mRNA, complete cds,
(clvii) X75342 *H. sapiens* SHB mRNA,
(clviii) U83115 Human non-lens beta gamma-crystallin like protein (AIM1) mRNA, partial cds,
(clix) U88629 Human RNA polymerase II elongation factor ELL2, complete cds,
(clx) S78825 2Id1,
(clxi) U28811 Human cysteine-rich fibroblast growth factor receptor(CFR-1) mRNA, complete cds,
(clxii) M58286 *H. sapiens* tumor necrosis factor receptor mRNA, complete cds,
(clxiii) D78129 *H. sapiens* mRNA for squalene epoxidase, partial cds,
(clxiv) D14874 *H. sapiens* mRNA for adrenomedullin precursor, complete cds,
(clxv) Z26317 *H. sapiens* mRNA for desmoglein 2,
(clxvi) L19267 *H. sapiens* 59 protein mRNA, 3' end,
(clxvii) J00120 Proto-Oncogene C-Myc, Alt. Splice 3, Orf 114,
(clxviii) U33821 Human tax1-binding protein TXBP151 mRNA, complete cds,
(clxix) U52100 Human XMP mRNA, complete cds,
(clxx) L31801 *H. sapiens* monocarboxylate transporter 1 (SLC16A1) mRNA, complete cds,
(clxxi) L00058 Human (GH) germline c-myc proto-oncogene, exon 3 and 3' flank,
(clxxii) U52426 *H. sapiens* GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 *H. sapiens* ADP-ribosylation factor mRNA, complete cds,
(clxxvi) U14603 Human protein-tyrosine phosphatase (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 *H. sapiens* mRNA for TGIF protein,
(clxxx) D85429 *H. sapiens* gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 *H. sapiens* OXA1Hs mRNA,
(clxxxiv) M54915 Human h-pim-1 protein (h-pim-1) mRNA, complete cds,
(clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 *H. sapiens* mRNA for chloride channel (putative) 2139 bp,
(cxci) D14520 Human mRNA for GC-Box binding protein BTEB2, complete cds,
(cxcii) D87462 Human mRNA for KIAA0272 gene, partial cds,
(cxciii) X80692 *H. sapiens* ERK3 mRNA,
(cxciv) X90858 *H. sapiens* mRNA for uridine phosphorylase,
(cxcv) M57763 Human ADP-ribosylation factor (hARF6) mRNA, complete cds,
(cxcvi) X92720 *H. sapiens* mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 *H. sapiens* HBZ17 mRNA,
(cciii) X76534 *H. sapiens* NMB mRNA,
(cciv) U37519 Human aldehyde dehydrogenase (ALDH8) mRNA, complete cds,
(ccv) M83667 Human NF-IL6-beta protein mRNA, complete cds,
(ccvi) U53347 Human neutral amino acid transporter B mRNA, complete cds,
(ccvii) L9229 Human long-chain acyl-coenzyme A synthetase (FACL1) mRNA, complete cds,
(ccviii) S73591 brain-expressed HHCPA78 homolog [human, HL-60 acute promyelocytic leukemia cells,
(ccix) M13929 Human c-myc-P64 mRNA, initiating from promoter P0, (HLmyc2.5) partial cds,
(ccx) M55268 Human casein kinase II alpha' subunit mRNA, complete cds,
(ccxi) M77836 Human pyrroline 5-carboxylate reductase mRNA, complete cds,
(ccxii) HG2724-HT2820_at S75762 Oncogene Tls/Chop, Fusion Activated,
(ccxiii) U72066 *H. sapiens* CtBP interacting protein CtIP (CtIP) mRNA, complete cds,
(ccxiv) U42031 Human 54 kDa progesterone receptor-associated immunophilin FKBP54 mRNA, partial, (ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase, complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 *H. sapiens* HLH 1R21 mRNA for helix-loop-helix protein.

20. The method according to claim 19, wherein the pattern consists of the first response group.

21. The method according to claim 19, wherein the pattern consists of the second response group.

22. The method according to claim 19, wherein the pattern consists of the third response group.

23. The method according to claim 19, wherein the pattern consists of the first response group and the second response group.

24. The method according to claim 19, wherein the pattern consists of the first response group and the third response group.

25. The method according to claim 19, wherein the pastern consists of the second response group and the third response group.

26. The method according to claim 19, wherein the pattern consists of the first response group, the second response group, and the third response group.

27. A method for detecting exposure of a cell to ultraviolet radiation comprising:
(a) measuring the levels of a plurality of RNA molecules in the cell by expression array analysis, comprising:
(i) isolating RNA from the cell post-ultraviolet radiation exposure;
(ii) creating a test expression array through nucleic acid hybridization between a labeled probe complementary to the RNA and an expression array substrate;
(iii) analyzing the test expression array to create a test expression array data set; and
(iv) comparing the test expression array data set to a control expression array data set; and
(b) analyzing the levels of the plurality of RNA molecules to establish a pattern of expression for the cell, the response of the cell to ultraviolet radiation exposure comprising at least one of the following:
(i) a first response comprising altered expression of at least one nucleic acid molecule encoding a transcription factor protein, at least one nucleic acid molecule encoding a signal transducing protein, and at least one nucleic acid molecule encoding a mitochondrial protein;
(ii) a second response comprising altered expression of at least one nucleic acid molecule molecule encoding a secreted growth factor, at least one nucleic acid encoding a cytokine, and at least one nucleic acid encoding a chemokine; and
(iii) a third response comprising altered expression of at least one nucleic acid molecule encoding an actin-binding protein, at least one nucleic acid molecule encoding a desmosomal protein, and at least one nucleic acid molecule encoding a tubulin protein,
wherein if the pattern of expression for the cell is substantially similar to the response of the cell to ultraviolet radiation, the cell was exposed to ultraviolet radiation.

28. The method according to claim 27, wherein the pattern consists of the first response.

29. The method according to claim 27, wherein the pattern consists of the second response.

30. The method according to claim 27, wherein the pattern consists of the third response.

31. The method according to claim 27, wherein the pattern consists of the first response and the second response.

32. The method according to claim 27, wherein the pattern consists of the first response and the third response.

33. The method according to claim 27, wherein the pattern consists of the second response and the third response.

34. The method according to claim 27, wherein the pattern consists of the first response, the second response, and the third response.

35. The method according to claim 27, wherein the cell is selected from the group consisting of a keratinocyte, a Langerhans cell, a melanocyte, and a fibroblast cell.

36. The method according to claim 27, wherein the ultraviolet radiation exposure comprises energy at a wavelength in the range of about 220 nm to about 440 nm.

37. The method according to claim 36, wherein the ultraviolet radiation exposure comprises energy at a wavelength of about 290 nm to about 320 nm.

38. The method according to claim 36, wherein the ultraviolet radiation exposure comprises energy at a wavelength of about 320 to about 440 nm.

39. The method according to claim 27, wherein the ultraviolet radiation exposure comprises a total energy exposure in the range of about 0.2 mJ/cm$^2$ to about 40 mJ/cm$^2$.

40. The method according to claim 27, wherein the pattern is further characterized by:
(a) the first response occurring from about 0.5 hours to about 2 hours post-exposure to ultraviolet radiation;
(b) the second response occurring from about 4 hours to about 8 hours post-exposure to ultraviolet radiation; and
(c) the third response occurring from about 16 hours to about 24 hours post-exposure to ultraviolet radiation.

41. The method according to claim 27, wherein altered expression comprises an increase or decrease in the level of RNA.

42. The method according to claim 27, wherein:
(a) the first response further comprises altered expression of at least three nucleic acid molecules, each one at least 90% identical to a polynucleotide selected from the group consisting of:
(i) M62831 Human transcription factor ETR101 mRNA, complete cds,
(ii) X68277 *H. sapiens* CL 100 mRNA for protein tyrosine phosphatase,
(iii) L04731 *H. sapiens* translocation T(4:11) of ALL-1 gene to chromosome 4,
(iv) X56681 Human junD mRNA,
(v) U20734 Human transcription factor junB (junB) gene, 5' region and complete cds,
(vi) L38951 *H. sapiens* importin beta subunit mRNA, complete cds,
(vii) D87071 Human mRNA for KIAA0233 gene, complete cds,
(viii) M72885 Human GOS2 gene, 5' flank and cds,
(ix) M92843 *H. sapiens* zinc finger transcriptional regulator mRNA, complete cds,
(x) S81914 IEX-1=radiation-inducible immediate-early gene [human, placenta, mRNA Partial,
(xi) U72649 Human BTG2 (BTG2) mRNA, complete cds, (xii) D86988 Human mRNA for KIAA0221 gene, complete cds,
(xiii) L19779 *H. sapiens* histone H2A.2 mRNA, complete cds,
(xiv) U62317 Chromosome 22q13 BAC Clone CIT987SK-384D8 complete sequence,
(xv) X04412 Human mRNA for plasma gelsolin,
(xvi) L27706 Human chaperonin protein (Tcp20) gene complete cds,
(xvii) X61123 Human BTG1 mRNA,
(xviii) M60974 growth arrest and DNA damage-inducible protein (gadd45) mRNA, complete cds,
(xix) L19437 Human transaldolase mRNA containing transposable element, complete cds,
(xx) X57985 *H. sapiens* genes for histones H2B.1 and H2A,
(xxi) D90086 Human pyruvate dehydrogenase (EC 1.2.4.1) beta subunit gene, exons 1–10,
(xxii) M34182 Human testis-specific protein kinase gamma-subunit mRNA, complete cds,
(xxiii) L16862 *H. sapiens* G protein-coupled receptor kinase (GRK6) mRNA, complete cds,
(xxiv) D13705 Human mRNA for fatty acids omega-hydroxylase (cytochrome P-450HKV), complete cd,
(xxv) U37122 Human adducin gamma subunit mRNA, complete cds,
(xxvi) D45906 *H. sapiens* mRNA for LIMK-2, complete cds,
(xxvii) U07664 Human HB9 homeobox gene, exons 2 and 3 and complete cds,
(xxviii) D87438 Human mRNA for KIAA0251 gene, partial cds,
(xxix) L37042 *H. sapiens* casein kinase I alpha isoform (CSNK1A1) mRNA, complete cds,
(xxx) D14043 Human mRNA for MGC-24, complete cds,
(xxxi) D13988 Human rab GDI mRNA, complete cds,
(xxxii) U28480 Uncoupling Protein Uc,
(xxxiii) D50840 *H. sapiens* mRNA for ceramide glucosyltransferase, complete cds,
(xxxiv) M55265 Human casein kinase II alpha subunit mRNA, complete cds,
(xxxv) M96803 Human general beta-spectrin (SPTBN1) mRNA, complete cds,
(xxxvi) U89336 Human HLA class III region containing NOTCH4 gene, partial sequence, homeobox P,
(xxxvii) D87442 Human mRNA for KIAA0253 gene, partial cds,
(xxxviii) J03161 Human serum response factor (SRF) mRNA, complete cds,
(xxxix) D86965 Human mRNA for KIAA0210 gene, complete cds,
(xl) U17327 Human neuronal nitric oxide synthase (NOS1) mRNA, complete cds,
(xli) D86966 Human mRNA for KIAA0211 gene, complete cds,
(xlii) D85527 *H. sapiens* mRNA for LIM domain, partial cds,
(xliii) U42031 Human 54 kDa progesterone receptor-associated immunophilin FKBP54 mRNA, partial,
(xliv) X59434 Human rohu mRNA for rhodanese,
(xlv) M13929 Human c-myc-P64 mRNA, initiating from promoter P0, (HLmyc2.5) partial cds, and
(xlvi) J05211 Desmoplakin;
(b) the second response further comprises altered expression of at least three nucleic acid molecules, each one at last 90% identical to a polynucleotide selected from the group consisting of:

(i) M57731 Human gro-beta mRNA, complete cds,
(ii) S81914 IEX-1=radiation-inducible immediate-early gene [human, placenta, mRNA Partial, 1,
(iii) Y00787 Human mRNA for MDNCF (monocyte-derived neutrophil chemotactic factor),
(iv) X54489 Human gene for melanoma growth stimulatory activity (MGSA),
(v) M72885 Human GOS2 gene, 5' flank and cds,
(vi) M62831 Human transcription factor ETR101 mRNA, complete cds,
(vii) M28130 Human interleukin 8 (IL8) gene, complete cds,
(viii) X57985 *H. sapiens* genes or histones H2B.1 and H2A,
(ix) X53800 Human mRNA for macrophage inflammatory protein-2beta (MIP2beta),
(x) L19779 *H. sapiens* histone H2A.2 mRNA, complete cds,
(xi) AF001294 *H. sapiens* IPL (IPL) mRNA, complete cds,
(xii) X56681 Human junD mRNA,
(xiii) S75762 Oncogene Tls/Chop, Fusion Activate,
(xiv) M84739 Human autoantigen calreticulin mRNA, complete cds,
(xv) M21302 Human small proline rich protein (sprII) mRNA, clone 174N,
(xvi) V00599 Tubulin, Bet,
(xvii) X70326 Macmarck,
(xviii) D10923 Human mRNA for HM74,
(xix) D64142 Human mRNA for histone H1x, complete cds,
(xx) D86974 Human mRNA for KIAA0220 gene, partial cds,
(xxi) M60974 Human growth arrest and DNA-damage-inducible protein (gadd45) mRNA, complete cds,
(xxii) X68277 *H. sapiens* CL 100 mRNA for protein tyrosine phosphatase,
(xxiii) L13391 Human helix-loop-helix basic phosphoprotein (GOS8) gene, complete cds,
(xxiv) M31627 Human X box binding protein-1 (XBP-1) mRNA, complete cds,
(xxv) U40369 Human spermidine/spermine N1-acetyltransferase (SSAT) gene, complete cds,
(xxvi) X52560 Nuclear Factor Nf-II,
(xxvii) X61123 Human BTG1 mRNA,
(xxviii) U20734 Human transcription factor junB (junB) gene, 5' region and complete cds,
(xxix) U35048 Human TSC-22 protein mRNA, complete cds,
(xxx) M69043 *H. sapiens* MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 *H. sapiens* mRNA for TGIF protein,
(xxxiv) X69111 *H. sapiens* HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 *H. sapiens* mRNA for TGF-betaIIR alpha, complete cds,
(xxxviii) M92843 *H. sapiens* zinc finger transcriptional regulator mRNA, complete cds,
(xxxix) X91247 *H. sapiens* mRNA for thioredoxin reductase, (xl) U05875 Human clone pSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 *H. sapiens* gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1alpha mRNA, complete cds,
(li) L77886 Human protein tyrosine phosphatase mRNA, complete cds,
(lii) X64330 *H. sapiens* mRNA for ATP-citrate lyase,
(liii) U37122 Human adducin gamma subunit mRNA, complete cds,
(liv) X74008 *H. sapiens* mRNA for protein phosphatase 1 gamma,
(lv) U60205 Human methyl sterol oxidase (ERG25) mRNA, complete cds,
(lvi) X76534 *H. sapiens* NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 *H. sapiens* CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, *E. coli* DnaJ homologue mRNA, complete cds,
(lxix) D50840 *H. sapiens* mRNA for ceramide glucosyltransferase, complete cds,
(lxx) L31801 *H. sapiens* monocarboxylate transporter 1 (SLC16A1) mRNA, complete cds,
(lxxi) S74017 Nrf2 32 NF-E2-like basic leucine zipper transcriptional activator [human, hemin-in,
(lxxii) X87241 *H. sapiens* mRNA for hFat protein,
(lxxiii) X52425 Human IL-4-R mRNA for the interleukin 4 receptor,
(lxxiv) D79994 Human mRNA for KIAA0172 gene, partial cds,
(lxxv) M58286 *H. sapiens* tumor necrosis factor receptor mRNA, complete cds,
(lxxvi) M13829 Human putative raf related protein (pks/a-raf) mRNA, partial cds,
(lxxvii) X78992 *H. sapiens* ERF-2 mRNA,
(lxxviii) U42031 Human 54 kDa progesterone receptor-associated immunophilin FKBP54 mRNA, partial,
(lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GH) germline c-myc proto-oncogene, exon 3 and 3' flank,
(lxxxiii) L26336 Heat Shock Protein, 70 Kda (Gb:Y00371,
(lxxxiv) L08246 Human myeloid cell differentiation protein (MCL1) mRNA,
(lxxxv) S73591 brain-expressed HHCPA78 homolog [human, HL-60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 *H. sapiens* mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HLmyc2.5) partial cds,
(xcii) D78129 *H. sapiens* mRNA for squalene epoxidase, partial cds,
(xciii) X80692 *H. sapiens* ERK3 mRNA, and
(xciv) J00120 Proto-Oncogene C-Myc, Alt. Splice 3, Orf 114; and
(c) the third response further comprises altered expression of at least three nucleic acid molecules, each one at least 90% identical to a polynucleotide selected from the group consisting of:
(i) M20030 Human small proline rich protein (sprII) mRNA, clone 930,
(ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 *H. sapiens* genes for histones H2B.1 and H2A,
(x) L05188 *H. sapiens* small proline-rich protein 2 (SPRR2B) gene, complete cds,
(xi) X70326 Macmarcks,
(xii) X67325 *H. sapiens* p27 mRNA,
(xiii) L19779 *H. sapiens* histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 *H. sapiens* thiol-specific antioxidant protein mRNA,
(xvii) M22918 Myosin, Light Chain, Alkali, Smooth Muscle (Gb:U02629), Non-Muscle, Alt. Splice, (xviii) X06956 Tubulin, Alpha 1, Isoform 44,
(xix) V00594 Human mRNA for metallothionein from cadmium-treated cells,
(xx) M80254 *H. sapiens* cyclophilin isoform (hCyP3) mRNA, complete cds,
(xxi) U04636 Human cyclooxygenase-2 (hCox-2) gene, complete cds,
(xxii) Z14244 *H. sapiens* cox VIIb mRNA for cytochrome c oxidase subunit VIIb,
(xxiii) X99920 *H. sapiens* mRNA for S100 calcium-binding protein A13,
(xxiv) U62800 Human cystatin M (CST6) mRNA, complete cds,
(xxv) L08069 Human heat shock protein, *E. coli* DnaJ homologue mRNA, complete cds,
(xxvi) U20688 Human GDP-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cd,
(xxix) AF001294 *H. sapiens* IPL (IPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl,
(xxxii) D42040 Human mRNA for KIAA9001 gene, complete cds,
(xxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 *H. sapiens* mRNA for smoothelin,
(xxxviii) L24564 Human Rad mRNA, complete cds,
(xxxix) D49824 Human HLA-B null allele mRNA,
(xl) M59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 *H. sapiens* L23-related mRNA,
(xliii) M22919 Myosin, light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 *H. sapiens* Arp2/3 protein complex subunit p41-Arc (ARC4t) mRNA, complete cds,
(xlvi) X62083 *H. sapiens* mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} {human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X
(liii) M14328 Human alpha enolase mRNA, complete cds,
(liv) U07919 Human aldehyde dehydrogenase 6 mRNA, complete cds,
(lv) M28130 Human interleukin 8 (IL8) gene, complete cds,
(lvi) Z21507 *H. sapiens* EF-1delta gene encoding human elongation factor-1-delta,
(lvii) M92934 Human connective tissue growth factor, complete cds,
(lviii) M27436 Human tissue factor gene, complete cds, with a Alu repetitive sequence in the 3',
(lix) X74874 *H. sapiens* gene for RNA pol II largest subunit, exon 1,
(lx) X57351 Human 1-8D gene from interferon-inducible gene family,
(lxi) X52979 Human gene for small nuclear ribonucleoproteins SmB and SmB',
(lxii) U41515 Human deleted in split hand/split foot 1 (DSS1) mRNA, complete cds,
(lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 *H. sapiens* mRNA for ceramide glucosyltransferase, complete cds,
(lxvii) U52101 Human YMP mRNA, complete cds,
(lxviii) D13413 Human mRNA for tumor-associated 120 kDa nuclear protein p120, partial cds(carbox,
(lxix) L42379 *H. sapiens* bone-derived growth factor (BPGF-1) mRNA, complete cds,
(lxx) X52426 *H. sapiens* mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 *H. sapiens* mRNA for ITBA2 protein,
(lxxvi) Z69043 *H. sapiens* mRNA translocon-associated protein delta subunit precursor,
(lxxvii) L76568 *H. sapiens* excision and cross link repair protein (ERCC4) gene, complete genom,
(lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver-specific cytochrome c oxidase (EC 1.9.3.1.),
(lxxxi) M34516 Human omega light chain protein 14.1 (Ig lambda chain related) gene, exon 3,
(lxxxii) U53830 *H. sapiens* interferon regulatory factor 7A mRNA, complete cds,
(lxxxiii) X82693 *H. sapiens* mRNA for E48 antigen,
(lxxxiv) M58026 Human NB-1 mRNA, complete cds,
(lxxxv) M90657 Human tumor antigen (L6) mRNA, complete cds,
(lxxxvi) X57579 *H. sapiens* activin beta-A subunit (exon 2),
(lxxxvii) D38251 Human mRNA for RPB5 (XAP4), complete cds,
(lxxxviii) D89667 *H. sapiens* mRNA for c-myc binding protein, complete cds,
(lxxxix) AB000584 *H. sapiens* mRNA for TGF-beta superfamily protein, complete cds,
(xc) L76200 Human guanylate kinase (GUK1) mRNA, complete cds,
(xci) J04794 Human aldehyde reductase mRNA, complete cds, (xcii) X52882 Human t-complex polypeptide 1 gene,
(xciii) M79463 Human PML-2 mRNA, complete CDS,
(xciv) Y09022 *H. sapiens* mRNA for Not56-like protein,
(xcv) M12529 Human apolipoprotein E mRNA, complete cds,
(xcvi) X71129 *H. sapiens* mRNA for electron transfer flavoprotein beta subunit,
(xcvii) X83416 *H. sapiens* PrP gene, exon 2,
(xcviii) D89052 *H. sapiens* mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb:M21533),
(ciii) Z29505 *H. sapiens* mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 *H. sapiens* mRNA for proliferation-associated gene (pag),
(cvii) J04611 Human lupus p70 (Ku) autoantigen protein mRNA, complete cds,
(cviii) U09578 *H. sapiens* MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 KDa subunit,
(cxvii) X77794 *H. sapiens* mRNA for cyclin G 1,
(cxviii) M29064 Human hnRNP B1 protein mRNA,
(cxix) D21853 Human mRNA for KIAA0111 gene, complete cds,
(cxx) X78687 *H. sapiens* G9 gene encoding sialidase,
(cxxi) X15729 Human mRNA for nuclear p68 protein,
(cxxii) X04828 Human mRNA for G(i) protein alpha-subunit (adenylate cyclase inhibiting GTP-bind,
(cxxiii) L27943 *H. sapiens* cytidine deaminase (CDA) mRNA, complete cds,
(cxxiv) L40391 *H. sapiens* (clone s153) mRNA fragment,
(cxxv) D42123 *H. sapiens* mRNA for ESP1/CRP2, complete cds,
(cxxvi) X74104 *H. sapiens* mRNA for TRAP beta subunit,
(cxxvii) M84332 Human ADP-ribosylation factor 1 gene, exons 2–5,
(cxxviii) L37127 *H. sapiens* RNA polymerase II mRNA, complete cds,
(cxxix) M92843 *H. sapiens* zinc finger transcriptional regulator mRNA, complete cds,
(cxxx) U07664 Human HB9 homeobox gene, exons 2 and 3 and complete cds,
(cxxxi) L48546 *H. sapiens* tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds,
(cxxxiv) L11066 Human mRNA sequence,
(cxxxv) J04444 Human cytochrome c-1 gene, complete cds,
(cxxxvi) M95787 Human 22 kDa smooth muscle protein (SM22) mRNA, complete cds,
(cxxxvii) L07517 Mucin 6, Gastric (Gb:L07517),
(cxxxviii) X91247 *H. sapiens* mRNA for thioredoxin reductase,
(cxxxix) L11672 Human Kruppel related zinc finger protein (HTF10) mRNA, complete cds,
(cxl) U30999 Human (memc) mRNA, 3' UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 *H. sapiens* mRNA for alpha 4 protein,
(cxlvii) M24547 Amyloid Beta (A4) Precursor Protein, Alt. Splice 2, A4(751),
(cxlviii) X76717 *H. sapiens* MT-11 mRNA,
(cxlix) M64347 Human novel growth factor receptor mRNA, 3' cds,
(cl) X05409 Human RNA for mitochondrial aldehyde dehydrogenase I ALDH I (EC 1.2.1.3),
(cli) D87469 Human mRNA for KIAA0279 gene, partial cds,
(clii) M58603 Human nuclear factor kappa-B DNA binding subunit (NF-kappa-B) mRNA, complete cds,
(cliii) M76482 Human 130-kD pemphigus vulgaris antigen mRNA, complete cds,
(cliv) X06323 Human MRL3 mRNA for ribosomal protein L3 homologue (MRL3=mammalian ribosome L,
(clv) X78992 *H. sapiens* ERF-2 mRNA,
(clvi) L41351 *H. sapiens* prostasin mRNA, complete cds,
(clvii) X75342 *H. sapiens* SHB mRNA,
(clviii) U83115 Human non-lens beta gamma-crystallin like protein (AIM1) mRNA, partial cds,
(clix) U88629 Human RNA polymerase II elongation factor ELL2, complete cds,
(clx) S78825 Id1,
(clxi) U28811 Human cysteine-rich fibroblast growth factor receptor (CFR-1) mRNA, complete cds,
(clxii) M58286 *H. sapiens* tumor necrosis factor receptor mRNA, complete cds,
(clxiii) D78129 *H. sapiens* mRNA for squalene epoxidase, partial cds,
(clxiv) D14874 *H. sapiens* mRNA for adrenomedullin precursor, complete cds,
(clxv) Z26317 *H. sapiens* mRNA for desmoglein 2,
(clxvi) L19267 *H. sapiens* 59 protein mRNA, 3' end,
(clxvii) J00120 Proto-Oncogene C-Myc, Alt. Spice 3, Orf 114,
(clxviii) U33821 Human tax1-binding protein TXBP151 mRNA, complete cds, (clxix) U52100 Human XMP mRNA, complete cds,
(clxx) L31801 *H. sapiens* monocarboxylate transporter 1 (SLC16A1) mRNA, complete cds,
(clxxi) L00058 Human (GH) germline c-myc proto-oncogene, exon 3 and 3' flank,
(clxxii) U52426 *H. sapiens* GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 *H. sapiens* ADP-ribosylation factor mRNA, complete cds,
(clxxvi) U14603 Human protein-tyrosine phosphatase (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 *H. sapiens* mRNA for TGIF protein,
(clxxx) D85429 *H. sapiens* gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 *H. sapiens* OXA1Hs mRNA,
(clxxxiv) M54915 Human h-pim-1 protein (h-pim-1) mRNA, complete cds,
(clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 *H. sapiens* mRNA for chloride channel (putative) 2139 bp,
(cxci) D14520 Human mRNA for GC-Box binding protein BTEB2, complete cds,
(cxcii) D87462 Human mRNA for KIAA0272 gene, partial cds,
(cxciii) X80692 *H. sapiens* ERK3 mRNA,
(cxciv) X90858 *H. sapiens* mRNA for uridine phosphorylase,
(cxcv) M57763 Human ADP-ribosylation factor (hARF6) mRNA, complete cds,
(cxcvi) X92720 *H. sapiens* mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 *H. sapiens* HBZ17 mRNA,
(cciii) X76534 *H. sapiens* NMB mRNA,
(cciv) U37519 Human aldehyde dehydrogenase (ALDH8) mRNA, complete cds,
(ccv) M83667 Human NF-IL6-beta protein mRNA, complete cds,
(ccvi) U53347 Human neutral amino acid transporter B mRNA, complete cds,
(ccvii) L09229 Human long-chain acyl-coenzyme A synthetase (FACL1) mRNA, complete cds,
(ccviii) S73591 brain-expressed HHCPA78 homolog [human, HL-60 acute promyelocytic leukemia cells,
(ccix) M13929 Human c-myc-P64 mRNA, initiating from promoter P0, (HLmyc2.5) partial cds,
(ccx) M55268 Human casein kinase II alpha' subunit mRNA, complete cds,
(ccxi) M77836 Human pyrroline 5-carboxylate reductase mRNA, complete cds,
(ccxii) HG2724-HT2820_at S75762 Oncogene Tls/Chop, Fusion Activated,
(ccxiii) U72066 *H. sapiens* CtBP interacting protein CtIP (CtIP) mRNA, complete cds,
(ccxiv) U42031 Human 54 kDa progesterone receptor-associated immunophilin FKBP54 mRNA, partial,
(ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase, complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 *H. sapiens* HLH 1R21 mRNA for helix-loop-helix protein.

43. The method according to claim 42, wherein the pattern consists of the first response group.

44. The method according to claim 42, wherein the pattern consists of the second response group.

45. The method according to claim 42, wherein the pattern consists of the third response group.

46. The method according to claim 42, wherein the pattern consists of the first response group and the second response group.

47. The method according to claim 42, wherein the pattern consists of the first response group and the third response group.

48. The method according to claim 42, wherein the pattern consists of the second response group and the third response group.

49. The method according to claim 42, wherein the pattern consists of the first response group, the second response group, and the third response group.

50. A method for detecting exposure of a cell to ultraviolet radiation, comprising measuring the levels of a plurality of protein molecules in the cell for at least one time point after ultraviolet radiation exposure to establish a pattern of expression, the response of the cell to ultraviolet radiation exposure comprising at least one of the following:
(a) a first response comprising altered expression of at least one transcription factor protein, at least one signal transduction protein, and at least one mitochondrial protein;
(b) a second response comprising altered expression of at least one secreted growth factor protein, at least one cytokine protein, and at least one chemokine protein; and
(c) a third response comprising altered expression of at least one actin-binding protein, at least one desmosomal protein, and at least one tubulin protein,
wherein if the pattern of expression for the cell is substantially similar to the response of the cell to ultraviolet radiation, the cell was exposed to ultraviolet radiation.

51. The method according to claim 50, wherein the cell is selected from the group consisting of a keratinocyte, a Langerhans cell, a melanocyte, and a fibroblast cell.

52. The method according to claim 50, wherein the ultraviolet radiation exposure comprises energy at a wavelength in the range of about 220 nm to about 440 nm.

53. The method according to claim 52, wherein the ultraviolet radiation exposure comprises energy at a wavelength of about 290 nm to about 320 nm.

54. The method according to claim 52, wherein the ultraviolet radiation exposure comprises energy at a wavelength of about 320 to about 440 nm.

55. The method according to claim 50, wherein the ultraviolet radiation exposure comprises energy in the range of about 0.2 mJ/cm$^2$ to about 40 mJ/cm$^2$.

56. The method according to claim 50, wherein the pattern is characterized by:
  (a) the first response occurring from about 0.5 hours to about 2 hours post-exposure to ultraviolet radiation exposure;
  (b) the second response occurring from about 4 hours to about a 8 hours post-exposure to ultraviolet radiation exposure; and
  (c) the third response occurring from about 16 hours to about 24 hours post-exposure to ultraviolet radiation exposure.

57. The method according to claim 50, wherein altered regulation comprises an increase or decrease in protein level.

58. The method according to claim 50, wherein:
  (a) the first response further comprises altered expression of at least three proteins, each one encoded by a nucleic acid molecule that is at least 90% identical to a polynucleotide selected from the group consisting of:
    (i) M62831 Human transcription factor ETR101 mRNA, complete cds,
    (ii) X68277 H. sapiens CL 100 mRNA for protein tyrosine phosphatase,
    (iii) L04731 H. sapiens translocation T(4:11) of ALL-1 gene to chromosome 4,
    (iv) X56681 Human junD mRNA,
    (v) U20734 Human transcription factor junB (junB) gene, 5' region and complete cds,
    (vi) L38951 H. sapiens importin beta subunit mRNA, complete cds,
    (vii) D87071 Human mRNA for KIAA0233 gene, complete cds,
    (viii) M72885 Human GOS2 gene, 5' flank and cds,
    (ix) M92843 H. sapiens zinc finger transcriptional regulator mRNA, complete cds,
    (x) S81914 IEX-1=radiation-inducible immediate-early gene [human, placenta, mRNA Partial,
    (xi) U72649 Human BTG2 (BTG2) mRNA, complete cds,
    (xii) D86998 Human mRNA for KIAA0221 gene, complete cds,
    (xiii) L19779 H. sapiens histone H2A.2 mRNA, complete cds,
    (xiv) U62317 Chromosome 22q13 BAC Clone CIT987SK-384D8 complete sequence,
    (xv) X04412 Human mRNA for plasma gelsolin,
    (xvi) L27706 Human chaperonin protein (Tcp20) gene complete cds,
    (xvii) X61123 Human BTG1 mRNA,
    (xviii) M60974 growth arrest and DNA-damage-inducible protein (gadd45) mRNA, complete cds,
    (xix) L19437 Human transaldolase mRNA containing transposable element, complete cds,
    (xx) X57985 H. sapiens genes for histones H2B.1 and H2A.
    (xxi) D90086 Human pyruvate dehydrogenase (EC 1.2.4.1) beta subunit gene, exons 1–10,
    (xxii) M34182 Human testis-specific protein kinase gamma-subunit mRNA, complete cds,
    (xxiii) L16862 H. sapiens G protein-coupled receptor kinase (GRK6) mRNA, complete cds,
    (xxiv) D13705 Human mRNA for fatty acids omega-hydroxylase (cytochrome P-450HKV), complete cd,
    (xxv) U37122 Human adducin a subunit mRNA, complete cds,
    (xxvi) D45906 H. sapiens mRNA for LIMK-2, complete cds,
    (xxvii) U07664 Human HB9 homeobox gene, exons 2 and 3 and complete cds,
    (xxviii) D87438 Human mRNA for KIAA0251 gene, partial cds,
    (xxix) L37042 H. sapiens casein kinase I alpha isoform (CSNK1A1) mRNA, complete cds,
    (xxx) D14043 Human mRNA for MGC-24, complete cds,
    (xxxi) D13988 Human rab GDI mRNA, complete cds,
    (xxxii) U28480 Uncoupling Protein Uc,
    (xxxiii) D50840 H. sapiens mRNA for ceramide glucosyltransferase, complete cds,
    (xxxiv) M55265 Human casein kinase II alpha subunit mRNA, complete cds,
    (xxxv) M96803 Human general beta-spectrin (SPIN1) mRNA, complete cds,
    (xxxvi) U89336 Human HLA class III region containing NOTCH4 gene, partial sequence, homeobox P,
    (xxxvii) D87442 Human mRNA for KIAA0253 gene, partial cds,
    (xxxviii) J03161 Human serum response factor (SRF) mRNA, complete cds,
    (xxxix) D86965 Human mRNA for KIAA0210 gene, complete cds,
    (xl) U17327 Human neuronal nitric oxide synthase (NOS1) mRNA, complete cds,
    (xli) D86966 Human mRNA for KIAA0211 gene, complete cds,
    (xlii) D85527 H. sapiens mRNA for LIM domain, partial cds,
    (xliii) U42031 Human 54 kDa progesterone receptor-associated immunophilin FKBP54 mRNA, partial,
    (xliv) X59434 Human rohu mRNA for rhodanese,
    (xlv) M13929 Human c-myc-P64 mRNA, initiating from promoter P0, (HLmyc2.5) partial cds, and
    (xlvi) J05211 Desmoplakin;
  (b) the second response further comprises altered expression of at least three proteins, each one encoded by a nucleic acid molecule that is at least 90% identical to a polynucleotide selected from the group consisting of:
    (i) M57731 Human gro-beta mRNA, complete cds,
    (ii) S81914 IEX-1=radiation-inducible immediate-early gene [human, placenta, mRNA Partial, 1,
    (iii) Y00787 Human mRNA for MDNCF (monocyte-derived neutrophil chemotactic factor),
    (iv) X54489 Human gene for melanoma growth stimulatory activity (MGSA),
    (v) M72885 Human GOS2 gene, 5' flank and cds,
    (vi) M62831 Human transcription factor ETR101 mRNA, complete cds,
    (vii) M28130 Human interleukin 8 (IL8) gene, complete cds,
    (viii) X57985 H. sapiens genes for histones H2B.1 and H2A, (ix) X53800 Human mRNA for macrophage inflammatory protein-2beta (MIP2beta),
(x) L19779 H. sapiens histone H2A.2 mRNA, complete cds,
(xi) AF001294 H. sapiens IPL (IPL) mRNA, complete cds,
(xii) X56681 Human junD mRNA,
(xiii) S75762 Oncogene Tls/Chop, Fusion Activate,
(xiv) M84739 Human autoantigen calreticulin mRNA, complete cds,
(xv) M21302 Human small proline rich protein (sprII) mRNA, clone 174N,
(xvi) V00599 Tubulin, Bet,
(xvii) X70326 Macmarck,
(xviii) D10923 Human mRNA for HM74,
(xix) D64142 Human mRNA for histone H1x, complete cds,
(xx) D86974 Human mRNA for KIAA0220 gene, partial cds,
(xxi) M60974 Human growth arrest and DNA-damage-inducible protein (gadd45) mRNA, complete cds,
(xxii) X68277 H. sapiens CL 100 mRNA for protein tyrosine phosphatase,
(xxiii) L13391 Human helix-loop-helix basic phosphoprotein (GOS8) gene, complete cds,
(xxiv) M31627 Human X box binding protein-1 (XBP-1) mRNA, complete cds,
(xxv) U40369 Human spermidine-spermine N1-acetyltransferase (SSAT) gene, complete cds,
(xxvi) X52560 Nuclear Factor Nf-Il,
(xxvii) X61123 Human BTG1 mRNA,
(xxviii) U20734 Human transcription factor junB (junB) gene, 5' region and complete cds,
(xxix) U35048 Human TSC-22 protein mRNA, complete cds,
(xxx) M69043 H. sapiens MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 H. sapiens mRNA for TGIF protein,
(xxxiv) X69111 H. sapiens HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 H. sapiens mRNA for TGF-betaIIR alpha, complete cds,
(xxxviii) M92843 H. sapiens zinc finger transcriptional regulator mRNA, complete cds,
(xxxix) X91247 H. sapiens mRNA for thioredoxin reductase,
(xl) U05875 Human clone PSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 H. sapiens gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1alpha mRNA, complete cds,
(li) L77886 Human protein tyrosine phosphatase mRNA, complete cds,
(lii) X64330 H. sapiens mRNA for ATP-citrate lyase,
(liii) U37122 Human adducin gamma subunit mRNA, complete cds,
(liv) X74008 H. sapiens mRNA for protein phosphatase 1 gamma,
(lv) U60205 Human methyl sterol oxidase (ERG25) mRNA, complete cds,
(lvi) X76534 H. sapiens NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 H. sapiens CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, E. coli DnaJ homologue mRNA, complete cds,
(lxix) D50840 H. sapiens mRNA for ceramide glucosyltransferase, complete cds,
(lxx) L31801 H. sapiens monocarboxylate transporter 1 (SLC16A1) mRNA, complete cds,
(lxxi) S74017 Nrf2=NF-F2-like basic leucine zipper transcriptional activator [human, hemin-in,
(lxxii) X87241 H. sapiens mRNA for hFat protein,
(lxxii) X52425 Human IL-4-R mRNA for the interleukin 4 receptor,
(lxxiv) D79994 Human mRNA for KIAA0172 gene, partial cds,
(lxxv) M58286 H. sapiens tumor necrosis factor receptor mRNA complete cds,
(lxxvi) M13829 Human putative raf related protein (pks/a-raf) mRNA, partial cds,
(lxxvii) X78992 H. sapiens ERF-2 mRNA,
(lxxviii) U42031 Human 54 kDa progesterone receptor-associated immunophilin FKBP54 mRNA, partial,
(lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GH) germline c-myc proto-oncogene, exon 3 and 3' flank, (lxxxiii) L26336 Heat Shock Protein, 70 Kda (Gb:Y00371),
(lxxxiv) L08246 Human myeloid cell differentiation protein (MCL1) mRNA,
(lxxxv) S73591 brain-expressed HHCPA78 homolog [human, HL-60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 H. sapiens mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HL-myc2.5) partial cds,
(xcii) D78129 H. sapiens mRNA for squalene epoxidase, partial cds,
(xciii) X80692 H. sapiens ERK3 mRNA, and
(xciv) J00120 Proto-Oncogene C-Myc, Alt. Splice 3, Orf 114; and (c) the third response further comprises altered expression of at least three proteins, each one encoded by a nucleic acid molecule that is at least 90% identical to a polynucleotide selected from the group consisting of:

(i) M20030 Human small proline rich protein (sprII) mRNA, clone 930,
(ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 H. sapiens genes for histones H2B.1 and H2A,
(x) L05188 H. sapiens small proline-rich protein 2 (SPRR2B) gene, complete cds,
(xi) X70326 Macmarcks,
(xii) X67325 H. sapiens p27 mRNA,
(xiii) L19779 H. sapiens histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 H. sapiens thiol-specific antioxidant protein mRNA,
(xvii) M22918 Myosin, Light Chain, Alkali, Smooth Muscle (Gb:U02629), Non-Muscle, Alt. Splice,
(xviii) X06956 Tubulin, Alpha 1, Isoform 44,
(xix) V00594 Human mRNA for metallothionein from cadmium-treated cells,
(xx) M80254 H. sapiens cyclophilin isoform (hCyP3) mRNA, complete cds,
(xxi) U04636 Human cyclooxygenase-2 (hCox-2) gene, complete cds,
(xxii) Z14244 H. sapiens cox VIIb mRNA for cytochrome c oxidase subunit VIIb,
(xxiii) X99920 H. sapiens mRNA for S100 calcium-binding protein A13,
(xxiv) U62800 Human cystatin M (CST6) mRNA, complete cds,
(xxv) L08069 Human heat shock protein, E. coli DnaJ homologue mRNA, complete cds,
(xxvi) L20688 Human GDP-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cds,
(xxix) AF001294 H. sapiens IPL (IPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl,
(xxxii) D42040 Human mRNA for KIAA9001 gene, complete cds,
(xxxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 H. sapiens mRNA for smoothelin,
(xxxviii) L24564 Human Rad mRNA, complete cds,
(xxxix) D49824 Human HLA-B null allele mRNA,
(xl) M59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 H. sapiens L23-related mRNA,
(xliii) M22919 Myosin, Light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 H. sapiens Arp2/3 protein complex subunit p41-Arc (ARC41) mRNA, complete cds,
(xlvi) X62083 H. sapiens mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} [human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X,
(liii) M14328 Human alpha enolase mRNA, complete cds,
(liv) U07919 Human aldehyde dehydrogenase 6 mRNA, complete cds,
(lv) M28130 Human interleukin 8 (IL8) gene, complete cds,
(lvi) Z21507 H. sapiens EF-1delta gene encoding human elongation factor-1-delta,
(lvii) M92934 Human connective tissue growth factor, complete cds,
(lviii) M27436 Human tissue factor gene, complete cds, with a Alu repetitive sequence in the 3',
(lix) X74874 H. sapiens gene for RNA pol II largest subunit, exon 1,
(lx) X57351 Human 1-8D gene from interferon-inducible gene family,
(lxi) X52979 Human gene for small nuclear ribonucleoproteins SmB and SmB'.
(lxii) U41515 Human deleted in split hand/split foot 1 (DSS1) mRNA, complete cds, (lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 *H. sapiens* mRNA for ceramide glucosyltransferase, complete cds,
(lxvii) U52101 Human YMP mRNA, complete cds,
(lxviii) D13413 Human mRNA for tumor-associated 120 kDa nuclear protein p120, partial cds(carbox,
(lxix) L42379 *H. sapiens* bone-derived growth factor (BPGF-1) mRNA, complete cds,
(lxx) X52426 *H. sapiens* mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 *H. sapiens* mRNA for ITBA2 protein,
(lxxvi) Z69043 *H. sapiens* mRNA translocon-associated protein delta subunit precursor,
(lxxvii) L76568 *H. sapiens* excision and cross link repair protein (ERCC4) gene, complete genom,
(lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver-specific cytochrome c oxidase (EC 1.9.3.1.),
(lxxxi) M34516 Human omega light chain protein 14.1 (Ig lambda chain related) gene, exon 3,
(lxxxii) U53830 *H. sapiens* interferon regulatory factor 7A mRNA, complete cds,
(lxxxiii) X82693 *H. sapiens* mRNA for E48 antigen,
(lxxxiv) M58026 Human NB-1 mRNA, complete cds,
(lxxxv) M90657 Human tumor antigen (L6) mRNA, complete cds,
(lxxxvi) X57579 *H. sapiens* activin beta-A subunit (exon 2),
(lxxxvii) D38251 Human mRNA for RPB5 (XAP4), complete cds,
(lxxxviii) D89667 *H. sapiens* mRNA for c-myc binding protein, complete cds,
(lxxxix) AB000584 *H. sapiens* mRNA for TGF-beta superfamily protein, complete cds,
(xc) L76200 Human guanylate kinase (GUK1) mRNA, complete cds,
(xci) J04794 Human aldehyde reductase mRNA, complete cds,
(xcii) X52882 Human t-complex polypeptide 1 gene,
(xciii) M79463 Human PML-2 mRNA, complete CDS.
(xciv) Y09022 *H. sapiens* mRNA for Not56like protein,
(xcv) M12529 Human apolipoprotein E mRNA, complete cds,
(xcvi) X71129 *H. sapiens* mRNA for electron transfer flavoprotein beta subunit,
(xcvii) X83416 *H. sapiens* PrP gene, exon 2,
(xcviii) D89052 *H. sapiens* mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb:M21533),
(ciii) Z29505 *H. sapiens* mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 *H. sapiens* mRNA for proliferation-associated gene (pag),
(cvii) J04611 Human lupus p70 (Ku) autoantigen protein mRNA, complete cds,
(cviii) U09578 *H. sapiens* MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 kDa subunit,
(cxvii) X77794 *H. sapiens* mRNA for cyclin G1,
(cxviii) M29064 Human hnRNP B1 protein mRNA,
(cxix) D21853 Human mRNA for KIAA0111 gene, complete cds,
(cxx) X78687 *H. sapiens* G9 gene encoding sialidase,
(cxxi) X15729 Human mRNA for nuclear p68 protein,
(cxii) X04828 Human mRNA for G(i) protein alpha-subunit (adenylate cyclase inhibiting GTP-bind,
(cxxiii) L27943 *H. sapiens* cytidine deaminase (CDA) mRNA, complete cds,
(cxxiv) L40391 *H. sapiens* (clone s153) mRNA fragment,
(cxxv) D42123 *H. sapiens* mRNA for ESP1/CRP2, complete cds,
(cxxvi) X74104 *H. sapiens* mRNA for TRAP beta subunit,
(cxxvii) M84332 Human ADP-ribosylation factor 1 gene, exons 2–5,
(cxxviii) L37127 *H. sapiens* RNA polymerase II mRNA, complete cds,
(cxxix) M92843 *H. sapiens* zinc finger transcriptional regulator mRNA, complete cds,
(cxxx) U07664 Human HB9 homeobox gene, exons 2 and 3 and complete cds,
(cxxxi) L48546 *H. sapiens* tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds,
(cxxxiv) L11066 Human mRNA sequence,
(cxxxv) J04444 Human cytochrome c-1 gene, complete cds,
(cxxxvi) M95787 Human 22 kDa smooth muscle protein (SM22) mRNA, complete cds,
(cxxxvii) L07517 Mucin 6, Gastric (Gb:L07517),
(cxxxviii) X91247 *H. sapiens* mRNA for thioredoxin reductase, (cxxxix) L11672 Human Kruppel related zinc finger protein (HTF10) mRNA, complete cds,
(cxl) U30999 Human (memc) mRNA, 3'UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 H. sapiens mRNA for alpha 4 protein,
(cxlvii) M24547 Amyloid Beta (A4) Precursor Protein, Alt. Splice 2, A4(751),
(cxlviii) X76717 H. sapiens MT-11 mRNA,
(cxlix) M64347 Human novel growth factor receptor mRNA, 3' cds,
(cl) X05409 Human RNA for mitochondrial aldehyde dehydrogenase I ALDH I (EC 1.21.3),
(cli) D87469 Human mRNA for KIAA0279 gene, partial cds,
(clii) M58603 Human nuclear factor kappa-B DNA binding subunit NF-kappa-B) mRNA, complete cds,
(cliii) M76482 Human 130-kD pemphigus vulgaris antigen mRNA, complete cds,
(cliv) X06323 Human MRL3 mRNA for ribosomal protein L3 homologue (MRL3= mammalian ribosome L,
(clv) X78992 H. sapiens ERF-2 mRNA,
(clvi) L41351 H. sapiens prostasin mRNA, complete cds,
(clvii) X75342 H. sapiens SHB mRNA,
(clviii) U83115 Human non-lens beta gamma-crystallin like protein (AIM1) mRNA, partial cds,
(clix) U88629 Human RNA polymerase II elongation factor ELL2, complete cds,
(clx) S78825 Id1,
(clxi) U28811 Human cysteine-rich fibroblast growth factor receptor (CFR-1) mRNA, complete cds,
(clxii) M58286 H. sapiens tumor necrosis factor receptor mRNA, complete cds,
(clxiii) D78129 H. sapiens mRNA for squalene epoxidase, partial cds,
(clxiv) D14874 H. sapiens mRNA for adrenomedullin precursor, complete cds,
(clxv) Z26317 H. sapiens mRNA for desmoglein 2,
(clxvi) L19267 H. sapiens 59 protein mRNA, 3' end,
(clxvii) J00120 Proto-Oncogene C-Myc, Alt. Splice 3, Orf 114,
(clxviii) U33821 Human tax1-binding protein TXBP151 mRNA, complete cds,
(clxix) U52100 Human XMP mRNA, complete cds,
(clxx) L31801 H. sapiens monocarboxylate transporter 1 (SLC16A1) mRNA, complete cds,
(clxxi) L00058 Human (GH) germline c-myc proto-oncogene, exon 3 and 3' flank,
(clxxii) U52426 H. sapiens GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 H. sapiens ADP-ribosylation factor mRNA, complete cds,
(clxxvi) U14603 Human protein-tyrosine phosphatase (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 H. sapiens mRNA for TGIF protein,
(clxxx) D85429 H. sapiens gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 H. sapiens OXA1Hs mRNA,
(clxxxiv) M54915 Human h-pim-1 protein (h-pim-1) mRNA, complete cds,
(clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 H. sapiens mRNA for chloride channel (putative) 2139 bp,
(cxci) D14520 Human mRNA for GC-Box binding protein BTEB2, complete cds,
(cxcii) D87462 Human mRNA for KIAA0272 gene, partial cds,
(cxciii) X80692 H. sapiens ERK3 mRNA,
(cxciv) X90858 H. sapiens mRNA for uridine phosphorylase,
(cxcv) M57763 Human ADP-ribosylation factor (hARF6) mRNA, complete cds,
(cxcvi) X92720 H. sapiens mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 H. sapiens HBZ17 mRNA,
(cciii) X76534 H. sapiens NMB mRNA,
(cciv) U37519 Human aldehyde dehydrogenase (ALDH8) mRNA, complete cds,
(ccv) M83667 Human NF-IL-6-beta protein mRNA, complete cds,
(ccvi) U53347 Human neutral amino acid transporter B mRNA, complete cds,
(ccvii) L09229 Human long-chain acyl-coenzyme A synthetase (FACL1) mRNA, complete cds,
(ccviii) S73591 brain-expressed HHCPA78 homolog [human, HL-60 acute promyelocytic leukemia cells,
(ccix) M13929 Human c-myc-P64 mRNA, initiating from promoter P0, (HLmyc2.5) partial cds,
(ccx) M55268 Human casein kinase II alpha' subunit mRNA, complete cds,
(ccxi) M77836 Human pyrroline 5-carboxylate reductase mRNA, complete cds,
(ccxii) HG2724-HT2820_at S75762 Oncogene Tls/Chop, Fusion Activated,
(ccxiii) U72066 H. sapiens CtBP interacting protein CtIp (CtIP) mRNA, complete cds,
(ccxiv) U42031 Human 54 kDa progesterone receptor-associated immunophilin FKBP54 mRNA, partial, (ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase, complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 *H. sapiens* HLH 1R21mRNA for helix-loop-helix protein.

59. The method according to claim 50, wherein the levels of the plurality of protein molecules are measured by ELISA.

60. A method for detecting exposure of a cell to ultraviolet radiation comprising measuring the levels of a plurality of RNA molecules in the cell for at least one time point,
wherein an altered pattern of expression is established and is indicative of ultraviolet radiation exposure, the pattern comprising the following:
   (a) a first response comprising an altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein;
   (b) a second response comprising an altered pattern of expression of at least one polynucleotide selected from the group consisting of a nucleic acid molecule encoding a secreted growth factor, a nucleic acid molecule encoding a cytokine and a nucleic acid molecule encoding a chemokine; and
   (c) a third response comprising an altered pattern of expression of at least one polynucleotide selected from the group consisting of a nucleic acid molecule encoding an actin-binding protein, a nucleic acid molecule encoding a desmosomal protein, and a nucleic acid molecule encoding a tubulin protein.

61. The method according to claim 60, wherein the cell is selected from the group consisting of a keratinocyte, a Langerhans cell, a melanocyte, and a fibroblast cell.

62. The method according to claim 60, wherein the ultraviolet radiation exposure comprises ultraviolet radiation energy at a wavelength in the range of about 220 nm to about 440 nm.

63. The method according to claim 60, wherein the ultraviolet radiation exposure comprises ultraviolet radiation energy at a wavelength of about 290 nm to about 320 nm.

64. The method according to claim 60, wherein the ultraviolet radiation exposure comprises ultraviolet radiation energy at a wavelength in the range of about 320 nm to about 440 nm.

65. The method according to claim 60, wherein the ultraviolet radiation exposure comprises a total ultraviolet radiation energy exposure in the range of about 0.2 mJ/cm$^2$ to about 40 mJ/cm$^2$.

66. The method according to claim 60, wherein the pattern further comprises the first response being from about 0.5 hours to about two hours post-exposure to ultraviolet radiation.

67. The method according to claim 60, wherein the pattern further comprises the second response being from about four hours to about eight hours post-exposure to ultraviolet radiation.

68. The method according to claim 60, wherein the pattern further comprises the third response being from about sixteen hours to about twenty-four hours post-exposure to ultraviolet radiation.

69. The method according to claim 60, wherein the pattern is further characterized by:
   (a) the first response occurring from about 0.5 hours to about two hours post-exposure to ultraviolet radiation;
   (b) the second response occurring from about four hours to about eight hours post-exposure to ultraviolet radiation; and
   (c) the third response occurring from about sixteen hours to about twenty-four hours post-exposure to ultraviolet radiation.

70. The method according to claim 60, wherein altered expression comprises an increase or decrease in RNA level.

71. The method according to claim 60, wherein:
   (a) the first response further comprises an altered pattern of expression of at least one nucleic acid molecule that is at least 90% identical to a polynucleotide selected from the group consisting of:
      (i) M62831 Human transcription factor ETR101 mRNA, complete cds,
      (ii) X68277 *H. sapiens* CL 100 mRNA for protein tyrosine phosphatase,
      (iii) L04731 *H. sapiens* translocation T(4:11) of ALL-1 gene to chromosome 4,
      (iv) X56681 Human junD mRNA,
      (v) U20734 Human transcription factor junB (junB) gene, 5' region and complete cds,
      (vi) L38951 *H. sapiens* importin beta subunit mRNA, complete cds,
      (vii) D87071 Human mRNA for KIAA0233 gene, complete cds,
      (viii) M72885 Human GOS2 gene, 5' flank and cds,
      (ix) M92843 *H. sapiens* zinc finger transcriptional regulator mRNA, complete cds,
      (x) S81914 IEX-1=radiation-inducible immediate-early gene (human, placenta, mRNA Partial,
      (xi) U72649 Human BTG2 (BTG2) mRNA, complete cds,
      (xii) D86988 Human mRNA for KIAA0221 gene, complete cds,
      (xiii) L19779 *H. sapiens* histone H2A.2 mRNA, complete cds,
      (xiv) U62317 Chromosome 22q13 BAC Clone CIT987SK-384D8 complete sequence,
      (xv) X04412 Human mRNA for plasma gelsolin,
      (xvi) L27706 Human chaperonin protein (Tcp20) gene complete cds,
      (xvii) X61123 Human BTG1 mRNA,
      (xviii) M60974growth arrest and DNA-damage-inducible protein (gadd45) mRNA, complete cds,
      (xix) L19437 Human transaldolase mRNA containing transposable element, complete cds,
      (xx) X57985 *H. sapiens* genes for histones H2B.1 and H2A,
      (xxi) D90086 Human pyruvate dehydrogenase (EC 1.2.4.1) beta subunit gene, exons 1–10,
      (xxii) M34182 Human testis-specific protein kinase gamma-subunit mRNA, complete cds,
      (xxiii) L16862 *H. sapiens* G protein-coupled receptor kinase (GRK6) mRNA, complete cds,
      (xxiv) D13705 Human mRNA for fatty acids omega-hydroxylase (cytochrome P-450HKV), complete cd,
      (xxv) U37122 Human adducin gamma subunit mRNA, complete cds,
      (xxvi) D45906 *H. sapiens* mRNA for LIMK-2, complete cds, (xxvii) U07664 Human HB9 homeobox gene, exons 2 and 3 and complete cds,
(xxviii) D87438 Human mRNA for KIAA0251 gene, partial cds,
(xxix) L37042 *H. sapiens* casein kinase I alpha isoform (CSNK1A1) mRNA, complete cds,
(xxx) D14043 Human mRNA for MGC-24, complete cds,
(xxxi) D13988 Human rab GDI mRNA, complete cds,
(xxxii) U28480 Uncoupling Protein Uc,
(xxxiii) D50840 *H. sapiens* mRNA for ceramide glucosyltransferase, complete cds,
(xxxiv) M55265 Human casein kinase II alpha subunit mRNA, complete cds,
(xxxv) M96803 Human general beta-spectrin (SPTBN1) mRNA, complete cds,
(xxxvi) U89336 Human HLA class III region containing NOTCH4 gene, partial sequence, homeobox P,
(xxxvii) D87442 Human mRNA for KIAA0253 gene, partial cds,
(xxxviii) J03161 Human serum response factor (SRF3) mRNA, complete cds,
(xxxix) D86965 Human mRNA for KIAA0210 gene, complete cds,
(xl) U17327 Human neuronal nitric oxide synthase (NOS1) mRNA, complete cds,
(xli) D86966 Human mRNA for KIAA0211 gene, complete cds,
(xlii) D85527 *H. sapiens* mRNA for LIM domain, partial cds,
(xliii) U42031 Human 54 kDa progesterone receptor-associated immunophilin FKBP54 mRNA, partial,
(xliv) X59434 Human rohu mRNA for rhodanese,
(xlv) M13929 Human c-myc-P64 mRNA, initiating from promoter P0, (HLmyc2.5) partial cds, and
(xlvi) J05211 Desmoplakin;
(b) the second response further comprises an altered pattern of expression of at least one nucleic acid molecule that is at least 90% identical to a polynucleotide selected from the group consisting of; and
(i) M57731 Human gro-beta mRNA, complete cds,
(ii) S81914 IEX-1=radiation-inducible immediate-early gene [human, placenta, mRNA Partial, 1,
(iii) Y00787 Human mRNA for MDNCF (monocyte-derived neutrophil chemotactic factor),
(iv) X54489 Human gene for melanoma growth stimulatory activity (MGSA),
(v) M72885 Human GOS2 gene, 5' flank and cds,
(vi) M62831 Human transcription factor ETR101 mRNA, complete cds,
(vii) M28130 Human interleukin 8 (IL8) gene, complete cds,
(viii) X57985 *H. sapiens* genes for histones H2B.1 and H2A,
(ix) X53800 Human mRNA for macrophage inflammatory protein-2beta (MIP2beta),
(x) L19779 *H. sapiens* histone H2A.2 mRNA, complete cds,
(xi) AF001294 *H. sapiens* IPL (IPL) mRNA, complete cds,
(xii) X56681 Human junD mRNA,
(xiii) S75762 Oncogene Tls/Chop, Fusion Activate,
(xiv) M84739 Human autoantigen calreticulin mRNA, complete cds,
(xv) M21302 Human small proline rich protein (sprII) mRNA, clone 174N,
(xvi) V00599 Tubulin, Bet,
(xvii) X70326 Macmarck,
(xviii) D10923 Human mRNA for HM74,
(xix) D64142 Human mRNA for histone H1x, complete cds,
(xx) D86974 Human mRNA for KIAA0220 gene, partial cds,
(xxi) M60974 Human growth arrest and DNA-damage-inducible protein (gadd45) mRNA, complete cds,
(xxii) X68277 *H. sapiens* CL 100 mRNA for protein tyrosine phosphatase,
(xxiii) L13391 Human helix-loop-helix basic phosphoprotein (GOS8) gene, complete cds,
(xxiv) M31627 Human X box binding protein-1 (XBP-1) mRNA, complete cds,
(xxv) U40369 Human spermidine/spermine N1-acetyltransferase (SSAT) gene, complete cds,
(xxvi) X52560 Nuclear Factor Nf-Il,
(xxvii) X61123 Human BTG1 mRNA,
(xxviii) U20734 Human transcription factor junB (junB) gene, 5∝ region and complete cds,
(xxix) U35048 Human TSC-22 protein mRNA, complete cds,
(xxx) M69043 *H. sapiens* MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 *H. sapiens* mRNA for TGIF protein,
(xxxiv) X69111 *H. sapiens* HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 *H. sapiens* mRNA for TGF-betaIIR alpha, complete cds,
(xxxviii) M92843 *H. sapiens* zinc finger transcriptional regulator mRNA, complete cds,
(xxxix) X91247 *H. sapiens* mRNA for thioredoxin reductase,
(xi) U05875 Human clone pSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 *H. sapiens* gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1 alpha mRNA, complete cds,
(li) L77886 Human protein tyrosine phosphatase mRNA, complete cds,
(lii) X64330 *H. sapiens* mRNA for ATP-citrate lyase,
(liii) U37122 Human adducin gamma subunit mRNA, complete cds,
(liv) X74008 *H. sapiens* mRNA for protein phosphatase 1 gamma, (lv) U60205 Human methyl sterol oxidase (ERG25) mRNA, complete cds,
(lvi) X76534 H. sapiens NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 H. sapiens CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, E. coli DnaJ homologue mRNA, complete cds,
(lxix) D50840 H. sapiens mRNA for ceramide glucosyltransferase, complete cds,
(lxx) L31801 H. sapiens monocarboxylate transporter 1 (SLC16A1) mRNA, complete cds,
(lxxi) S74017 Nrf2=NF-E2-like basic leucine zipper transcriptional activator [human, hemin-in,
(lxxii) X87241 H. sapiens mRNA for hFat protein,
(lxxiii) X52425 Human IL-4-R mRNA for the interleukin 4 receptor,
(lxxiv) D79994 Human mRNA for KIAA0172 gene, partial cds,
(lxxv) M58286 H. sapiens tumor necrosis factor receptor mRNA, complete cds,
(lxxvi) M13829 Human putative raf related protein (pks/a-raf) mRNA, partial cds,
(lxxvii) X78992 H. sapiens ERF-2 mRNA,
(lxxviii) U42031 Human 54 kDa progesterone receptor-associated immunophilin FKBP54 mRNA, partial,
(lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GH) germline c-myc proto-oncogene, exon 3 and 3' flank,
(lxxxiii) U26336 Heat Shock Protein, 70 Kda (Gb:Y00371,
(lxxxiv) L08246 Human myeloid cell differentiation protein (MCL1) mRNA,
(lxxxv) S73591 brain-expressed HHCPA78 homolog [human, HL-60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 H. sapiens mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HLmyc2.5) partial cds,
(xcii) D78129 H. sapiens mRNA for squalene epoxidase, partial cds,
(xciii) X80692 H. sapiens ERK3 mRNA, and
(xciv) J00120 Proto-Oncogene C-Myc, Alt. Splice 3, Orf 114; and
(c) the third response further comprises an altered pattern of expression of at least one nucleic acid molecule that is at least 90% identical to a polynucleotide selected from the group consisting of:
(i) M20030 Human small proline rich protein (sprII) mRNA, clone 930,
(ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 H. sapiens genes for histones H2B.1 and H2A,
(x) L05188 H. sapiens small proline-rich protein 2 (SPRR2B) gene, complete cds,
(xi) X70326 Macmarcks,
(xii) X67325 H. sapiens p27 mRNA,
(xiii) L19779 H. sapiens histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 H. sapiens thiol-specific antioxidant protein mRNA,
(xvii) M22918 Myosin, Light Chain, Alkali, Smooth Muscle (Gb:U02629), Non-Muscle, Alt. Splice,
(xviii) X06956 Tubulin, Alpha 1, Isoform 44,
(xix) V00594 Human mRNA for metallothionein from cadmium-treated cells,
(xx) M80254 H. sapiens cyclophilin isoform (hCyP3) mRNA, complete cds,
(xxi) U04636 Human cyclooxygenase-2 (hCox-2) gene, complete cds,
(xxii) Z14244 H. sapiens cox VIIb mRNA for cytochrome c oxidase subunit VIIb,
(xxiii) X99920 H. sapiens mRNA for S100 calcium-binding protein A13,
(xxiv) U62800 Human cystatin M (CST6) mRNA, complete cds,
(xxv) L08069 Human heat shock protein, E. coli DnaJ homologue mRNA, complete cds,
(xxvi) L20688 Human GDP-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cds,
(xxix) AF001294 H. sapiens IPL (IPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl, (xxxii) D42040 Human mRNA for KIAA9001 gene, complete cds,
(xxxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 *H. sapiens* mRNA for smoothelin,
(xxxviii) L24564 Human Rad mRNA, complete cds,
(xxxix) D49824 Human HLA-B null allele mRNA,
(xl) M59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 *H. sapiens* L23-related mRNA,
(xliii) M22919 Myosin, Light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 *H. sapiens* Arp2/3 protein complex subunit p41-Arc (ARC41) mRNA, complete cds,
(xlvi) X62083 *H. sapiens* mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} [human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X,
(liii) M14328 Human alpha enolase mRNA, complete cds,
(liv) U07919 Human aldehyde dehydrogenase 6 mRNA, complete cds,
(lv) M281330 Human interleukin 8 (IL8) gene, complete cds,
(lvi) Z21507 *H. sapiens* EF-1delta gene encoding human elongation factor-1-delta,
(lvii) M92934 Human connective tissue growth factor, complete cds,
(lviii) M27436 Human tissue factor gene, complete cds, with a Alu repetitive sequence in the 3',
(lix) X74874 *H. sapiens* gene for RNA pol II largest subunit, exon 1,
(lx) X57351 Human 1-8D gene from interferon-inducible gene family,
(lxi) X52979 Human gene for small nuclear ribonucleoproteins SmB and SmB',
(lxii) U41515 Human deleted in split hand/split foot 1 (DSS1) mRNA, complete cds,
(lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 *H. sapiens* mRNA for ceramide glucosyltransferase, complete cds,
(lxvii) U52101 Human YMP mRNA, complete cds,
(lxviii) D13413 Human mRNA for tumor-associated 120 kDa nuclear protein p120, partial cds(carbox,
(lxix) L42379 *H. sapiens* bone-derived growth factor (BPGF-1) mRNA, complete cds,
(lxx) X52426 *H. sapiens* mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 *H. sapiens* mRNA for ITBA2 protein,
(lxxvi) Z69043 *H. sapiens* mRNA translocon-associated protein delta subunit precursor,
(lxxvii) L76568 *H. sapiens* excision and cross link repair protein (ERCC4) gene, complete genom,
(lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver-specific cytochrome c oxidase (EC 1.9.3.1.),
(lxxxi) M34516 Human omega light chain protein 14.1 (Ig Lambda chain related) gene, exon 3,
(lxxxii) U53830 *H. sapiens* interferon regulatory factor 7A mRNA, complete cds,
(lxxxiii) X82693 *H. sapiens* mRNA for E48 antigen,
(lxxxiv) M58026 Human NB-1 mRNA, complete cds,
(lxxxv) M90657 Human tumor antigen (L6) mRNA, complete cds,
(lxxxvi) X57579 *H. sapiens* activin beta-A subunit (exon 2),
(lxxxvii) D38251 Human mRNA for RPB5 (XAP4), complete cds,
(lxxxviii) D89667 *H. sapiens* mRNA for c-myc binding protein, complete cds,
(lxxxix) AB000584 *H. sapiens* mRNA for TGF-beta superfamily protein, complete cds,
(xc) L76200 Human guanylate kinase (GUK1) mRNA, complete cds,
(xci) J04794 Human aldehyde reductase mRNA, complete cds,
(xcii) X52882 Human t-complex polypeptide 1 gene,
(xciii) M79463 Human PML-2 mRNA, complete CDS,
(xciv) Y09022 *H. sapiens* mRNA for Not56-like protein,
(xcv) M12529 Human apolipoprotein E mRNA, complete cds,
(xcvi) X71129 *H. sapiens* mRNA for electron transfer flavoprotein beta subunit,
(xcvii) X83416 *H. sapiens* PrP gene, exon 2,
(xcviii) D89052 *H. sapiens* mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb:M21533),
(ciii) Z29505 *H. sapiens* mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 *H. sapiens* mRNA for proliferation-associated gene (pag),
(cvii) J04611 Human lupus p70 (Ku) autoantigen protein mRNA, complete cds, (cviii) U09578 *H. sapiens* MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 kDa subunit,
(cxvii) X77794 *H. sapiens* mRNA for cyclin G1,
(cxviii) M29064 Human hnRNP B1 protein mRNA,
(cxix) D21853 Human mRNA for KIAA0111 gene, complete cds,
(cxx) X78687 *H. sapiens* G9 gene encoding sialidase,
(cxxi) X15729 Human mRNA for nuclear p68 protein,
(cxxii) X04828 Human mRNA for G(i) protein alpha-subunit (adenylate cyclase inhibiting GTP-bind,
(cxxiii) L27943 *H. sapiens* cytidine deaminase (CDA) mRNA, complete cds,
(cxxiv) L40391 *H. sapiens* (clone s153) mRNA fragment,
(cxxv) D42123 *H. sapiens* mRNA for ESP1/CRP2, complete cds,
(cxxvi) X74104 *H. sapiens* mRNA for TRAP beta subunit,
(cxxvii) M84332 Human ADP-ribosylation factor 1 gene, exons 2–5,
(cxxviii) L37127 *H. sapiens* RNA polymerase II mRNA, complete cds,
(cxxix) M92843 *H. sapiens* zinc finger transcriptional regulator mRNA, complete cds,
(cxxx) U07664 Human HB9 homeobox gene, exons 2 and 3 and complete cds,
(cxxxi) L48546 *H. sapiens* tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds,
(cxxxiv) L11066 Human mRNA sequence,
(cxxxv) J04444 Human cytochrome c-1 gene, complete cds,
(cxxxvi) M95787 Human 22 kDA smooth muscle protein (SM22) mRNA, complete cds,
(cxxxvii) L07517 Mucin 6, Gastric (Gb:L07517),
(cxxxviii) X91247 *H. sapiens* mRNA for thioredoxin reductase,
(cxxxix) L11672 Human Kruppel related zinc finger protein (HTF10) mRNA, complete cds,
(cxl) U30999 Human (memc) mRNA, 3'UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 *H. sapiens* mRNA for alpha 4 protein,
(cxlvii) M24547 Amyloid Beta (A4) Precursor Protein, Alt. Splice 2, A4(751),
(cxlviii) X76717 *H. sapiens* MT-11 mRNA,
(cxlix) M64347 Human novel growth factor receptor mRNA, 3' cds,
(cl) X05409 Human RNA for mitochondrial aldehyde dehydrogenase I ALDH I (EC 1.2.1.3),
(cli) D87469 Human mRNA for KIAA0279 gene, partial cds,
(clii) M58603 Human nuclear factor kappa-B DNA binding subunit (NF-kappa-B) mRNA, complete cds,
(cliii) M76482 Human 130-kD pemphigus vulgaris antigen mRNA, complete cds,
(cliv) X06323 Human MRL3 mRNA for ribosomal protein L3 homologue (MRL3=mammalian ribosome L,
(clv) X78992 *H. sapiens* ERF-2 mRNA,
(clvi) L41351 *M. sapiens* prostasin mRNA, complete cds,
(clvii) X75342 *H. sapiens* SHB mRNA,
(clviii) U83115 Human non-lens beta gamma-crystallin like protein (AIM1) mRNA, partial cds,
(clix) U88629 Human RNA polymerase II elongation factor ELL2, complete cds,
(clx) S78825 Id1,
(clxi) U28811 Human cysteine-rich fibroblast growth factor receptor (CFR-1) mRNA, complete cds,
(clxii) M58286 *H. sapiens* tumor necrosis factor receptor mRNA, complete cds,
(clxiii) D78129 *H. sapiens* mRNA for squalene epoxidase, partial cds,
(clxiv) D14874 *H. sapiens* mRNA for adrenomedullin precursor, complete cds,
(clxv) Z26317 *H. sapiens* mRNA for desmoglein 2,
(clxvi) L19267 *H. sapiens* 59 protein mRNA, 3' end,
(clxvii) J00120 Proto-Oncogene C-Myc, Alt. Splice 3, Orf 114,
(clxviii) U33821 Human tax1-binding protein TXBP151 mRNA, complete cds,
(clxix) U52100 Human XMP mRNA, complete cds,
(clxx) L31801 *H. sapiens* monocarboxylate transporter 1 (SLC16A1) mRNA, complete cds,
(clxxi) L00058 Human (GH) germline c-myc proto-oncogene, exon 3 and 3' flank,
(clxxii) U52426 *H. sapiens* GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 *H. sapiens* ADP-ribosylation factor mRNA, complete cds,
(clxxvi) U14603 Human protein-tyrosine phosphate (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 *H. sapiens* mRNA for TGIF protein,
(clxxx) D85429 *H. sapiens* gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 *H. sapiens* OXA1Hs mRNA,
(clxxxiv) M54915 Human h-pim-1 protein (h-pim-1) mRNA, complete cds, (clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 H. sapiens mRNA for chloride channel (putative) 2139 bp,
(cxci) D14520 Human mRNA for GC-Box binding protein BTEB2, complete cds,
(cxcii) D87462 Human mRNA for KIAA0272 gene, partial cds,
(cxciii) X80692 H. sapiens ERK3 mRNA,
(cxciv) X90858 H. sapiens mRNA for uridine phosphorylase,
(cxcv) M57763 Human ADP-ribosylation factor (hARF6) mRNA, complete cds,
(cxcvi) X92720 H. sapiens mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 H. sapiens HBZ17 mRNA,
(cciii) X76534 H. sapiens NMB mRNA,
(cciv) U37519 Human aldehyde dehydrogenase (ALDH8) mRNA, complete cds,
(ccv) M83667 Human NF-IL6beta protein mRNA, complete cds,
(ccvi) U53347 Human neutral amino acid transporter B mRNA, complete cds,
(ccvii) L09229 Human long-chain acyl-coenzyme A synthetase (FACL1) mRNA, complete cds,
(ccviii) S73591 brain-expressed HHCPA78 homolog [human, HL-60 acute promyelocytic leukemia cells,
(ccix) M13929 Human c-myc-P64 mRNA, initiating from promoter P0, (HLmyc2.5) partial cds,
(ccx) M55268 Human casein kinase II alpha' subunit mRNA, complete cds,
(ccxi) M77836 Human pyrroline 5-carboxylate reductase mRNA, complete cds,
(ccxii) HG2724-HT820 at S75762 Oncogene Tls/Chop, Fusion Activated,
(ccxiii) U72066 H. sapiens CtBP interacting protein CtIP (CtIP) mRNA, complete cds,
(ccxiv) U42031 Human 54 kDA progesterone receptor-associated immunophilin FKBP54 mRNA, partial,
(ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase, complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 H. sapiens HLH 1R21 mRNA for helix-loop-helix protein.

72. A method to detect exposure of a cell to ultraviolet radiation comprising:
(a) measuring the levels of a plurality of RNA molecules in the cell by expression array analysis, comprising:
(i) isolating RNA from the cell post ultraviolet radiation exposure;
(ii) creating a test expression array through nucleic acid hybridization between a labeled probe complementary to the RNA and an expression array substrate;
(iii) analyzing the test expression array to create a test expression array data set; and
(iv) comparing the test expression array data set to a control expression array data; and
(b) analyzing the levels of the plurality of RNA molecules and thereby establishing a response pattern of the cell, wherein exposure of the cell to ultraviolet radiation is indicated by the altered pattern of expression comprising the following:
(i) a first response comprising the altered pattern of expression of at least one polynucleotide selected from the group consisting of a nucleic acid molecule encoding a transcription factor protein, a nucleic acid molecule encoding a signal transducing protein, and a nucleic acid molecule encoding a mitochondrial protein;
(ii) a second response comprising the altered pattern of expression of at least one polynucleotide selected from the group consisting of a nucleic acid molecule encoding a secreted growth factor, a nucleic acid molecule encoding a cytokine, and a nucleic acid molecule encoding a chemokine; and
(iii) a third response comprising the altered pattern of expression of at least one polynucleotide selected from the group consisting of a nucleic acid molecule encoding an actin-binding protein, a nucleic acid molecule encoding a desmosomal protein, and a nucleic acid molecule encoding a tubulin protein.

73. The method according to claim 72, wherein the cell is selected from the group consisting of a keratinocyte, a Langerhans cell, a melanocyte, and a fibroblast cell.

74. The method according to claim 72, wherein the ultraviolet radiation exposure comprises ultraviolet radiation energy at a wavelength in the range of 220 nm to 440 nm.

75. The method according to claim 72, wherein the ultraviolet radiation exposure comprises ultraviolet radiation energy at a wavelength of about 290 nm to about 320 nm.

76. The method according to claim 72, wherein the ultraviolet radiation exposure comprises ultraviolet radiation energy at a wavelength in the range of about 320 nm to about 440 nm.

77. The method according to claim 72, wherein the ultraviolet radiation exposure comprises a total ultraviolet radiation energy exposure in the range of 0.2 mJ/cm$^2$ to 40 mJ/cm$^2$.

78. The method according to claim 72, wherein the pattern is further characterized by:
(a) the first response occurring from about 0.5 hours to about 2 hours post-exposure to ultraviolet radiation
(b) the second response occurring from about 4 hours to about 8 hours post-exposure to ultraviolet radiation; and
(c) the third response occurring from about 16 hours to about 24 hours post-exposure to ultraviolet radiation.

79. The method according to claim 72, wherein altered expression comprises an increase or decrease in the level of RNA.

80. The method according to claim 72, wherein:
(a) the first response further comprises an altered pattern of expression of at least one nucleic acid molecule that is at least 90% identical to a polynucleotide selected from the group consisting of:
  (i) M62831 Human transcription factor ETR101 mRNA, complete cds,
  (ii) X68277 H. sapiens CL 100 mRNA for protein tyrosine phosphatase,
  (iii) L04731 H. sapiens translocation T(4:11) of ALL1 gene to chromosome 4,
  (iv) X56681 Human junD mRNA,
  (v) U20734 Human transcription factor junB (junB) gene, 5' region and complete cds,
  (vi) L38951 H. sapiens importin beta subunit mRNA, complete cds,
  (vii) D87071 Human mRNA for KIAA0233 gene, complete cds,
  (viii) M72885 Human GOS2 gene, 5' flank and cds,
  (ix) M92843 H. sapiens zinc finger transcriptional regulator mRNA, complete cds,
  (x) S81914 IEX-1=radiation-inducible immediate-early gene [human, placenta, mRNA Partial,
  (xi) U72649 Human BTG2 (BTG2) mRNA, complete cds,
  (xii) D86988 Human mRNA for KIAA0221 gene, complete cds,
  (xiii) L19779 H. sapiens histone H2A.2 mRNA, complete cds,
  (xiv) U62317 Chromosome 22q13 BAC Clone CIT987SK-384D8 complete sequence,
  (xv) X04412 Human mRNA for plasma gelsolin,
  (xvi) L27706 Human chaperonin protein (Tcp20) gene complete cds,
  (xvii) X61123 Human BTG1 mRNA,
  (xviii) M60974 growth arrest and DNA-damage-inducible protein (gadd45) mRNA, complete cds,
  (xix) L19437 Human transaldolase mRNA containing transposable element, complete cds,
  (xx) X57985 H. sapiens genes for histones H2B.1 and H2A,
  (xxi) D90086 Human pyruvate dehydrogenase (EC 1.2.4.1) beta subunit gene, exons 1–10,
  (xxii) M34182 Human testis-specific protein kinase gamma-subunit mRNA, complete cds,
  (xxiii) L16862 H. sapiens G protein-coupled receptor kinase (GRK6) mRNA, complete cds,
  (xxiv) D13705 Human mRNA for fatty acids omega-hydroxylase (cytochrome P-450HKV), complete cd,
  (xxv) U37122 Human adducin gamma subunit mRNA, complete cds,
  (xxvi) D45906 H. sapiens mRNA for LIMK-2, complete cds,
  (xxvii) U07664 Human HB9 homeobox gene, exons 2 and 3 and complete cds,
  (xxviii) D87438 Human mRNA for KIAA0251 gene, partial cds,
  (xxix) L37042 H. sapiens casein kinase I alpha isoform (CSNK1A1) mRNA, complete cds,
  (xxx) D14043 Human mRNA for MGC-24, complete cds,
  (xxxi) D13988 Human rab GDI mRNA, complete cds,
  (xxxii) U28480 Uncoupling Protein Uc,
  (xxxiii) D50840 H. sapiens mRNA for ceramide glucosyltransferase, complete cds,
  (xxxiv) M55265 Human casein kinase II alpha subunit mRNA, complete cds,
  (xxxv) M96803 Human general beta-spectrin (SPTBN1) mRNA, complete cds,
  (xxxvi) U89336 Human HLA class III region containing NOTCH4 gene, partial sequence, homeobox P,
  (xxxvii) D87442 Human mRNA for KIAA0253 gene, partial cds,
  (xxxviii) J03161 Human serum response factor (SRF) mRNA, complete cds,
  (xxxix) D86965 Human mRNA for KIAA0210 gene, complete cds,
  (xl) U17327 Human neuronal nitric oxide synthase (NOS1) mRNA, complete cds,
  (xli) D86966 Human mRNA for KIAA0211 gene, complete cds,
  (xlii) D85527 H. sapiens mRNA for LIM domain, partial cds,
  (xliii) U42031 Human 54 kDA progesterone receptor-associated immunophilin FKBP54 mRNA, partial,
  (xliv) X59434 Human rohu mRNA for rhodanese,
  (xlv) M13929 Human c-myc-P64 mRNA, initiating from promoter P0, (HLmyc2.5) partial cds, and
  (xlvi) J05211 Desmoplakin;
(b) the second response further comprises an altered pattern of expression of at least three nucleic acid molecule that is at least 90% identical to a polynucleotide selected from the group consisting of; and
  (i) M57731 Human gro-beta mRNA, complete cds,
  (ii) S81914 IEX-1=radiation-inducible immediate-early gene [human, placenta, mRNA Partial, 1,
  (iii) Y00787 Human mRNA for MDNCF (monocyte-derived neutrophil chemotactic factor),
  (iv) X54489 Human gene for melanoma growth stimulatory activity (MGSA),
  (v) M72885 Human GOS2 gene, 5' flank and cds,
  (vi) M62831 Human transcription factor ETR101 mRNA, complete cds,
  (vii) M28130 Human interleukin 8 (IL8) gene, complete cds,
  (viii) X57985 M. sapiens genes for histones H2B.1 and H2A,
  (ix) X53800 Human mRNA for macrophage inflammatory protein-2beta (MIP2beta),
  (x) L19779 H. sapiens histone H2A.2 mRNA, complete cds,
  (xi) AF001294 H. sapiens IPL (IPL) mRNA, complete cds,
  (xii) X56681 Human junD mRNA,
  (xiii) S75762 Oncogene Tls/Chop, Fusion Activate,
  (xiv) M84739 Human autoantigen calreticulin mRNA, complete cds,
  (xv) M21302 Human small proline rich protein (sprII) mRNA, clone 174N,
  (xvi) V00599 Tubulin, Bet,
  (xvii) X70326 Macmarck,
  (xviii) D10923 Human mRNA for HM74,
  (xix) D64142 Human mRNA for histone H1x, complete cds,
  (xx) D86974 Human mRNA for KIAA0220 gene, partial cds,
  (xxi) M60974 Human growth arrest and DNA-damage-inducible protein (gadd45) mRNA, complete cds,
  (xxii) X68277 H. sapiens CL 100 mRNA for protein tyrosine phosphatase,
  (xxiii) L13391 Human helix-loop-helix basic phosphoprotein (GOS8) gene, complete cds,
  (xxiv) M31627 Human X box binding protein-1 (XBP-1) mRNA, complete cds, (xxv) U40369 Human spermidine/spermine N1-acetyltransferase (SSAT) gene, complete cds,
(xxvi) X52560 Nuclear Factor Nf-Il,
(xxvii) X61123 Human BTG1 mRNA,
(xxviii) U20734 Human transcription factor junB (junB) gene, 5' region and complete cds,
(xxix) U35048 Human TSC-22 protein mRNA, complete cds,
(xxx) M69043 *H. sapiens* MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 *H. sapiens* mRNA for TGIF protein,
(xxxiv) X69111 *H. sapiens* HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 *H. sapiens* mRNA for TGF-betaIIR alpha, complete cds,
(xxxviii) M92843 *H. sapiens* zinc finger transcriptional regulator mRNA, complete cds,
(xxxix) X91247 *H. sapiens* mRNA for thioredoxin reductase,
(xl) U05875 Human clone pSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 *H. sapiens* gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1alpha mRNA, complete cds,
(li) L77886 Human protein tyrosine phosphatase mRNA, complete cds,
(lii) X64330 *H. sapiens* mRNA for ATP-citrate lyase,
(liii) U37122 Human adducin gamma subunit mRNA, complete cds,
(liv) X74008 *H. sapiens* mRNA for protein phosphatase 1 gamma,
(lv) U60205 Human methyl sterol oxidase (ERG25) mRNA, complete cds,
(lvi) X76534 *H. sapiens* NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 *H. sapiens* CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, *E. coli* DnaJ homologue mRNA, complete cds,
(lxix) D50840 *H. sapiens* mRNA for ceramide glucosyltransferase, complete cds,
(lxx) L31801 *H. sapiens* monocarboxylate transporter I (SLC16A1) mRNA, complete cds,
(lxxi) S74017 Nrf2=NF-E2-like basic leucine zipper transcriptional activator [human, hemin-in,
(lxxii) X87241 *H. sapiens* mRNA for hFat protein,
(lxxiii) X52425 Human IL-4-R mRNA for the interleukin 4 receptor,
(lxxiv) D79994 Human mRNA for KIAA0172 gene, partial cds,
(lxxv) M58286 *H. sapiens* tumor necrosis factor receptor mRNA, complete cds,
(lxxvi) M13829 Human putative raf related protein (pks/a-raf) mRNA, partial cds,
(lxxvii) X78992 *H. sapiens* ERF-2 mRNA,
(lxxviii) U42031 Human 54 kDA progesterone receptor-associated immunophilin FKBP54 mRNA, partial,
(lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GH) germline c-myc proto-oncogene, exon 3 and 3' flank,
(lxxxiii) L26336 Heat Shock Protein, 70 Kda (Gb:Y00371,
(lxxxiv) L08246 Human myeloid cell differentiation protein (MCL1) mRNA,
(lxxxv) S73591 brain-expressed HHCPA78 homolog [human, HL-60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 *H. sapiens* mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HLmyc2.5) partial cds,
(xcii) D78129 *H. sapiens* mRNA for squalene epoxidase, partial cds,
(xciii) X80692 *H. sapiens* ERK3 mRNA, and
(xciv) J00120 Proto-Oncogene C-Myc, Alt. Splice 3, Orf 114; and
(c) the third response further comprises an altered pattern of expression of at least one nucleic acid molecule that is at least 90% identical to a polynucleotide selected from the group consisting of:
(i) M20030 Human small proline rich protein (sprII) mRNA, clone 930, (ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 *H. sapiens* genes for histones H2B.1 and H2A,
(x) L05188 *H. sapiens* small proline-rich protein 2 (SPRR2B) gene, complete cds,
(xi) X70326 Macmarcks,
(xii) X67325 *H. sapiens* p27 mRNA,
(xiii) L19779 *H. sapiens* histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 *H. sapiens* thiol-specific antioxidant protein mRNA,
(xvii) M22918 Myosin, Light Chain, Alkali, Smooth Muscle (Gb:U02629), Non-Muscle, Alt. Splice,
(xviii) X06956 Tubulin, Alpha 1, Isoform 44,
(xix) V00594 Human mRNA for metallothionein from cadmium-treated cells,
(xx) M80254 *H. sapiens* cyclophilin isoform (hCyP3) mRNA, complete cds,
(xxi) U04636 Human cyclooxygenase-2 (hCox-2) gene, complete cds,
(xxii) Z14244 *H. sapiens* cox VIIb mRNA for cytochrome c oxidase subunit VIIb,
(xxiii) X99920 *H. sapiens* mRNA for S100 calcium-binding protein A13,
(xxiv) U62800 Human cystatin M (CST6) mRNA, complete cds,
(xxv) L08069 Human heat shock protein, *E. coli* DnaJ homologue mRNA, complete cds,
(xxvi) L20688 Human GDP-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cds,
(xxix) AF001294 *H. sapiens* IPL (IPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl,
(xxxii) D42040 Human mRNA for KIAA9001 gene, complete cds,
(xxxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 *H. sapiens* mRNA for smoothelin,
(xxxviii) L24564 Human Rad mRNA, complete cds,
(xxxix) D49824 Human HLA-B null allele mRNA,
(xl) M59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 *H. sapiens* L23related mRNA,
(xliii) M22919 Myosin, Light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 *H. sapiens* Arp2/3 protein complex subunit p41-Arc (ARC41) mRNA, complete cds,
(xlvi) X62083 *H. sapiens* mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} [human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X,
(liii) M14328 Human alpha enolase mRNA, complete cds,
(liv) U07919 Human aldehyde dehydrogenase 6 mRNA, complete cds,
(lv) M28130 Human interleukin 8 (IL8) gene, complete cds,
(lvi) Z21507 *H. sapiens* EF-1 delta gene encoding human elongation factor-1-delta,
(lvii) M92934 Human connective tissue growth factor, complete cds,
(lviii) M27436 Human tissue factor gene, complete cds, with a Alu repetitive sequence in the 3',
(lix) X74874 *H. sapiens* gene for RNA pol II largest subunit, exon 1,
(lx) X57351 Human 1-8D gene from interferon-inducible gene family,
(lxi) X52979 Human gene for small nuclear ribonucleoproteins SmB and SmB',
(lxii) U41515 Human deleted in split hand/split foot 1 (DSS1) mRNA, complete cds,
(lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 *H. sapiens* mRNA for ceramide glucosyltransferase, complete cds,
(lxvii) U52101 Human YMP mRNA, complete cds,
(lxviii) D13413 Human mRNA for tumor-associated 120 kDA nuclear protein p120, partial cds(carbox,
(lxix) L42379 *H. sapiens* bone-derived growth factor (BPGF-1) mRNA, complete cds,
(lxx) X52426 *H. sapiens* mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 *H. sapiens* mRNA for ITBA2 protein,
(lxxvi) Z69043 *H. sapiens* mRNA translocon-associated protein delta subunit precursor,
(lxxvii) L76568 *H. sapiens* excision and cross link repair protein (ERCC4) gene, complete genom, (lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver-specific cytochrome c oxidase (EC 1.9.3.1.),
(lxxxi) M34516 Human omega light chain protein 14.1 (Ig lambda chain related) gene, exon 3,
(lxxxii) U53830 H. sapiens interferon regulatory factor 7A mRNA, complete cds,
(lxxxiii) X82693 H. sapiens mRNA for E48 antigen,
(lxxxiv) M58026 Human NB-1 mRNA, complete cds,
(lxxxv) M90657 Human tumor antigen (L6) mRNA, complete cds,
(lxxxvi) X57579 H. sapiens activin beta-A subunit (exon 2),
(lxxxvii) D38251 Human mRNA for RPB5 (XAP4), complete cds.
(lxxxviii) D89667 H. sapiens mRNA for c-myc binding protein, complete cds,
(lxxxix) AB000584 H. sapiens mRNA for TGF-beta superfamily protein, complete cds,
(xc) L76200 Human guanylate kinase (GUK1) mRNA, complete cds,
(xci) J04794 Human aldehyde reductase mRNA, complete cds,
(xcii) X52882 Human t-complex polypeptide 1 gene,
(xciii) M79463 Human PML-2 mRNA, complete CDS,
(xciv) Y09022 H. sapiens mRNA for Not56-like protein,
(xcv) M12529 Human apolipoprotein E mRNA, complete cds,
(xcvi) X71129 H. sapiens mRNA for electron transfer flavoprotein beta subunit,
(xcvii) X83416 H. sapiens PrP gene, exon 2,
(xcviii) D89052 H. sapiens mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb:M21533),
(ciii) Z29505 H. sapiens mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 H. sapiens mRNA for proliferation-associated gene (pag),
(cvii) J04611 Human lupus p70 (Ku) autoantigen protein mRNA, complete cds,
(cviii) U09578 H. sapiens MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 kDA subunit,
(cxvii) X77794 H. sapiens mRNA for cyclin G1.
(cxviii) M29064 Human hnRNP B1 protein mRNA,
(cxix) D21853 Human mRNA for KIAA0111 gene, complete cds,
(cxx) X78687 H. sapiens G9 gene encoding sialidase,
(cxxi) X15729 Human mRNA for nuclear p68 protein,
(cxxii) X04828 Human mRNA for G(i) protein alpha-subunit (adenylate cyclase inhibiting GTP-bind,
(cxxiii) L27943 H. sapiens cytidine deaminase (CDA) mRNA, complete cds,
(cxxiv) L40391 H. sapiens (clone s153) mRNA fragment,
(cxxv) D42123 H. sapiens mRNA for ESP1/CRP2, complete cds,
(cxxvi) X74104 H. sapiens mRNA for TRAP beta subunit,
(cxxvii) M84332 Human ADP-ribosylation factor 1 gene, exons 2–5,
(cxxviii) L37127 H. sapiens RNA polymerase II mRNA, complete cds,
(cxxix) M92843 H. sapiens zinc finger transcriptional regulator mRNA, complete cds,
(cxxx) U07664 Human HB9 homeobox gene, exons 2 and 3 and complete cds,
(cxxxi) L48546 H. sapiens tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds,
(cxxxiv) L11066 Human mRNA sequence,
(cxxxv) J04444 Human cytochrome c-1 gene, complete cds,
(cxxxvi) M95787 Human 22 kDA smooth muscle protein (SM22) mRNA, complete cds,
(cxxxvii) L07517 Mucin 6, Gastric (Gb:L07517),
(cxxxviii) X91247 H. sapiens mRNA for thioredoxin reductase,
(cxxxix) L11672 Human Kruppel related zinc finger protein (HTF10) mRNA, complete cds,
(cxl) U30999 Human (memc) mRNA, 3'UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 H. sapiens mRNA for alpha 4 protein,
(cxlvii) M24547 Amyloid Beta (A4) Precursor Protein, Alt. Splice 2, A4(751),
(cxlviii) X76717 H. sapiens MT-11 mRNA,
(cxlix) M64347 Human novel growth factor receptor mRNA, 3' cds,
(cl) X05409 Human RNA for mitochondrial aldehyde dehydrogenase I ALDH I (EC 1.2.1.3),
(cli) D87469 Human mRNA for KIAA0279 gene, partial cds,
(clii) M58603 Human nuclear factor kappa-B DNA binding subunit (NF-kappa-B) mRNA, complete cds,
(cliii) M76482 Human 130-kD pemphigus vulgaris antigen mRNA, complete cds, (cliv) X06323 Human MRL3 mRNA for ribosomal protein L3 homologue (MRL3=mammalian ribosome L,
(clv) X78992 *H. sapiens* ERF-2 mRNA,
(clvi) L41351 *H. sapiens* prostasin mRNA, complete cds,
(clvii) X75342 *H. sapiens* SHB mRNA,
(clviii) U83115 Human non-lens beta gamma-crystallin like protein (AIM1) mRNA, partial cds,
(clix) U88629 Human RNA polymerase II elongation factor ELL2, complete cds,
(clx) S78825 Id1,
(clxi) U28811 Human cysteine-rich fibroblast growth factor receptor (CFR-1) mRNA, complete cds,
(clxii) M58286 *H. sapiens* tumor necrosis factor receptor mRNA, complete cds,
(clxiii) D78129 *H. sapiens* mRNA for squalene epoxidase, partial cds,
(clxiv) D14874 *H. sapiens* mRNA for adrenomedullin precursor, complete cds,
(clxv) Z26317 *H. sapiens* mRNA for desmoglein 2,
(clxvi) L19267 *H. sapiens* 59 protein mRNA, 3' end,
(clxvii) J00120 Proto-Oncogene C-Myc, Alt. Splice 3, Orf 114,
(clxviii) U33821 Human tax 1-binding protein TXBP151 mRNA, complete cds,
(clxix) U52100 Human XMP mRNA, complete cds,
(clxx) L31801 *H. sapiens* monocarboxylate transporter 1 (SLC16A1) mRNA, complete cds,
(clxxi) L00058 Human (GH) germline c-myc proto-oncogene, exon 3 and 3' flank,
(clxxii) U52426 *H. sapiens* GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 *H. sapiens* ADP-ribosylation factor mRNA, complete cds,
(clxxvi) U14603 Human protein-tyrosine phosphatase (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 *H. sapiens* mRNA for TGIF protein,
(clxxx) D85429 *H. sapiens* gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 *H. sapiens* OXA1Hs mRNA,
(clxxxiv) M54915 Human h-pim-1 protein (h-pim-1) mRNA, complete cds,
(clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 *H. sapiens* mRNA for chloride channel (putative) 2139 bp,
(cxci) D14520 Human mRNA for GC-Box binding protein BTEB2, complete cds,
(cxcii) D87462 Human mRNA for KIAA0272 gene, partial cds,
(cxciii) X80692 *H. sapiens* ERK3 mRNA,
(cxciv) X90858 *H. sapiens* mRNA for uridine phosphorylase,
(cxcv) M57763 Human ADP-ribosylation factor (hARF6) mRNA, complete cds,
(cxcvi) X92720 *H. sapiens* mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 *H. sapiens* HBZ17 mRNA,
(cciii) X76534 *H. sapiens* NMB mRNA,
(cciv) U37519 Human aldehyde dehydrogenase (ALDH8) mRNA, complete cds,
(ccv) M83667 Human NF-IL6-beta protein mRNA, complete cds.
(ccvi) U53347 Human neutral amino acid transporter B mRNA, complete cds,
(ccvii) L09229 Human long-chain acyl-coenzyme A synthetase (FACL1) mRNA, complete cds,
(ccviii) S73591 brain-expressed HHCPA78 homolog [human, HL60 acute promyelocytic leukemia cells,
(ccix) M13929 Human c-myc-P64 mRNA, initiating from promoter P0, (HLmyc2.5) partial cds,
(ccx) M55268 Human casein kinase II alpha' subunit mRNA, complete cds,
(ccxi) M77836 Human pyrroline 5-carboxylate reductase mRNA, complete cds,
(ccxii) HG2724-HT2820_at S75762 Oncogene Tls/Chop, Fusion Activated,
(ccxiii) U72066 *H. sapiens* CtBP interacting protein CtIP (CtIP) mRNA, complete cds,
(ccxiv) U42031 Human 54 kDA progesterone receptor-associated immunophilin FKBP54 mRNA, partial,
(ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 *H. sapiens* HLH 1R21 mRNA for helix-loop-helix protein.

81. A method for detecting exposure of a cell to ultraviolet radiation comprising measuring the levels of a plurality of proteins in the cell, wherein an altered pattern of expression is established and is indicative of ultraviolet radiation exposure, the pattern comprising the following:

(a) a first response comprising an altered pattern of expression of at least one protein selected from the group consisting of a transcription factor protein, a signal transduction protein, and a mitochondrial protein;

(b) a second response comprising an altered pattern of expression of at least one protein selected from the group consisting of a secreted growth factor protein, a cytokine protein, and a chemokine protein; and (c) a third response comprising an altered pattern of expression of at least one protein selected from the group consisting of an actin-binding protein, a desmosomal protein, and a tubulin protein.

82. The method according to claim 81, wherein the cell is selected from the group consisting of a keratinocyte, a Langerhans cell, a melanocyte, and a fibroblast cell.

83. The method according to claim 81, wherein the ultraviolet radiation exposure comprises ultraviolet radiation energy at a wavelength in the range of 220 nm to 440 nm.

84. The method according to claim 81, wherein the ultraviolet radiation exposure comprises ultraviolet radiation energy at a wavelength of about 290 nm to about 320 nm.

85. The method according to claim 81, wherein the ultraviolet radiation exposure comprises ultraviolet radiation energy at a wavelength in the range of about 320 nm to about 440 nm.

86. The method according to claim 81, wherein the ultraviolet radiation exposure comprises ultraviolet radiation energy in the range of about 0.2 mJ/cm$^2$ to about 40 mJ/cm$^2$.

87. The method according to claim 81, wherein the pattern of expression is further characterized by:

(a) the first response occurring from about 0.5 hours to about 2 hours post-exposure to ultraviolet radiation exposure;

(b) the second response occurring from about 4 hours to about 8 hours post-exposure to ultraviolet radiation exposure; and (c) the third response occurring from about 16 hours to about 24 hours post-exposure to ultraviolet radiation exposure.

88. The method according to claim 81, wherein the altered pattern of expression of comprises an increase or decrease in protein level.

89. The method according to claim 81, wherein:

(a) the fast response further comprises an altered pattern of expression of at least one protein that is at least 90% identical to a polypeptide encoded by a polynucleotide selected from the group consisting of:

(i) M62831 Human transcription factor ETR101 mRNA, complete cds, (ii) X68277 *H. sapiens* CL 100 mRNA for protein tyrosine phosphatase, (iii) L04731 *H. sapiens* translocation T(4:11) of ALL-1 gene to chromosome 4, (iv) X56681 Human junD mRNA, (v) U20734 Human transcription factor junB (junB) gene, 5' region and complete cds, (vi) L38951 *H. sapiens* importin beta subunit mRNA, complete cds, (vii) D87071 Human mRNA for KIAA0233 gene, complete cds, (viii) M72885 Human GOS2 gene, 5' flank and cds, (ix) M92843 *H. sapiens* zinc finger transcriptional regulator mRNA, complete cds, (x) S81914 IEX-1=radiation-inducible immediate-early gene [human, placenta, mRNA Partial, (xi) U72649 Human BTG2 (BTG2) mRNA, complete cds, (xii) D86988 Human mRNA for KIAA0221 gene, complete cds, (xiii) L19779 *H. sapiens* histone H2A.2 mRNA, complete cds, (xiv) U62317 Chromosome 22q13 BAC Clone CIT987SK-384D8 complete sequence, (xv) X04412 Human mRNA for plasma gelsolin, (xvi) L27706 Human chaperonin protein (Tcp20) gene complete cds, (xvii) X61123 Human BTG1 mRNA, (xviii) M60974 growth arrest and DNA-damage-inducible protein (gadd45) mRNA, complete cds, (xix) L19437 Human transaldolase mRNA containing transposable element, complete cds, (xx) X57985 *H. sapiens* genes for histones H2B.1 and H2A, (xxi) D90086 Human pyruvate dehydrogenase (EC 1.2.4.1) beta subunit gene, exons 1–10, (xxii) M34182 Human testis-specific protein kinase gamma-subunit mRNA, complete cds, (xxiii) L16862 *H. sapiens* G protein-coupled receptor kinase (GRK6) mRNA, complete cds, (xxiv) D13705 Human mRNA for fatty acids omega-hydroxylase (cytochrome P-450HKV), complete cd, (xxv) U37122 Human adducin gamma subunit mRNA, complete cds, (xxvi) D45906 *H. sapiens* mRNA for LIMK-2, complete cds, (xxvii) U07664 Human HB9 homeobox gene, exons 2 and 3 and complete cds, (xxviii) D87438 Human mRNA for KIAA0251 gene, partial cds, (xxix) L37042 *H. sapiens* casein kinase I alpha isoform (CSNK1 A1) mRNA, complete cds, (xxx) D14043 Human mRNA for MGC-24, complete cds, (xxxi) D13988 Human rab GDI mRNA, complete cds, (xxxii) U28480 Uncoupling Protein Uc, (xxxiii) D50840 *H. sapiens* mRNA for ceramide glucosyltransferase, complete cds, (xxxiv) M55265 Human casein kinase II alpha subunit mRNA, complete cds, (xxxv) M96803 Human general beta-spectrin (SPTBN1) mRNA, complete cds, (xxxvi) U89336 Human HLA class III region containing NOTCH4 gene, partial sequence, homeobox P, (xxxvii) D87442 Human mRNA for KIAA0253 gene, partial cds, (xxxviii) J03161 Human serum response factor (SRF) mRNA, complete cds, (xxxix) D86965 Human mRNA for KIAA0210 gene, complete cds, (xl) U17327 Human neuronal nitric oxide synthase (NOS1) mRNA, complete cds, (xli) D86966 Human mRNA for KIAA0211 gene, complete cds, (xlii) D85527 *H. sapiens* mRNA for LIM domain, partial cds, (xliii) U42031 Human 54 kDA progesterone receptor-associated immunophilin FKBP54 mRNA, partial, (xliv) X59434 Human rohu mRNA for rhodanese, (xlv) M13929 Human c-myc-P64 mRNA, initiating from promoter P0, (HLmyc2.5) partial cds, and (xlvi) J05211 Desmoplakin;

(b) the second response further comprises an altered pattern of expression of at least one protein that is at least 90% identical to a polypeptide encoded by a polynucleotide selected from the group consisting of; and (i) M57731 Human gro-beta mRNA, complete cds, (ii) S81914 IEX-1=radiation-inducible immediate-early gene [human, placenta, mRNA Partial, 1, (iii) Y00787 Human mRNA for MDNCF (monocyte-derived neutrophil chemotactic factor), (iv) X54489 Human gene for melanoma growth stimulatory activity (MGSA),
(v) M72885 Human GOS2 gene, 5' flank and cds,
(vi) M62831 Human transcription factor ETR101 mRNA, complete cds,
(vii) M28130 Human interleukin 8 (IL8) gene, complete cds,
(viii) X57985 H. sapiens genes for histones H2B.1 and H2A,
(ix) X53800 Human mRNA for macrophage inflammatory protein-2beta (MIP2beta),
(x) L19779 H. sapiens histone H2A.2 mRNA, complete cds,
(xi) AF001294 H. sapiens IPL (IPL) mRNA, complete cds,
(xii) X56681 Human junD mRNA,
(xiii) S75762 Oncogene Tls/Chop, Fusion Activate,
(xiv) M84739 Human autoantigen calreticulin mRNA, complete cds,
(xv) M21302 Human small proline rich protein (sprII) mRNA, clone 174N,
(xvi) V00599 Tubulin, Bet,
(xvii) X70326 Macmarck,
(xviii) D10923 Human mRNA for HM74,
(xix) D64142 Human mRNA for histone H1x, complete cds,
(xx) D86974 Human mRNA for KIAA0220 gene, partial cds,
(xxi) M60974 Human growth arrest and DNA damage-inducible protein (gadd45) mRNA, complete cds,
(xxii) X68277 H. sapiens CL 100 mRNA for protein tyrosine phosphatase,
(xxiii) L13391 Human helix-loop-helix basic phosphoprotein (GOS8) gene, complete cds,
(xxiv) M31627 Human X box binding protein-1 (XBP-1) mRNA, complete cds,
(xxv) U40369 Human spermidine/spermine N1-acetyltransferase (SSAT) gene, complete cds,
(xxvi) X52560 Nuclear Factor Nf-Il,
(xxvii) X61123 Human BTG1 mRNA,
(xxviii) U20734 Human transcription factor junB (junb) gene, 5' region and complete cds,
(xxix) U35048 Human TSC-22 protein mRNA, complete cds,
(xxx) M69043 H. sapiens MAD-3 mRNA encoding IkB-like activity, complete cds,
(xxxi) X51345 Human jun-B mRNA for JUN-B protein,
(xxxii) S68616 Na+/H+ exchanger NHE-1 isoform [human, heart, mRNA, 4516 nt],
(xxxiii) X89750 H. sapiens mRNA for TGIF protein,
(xxxiv) X69111 H. sapiens HLH 1R21 mRNA for helix-loop-helix protein,
(xxxv) U14603 Human protein-tyrosine phosphatase (HU-PP-1) mRNA, partial sequence,
(xxxvi) X52541 Human mRNA for early growth response protein 1 (hEGR1),
(xxxvii) D50683 H. sapiens mRNA for TGF-betaIIR alpha, complete cds,
(xxxviii) M92843 H. sapiens zinc finger transcriptional regulator mRNA, complete cds,
(xxxix) X91247 H. sapiens mRNA for thioredoxin reductase,
(xl) U05875 Human clone pSK1 interferon gamma receptor accessory factor-1 (AF-1) mRNA, comp,
(xli) L19314 Human HRY gene, complete cds,
(xlii) M30703 Human amphiregulin (AR) gene, exon 6, clones lambda-ARH(6,12),
(xliii) U34252 Human gamma-aminobutyraldehyde dehydrogenase mRNA, complete cds,
(xliv) S78825 Id1,
(xlv) D85429 H. sapiens gene for heat shock protein 40, complete cds,
(xlvi) U41766 Human metalloprotease/disintegrin/cysteine-rich protein precursor (MDC9) mRNA,
(xlvii) U89336 Human HLA class III region containing NOTCH4 gene, partial sequence, homeobox PB,
(xlviii) M69181 Human nonmuscle myosin heavy chain-B (MYH10) mRNA, partial cds,
(xlix) D15050 Human mRNA for transcription factor AREB6, complete cds,
(l) U28386 Human nuclear localization sequence receptor hSRP1alpha mRNA, complete cds,
(li) L77886 Human protein tyrosine phosphatase mRNA, complete cds,
(lii) X64330 H. sapiens mRNA for ATP-citrate lyase,
(liii) U37122 Human adducin gamma subunit mRNA, complete cds,
(liv) X74008 H. sapiens mRNA for protein phosphatase 1 gamma,
(lv) U60205 Human methyl sterol oxidase (ERG25) mRNA, complete cds,
(lvi) X76534 H. sapiens NMB mRNA,
(lvii) D87071 Human mRNA for KIAA0233 gene, complete cds,
(lviii) U90716 Human cell surface protein HCAR mRNA, complete cds,
(lix) M91083 Human DNA-binding protein (HRC1) mRNA, complete cds,
(lx) U29607 Human methionine aminopeptidase mRNA, complete cds,
(lxi) M76482 Human 130-kD pemphigus vulgaris antigen mRNA, complete cds,
(lxii) U72066 H. sapiens CtBP interacting protein CtIP (CtIP) mRNA, complete cds,
(lxiii) K03195 Human (HepG2) glucose transporter gene mRNA, complete cds,
(lxiv) X12953 Human rab2 mRNA, YPT1-related and member of ras family,
(lxv) M60483 Human protein phosphatase 2A catalytic subunit-alpha gene, complete cds,
(lxvi) U72649 Human BTG2 (BTG2) mRNA, complete cds,
(lxvii) D14520 Human mRNA for GC-Box binding protein BTEB2, complete cds,
(lxviii) L08069 Human heat shock protein, E. coli DnaJ homologue mRNA, complete cds,
(lxix) D50840 H. sapiens mRNA for ceramide glucosyltransferase, complete cds,
(lxx) L31801 H. sapiens monocarboxylate transporter 1 (SLC16A1) mRNA, complete cds,
(lxxi) S74017 Nrf2=NF-E2-like basic leucine zipper transcriptional activator [human, hemin-in,
(lxxii) X87241 H. sapiens mRNA for hFat protein,
(lxxiii) X52425 Human IL-4-R mRNA for the interleukin 4 receptor,
(lxxiv) D79994 Human mRNA for KIAA0172 gene, partial cds,
(lxxv) M58286 H. sapiens tumor necrosis factor receptor mRNA, complete cds,
(lxxvi) M13829 Human putative raf related protein (pks/a-raf) mRNA, partial cds,
(lxxvii) X78992 H. sapiens ERF-2 mRNA,
(lxxviii) U42031 Human 54 kDA progesterone receptor-associated immunophilin FKBP54 mRNA, partial, (lxxix) U88629 Human RNA polymerase II elongation factor ELL2, complete cds,
(lxxx) X52611 Human mRNA for transcription factor AP-2,
(lxxxi) U28749 Human high-mobility group phosphoprotein isoform I-C (HMGIC) mRNA, complete cds,
(lxxxii) L00058 Human (GM) germline c-myc proto-oncogene, exon 3 and 3' flank,
(lxxxiii) L26336 Heat Shock Protein, 70 Kda (Gb:Y00371,
(lxxxiv) L08246 Human myeloid cell differentiation protein (MCL1) mRNA,
(lxxxv) S73591 brain-expressed HHCPA78 homolog [human, HL60 acute promyelocytic, leukemia cells
(lxxxvi) J05211 Desmoplakin,
(lxxxvii) L00352 Human low density lipoprotein receptor gene, exon 18,
(lxxxviii) Y13647 Stearoyl-Coenzymea Desaturase,
(lxxxix) X77794 H. sapiens mRNA for cyclin G1,
(xc) M90656 Human gamma-glutamylcysteine synthetase (GCS) mRNA, complete cds,
(xci) M13929 Human c-myc-P64 mRNA, initiating from promoter P0, (HLmyc2.5) partial cds,
(xcii) D78129 H. sapiens mRNA for squalene epoxidase, partial cds,
(xciii) X80692 H. sapiens ERK3 mRNA, and
(xciv) J00120 Proto-Oncogene C-Myc, Alt. Splice 3, Orf 114; and (c) the third response further comprises an altered pattern of expression of at least one protein that is at least 90% identical to a polypeptide encoded by a polynucleotide selected from the group consisting of:

(i) M20030 Human small proline rich protein (sprII) mRNA, clone 930,
(ii) X53065,
(iii) M13903 Human involucrin gene, exon 2,
(iv) M22918 Myosin, Light Chain, Alkali, Smooth Muscle (Gb:U02629), Non-Muscle, Alt. Splice,
(v) L10343 Human elafin gene, complete cds,
(vi) M63573 Human secreted cyclophilin-like protein (SCYLP) mRNA, complete cds,
(vii) M21302 Human small proline rich protein (sprII) mRNA, clone 174N,
(viii) Y00787 Human mRNA for MDNCF (monocyte-derived neutrophil chemotactic factor),
(ix) X57985 H. sapiens genes for histones H2B.1 and H2A,
(x) L05188 H. sapiens small proline-rich protein 2 (SPRR2B) gene, complete cds,
(xi) X70326 Macmarcks,
(xii) X67325 H. sapiens p27 mRNA,
(xiii) L19779 H. sapiens histone H2A.2 mRNA, complete cds,
(xiv) S81914 IEX-1=radiation-inducible immediate-early gene [human, placenta, mRNA Partial, 1,
(xv) D45248 Human mRNA for proteasome activator hPA28 subunit beta, complete cds,
(xvi) Z22548 H. sapiens thiol-specific antioxidant protein mRNA,
(xvii) M22918 Myosin, Light Chain, Alkali, Smooth Muscle (Gb:U02629), Non-Muscle, Alt. Splice,
(xviii) X06956 Tubulin, Alpha 1, Isoform 44,
(xix) V00594 Human mRNA for metallothionein from cadmium-treated cells,
(xx) M80254 H. sapiens cyclophilin isoform (hCyP3) mRNA, complete cds,
(xxi) U04636 Human cyclooxygenase-2 (hCox-2) gene, complete cds,
(xxii) Z14244 H. sapiens cox VIIb mRNA for cytochrome c oxidase subunit VIIb,
(xxiii) X99920 H. sapiens mRNA for S100 calcium-binding protein A13,
(xxiv) U62800 Human cystatin M (CST6) mRNA, complete cds,
(xxv) L08069 Human heat shock protein, E. coli DnaJ homologue mRNA, complete cds,
(xxvi) L20688 Human GDP-dissociation inhibitor protein (Ly-GDI) mRNA, complete cds,
(xxvii) M13755 Human interferon-induced 17-kDa/15-kDa protein mRNA, complete cds,
(xxviii) M60278 Human heparin-binding EGF-like growth factor mRNA, complete cds,
(xxix) AF001294 H. sapiens IPL (lPL) mRNA, complete cds,
(xxx) X54489 Human gene for melanoma growth stimulatory activity (MGSA),
(xxxi) M21186 Human neutrophil cytochrome b light chain p22 phagocyte b-cytochrome mRNA, compl,
(xxxii) D42040 Human mRNA for KIAA9001 gene, complete cds,
(xxxiii) V00599 Tubulin, Beta,
(xxxiv) U37690 Human RNA polymerase II subunit (hsRPB10) mRNA, complete cds,
(xxxv) M21005 Human migration inhibitory factor-related protein 8 (MRP8) gene, complete cds,
(xxxvi) M37583 Human histone (H2A.Z) mRNA, complete cds,
(xxxvii) Z49989 H. sapiens mRNA for smoothelin,
(xxxviii) L24564 Human Rad mRNA, complete cds,
(xxxix) D49824 Human HLA-B null allele mRNA,
(xl) M59465 Human tumor necrosis factor alpha inducible protein A20 mRNA, complete cds,
(xli) S54005 thymosin beta-10 [human, metastatic melanoma cell line, mRNA, 453 nt],
(xlii) Z49254 H. sapiens L23-related mRNA,
(xliii) M22919 Myosin, Light Chain, Alkali, Smooth Muscle (Gb:U02629), Smooth Muscle, Alt. Spli,
(xliv) U70660 Human copper transport protein HAH1 (HAH1) mRNA, complete cds,
(xlv) AF006084 H. sapiens Arp2/3 protein complex subunit p41-Arc (ARC41) mRNA, complete cds,
(xlvi) X62083 H. sapiens mRNA for Drosophila female sterile homeotic (FSH) homologue,
(xlvii) D86974 Human mRNA for KIAA0220 gene, partial cds,
(xlviii) M72885 Human GOS2 gene, 5' flank and cds,
(xlix) S80437 fatty acid synthase {3' region} [human, breast and HepG2 cells, mRNA Partial, 22,
(l) X04654 Human mRNA for U1 RNA-associated 70K protein,
(li) t M26311 Human cystic fibrosis antigen mRNA, complete cds,
(lii) X14850 Human H2A.X mRNA encoding histone H2A.X,
(liii) M14328 Human alpha enolase mRNA, complete cds,
(liv) U07919 Human aldehyde dehydrogenase 6 mRNA, complete cds,
(lv) M28130 Human interleukin 8 (IL8) gene, complete cds,
(lvi) Z21507 H. sapiens EF-1delta gene encoding human elongation factor-1-delta,
(lvii) M92934 Human connective tissue growth factor, complete cds,
(lviii) M27436 Human tissue factor gene, complete cds, with a Alu repetitive sequence in the 3', (lix) X74874 H. sapiens gene for RNA pol II largest subunit, exon 1,
(lx) X57351 Human 1-8D gene from interferon-inducible gene family,
(lxi) X52979 Human gene for small nuclear ribonucleoproteins SmB and SmB',
(lxii) U41515 Human deleted in split hand/split foot 1 (DSS1) mRNA, complete cds,
(lxiii) D28235 Human PTGS2 gene for prostaglandin endoperoxide synthase-2, complete cds,
(lxiv) Y00503 Human mRNA for keratin 19,
(lxv) M57731 Human gro-beta mRNA, complete cds,
(lxvi) D50840 H. sapiens mRNA for ceramide glucosyltransferase, complete cds,
(lxvii) U52101 Human YMP mRNA, complete cds,
(lxviii) D13413 Human mRNA for tumor-associated 120 kDA nuclear protein p120, partial cds(carbox,
(lxix) L42379 H. sapiens bone-derived growth factor (BPGF-1) mRNA, complete cds,
(lxx) X52426 H. sapiens mRNA for cytokeratin 13,
(lxxi) J04456 Human 14 kd lectin mRNA, complete cds,
(lxxii) S78771 NAT=CpG island-associated gene [human, mRNA, 1741 nt],
(lxxiii) M26730 Human mitochondrial ubiquinone-binding protein (QP) gene, exon 4,
(lxxiv) U26727 Human p16INK4/MTS1 mRNA, complete cds,
(lxxv) X92896 H. sapiens mRNA for ITBA2 protein,
(lxxvi) Z69043 H. sapiens mRNA translocon-associated protein delta subunit precursor,
(lxxvii) L76568 H. sapiens excision and cross link protein (ERCC4) gene, complete genom,
(lxxviii) M12125 Human fibroblast muscle-type tropomyosin mRNA, complete cds,
(lxxix) U09937 Human urokinase-type plasminogen receptor, exon 7,
(lxxx) X15822 Human COX VIIa-L mRNA for liver-specific cytochrome c oxidase (EC 1.9.3.1.),
(lxxxi) M34516 Human omega light chain protein 14.1 (Ig lambda chain related) gene, exon 3,
(lxxxii) U53830 H. sapiens interferon regulatory factor 7A mRNA, complete cds,
(lxxxiii) X82693 H. sapiens mRNA for E48 antigen,
(lxxxiv) M58026 Human NB-1 mRNA, complete cds,
(lxxxv) M90657 Human tumor antigen (L6) mRNA, complete cds,
(lxxxvi) X57579 H. sapiens activin beta-A subunit (exon 2),
(lxxxvii) D38251 Human mRNA for RPB5 (XAP4), complete cds,
(lxxxviii) D89667 H. sapiens mRNA for c-myc binding protein, complete cds,
(lxxxix) AB000584 H. sapiens mRNA for TGF-beta superfamily protein, complete cds,
(xc) L76200 Human guanylate kinase (GUK1) mRNA, complete cds,
(xci) J04794 Human aldehyde reductase mRNA, complete cds,
(xcii) X52882 Human t-complex polypeptide 1 gene,
(xciii) M79463 Human PML-2 mRNA, complete CDS,
(xciv) Y09022 H. sapiens mRNA for Not56-like protein,
(xcv) M12529 Human apolipoprotein E mRNA, complete cds,
(xcvi) X71129 H. sapiens mRNA for electron transfer flavoprotein beta subunit,
(xcvii) X83416 H. sapiens PrP gene, exon 2,
(xcviii) D89052 H. sapiens mRNA for proton-ATPase-like protein, complete cds,
(xcix) M60974 Human growth arrest and DNA-damage-inducible protein (gadd45) mRNA, complete cds,
(c) M16364 Human creatine kinase-B mRNA, complete cds,
(ci) D38305 Human mRNA for Tob, complete cds,
(cii) X87679 Major Histocompatibility Complex, Class I, E (Gb:M21533),
(ciii) Z29505 H. sapiens mRNA for nucleic acid binding protein sub2.3,
(civ) K02574,
(cv) U09813 Human mitochondrial ATP synthase subunit 9, P3 gene copy, mRNA, nuclear gene enc,
(cvi) X67951 H. sapiens mRNA for proliferation-associated gene (pag),
(cvii) J04611 Human lupus p70 (Ku) autoantigen protein mRNA, complete cds,
(cviii) U09578 H. sapiens MAPKAP kinase (3 pK) mRNA, complete cds,
(cix) X53800 Human mRNA for macrophage inflammatory protein-2beta (MIP2beta),
(cx) V00599 Tubulin, Beta 2,
(cxi) U69126 Human FUSE binding protein 2 (FBP2) mRNA, partial cds,
(cxii) X53416 Human mRNA for actin-binding protein (filamin) (ABP-280),
(cxiii) U90546 Human butyrophilin (BTF4) mRNA, complete cds,
(cxiv) M58459 Human ribosomal protein (RPS4Y) isoform mRNA, complete cds,
(cxv) M19961 Human cytochrome c oxidase subunit Vb (cox Vb) mRNA, complete cds,
(cxvi) U65579 Human mitochondrial NADH dehydrogenase-ubiquinone Fe—S protein 8, 23 kDA subunit,
(cxvii) X77794 H. sapiens mRNA for cyclin G1,
(cxviii) M29064 Human hnRNP B1 protein mRNA,
(cxix) D21853 Human mRNA for KIAA0111 gene, complete cds,
(cxx) X78687 H. sapiens G9 gene encoding sialidase,
(cxxi) X15729 Human mRNA for nuclear p68 protein,
(cxxii) X04828 Human mRNA for G(i) protein alpha-subunit (adenylate cyclase inhibiting GTP-bind,
(cxxiii) L27943 H. sapiens cytidine deaminase (CDA) mRNA, complete cds,
(cxxiv) L40391 H. sapiens (clone s153) mRNA fragment,
(cxxv) D42123 H. sapiens mRNA for ESP1/CRP2, complete cds,
(cxxvi) X74104 H. sapiens mRNA for TRAP beta subunit,
(cxxvii) M84332 Human ADP-ribosylation factor 1 gene, exons 2–5,
(cxxviii) L37127 H. sapiens RNA polymerase II mRNA, complete cds,
(cxxix) M92843 H. sapiens zinc finger transcriptional regulator mRNA, complete cds,
(cxxx) U07664 Human HB9 homeobox gene, exons 2 and 3 and complete cds,
(cxxxi) L48546 H. sapiens tuberin (TSC2) gene, exons 38, 39, 40 and 41,
(cxxxii) X53586 Human mRNA for integrin alpha 6,
(cxxxiii) t D21852 Human mRNA for KIAA0029 gene, partial cds, (cxxxiv) L11066 Human mRNA sequence,
(cxxxv) J04444 Human cytochrome c-1 gene, complete cds,
(cxxxvi) M95787 Human 22 kDA smooth muscle protein (SM22) mRNA, complete cds,
(cxxxvii) L07517 Mucin 6, Gastric (Gb:L07517),
(cxxxviii) X91247 H. sapiens mRNA for thioredoxin reductase,
(cxxxix) L11672 Human Kruppel related zinc finger protein (HTF10) mRNA, complete cds,
(cxl) U30999 Human (memc) mRNA, 3'UTR,
(cxli) U01337 Human Ser/Thr protein kinase (A-RAF-1) gene, complete cds,
(cxlii) U28480 Uncoupling Protein Ucp,
(cxliii) X12794 Human v-erbA related ear-2 gene,
(cxliv) L22005 Human ubiquitin conjugating enzyme mRNA, partial cds,
(cxlv) M12886 Human T-cell receptor active beta-chain mRNA, complete cds,
(cxlvi) Y08915 H. sapiens mRNA for alpha 4 protein,
(cxlvii) M24547 Amyloid Beta (A4) Precursor Protein, Alt. Splice 2, A4(751),
(cxlviii) X76717 H. sapiens MT-11 mRNA,
(cxlix) M64347 Human novel growth factor receptor mRNA, 3' cds,
(cl) X05409 Human RNA for mitochondrial aldehyde dehydrogenase I ALDH I (EC 1.2.1.3),
(cli) D87469 Human mRNA for KIAA0279 gene, partial cds,
(clii) M58603 Human nuclear factor kappa-B DNA binding subunit (NF-kappa-B) mRNA, complete cds,
(cliii) M76482 Human 130-kD pemphigus vulgaris antigen mRNA, complete cds,
(cliv) X06323 Human MRL3 mRNA for ribosomal protein L3 homologue (MRL3=mammalian ribosome L,
(clv) X78992 H. sapiens ERF-2 mRNA,
(clvi) L41351 H. sapiens prostasin mRNA, complete cds,
(clvii) X75342 H. sapiens SHB mRNA,
(clviii) U83115 Human non-lens beta gamma-crystallin like protein (AIM1) mRNA, partial cds,
(clix) U88629 Human RNA polymerase II elongation factor ELL7, complete cds,
(clx) S78825 Id1,
(clxi) U28811 Human cysteine-rich fibroblast growth factor receptor (CFR-1) mRNA, complete cds,
(clxii) M58286 H. sapiens tumor necrosis factor receptor mRNA, complete cds,
(clxiii) D78129 H. sapiens mRNA for squalene epoxidase, partial cds,
(clxiv) D14874 H. sapiens mRNA for adrenomedullin precursor, complete cds,
(clxv) Z26317 H. sapiens mRNA for desmoglein 2,
(clxvi) L19267 H. sapiens 59 protein mRNA, 3' end,
(clxvii) J00120 Proto-Oncogene C-Myc, Alt. Splice 3, Orf 114,
(clxviii) U33821 Human tax 1-binding protein TXBP151 mRNA, complete cds,
(clxix) U52100 Human XMP mRNA, complete cds,
(clxx) L31801 H. sapiens monocarboxylate transporter 1 (SLC16A1) mRNA, complete cds,
(clxxi) L00058 Human (GH) germline c-myc proto-oncogene, exon 3 and 3' flank,
(clxxii) U52426 H. sapiens GOK (STIM1) mRNA, complete cds,
(clxxiii) M80244 Human E16 mRNA, complete cds,
(clxxiv) U56418 Human lysophosphatidic acid acyltransferase-beta mRNA, complete cds,
(clxxv) L38490 H. sapiens ADP-ribosylation factor mRNA, complete cds,
(clxxvi) U14603 Human protein-tyrosine phosphatase (HU-PP-1) mRNA, partial sequence,
(clxxvii) L77886 Human protein tyrosine phosphatase mRNA, complete cds,
(clxxviii) M38258 Human retinoic acid receptor gamma 1 mRNA, complete cds,
(clxxix) X89750 H. sapiens mRNA for TGIF protein,
(clxxx) D85429 H. sapiens gene for heat shock protein 40, complete cds,
(clxxxi) J05211 Desmoplakin I,
(clxxxii) M31627 Human X box binding protein-1 (XBP-1) mRNA, complete cds,
(clxxxiii) X80695 H. sapiens OXA1Hs mRNA,
(clxxxiv) M54915 Human h-pim-1 protein (h-pim-1) mRNA, complete cds,
(clxxxv) D83777 Human mRNA for KIAA0193 gene, complete cds,
(clxxxvi) D31883 Human mRNA for KIAA0059 gene, complete cds,
(clxxxvii) U00968 Human SREBP-1 mRNA, complete cds,
(clxxxviii) K03195 Human (HepG2) glucose transporter gene mRNA, complete cds,
(clxxxix) D86965 Human mRNA for KIAA0210 gene, complete cds,
(cxc) Z30643 H. sapiens mRNA for chloride channel (putative) 2139 bp.
(cxci) D14520 Human mRNA for GC-Box binding protein BTEB2, complete cds,
(cxcii) D87462 Human mRNA for KIAA0272 gene, partial cds,
(cxciii) X80692 H. sapiens ERK3 mRNA,
(cxciv) X90858 H. sapiens mRNA for uridine phosphorylase,
(cxcv) M57763 Human ADP-ribosylation factor (hARF6) mRNA, complete cds,
(cxcvi) X92720 H. sapiens mRNA for phosphoenolpyruvate carboxykinase,
(cxcvii) M81601 Human transcription elongation factor (SII) mRNA, complete cds,
(cxcviii) X52611 Human mRNA for transcription factor AP-2,
(cxcix) U09587 Human glycyl-tRNA synthetase mRNA, complete cds,
(cc) U14550 Human sialyltransferase SThM (sthm) mRNA, complete cds,
(cci) D90209 Human mRNA for DNA binding protein TAXREB67,
(ccii) X77366 H. sapiens HBZ17 mRNA,
(cciii) X76534 H. sapiens NMB mRNA,
(cciv) U37519 Human aldehyde dehydrogenase (ALDH8) mRNA, complete cds,
(ccv) M83667 Human NF-IL6-beta protein mRNA, complete cds,
(ccvi) U53347 Human neutral amino acid transporter B mRNA, complete cds,
(ccvii) L09229 Human long-chain acyl-coenzyme A synthetase (FACL1) mRNA, complete cds,
(ccviii) S73591 brain-expressed HHCPA78 homolog [human, HL-60 acute promyelocytic leukemia cells,
(ccix) M13929 Human c-myc-P64 mRNA, initiating from promoter P0, (HLmyc2.5) partial cds, (ccx) M55268 Human casein kinase II alpha' subunit mRNA, complete cds,
(ccxi) M77836 Human pyrroline 5-carboxylate reductase mRNA, complete cds,
(ccxii) HG2724-HT2820$_{\_l\ at\ s}$75762 Oncogene Tls/ Chop, Fusion Activated,
(ccxiii) U72066 *H. sapiens* CtBP interacting protein CtIP (CtIP) mRNA, complete cds,
(ccxiv) U42031 Human 54 kDa progesterone receptor-associated immunophilin FKBP54 mRNA, partial,
(ccxv) M27396 Human asparagine synthetase mRNA, complete cds,
(ccxvi) X01630 Human mRNA for argininosuccinate synthetase,
(ccxvii) D32050 Human mRNA for alanyl-tRNA synthetase, complete cds,
(ccxviii) M90656 Human gamma-glutamylcysteine synthetase (GCS) mRNA, complete cds,
(ccxix) J04102 Human erythroblastosis virus oncogene homolog 2 (ets-2) mRNA, complete cds, and
(ccxx) X69111 *H. sapiens* HLH 1R21 mRNA for helix-loop-helix protein.

90. The method according to claim 81, wherein the levels of the plurality of proteins are measured by ELISA.

91. A method for detecting exposure of a cell to ultraviolet radiation by screening for a response of the cell to ultraviolet radiation exposure, the response being an altered pattern of expression determined by gene expression array analysis, comprising:

(a) measuring the levels of a plurality of RNA molecules in the cell for at least one time point after ultraviolet radiation exposure to establish a test pattern of expression; and (b) comparing the test pattern of expression to the response of a cell to ultraviolet radiation exposure;

wherein if the pattern of expression for the cell is substantially similar to the response of the cell to ultraviolet radiation, the cell was exposed to ultraviolet radiation.

92. A method for detecting exposure of a cell to ultraviolet radiation by screening for a response of the cell to ultraviolet radiation exposure, the response being an altered pattern of expression determined by gene expression array analysis, comprising:

(a) measuring the levels of a plurality of proteins in the cell for at least one time point after ultraviolet radiation exposure to establish a test pattern of expression; and (b) comparing the test pattern of expression to the response of a cell to ultraviolet radiation exposure;

(e) wherein if the pattern of expression for the cell is substantially similar to the response of the cell to ultraviolet radiation, the cell was exposed to ultraviolet radiation.

* * * * *

UNITED STATES PATENT AND TRADEMARK OFFICE
CERTIFICATE OF CORRECTION

PATENT NO. : 6,794,137 B2
DATED : September 21, 2004
INVENTOR(S) : Blumenberg

It is certified that error appears in the above-identified patent and that said Letters Patent is hereby corrected as shown below:

Column 1,
Line 10, before "Cross-Reference to Related Application" insert:
-- Statement Regarding Federally Sponsored Research The research described herein was funded in-part by National Institutes of Health (NIH), 9000 Rockville Pike, Bethesda, Maryland 20892. Accordingly, the U.S. government may have certain rights in this invention. --

Signed and Sealed this

Eleventh Day of January, 2005

JON W. DUDAS
*Director of the United States Patent and Trademark Office*